United States Patent
Abraham et al.

(10) Patent No.: US 11,084,861 B2
(45) Date of Patent: Aug. 10, 2021

(54) GIP/GLP1 CO-AGONIST COMPOUNDS

(71) Applicant: Eli Lilly and Company, Indianapolis, IN (US)

(72) Inventors: Milata Mary Abraham, Indianapolis, IN (US); Jorge Alsina-Fernandez, Indianapolis, IN (US); Robert Andrew Brown, Carmel, IN (US); Over Cabrera, Carmel, IN (US); Tamer Coskun, Carmel, IN (US); Robert Chadwick Cummins, Carmel, IN (US); Mohamed ElSayed Hamed Elsayed, Fishers, IN (US); Hongchang Qu, Carmel, IN (US); James Lincoln Wallis, Indianapolis, IN (US); Amita Datta-Mannan, Indianapolis, IN (US); Xianyin Lai, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 16/518,468

(22) Filed: Jul. 22, 2019

(65) Prior Publication Data

US 2020/0024322 A1 Jan. 23, 2020

Related U.S. Application Data

(60) Provisional application No. 62/740,596, filed on Oct. 3, 2018, provisional application No. 62/730,563, filed on Sep. 13, 2018, provisional application No. 62/702,072, filed on Jul. 23, 2018.

(51) Int. Cl.
| | |
|---|---|
| *C07K 14/605* | (2006.01) |
| *A61P 3/04* | (2006.01) |
| *A61K 9/20* | (2006.01) |
| *A61K 9/48* | (2006.01) |
| *A61K 38/56* | (2006.01) |
| *A61K 9/00* | (2006.01) |

(52) U.S. Cl.
CPC .......... *C07K 14/605* (2013.01); *A61K 9/2013* (2013.01); *A61K 9/4858* (2013.01); *A61K 38/56* (2013.01); *A61P 3/04* (2018.01); *A61K 9/0019* (2013.01); *A61K 9/0053* (2013.01)

(58) Field of Classification Search
None
See application file for complete search history.

(56) References Cited

U.S. PATENT DOCUMENTS

| 9,474,780 B2 | 10/2016 | Bokvist et al. |
| 10,278,923 B2 | 5/2019 | Nielsen et al. |
| 2016/0199438 A1* | 7/2016 | Bokvist ............... C07K 14/575 514/7.2 |
| 2017/0112897 A1 | 4/2017 | Talbot |

FOREIGN PATENT DOCUMENTS

| WO | 2013/164483 | | 11/2013 |
| WO | WO 2013/164483 | * | 11/2013 |
| WO | 2014049610 | | 4/2014 |
| WO | WO 2014/049610 | * | 4/2014 |
| WO | 2014/177683 | | 5/2014 |
| WO | 2014152460 | | 9/2014 |
| WO | WO 2014/152460 | * | 9/2014 |
| WO | 2015/067715 | | 5/2015 |
| WO | WO 2015/067715 | * | 5/2015 |
| WO | 2016/111971 | | 7/2016 |
| WO | WO 2016/111971 | * | 7/2016 |
| WO | WO 2016111971 | * | 7/2016 |
| WO | WO 2017/112897 | * | 4/2017 |
| WO | 2019125929 | | 6/2019 |

OTHER PUBLICATIONS

Finan et al. "Unimolecular Dual Incretins Maximize Metabolic Benefits In Rodents, Monkeys, and Humans", Science Translational Medicine, vol. 5, No. 209ra151, Oct. 30, 2013, pp. 1-17.*
International Search Report of the International Searching Authority pertaining to International Application No. PCT/US2019/042822; dated Nov. 7, 2019; 12 pages.
Written Opinion of the International Searching Authority pertaining to International Application No. PCT/US2019/042822; dated Nov. 7, 2019; 14 pages.
Pratley, Richard, et. al. Oral semaglutide versus subcutaneous liraglutide and placebo in type 2 diabetes (PIONEER 4): a randomized, double blind, phase 3a tiral; The Lancet, (online Jun. 8, 2019).
Kaspar, Allan et. al.Future Directions for peptide therapeutics development; Drug Discovery Today vol. 18: No. 17/18 (Sep. 2013).
Finan, Brian, Unimolecular Dual Incretins Maximize Metabolic Benefits in Rodents, Monkeys, and Humans; Science Translational Medicine.org vol. 5; Issue 209 p. 1 www.ScienceTranslationlMedicine.org (Oct. 30, 2013).

* cited by examiner

*Primary Examiner* — Maury A Audet
(74) *Attorney, Agent, or Firm* — Macharri Vorndran-Jones

(57) ABSTRACT

The present invention relates to compounds having activity at both the human glucose-dependent insulinotropic polypeptide (GIP) and glucagon-like peptide-1 (GLP-1) receptors. The present invention also relates to compounds having an extended duration of action at each of these receptors. Furthermore, the present invention relates to compounds that may be administered orally. Compounds may be useful in the treatment of type 2 diabetes mellitus ("T2DM"). Also, the compounds may be useful in the treatment of obesity.

10 Claims, No Drawings

Specification includes a Sequence Listing.

GIP/GLP1 CO-AGONIST COMPOUNDS

The present invention relates to compounds having activity at both the human glucose-dependent insulinotropic polypeptide (GIP) and glucagon-like peptide-1 (GLP-1) receptors. The present invention also relates to compounds having an extended duration of action at each of these receptors. Furthermore, the present invention relates to compounds that may be administered orally. Compounds may be useful in the treatment of type 2 diabetes mellitus ("T2DM"). Also, the compounds may be useful in the treatment of obesity.

Over the past several decades, the prevalence of diabetes has continued to rise. T2DM is the most common form of diabetes accounting for approximately 90% of all diabetes. T2DM is characterized by high blood glucose levels associated mainly with insulin resistance. The current standard of care for T2DM includes diet and exercise, treatment with oral medications, and injectable glucose lowering drugs, including incretin-based therapies, such as GLP-1 receptor agonists. A variety of GLP-1 receptor agonists are currently available for treatment of T2DM, although currently marketed GLP-1 receptor agonists are generally dose-limited by gastrointestinal side effects such as nausea and vomiting. Subcutaneous injection is the typical route of administration for the available GLP-1 receptor agonists. When treatment with oral medications and incretin-based therapies are insufficient, insulin treatment is considered. Despite the advances in treatment available today, many patients with T2DM are unable to reach their glycemic control goals. Uncontrolled diabetes leads to several conditions associated with increased morbidity and mortality of patients. There is a need for a treatment to enable more patients with T2DM to reach their glycemic treatment goal.

Obesity is a complex medical disorder resulting in excessive accumulation of adipose tissue mass. Today obesity is a global public health concern that is associated with undesired health outcomes and morbidities. Desired treatments for patients with obesity strive to reduce excess body weight, improve obesity-related co-morbidities, and maintain long-term weight reduction. Available treatments for obesity are particularly unsatisfactory for patients with severe obesity. There is a need for alternative treatment options to induce therapeutic weight loss in patients in need of such treatment.

WO2016/111971 describes peptides stated to have GLP-1 and GIP activity. WO2013/164483 also discloses compounds stated to have GLP-1 and GIP activity.

There is a need for T2DM treatments capable of providing effective glucose control for a larger portion of the patients in need of such treatment. There is a further need for T2D treatments capable of providing effective glucose control and with a favorable side effect profile. There is a need for alternate treatment options to provide therapeutic weight loss in a patient in need of such treatment. There is a need for an alternate treatment option for a patient in need of treatment for severe obesity.

There is a desire for compounds having agonist activity at the GIP and GLP-1 receptors that are suitable for oral administration. Compounds with extended duration of action at each of the GIP and GLP-1 receptors are desirable to allow for less frequent dosing of the compound.

Accordingly, the present invention provides a compound of Formula I:

(SEQ ID NO: 3)
$R_1X_1X_2X_3GTX_6TSDX_{10}X_{11}X_{12}X_{13}X_{14}DX_{16}X_{17}AX_{19}X_{20}X_{21}X_{22}$
$X_{23}X_{24}X_{25}X_{26}X_{27}X_{28}X_{29}X_{30}X_{31}$ wherein:

$R_1$ is a modification of the N-terminal amino group wherein the modification is selected from the group consisting of Ac and absent;

$X_1$ is selected from the group consisting of Y, H, D-Tyr, F, desH, and desY, $X_2$ is selected from the group consisting of Aib, αMeP, A, P, and D-Ala;

or $X_1$ and $X_2$ combine to form desH-ψ[NHCO]-Aib;

$X_3$ is selected from the group consisting of E, N, Aad, and cTA;

$X_6$ is selected from the group consisting of F, αMeF, and αMeF(2F);

$X_{10}$ is selected from the group consisting of A, L, H, 3Pal, 4Pal, V, Y, E, αMeF, αMeF(2F), I, αMeY, Q, D-His, D-Tyr, cTA, and K(2-[2-(2-amino-ethoxy)-ethoxy]-acetyl)$_2$-(γ-Glu)-CO—(CH$_2$)qCO$_2$H;

$X_{11}$ is selected from the group consisting of S, αMeS, and D-Ser;

$X_{12}$ is selected from the group consisting of I, S, D-Ile, and K(2-[2-(2-amino-ethoxy)-ethoxy]-acetyl)$_2$-(γ-Glu)-CO—(CH$_2$)qCO$_2$H;

$X_{13}$ is selected from the group consisting of Nle, Aib, L, αMeL, and K(2-[2-(2-amino-ethoxy)-ethoxy]-acetyl)$_2$-(γ-Glu)-CO—(CH$_2$)qCO$_2$H;

$X_{14}$ is selected from the group consisting of L and K, wherein K is conjugated to a $C_{16}$-$C_{22}$ fatty acid wherein said fatty acid is optionally conjugated to said K via a linker;

$X_{16}$ is selected from the group consisting of K, E, Orn, Dab, Dap, S, T, H, Aib, αMeK, R, and K(2-[2-(2-amino-ethoxy)-ethoxy]-acetyl)$_2$-(γ-Glu)-CO—(CH$_2$)qCO$_2$H;

$X_{17}$ is selected from the group consisting of K, Q, I, and an amino acid conjugated to a $C_{16}$-$C_{22}$ fatty acid wherein said fatty acid is optionally conjugated to said amino acid via a linker;

$X_{19}$ is selected from the group consisting of Q, A, and K(2-[2-(2-amino-ethoxy)-ethoxy]-acetyl)$_2$-(γ-Glu)-CO—(CH$_2$)qCO$_2$H;

$X_{20}$ is selected from the group consisting of Aib, Q, H, R, K, αMeK, and K(2-[2-(2-amino-ethoxy)-ethoxy]-acetyl)$_2$-(γ-Glu)-CO—(CH$_2$)qCO$_2$H;

$X_{21}$ is selected from the group consisting of H, Aad, D, Aib, T, A, E, I, and K(2-[2-(2-amino-ethoxy)-ethoxy]-acetyl)$_2$-(γ-Glu)-CO—(CH$_2$)qCO$_2$H;

$X_{22}$ is selected from the group consisting of F and αMeF;

$X_{23}$ is selected from the group consisting of I, L, A, G, F, H, E, V, and K(2-[2-(2-amino-ethoxy)-ethoxy]-acetyl)$_2$-(γ-Glu)-CO—(CH$_2$)qCO$_2$H;

$X_{24}$ is selected from the group consisting of S, Aad, D-Glu, E, Aib, H, V, A, Q, D, P, and K(2-[2-(2-amino-ethoxy)-ethoxy]-acetyl)$_2$-(γ-Glu)-CO—(CH$_2$)qCO$_2$H;

$X_{25}$ is selected from the group consisting of Y and αMeY;

$X_{26}$ is selected from the group consisting of L, αMeL, and K(2-[2-(2-amino-ethoxy)-ethoxy]-acetyl)$_2$-(γ-Glu)-CO—(CH$_2$)qCO$_2$H;

$X_{27}$ is selected from the group consisting of L, I, and K(2-[2-(2-amino-ethoxy)-ethoxy]-acetyl)$_2$-(γ-Glu)-CO—(CH$_2$)qCO$_2$H;

$X_{28}$ is selected from the group consisting of E, A, S, D-Glu, and K(2-[2-(2-amino-ethoxy)-ethoxy]-acetyl)$_2$-(γ-Glu)-CO—(CH$_2$)qCO$_2$H;

$X_{29}$ is selected from the group consisting of Aib, G, A, and K(2-[2-(2-amino-ethoxy)-ethoxy]-acetyl)$_2$-(γ-Glu)-CO—(CH$_2$)qCO$_2$H;

$X_{30}$ is selected from the group consisting of C, G, G-R$_2$ and K(2-[2-(2-amino-ethoxy)-ethoxy]-acetyl)$_2$-(γ-Glu)-CO—(CH$_2$)$_q$—CO$_2$H;

$X_{31}$ is absent or is selected from the group consisting of PX$_{32}$X$_{33}$X$_{34}$—R$_2$ (SEQ ID NO:4), PX$_{32}$X$_{33}$X$_{34}$X$_{33}$X$_{36}$X$_{37}$X$_{38}$X$_{39}$—R$_2$ (SEQ ID NO: 5), PX$_{32}$X$_{33}$X$_{34}$X$_{33}$X$_{36}$X$_{37}$X$_{38}$X$_{39}$X$_{40}$—R$_2$ (SEQ ID NO:6), K[(2-[2-(2-amino-ethoxy)-ethoxy]-acetyl)$_2$-(γ-Glu)-CO—(CH$_2$)$_q$—CO$_2$H] X$_{32}$X$_{33}$X$_{34}$—R$_2$ (SEQ ID NO: 7), K[(2-[2-(2-amino-ethoxy)-ethoxy]-acetyl)$_2$-(γ-Glu)-CO—(CH$_2$)$_q$—CO$_2$H]
X$_{32}$X$_{33}$X$_{34}$X$_{33}$X$_{36}$X$_{37}$X$_{38}$X$_{39}$—R$_2$ (SEQ ID NO: 8), and K[(2-[2-(2-amino-ethoxy)-ethoxy]-acetyl)$_2$-(γ-Glu)-CO—(CH$_2$)$_q$—CO$_2$H]
X$_{32}$X$_{33}$X$_{34}$X$_{33}$X$_{36}$X$_{37}$X$_{38}$X$_{39}$X$_{40}$—R$_2$ (SEQ ID NO: 9);

wherein:

$X_{32}$ is S or K[(2-[2-(2-amino-ethoxy)-ethoxy]-acetyl)$_2$-(γ-Glu)-CO—(CH$_2$)$_q$—CO$_2$H];

$X_{33}$ is S or K[(2-[2-(2-amino-ethoxy)-ethoxy]-acetyl)$_2$-(γ-Glu)-CO—(CH$_2$)$_q$—CO$_2$H];

$X_{34}$ is selected from the group consisting of G, C, and K[(2-[2-(2-amino-ethoxy)-ethoxy]-acetyl)$_2$-(γ-Glu)-CO—(CH$_2$)$_q$—CO$_2$H];

$X_{35}$ is A or K[(2-[2-(2-amino-ethoxy)-ethoxy]-acetyl)$_2$-(γ-Glu)-CO—(CH$_2$)$_q$—CO$_2$H];

$X_{36}$ is P or K[(2-[2-(2-amino-ethoxy)-ethoxy]-acetyl)$_2$-(γ-Glu)-CO—(CH$_2$)$_q$—CO$_2$H];

$X_{37}$ is P or K[(2-[2-(2-amino-ethoxy)-ethoxy]-acetyl)$_2$-(γ-Glu)-CO—(CH$_2$)$_q$—CO$_2$H];

$X_{38}$ is P or K[(2-[2-(2-amino-ethoxy)-ethoxy]-acetyl)$_2$-(γ-Glu)-CO—(CH$_2$)$_q$—CO$_2$H];

$X_{39}$ is selected from the group consisting of C, S, and K[(2-[2-(2-amino-ethoxy)-ethoxy]-acetyl)$_2$-(γ-Glu)-CO—(CH$_2$)$_q$—CO$_2$H];

$X_{40}$ is selected from the group consisting of C and K[(2-[2-(2-amino-ethoxy)-ethoxy]-acetyl)$_2$-(γ-Glu)-CO—(CH$_2$)$_q$—CO$_2$H];

q is selected from the group consisting of 14, 15, 16, 17, 18, 19, and 20; and

R$_2$ is a modification of the C-terminal group, wherein the modification is NH$_2$ or absent;

or a pharmaceutically acceptable salt thereof;

wherein if $X_{30}$ is G-R$_2$, then $X_{31}$ is absent;

wherein no more than one of $X_{10}$, $X_{12}$, $X_{13}$, $X_{14}$, $X_{16}$, $X_{17}$, $X_{19}$, $X_{20}$, $X_{21}$, $X_{23}$, $X_{24}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$, $X_{37}$, $X_{38}$, $X_{39}$, and $X_{40}$ may be a substituent that contains a fatty acid; and wherein no more than one of $X_{30}$, $X_{34}$, $X_{39}$, and $X_{40}$ may be C; and wherein if one of $X_{30}$, $X_{34}$, $X_{39}$, and $X_{40}$ is C, then none of $X_{10}$, $X_{12}$, $X_{13}$, $X_{14}$, $X_{16}$, $X_{17}$, $X_{19}$, $X_{20}$, $X_{21}$, $X_{23}$, $X_{24}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$, $X_{37}$, $X_{38}$, $X_{39}$, and $X_{40}$ is a substituent that contains a fatty acid.

In an embodiment is a compound of Formula I, or a pharmaceutically acceptable salt thereof, wherein q is 16. In an embodiment is a compound of Formula I, or a pharmaceutically acceptable salt thereof, wherein $X_{31}$ is selected from the group consisting of SEQ ID NO:5 and SEQ ID NO:8. In an embodiment is a compound of Formula I, or a pharmaceutically acceptable salt thereof, wherein the $X_{17}$ amino acid that is conjugated to a fatty acid is a natural amino acid. In an embodiment is a compound of Formula I, or a pharmaceutically acceptable salt thereof, wherein $X_{17}$ is selected from the group consisting of K, Q and I.

In an embodiment is a compound of Formula I, or a pharmaceutically acceptable salt thereof, wherein K is conjugated to a C$_{16}$-C$_{22}$ fatty acid wherein said fatty acid is optionally conjugated to said K via a linker.

In an embodiment is a compound of Formula I, or a pharmaceutically acceptable salt thereof, wherein $X_{14}$ or $X_{17}$ is selected from the group consisting of K(2-[2-(2-Amino-ethoxy)-ethoxy]-acetyl)$_2$-(γ-Glu)-CO—(CH$_2$)$_{16}$—CO$_2$H, K(2-[2-(2-Amino-ethoxy)-ethoxy]-acetyl)$_2$-(γ-Glu)-CO—(CH$_2$)$_{18}$—CO$_2$H, K(2-[2-(2-Amino-ethoxy)-ethoxy]-acetyl)$_2$-(γ-Glu)-CO—(CH$_2$)$_{14}$—CO$_2$H, K(2-[2-(2-Amino-ethoxy)-ethoxy]-acetyl)$_2$-CO—(CH$_2$)$_{18}$—CO$_2$H, K(2-[2-(2-Amino-ethoxy)-ethoxy]-acetyl)-(γ-Glu)-(Trx)-CO—(CH$_2$)$_{18}$—CO$_2$H, K(2-[2-(2-Amino-ethoxy)-ethoxy]-acetyl)-(Trx)-(γ-Glu)-CO—(CH$_2$)$_{18}$—CO$_2$H, K(2-[2-(2-Amino-ethoxy)-et)-ethoxy]-acetyl)-(εK)-(γ-Glu)-CO—(CH$_2$)$_{18}$—CO$_2$H, K(2-[2-(2-Amino-ethoxy)-ethoxy]-acetyl)-(εK)-(εK)—CO—(CH$_2$)$_{18}$—CO$_2$H, K(2-[2-(2-Amino-ethoxy)-ethoxy]-acetyl)$_2$-(γ-Glu)$_2$-CO—(CH$_2$)$_{18}$—CO$_2$H, K(2-[2-(2-Amino-ethoxy)-ethoxy]-acetyl)$_2$-CO—(CH$_2$)$_{18}$—CO$_2$H, K(2-[2-(2-Amino-ethoxy)-ethoxy]-acetyl)$_2$-(εK)—CO—(CH$_2$)$_{16}$—CO$_2$H, K(2-[2-(2-Amino-ethoxy)-ethoxy]-acetyl)$_2$-(εK)—CO—(CH$_2$)$_{14}$—CO$_2$H, and KDab-(2-[2-(2-Amino-ethoxy)-ethoxy]-acetyl)-Dab-(2-[2-(2-Amino-ethoxy)-ethoxy]-acetyl)-CO—(CH$_2$)$_{18}$—CO$_2$H.

In an embodiment is a compound of Formula I, or a pharmaceutically acceptable salt thereof, wherein $X_{14}$ or $X_{17}$ is selected from the group consisting of K(2-[2-(2-Amino-ethoxy)-ethoxy]-acetyl)$_2$-(γ-Glu)-CO—(CH$_2$)$_{16}$—CO$_2$H, K(2-[2-(2-Amino-ethoxy)-ethoxy]-acetyl)$_2$-(γ-Glu)-CO—(CH$_2$)$_{18}$—CO$_2$H, K(2-[2-(2-Amino-ethoxy)-ethoxy]-acetyl)$_2$-(γ-Glu)-CO—(CH$_2$)$_{14}$—CO$_2$H, and K(2-[2-(2-Amino-ethoxy)-ethoxy]-acetyl)$_2$-CO—(CH$_2$)$_{18}$—CO$_2$H.

In an embodiment is a compound of Formula I, or a pharmaceutically acceptable salt thereof, wherein $X_{14}$ or $X_{17}$ is selected from the group consisting of K(2-[2-(2-Amino-ethoxy)-ethoxy]-acetyl)$_2$-(γ-Glu)-CO—(CH$_2$)$_{16}$—CO$_2$H, K(2-[2-(2-Amino-ethoxy)-ethoxy]-acetyl)$_2$-(γ-Glu)-CO—(CH$_2$)$_{18}$—CO$_2$H, and K(2-[2-(2-Amino-ethoxy)-ethoxy]-acetyl)$_2$-(γ-Glu)-CO—(CH$_2$)$_{14}$—CO$_2$H. In an embodiment is a compound of Formula I, or a pharmaceutically acceptable salt thereof, wherein $X_{14}$ or $X_{17}$ is selected from the group consisting of K(2-[2-(2-Amino-ethoxy)-ethoxy]-acetyl)$_2$-(γ-Glu)-CO—(CH$_2$)$_{18}$—CO$_2$H and K(2-[2-(2-Amino-ethoxy)-ethoxy]-acetyl)$_2$-(γ-Glu)-CO—(CH$_2$)$_6$—CO$_2$H. In an embodiment is a compound of Formula I, or pharmaceutically acceptable salt thereof, wherein $X_{14}$ or $X_{17}$ is K(2-[2-(2-amino-ethoxy)-ethoxy]-acetyl)$_a$-(γ-Glu)$_b$-CO—(CH$_2$)$_q$—CO$_2$H, wherein a is 2, b is 1, and q is selected from the group consisting of 18 and 20. In an embodiment is a compound of Formula I, or pharmaceutically acceptable salt thereof, wherein $X_{14}$ or $X_{17}$ is K(2-[2-(2-amino-ethoxy)-ethoxy]-acetyl)$_a$-(γ-Glu)$_b$-CO—(CH$_2$)$_q$—CO$_2$H, wherein a is 2, b is 1 and q is 18. In an embodiment is a compound of Formula I, or pharmaceutically acceptable salt thereof, wherein $X_{14}$ or $X_{17}$ is K(2-[2-(2-amino-ethoxy)-ethoxy]-acetyl)$_a$-(γ-Glu)$_b$-CO—(CH$_2$)$_q$—CO$_2$H, wherein, a is 2, b is 1, and q is 20.

In an embodiment is a Formula I compound, or pharmaceutically acceptable salt thereof, wherein $X_1$ and $X_2$ do not combine to form desH-ψ[NHCO]-Aib (hereafter a "Formula II" compound).

In an embodiment is a compound of Formula I, or pharmaceutically acceptable salt thereof, wherein:
$X_{17}$ is an amino acid conjugated to a $C_{16}$-$C_{22}$ fatty acid wherein said fatty acid is optionally conjugated to said amino acid via a linker; and
$X_{30}$ is selected from the group consisting of G-$R_2$ and G;
wherein if $X_{30}$ is G, then $X_{31}$ is selected from the group consisting of P$X_{32}X_{33}X_{34}$—$R_2$ (SEQ ID NO:4), wherein $X_{32}$ is S, $X_{33}$ is S and $X_{34}$ is G (SEQ ID NO:297), and P$X_{32}X_{33}X_{34}X_{35}X_{36}X_{37}X_{39}X_{39}$—$R_2$ (SEQ ID NO:5), wherein $X_{32}$ is S, $X_{33}$ is S, $X_{34}$ is G, $X_{35}$ is A, $X_{36}$ is P, $X_{37}$ is P, $X_{38}$ is P and $X_{39}$ is S (SEQ ID NO:298) (hereafter a "Formula III" compound).

In an embodiment is a compound of Formula III, or pharmaceutically acceptable salt thereof, wherein the $X_{17}$ amino acid is conjugated to the fatty acid via a linker (hereafter a "Formula IIIa" compound).

In an embodiment is a compound of Formula III and IIIa, or a pharmaceutically acceptable salt thereof, wherein:
$X_{10}$ is selected from the group consisting of A, L, H, 3Pal, 4Pal, V, Y, E, αMeF, αMeF(2F), I, αMeY, Q, D-His, D-Tyr, and cTA;
$X_{12}$ is selected from the group consisting of I, S, and D-Ile;
$X_{13}$ is selected from the group consisting of Nle, Aib, L, and αMeL;
$X_{14}$ is selected from the group consisting of L and K;
$X_{16}$ is selected from the group consisting of K, E, Orn, Dab, Dap, S, T, H, Aib, αMeK, and R;
$X_{19}$ is selected from the group consisting of Q, and A;
$X_{20}$ is selected from the group consisting of Aib, Q, H, R, K, and αMeK;
$X_{21}$ is selected from the group consisting of H, Aad, D, Aib, T, A, E, and I;
$X_{23}$ is selected from the group consisting of I, L, A, G, F, H, E, and V;
$X_{24}$ is selected from the group consisting of S, Aad, D-Glu, E, Aib, H, V, A, Q, D, and P;
$X_{26}$ is selected from the group consisting of L, and αMeL;
$X_{27}$ is selected from the group consisting of L, and I;
$X_{28}$ is selected from the group consisting of E, A, S, and D-Glu;
$X_{29}$ is selected from the group consisting of Aib, G, and A;
$X_{30}$ is selected from the group consisting of G and G-$R_2$;
wherein if $X_{30}$ is G; then $X_{31}$ is selected from the group consisting of P$X_{32}X_{33}X_{34}$—$R_2$ (SEQ ID NO:4), wherein $X_{32}$ is S, $X_{33}$ is S and $X_{34}$ is G (SEQ ID NO:297) and P$X_{32}X_{33}X_{34}X_{35}X_{36}X_{37}X_{39}X_{39}$—$R_2$ (SEQ ID NO:5), wherein $X_{32}$ is S, $X_{33}$ is S, $X_{34}$ is G, $X_{35}$ is A, $X_{36}$ is P, $X_{37}$ is P, $X_{38}$ is P and $X_{39}$ is S (SEQ ID NO:298) (hereafter a "Formula IIIb" compound).

In an embodiment, is a compound of Formula III, IIIa and IIIb, or a pharmaceutically acceptable salt thereof, wherein the linker comprises from 1 to 2 amino acids, and in a further embodiment of these particular Formula III, IIIa and IIIb compounds are those wherein the linker amino acids are independently selected from the group consisting of Glu and γ-Glu. In another embodiment is a compound of Formula III, IIIa and IIIb, or a pharmaceutically acceptable salt thereof, wherein the linker comprises from one or two (2-[2-(2-amino-ethoxy)-ethoxy]-acetyl) moieties and in a further particular embodiment of these particular formula III, IIIa and IIIb compounds are those where the linker is (2-[2-(2-amino-ethoxy)-ethoxy]-acetyl)$_a$-(γ-Glu)$_b$, wherein a is selected from the group consisting of 1 or 2; and b is selected from the group consisting of 1 or 2.

In an embodiment is a compound of Formula III, or a pharmaceutically acceptable salt thereof, wherein $X_{17}$ is an amino acid conjugated to a $C_{16}$-$C_{22}$ fatty acid, wherein the amino acid is K and wherein said fatty acid is optionally conjugated to said amino acid via a linker.

In an embodiment is a compound of Formula III, or pharmaceutically acceptable salt thereof, wherein:
$R_1$ is absent;
$X_1$ and $X_2$ do not combine to form desH-ψ[NHCO]-Aib;
$X_{17}$ is K conjugated to a $C_{16}$-$C_{22}$ fatty acid wherein said fatty acid is optionally conjugated to said amino acid via a linker.

In an embodiment is a compound of Formula III, or pharmaceutically acceptable salt thereof, wherein:
$X_1$ is Y;
$X_2$ is Aib;
$X_3$ is E;
$X_{10}$ is selected from the group consisting of A, L, H, 3Pal, 4Pal, V, and Y;
$X_{11}$ is S;
$X_{12}$ is I;
$X_{14}$ is L;
$X_{16}$ is selected from the group consisting of K, E, Orn, Dab, and Dap;
$X_{17}$ is K conjugated to a $C_{16}$-$C_{22}$ fatty acid wherein said fatty acid is optionally conjugated to said amino acid via a linker;
$X_{19}$ is Q;
$X_{20}$ is Aib;
$X_{21}$ is selected from the group consisting of H, Aad, D, Aib, T, A, and E;
$X_{22}$ is F;
$X_{23}$ is I,
$X_{24}$ is selected from the group consisting of S, Aad, D-Glu, and E;
$X_{26}$ is L; and
$X_{25}$ is selected from the group consisting of E and A.

In an embodiment is a compound of Formula III, or pharmaceutically acceptable salt thereof, wherein:
$X_1$ is Y;
$X_2$ is Aib;
$X_3$ is E;
$X_6$ is αMeF(2F);
$X_{10}$ is selected from the group consisting of Y, 4-Pal, and V;
$X_{11}$ is S;
$X_{12}$ is I;
$X_{13}$ is selected from the group consisting of L, Aib, and αMeL;
$X_{14}$ is L;
$X_{16}$ is selected from the group consisting of E, K, and Orn;
$X_{17}$ is K conjugated to a $C_{16}$-$C_{22}$ fatty acid wherein said fatty acid is optionally conjugated to said amino acid via a linker;
$X_{19}$ is Q;
$X_{20}$ is Aib
$X_{21}$ is selected from the group consisting of E, A, and T;
$X_{22}$ is F;
$X_{23}$ is I;
$X_{24}$ is D-Glu;
$X_{25}$ is selected from the group consisting of Y and αMeY;
$X_{26}$ is L;
$X_{27}$ is I;
$X_{28}$ is E;

X$_{29}$ is G;
X$_{30}$ is G; and
X$_{31}$ is PX$_{32}$X$_{33}$X$_{34}$X$_{38}$X$_{36}$X$_{37}$X$_{38}$X$_{39}$—R$_2$ (SEQ ID NO:5), wherein X$_{32}$ is S, X$_{33}$ is S, X$_{34}$ is G, X$_{35}$ is A, X$_{36}$ is P, X$_{37}$ is P, X$_{38}$ is P, X$_{39}$ is S (SEQ ID NO:298).

In an embodiment is a compound of Formula III, IIIa and IIIb, or a pharmaceutically acceptable salt thereof, wherein R$_2$ is absent.

In an embodiment is a compound of Formula III, IIIa and IIIb, or a pharmaceutically acceptable salt thereof, wherein R$_2$ is NH$_2$.

In an embodiment is a compound of Formula III, IIIa and IIIb, or a pharmaceutically acceptable salt thereof, wherein X$_{13}$ is αMeL.

In an embodiment is a compound of Formula III, IIIa and IIIb, or a pharmaceutically acceptable salt thereof, wherein X$_{25}$ is Y and X$_{13}$ is αMeL.

In an embodiment is a compound of Formula III, IIIa and IIIb, or a pharmaceutically acceptable salt thereof, wherein X$_{17}$ is K conjugated to a fatty acid via a linker to the epsilon-amino group of the K side-chain wherein said fatty acid and linker have the following formula:

(2-[2-(2-amino-ethoxy)-ethoxy]-acetyl)$_a$-(γ-Glu)$_b$-CO—(CH$_2$)$_q$—CO$_2$H, wherein a is 1 or 2; b is 1 or 2; and q is selected from the group consisting of 14 to 20.

In an embodiment is a compound of Formula III, IIIa and IIIb, or a pharmaceutically acceptable salt thereof, wherein X$_{16}$ is Orn, X$_{13}$ is αMeL, and X$_2$, is Y. In an embodiment is a compound of Formula III, IIIa and IIIb, or a pharmaceutically acceptable salt thereof, wherein X$_{16}$ is E, X$_{13}$ is αMeL, and X$_{25}$ is Y. In an embodiment is a compound of Formula III, IIIa and IIIb, or a pharmaceutically acceptable salt thereof, wherein X$_{16}$ is E, X$_{13}$ is αMeL, X$_{10}$ is Y, and X$_{25}$ is αMeY. In an embodiment is a compound of Formula III, IIIa and IIIb, or a pharmaceutically acceptable salt thereof, wherein X$_{16}$ is Orn, X$_{13}$ is αMeL, X$_{10}$ is 4Pal, and X$_{25}$ is Y. In an embodiment is a compound of Formula III, IIIa and IIIb, or a pharmaceutically acceptable salt thereof, wherein X$_{16}$ is Orn, X$_{13}$ is αMeL, X$_{10}$ is V, and X$_{25}$ is Y. In an embodiment is a compound of Formula III, IIIa and IIIb, or a pharmaceutically acceptable salt thereof, wherein X$_{16}$ is E, X$_{13}$ is αMeL, X$_{25}$ is Y, and X$_{17}$ is K(2-[2-(2-Amino-ethoxy)-ethoxy]-acetyl)$_a$-(γ-Glu)$_b$-CO—(CH$_2$)$_q$—CO$_2$H, wherein a is 2; b is 1; and q is selected from the group consisting of 14 to 20. In an embodiment is a compound of Formula III, IIIa and IIIb, or a pharmaceutically acceptable salt thereof, wherein X$_{16}$ is E, X$_{13}$ is αMeL, X$_{10}$ is Y, and X$_{25}$ is Y and and X$_{17}$ is K(2-[2-(2-Amino-ethoxy)-ethoxy]-acetyl)$_a$-(γ-Glu)$_b$-CO—(CH$_2$)$_q$—CO$_2$H, wherein a is 2; b is 1; and q is selected from the group consisting of 16 to 20.

In an embodiment is a compound of Formula I selected from the group consisting of SEQ ID NO:10, SEQ ID NO:11, SEQ ID NO:12, SEQ ID NO:13, and SEQ ID NO:14, or a pharmaceutically acceptable salt thereof. In an embodiment is a compound of Formula I that is SEQ ID NO:10, or a pharmaceutically acceptable salt thereof. In an embodiment is a compound of Formula I that is SEQ ID NO:11, or a pharmaceutically acceptable salt thereof. In an embodiment is a compound of Formula I that is SEQ ID NO:12, or a pharmaceutically acceptable salt thereof. In an embodiment is a compound of Formula I that is SEQ ID NO:13, or a pharmaceutically acceptable salt thereof. In an embodiment is a compound of Formula I that is SEQ ID NO:14, or a pharmaceutically acceptable salt thereof.

In an embodiment is a compound of Formula I, or a pharmaceutically acceptable salt thereof, wherein X$_1$ is selected from the group consisting of Y, F, and D-Tyr; X$_6$ is F; and X$_{13}$ is selected from the group consisting of Aib, L, and αMeL.

In an embodiment, is a compound of Formula I, or a pharmaceutically acceptable salt thereof, wherein R$_1$ is absent; X$_1$ is selected from the group consisting of Y, F, and D-Tyr; X$_6$ is F; X$_{13}$ is selected from the group consisting of Aib, L, and αMeL; X$_2$ is Aib; X$_3$ is E; X$_{10}$ is Y; X$_{11}$ is S; X$_{12}$ is I; X$_{14}$ is L; X$_{16}$ is selected from the group consisting of K, E, Orn, Dab, Dap, S, T, H, Aib, αMeK, and R; X$_{17}$ is an amino acid conjugated to a C$_{16}$-C$_{22}$ fatty acid wherein said fatty acid is optionally conjugated to said amino acid via a linker; X$_{19}$ is Q; X$_{20}$ is selected from the group consisting of Aib, Q, H, and K; X$_{21}$ is selected from the group consisting of H, D, T, A, and E; X$_{22}$ is F; X$_{23}$ is I; X$_{24}$ is selected from the group consisting of D-Glu and E; X$_{26}$ is L; X$_{27}$ is I; X$_{28}$ is selected from the group consisting of E, A, S, and D-Glu; X$_{29}$ is selected from the group consisting of Aib, G, and A; X$_{30}$ is selected from the group consisting of C, G, and G-R$_2$; X$_{31}$ is absent or is selected from the group consisting of PX$_{32}$X$_{33}$X$_{34}$—R$_2$ (SEQ ID NO:4), PX$_{32}$X$_{33}$X$_{34}$X$_{35}$X$_3$X$_{37}$X$_{39}$X$_{39}$—R$_2$ (SEQ ID NO:5), and PX$_{32}$X$_{33}$X$_{34}$X$_{35}$X$_{36}$X$_{37}$X$_{35}$X$_{39}$X$_{40}$—R$_2$ (SEQ ID NO:6); wherein: X$_{32}$ is S; X$_{33}$ is S; X$_{34}$ is selected from the group consisting of G and C; X$_{35}$ is A; X$_{36}$ is P; X$_{37}$ is P; X$_{38}$ is P; X$_{39}$ is selected from the group consisting of C and S; and X$_{40}$ is C.

In an embodiment, is a compound of Formula I, or a pharmaceutically acceptable salt thereof, wherein X$_1$ is selected from the group consisting of Y, F, and D-Tyr; X$_6$ is F; and X$_{13}$ is selected from the group consisting of Aib, L, and αMeL; X$_{25}$ is A; X$_{29}$ G; X$_{30}$ is G; X$_{31}$ is PX$_{32}$X$_{33}$X$_{34}$X$_{35}$X$_{36}$X$_{37}$X$_{38}$X$_{39}$—R$_2$ (SEQ ID NO:5); X$_{34}$ is G; and X$_{39}$ is S.

In an embodiment, is a compound of Formula I, or a pharmaceutically acceptable salt thereof, wherein X$_1$ is selected from the group consisting of Y and D-Tyr; and X$_{13}$ αMeL.

In an embodiment is a compound of Formula I selected from the group consisting of SEQ ID NO:303, SEQ ID NO:304, SEQ ID NO:305, SEQ ID NO:306, SEQ ID NO:307, and SEQ ID NO:308, or a pharmaceutically acceptable salt thereof. In an embodiment is a compound of Formula I that is SEQ ID NO:303, or a pharmaceutically acceptable salt thereof. In an embodiment is a compound of Formula I that is SEQ ID NO:304, or a pharmaceutically acceptable salt thereof. In an embodiment is a compound of Formula I that is SEQ ID NO:305, or a pharmaceutically acceptable salt thereof. In an embodiment is a compound of Formula I that is SEQ ID NO:306, or a pharmaceutically acceptable salt thereof. In an embodiment is a compound of Formula I that is SEQ ID NO:307, or a pharmaceutically acceptable salt thereof. In an embodiment is a compound of Formula I that is SEQ ID NO:308, or a pharmaceutically acceptable salt thereof. In an embodiment is a compound of Formula I that is SEQ ID NO:386, or a pharmaceutically acceptable salt thereof.

In an embodiment is a compound of Formula I, or a pharmaceutically acceptable salt thereof, wherein:
X$_{10}$ is selected from the group consisting of A, L, H, 3Pal, 4Pal, V, Y, αMeF, αMeF(2F), I, αMeY, Q, D-His, E, cTA, and D-Tyr;
X$_{12}$ is selected from the group consisting of I, D-Ile, and S;
X$_{13}$ is selected from the group consisting of Nle, Aib, L, and αMeL;
X$_{14}$ is L;

$X_{16}$ is selected from the group consisting of K, E, Orn, Dab, Dap, S, T, H, Aib, αMeK, and R;
$X_{17}$ is selected from the group consisting of K, Q, and I;
$X_{19}$ is selected from the group consisting of Q and A;
$X_{20}$ is selected from the group consisting of Aib, Q, H, R, K, and αMeK;
$X_{21}$ is selected from the group consisting of H, Aad, D, Aib, T, A, E, and I;
$X_{23}$ is selected from the group consisting of I, L, A, G, F, H, E, and V;
$X_{24}$ is selected from the group consisting of S, Aad, D-Glu, E, Aib, H, V, A, Q, D, and P;
$X_{26}$ is selected from the group consisting of L and αMeL;
$X_{27}$ is selected from the group consisting of L and I;
$X_{28}$ is selected from the group consisting of E, A, S, and D-Glu; and
$X_{29}$ is selected from the group consisting of Aib, G, and A (hereafter a "Formula IV" compound).

In an embodiment of is a compound of Formula IV, or a pharmaceutically acceptable salt thereof wherein $X_{39}$ is C.
In an embodiment is a compound of Formula IV, or a pharmaceutically acceptable salt thereof wherein $X_{40}$ is C.

In an embodiment is a compound of Formula IV, or a pharmaceutically acceptable salt thereof, wherein one, and only one, of $X_{30}$, $X_{34}$, $X_{39}$, and $X_{40}$ is C. In an embodiment is a compound of Formula IV, or a pharmaceutically acceptable salt thereof, wherein one, and only one, of $X_{30}$, $X_{34}$, $X_{39}$, and $X_{40}$ is C modified using time-extension technology. In an embodiment is a compound of Formula IV, or pharmaceutically acceptable salt thereof, wherein C is modified using time-extension technology wherein the time-extension technology is XTEN. In an embodiment is a compound of Formula IV, or pharmaceutically acceptable salt thereof, wherein C is modified using time-extension technology wherein the time-extension technology is a $(Glu)_m$ biotin wherein m is 0, 1, 2, or 3. In an embodiment is a compound of Formula IV, or a pharmaceutically acceptable salt thereof, wherein:
$X_1$ is Y;
$X_2$ is Aib;
$X_3$ is E;
$X_{10}$ is selected from the group consisting of A, L, H, 3Pal, 4Pal, V, and Y;
$X_{11}$ is S;
$X_{12}$ is I;
$X_{16}$ is selected from the group consisting of K, E, Orn, Dab, and Dap;
$X_9$ is Q;
$X_{20}$ is selected from the group consisting of Aib and K;
$X_{21}$ is selected from the group consisting of H, Aad, D, Aib, T, A, and E;
$X_{22}$ is F;
$X_{23}$ is I;
$X_{24}$ is selected from the group consisting of S, Aad, D-Glu, and E;
$X_{26}$ is L; and
$X_{28}$ is selected from the group consisting of E and A;
or a pharmaceutically acceptable salt thereof.

In an embodiment is a compound of Formula IV, or a pharmaceutically acceptable salt thereof, wherein
$X_1$ is Y;
$X_2$ is Aib;
$X_3$ is E;
$X_{10}$ is selected from the group consisting of A, L, H, 3Pal, 4Pal, V, and Y;
$X_{11}$ is S;
$X_{12}$ is I;
$X_{16}$ is selected from the group consisting of K, E, Orn, Dab, and Dap;
$X_{20}$ is Aib;
$X_{21}$ is selected from the group consisting of H, Aad, D, Aib, T, A, and E;
$X_{22}$ is F;
$X_{24}$ is selected from the group consisting of S, Aad, D-Glu, and E;
$X_{27}$ is I; and
$X_{28}$ is selected from the group consisting of E and A.

In an embodiment is a compound of Formula I, or a pharmaceutical salt thereof, wherein:
$X_{14}$ is L;
$X_{17}$ is selected from the group consisting of K, Q, and I;
$X_{30}$ is selected from the group consisting of G-$R_2$ and G; and
q is selected from the group consisting of 16, 18, and 20;
wherein if $X_{30}$ is G, then $X_{31}$ is selected from the group consisting of:
P$X_{32}X_{33}X_{34}$—$R_2$ (SEQ ID NO:4), wherein:
$X_{32}$ is S, $X_{33}$ is S, $X_{34}$ is G and $R_2$ is absent (SEQ ID NO:299) or
$X_{32}$ is S, $X_{33}$ is S, $X_{34}$ is G and $R_2$ is $NH_2$ (SEQ ID NO:300); and
P$X_{32}X_{33}X_{34}X_{35}X_{36}X_{37}X_{38}X_{39}$—$R_2$ (SEQ ID NO:5), wherein:
$X_{32}$ is S, $X_{33}$ is S, $X_{34}$ is G, $X_{35}$ is A, $X_{36}$ is P, $X_{37}$ is P, $X_{38}$ is P, $X_{39}$ is S and
$R_2$ is absent (SEQ ID NO:301) or
$X_{32}$ is S, $X_{33}$ is S, $X_{34}$ is G, $X_{35}$ is A, $X_{36}$ is P, $X_{37}$ is P, $X_{38}$ is P, $X_{39}$ is S and
$R_2$ is $NH_2$ (SEQ ID NO:302); and
wherein one of $X_{10}$, $X_{12}$, $X_{13}$, $X_{14}$, $X_{16}$, $X_{19}$, $X_{20}$, $X_{21}$, $X_{23}$, $X_{24}$, $X_{26}$, $X_{27}$, $X_{28}$, and $X_{29}$ is K(2-[2-(2-amino-ethoxy)-ethoxy]-acetyl)$_2$-γGlu-CO—$(CH_2)qCO_2H$ (hereafter a "Formula V" compound).

In an embodiment is a compound of Formula V, or a pharmaceutically acceptable salt thereof, wherein:
$X_1$ is Y;
$X_2$ is Aib;
$X_3$ is E;
$X_{10}$ is selected from the group consisting of A, L, H, 3Pal, 4Pal, V, Y, E, cTA, and K(2-[2-(2-amino-ethoxy)-ethoxy]-acetyl)$_2$-(γ-Glu)-CO—$(CH_2)qCO_2H$;
$X_{11}$ is S;
$X_{12}$ is selected from the group consisting of I, D-Ile, and K(2-[2-(2-amino-ethoxy)-ethoxy]-acetyl)$_2$-(γ-Glu)-CO—$(CH_2)qCO_2H$;
$X_{16}$ is selected from the group consisting of K, E, Orn, Dab, Dap, and K(2-[2-(2-amino-ethoxy)-ethoxy]-acetyl)$_2$-(γ-Glu)-CO—$(CH_2)qCO_2H$;
$X_{17}$ is selected from the group consisting of K and I;
$X_{19}$ is selected from the group consisting of Q and K(2-[2-(2-amino-ethoxy)-ethoxy]-acetyl)$_2$-(γ-Glu)-CO—$(CH_2)qCO_2H$;
$X_{20}$ is selected from the group consisting of Aib and K(2-[2-(2-amino-ethoxy)-ethoxy]-acetyl)$_2$-(γ-Glu)-CO—$(CH_2)qCO_2H$;
$X_{21}$ is selected from the group consisting of H, Aad, D, Aib, T, A, E, and K(2-[2-(2-amino-ethoxy)-ethoxy]-acetyl)$_2$-(γ-Glu)-CO—$(CH_2)qCO_2H$;
$X_{22}$ is F;
$X_{24}$ is selected from the group consisting of S, Aad, D-Glu, E, and K(2-[2-(2-amino-ethoxy)-ethoxy]-acetyl)$_2$-(γ-Glu)-CO—$(CH_2)qCO_2H$;

$X_{26}$ is selected from the group consisting of L and K(2-[2-(2-amino-ethoxy)-ethoxy]-acetyl)$_2$-(γ-Glu)-CO—(CH$_2$)qCO$_2$H;

$X_{27}$ is selected from the group consisting of L and I; and $X_{28}$ is selected from the group consisting of E, A, and K(2-[2-(2-amino-ethoxy)-ethoxy]-acetyl)$_2$-(γ-Glu)-CO—(CH$_2$)qCO$_2$H.

In an embodiment is a compound of Formula V, or a pharmaceutically acceptable salt thereof, wherein $X_{20}$ is K(2-[2-(2-amino-ethoxy)-ethoxy]-acetyl)$_2$-(γ-Glu)-CO—(CH$_2$)qCO$_2$H, wherein q is 16 or 18. In an embodiment is a compound of Formula V, or a pharmaceutically acceptable salt thereof, wherein $X_{31}$ is SEQ ID NO:301 or SEQ ID NO:302.

An embodiment provides a method of treating a condition selected from the group consisting of T2DM, obesity, nonalcoholic fatty liver disease (NAFLD), nonalcoholic steatohepatitis (NASH), dyslipidemia and metabolic syndrome, comprising administering to a subject in need thereof, an effective amount of a compound of Formula I or a pharmaceutically acceptable salt thereof. An embodiment provides a method for providing therapeutic weight loss comprising administering to a subject in need thereof, an effective amount of a compound of Formula I, or a pharmaceutically acceptable salt thereof. In one embodiment, the condition is NAFLD. In one embodiment, the condition is NASH.

An embodiment provides a compound of Formula I, or a pharmaceutically acceptable salt thereof, for use in therapy. An embodiment provides a compound of Formula I, or a pharmaceutically acceptable salt thereof, for use in therapy to treat a condition selected from the group consisting of T2DM, obesity, NAFLD, NASH, dyslipidemia and metabolic syndrome. In an embodiment, the condition is T2DM. In an embodiment, the condition is obesity. In an embodiment, the condition is NAFLD. In an embodiment, the condition is NASH. In an embodiment, the condition is metabolic syndrome.

The compounds of Formula I, or a pharmaceutically acceptable salt thereof, may be useful in the treatment of a variety of symptoms or disorders. For example, certain embodiments, provide a method for treatment of T2DM in a patient comprising administering to a subject in need of such treatment an effective amount of a compound of Formula I, or a pharmaceutically acceptable salt thereof. In an embodiment, is a method for treatment of obesity in a patient comprising administering to a subject in need of such treatment an effective amount of a compound of Formula I, or a pharmaceutically acceptable salt thereof. In an embodiment, the method is inducing non-therapeutic weight loss in a subject, comprising administering to a subject in need of such treatment an effective amount of a compound of Formula I, or a pharmaceutically acceptable salt thereof.

In certain embodiments, the present invention provides a method for treatment of metabolic syndrome in a patient comprising administering to a subject in need of such treatment an effective amount of a compound of Formula I, or a pharmaceutically acceptable salt thereof. In an embodiment, the method is treatment of NASH comprising administering to a subject in need of such treatment an effective amount of a compound of Formula I, or a pharmaceutically acceptable salt thereof.

Also provided herein is a compound of the present invention for use in simultaneous, separate and sequential combinations with one or more agents selected from metformin, a thiazolidinedione, a sulfonylurea, a dipeptidyl peptidase 4 inhibitor, a sodium glucose co-transporter, a SGLT-2 inhibitor, a growth differentiation factor 15 modulator ("GDF15"), a peptide tyrosine tyrosine modulator ("PYY"), a modified insulin, amylin, a dual amylin calcitonin receptor agonist, and oxyntomodulin agonist ("OXM") in the treatment of a condition selected from the group consisting of T2DM, obesity, NAFLD, NASH, dyslipidemia and metabolic syndrome. In an embodiment, a compound of the present invention is provided in a fixed dose combination with one or more agents selected from metformin, a thiazolidinedione, a sulfonylurea, a dipeptidyl peptidase 4 inhibitor, a sodium glucose co-transporter, a SGLT-2 inhibitor GDF15, PYY, a modified insulin, amylin, a dual amylin calcitonin receptor agonist, and OXM. In an embodiment is a compound of the present invention for use in simultaneous, separate and sequential combinations with one or more agents selected from metformin, a thiazolidinedione, a sulfonylurea, a dipeptidyl peptidase 4 inhibitor, a sodium glucose co-transporter, a SGLT-2 inhibitor, GDF15, PYY, a modified insulin, amylin, a dual amylin calcitonin receptor agonist, and OXM in the treatment of a condition selected from the group consisting of T2DM and obesity. In an embodiment is a compound of the present invention for use in simultaneous, separate and sequential combinations with one or more agents selected from metformin, a thiazolidinedione, a sulfonylurea, a dipeptidyl peptidase 4 inhibitor, a sodium glucose co-transporter, and a SGLT-2 inhibitor in the treatment of a condition selected from the group consisting of T2DM and obesity.

In other embodiments, the compounds, or a pharmaceutically acceptable salt thereof, may be useful to improve bone strength in subjects in need thereof. The compounds of the present invention, or a pharmaceutically acceptable salt thereof, may be useful in the treatment of other disorders such as Parkinson's disease or Alzheimer's disease. Incretins and incretin analogs having activity at one or more of the GIP, GLP-1 and/or glucagon receptors have been described as having the potential to have therapeutic value in a number of other diseases or conditions, including for example obesity, NAFLD and NASH, dyslipidemia, metabolic syndrome, bone related disorders, Alzheimer's disease, and Parkinson's disease. See, e.g., Jall S., et. al, *Monomeric GLP-1/GIP/glucagon triagonism corrects obesity, hepatosteatosis, and dyslipidemia in female mice*, MOL. METAB. 6(5):440-446 (March 2017); Carbone L. J., et. al., *Incretin-based therapies for the treatment of non-alcoholic fatty liver disease: A systematic review and meta-analysis*. J. GASTROENTEROL. HEPATOL., 31(1):23-31 (January 2016); B. Finan, et. al, *Reappraisal of GIP Pharmacology for Metabolic Diseases*. TRENDS MOL. MED., 22(5):359-76 (May 2016); Choi, I. Y., et al., *Potent body weight loss and efficacy in a NASH animal model by a novel long-acting GLP-1/Glucagon/GIP triple-agonist (HM15211)*, ADA 2017 Poster 1139-P; Ding, K. H., *Impact of glucose-dependent insulinotropic peptide on age-induced bone loss*, J. BONE MINER. RES., 23(4):536-43 (2008); Tai, J. et. al, *Neuroprotective effects of a triple GLP-1/GIP/glucagon receptor agonist in the APP/PSI transgenic mouse model of Alzheimer's disease*, BRAIN RES. 1678, 64-74 (2018); T. D. Müller et al., *The New Biology and Pharmacology of Glucagon*, PHYSIOL. REV. 97: 721-766 (2017); Finan, B. et. al, *Unimolecular Dual Incretins Maximize Metabolic Benefits in Rodents, Monkeys, and Humans*, SCI. TRANSL. MED., 5:209 (October 2013); Hölscher C, *Insulin, incretins and other growth factors as potential novel treatments for Alzheimer's and Parkinson's diseases*. BIOCHEM. SOC. TRANS. 42(2):593-0 (April 2014).

Another embodiment provides the use of a compound of the present invention, or a pharmaceutically acceptable salt thereof, in the manufacture of a medicament for the treatment of a condition selected from the group consisting of T2DM, obesity, NAFLD, NASH, dyslipidemia and metabolic syndrome. In an embodiment, the medicament is for the treatment of T2DM. In an embodiment, the medicament is for the treatment of obesity. In an embodiment, the medicament is for the treatment of NAFLD. In an embodiment, the medicament is for the treatment of NASH.

Another embodiment provides a pharmaceutical composition comprising a compound of Formula I, or a pharmaceutically acceptable salt thereof, and at least one selected from the group consisting of a carrier, diluent, and excipient.

In an embodiment is a pharmaceutical composition comprising a compound of Formula I, or a pharmaceutically acceptable salt thereof, at least one permeation enhancer and at least one protease inhibitor. In an embodiment, is a pharmaceutical composition comprising a compound of Formula I, or a pharmaceutically acceptable salt thereof, at least one permeation enhancer, and at least one selected from the group consisting of carrier, diluent, and excipient.

In an embodiment is a pharmaceutical composition comprising a compound of Formula I, or a pharmaceutically acceptable salt thereof, a permeation enhancer, a protease inhibitor, and at least one selected from the group consisting of carrier, diluent, and excipient. In an embodiment is a pharmaceutical composition comprising a compound of Formula I, or a pharmaceutically acceptable salt thereof, and a permeation enhancer. In an embodiment is a pharmaceutical composition comprising a compound of the present invention, or a pharmaceutically acceptable salt thereof, and a permeation enhancer. In an embodiment the permeation enhancer is selected from the group consisting of sodium decanoate ("C10"), sodium taurodeoxycholate ("NaTDC"), lauroyl carnitine ("LC"), dodecyl maltoside ("C12-maltoside"), dodecyl phosphatidylcholine ("DPC"), sodium N-[8-(2-hydroxybenzoyl)amino] caprylate ("SNAC") and a Rhamnolipid. In an embodiment the permeation enhancer is selected from the group consisting of C10 and LC. In an embodiment a protease inhibitor is selected from the group consisting of soybean trypsin inhibitor ("SBTI"), soybean trypsin-chymotrypsin inhibitor ("SBTCI"), ecotin, sunflower trypsin inhibitor ("SFTI"), leupeptin, citric acid, ethylenediaminetetraacetic acid ("EDTA"), sodium glycocholate and 4-(2-aminoethyl)benzenesulfonyl fluoride hydrochloride ("AEBSF"). In an embodiment, a protease inhibitor is selected from the group consisting of SBTI, SBTCI, and SFTI. In an embodiment, a protease inhibitor is SBTI.

As used herein, the term "treating" or "to treat" includes restraining, slowing, stopping, or reversing the progression or severity of a symptom, condition, or disorder.

Certain compounds of the present invention are generally effective over a wide dosage range. For example, dosages for once weekly parenteral dosing may fall within the range of 0.05 mg to about 30 mg per person per week.

The compounds of the present invention include novel amino acid sequences having affinity for the respective GLP-1 and GIP receptors, with desired potency at each of these receptors. GLP-1 is a 36 amino acid peptide, the major biologically active fragment of which is produced as a 30-amino acid, C-terminal amidated peptide (GLP-1$_{7-36}$) (SEQ ID NO:2).

GIP is a 42 amino acid peptide (SEQ ID NO:1), which, like GLP-1, is also known as an incretin, and plays a physiological role in glucose homeostasis by stimulating insulin secretion from pancreatic beta cells in the presence of glucose.

The compounds provide desired potency at each of the GIP and GLP-1 receptors. In an embodiment, compounds are suitable for oral administration. In an embodiment, compounds have desirable GIP and GLP receptor extended time action. In an embodiment, compounds have desirable GIP and GLP receptor activity wherein the GIP agonist potency is from 2.5 to 5 times the GLP1 receptor potency as measured by the casein cAMP assay described herein below, wherein the potency is normalized against native GIP and GLP on the day the assay is run. In an embodiment, compounds have desirable GIP and GLP receptor activity wherein the GIP agonist potency is from 2.5 to 10 times the GLP1 receptor potency as measured by the casein cAMP assay, wherein the potency is normalized against native GIP and GLP on the day the assay is run.

As used herein the term "amino acid" means both naturally occurring amino acids and unnatural amino acids. The amino acids are typically depicted using standard one letter codes (e.g., L=leucine), as well as alpha-methyl substituted residues of natural amino acids (e.g., α-methyl leucine, or αMeL and α-methyl lysine, or αMeK) and certain other unnatural amino acids, such as alpha amino isobutyric acid, or "Aib," "4Pal," "Orn," and the like. The structures of these amino acids appear below:

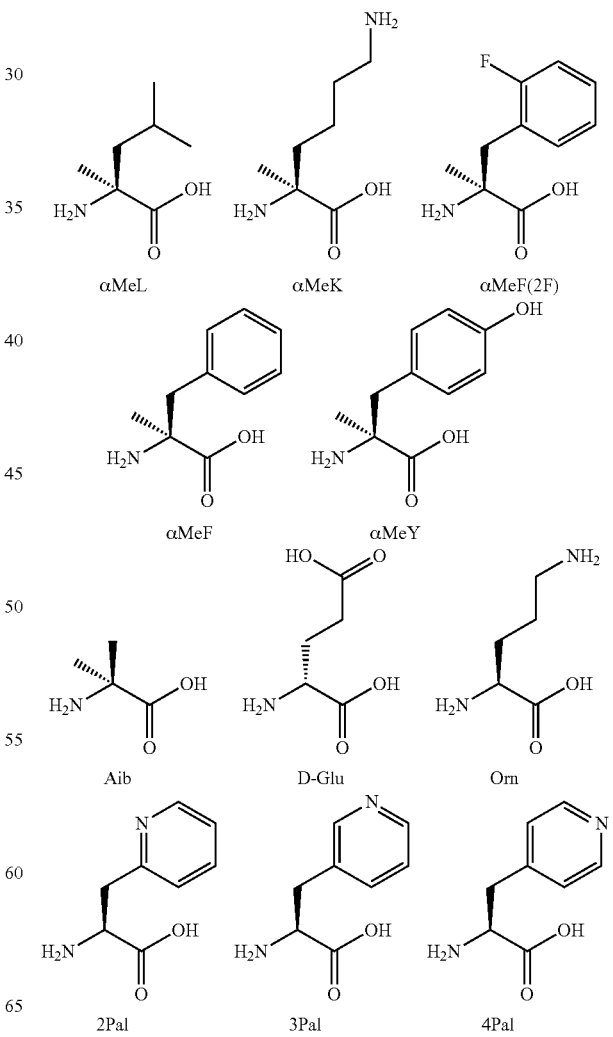

-continued

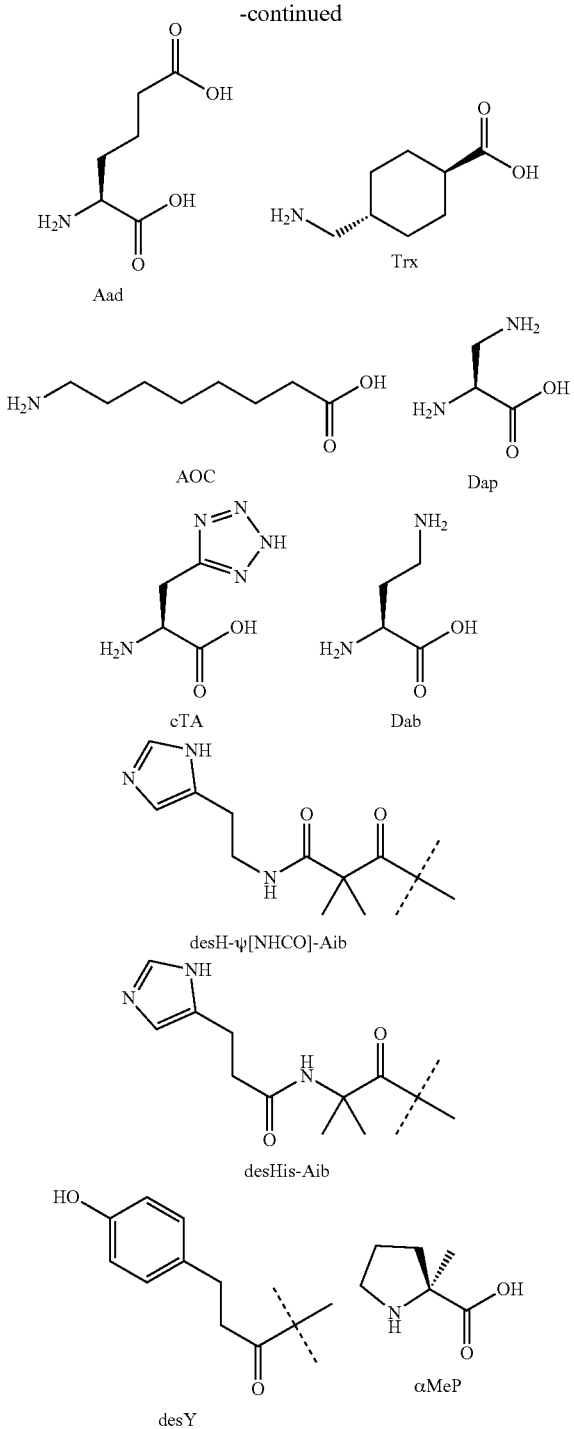

As used herein "Orn" means ornithine. As used herein "4Pal" means 3-(4-Pyridyl)-L-alanine. As used herein "αMeF(2F)" means alpha-methyl 2-F-phenylalanine. As used herein "αMeY," "αMeK," and "αMeL" mean alpha methyl tyrosine, alpha methyl lysine, and alpha methyl leucine, respectively. As used herein, "e" and "D-Glu" mean D-glutamic acid. As used herein "D-His" and "h" each mean D-histidine. As used herein "D-Tyr" and "y" each means D-tyrosine. As used herein "D-Ser" and "s" means means D-serine. As used herein "D-Ala" and "a" each means D-alanine. As used herein, "αMeF(2F)" means alpha-methyl-F(2F) and alpha-methyl-Phe(2F). As used herein, "αMeF", means alpha-methyl-F and alpha-methyl-Phe. As used herein, "αMeY", means alpha-methyl-Tyr. As used herein "αMeK", means alpha-methyl-Lys. As used herein, "αMeL", means alpha-methyl-Leu. As used herein, "αMeS", means alpha-methyl-serine and alpha-methyl-Ser. As used herein "αMeP", means alpha-methyl-proline and alpha-methyl-Pro. As used herein, "desH", means desHis. As used herein, "desY", means desTyr.

When $X_1$ is DesH and $X_2$ is Aib, and the DesH and Aib can combine to form a group as illustrated above, DesH-ψ[NHCO]-Aib.

When used herein, the term "amino acid conjugated to a $C_{16}$-$C_{22}$ fatty acid" refers to any natural or unnatural amino acid with a functional group that has been chemically modified to conjugate to a fatty acid by way of a covalent bond to the fatty acid or, preferably, by way of a linker. Examples of such functional groups include amino, carboxyl, chloro, bromo, iodo, azido, alkynyl, alkenyl, and thiol groups. Examples of natural amino acids which include such functional groups include K (amino), C (thiol), E (carboxyl) and D (carboxyl). In an embodiment the conjugated amino acid is K.

As noted above, in an embodiment of a compound of Formula I, II, III, IV, and V are compounds of the present invention wherein a fatty acid moiety is conjugated via a linker or a direct bond. In an embodiment, compounds of the present invention include a fatty acid moiety conjugated, preferably via a linker, to a K at position 14 or 17. In an embodiment, the conjugation is an acylation. In an embodiment, the conjugation is to the epsilon-amino group of the K side-chain. In an embodiment of the compounds of the present invention include a fatty acid moiety conjugated, via a linker, to a K at position 17.

In an embodiment, compounds of the present invention include a fatty acid moiety conjugated directly, without a linker, to a natural or unnatural amino acid with a functional group available for conjugation. In certain preferred embodiments the conjugated amino acid is selected from the group consisting of K, C, E and D. In particularly preferred embodiments the conjugated amino acid is K. In such embodiments, the conjugation is to the epsilon-amino group of the K side-chain.

In an embodiment, the linker comprises one to four amino acids, an amino polyethylene glycol carboxylate, or mixtures thereof. In an embodiment, the amino polyethylene glycol carboxylate has the following formula:

H—{NH—CH2-CH2-[O—CH2-CH2]$_p$-O—(CH2)$_z$-CO}$_r$—OH, wherein p is any integer from 1 to 12, z is any integer from 1 to 20, and r is 1 or 2.

In an embodiment is a compound of Formula I which comprises an amino acid conjugated to a fatty acid via a linker, wherein the linker is one to two amino acids selected from the group consisting of Glu and r-Glu. In an embodiment the linker is one to two (2-[2-(2-Amino-ethoxy)-ethoxy]-acetyl) moieties. The compounds of the present invention utilize a $C_{16}$-$C_{22}$ fatty acid chemically conjugated to the functional group of an amino acid either by a direct bond or by a linker. In an embodiment, the fatty acid moiety is conjugated to a lysine at position 17 via a linker between the lysine and the fatty acid. In an embodiment, the fatty acid moiety is conjugated to a lysine at position 20 via a linker between the lysine and fatty acid. In an embodiment, the fatty acid chain is any single chain $C_{16}$-$C_{22}$ fatty acid.

In an embodiment is a compound of Formula I, or a pharmaceutically acceptable salt thereof, wherein the fatty acid is conjugated with a linker, and the linker comprises one or more (2-[2-(2-Amino-ethoxy)-ethoxy]-acetyl) moieties, in combination with zero or one to four amino acids. In an embodiment, the linker may comprise one to four Glu or γ-Glu amino acid residues. In an embodiment, the linker may comprise 1 or 2 Glu or γ-Glu amino acid residues. In an embodiment is a compound of Formula I, or a pharmaceutically acceptable salt thereof, comprises a fatty acid conjugated via a linker wherein, the linker comprises either 1 or 2 γ-Glu amino acid residues. In an embodiment is a compound of Formula I, or a pharmaceutically acceptable salt thereof, comprises a fatty acid conjugated via a linker wherein the linker may comprise one to four amino acid residues (such as, for example Glu and r-Glu amino acids) used in combination with up to 36 (2-[2-(2-Amino-ethoxy)-ethoxy]-acetyl) moieties. Specifically, in an embodiment is a Formula I compound, or a pharmaceutically acceptable salt thereof, which comprises a fatty acid conjugated via a linker wherein, the linker constitutes combinations of one to four Glu and r-Glu amino acids and one to four (2-[2-(2-Amino-ethoxy)-ethoxy]-acetyl) moieties. In an embodiment is a Formula I compound, or a pharmaceutically acceptable salt thereof, which comprises a fatty acid conjugated via a linker wherein the linker is comprised of combinations of one or two γ-Glu amino acids and one or two (2-[2-(2-Amino-ethoxy)-ethoxy]-acetyl) moieties. In an embodiment is a Formula I compound, or a pharmaceutically acceptable salt thereof, which comprises a fatty acid conjugated via a linker wherein the linker and fatty acid components have the following formula:

(2-[2-(2-Amino-ethoxy)-ethoxy]-acetyl)$_a$-(γ-Glu)$_b$-CO—(CH$_2$)$_q$—CO$_2$H, wherein a is 1 or 2, b is 1 or 2 and q is 16 or 18. In an embodiment, a is 2, b is 1 and q is 18; and the structure is:

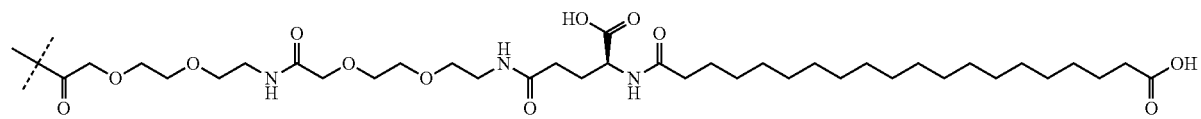

In an embodiment, a is 1, b is 2 and q is 18; and the structure is:

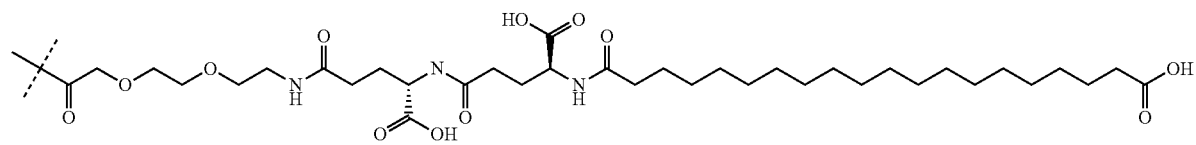

In an embodiment a is 1, b is 1, and q is 18; and the structure is:

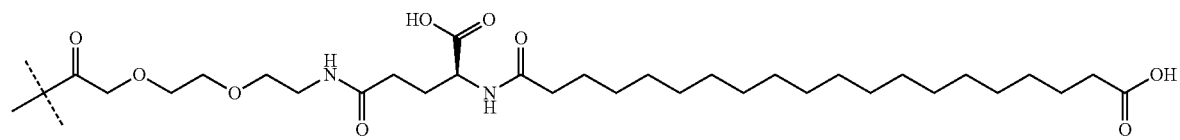

The term "$C_{16}$-$C_{22}$ fatty acid" as used herein means a carboxylic acid with between 16 and 22 carbon atoms. In an embodiment, the $C_{16}$-$C_{22}$ fatty acid suitable for use herein can be a saturated diacid. In an embodiment, the fatty acid is $C_{20}$-$C_{22}$. In an embodiment q is selected from the group consisting of 14, 16, 18, and 20. In an embodiment q is selected from 18 and 20. In an embodiment q is 18. In an embodiment q is 20.

In an embodiment, specific saturated $C_{16}$-$C_{22}$ fatty acids that are suitable for the compounds and uses thereof disclosed herein include, but are not limited to, hexadecanedioic acid ($C_{16}$ diacid), heptadecanedioic acid ($C_{17}$ diacid), octadecanedioic acid (Cis diacid), nonadecanedioic acid ($C_{19}$ diacid), eicosanedioic acid ($C_{20}$ diacid), heneicosanedioic acid ($C_{21}$ diacid), docosanedioic acid ($C_{22}$ diacid), including branched and substituted derivatives thereof.

In an embodiment, the $C_{16}$-$C_{22}$ fatty acid is selected from the group consisting of a saturated $C_{18}$ diacid, a saturated $C_{19}$ diacid, a saturated $C_{20}$ diacid, and branched and substituted derivatives thereof. In an embodiment, the $C_{16}$-$C_{22}$ fatty acid is selected from the group consisting of stearic acid, arachadic acid and eicosanedioic acid. In an embodiment, the $C_{16}$-$C_{22}$ fatty acid is arachadic acid.

As shown in the chemical structures of Examples 1-5 below, in an embodiment the linker-fatty acid moieties described above link to the epsilon-amino group of the lysine side-chain.

In an embodiment, is a compound of Formula I, or a pharmaceutically acceptable salt thereof, wherein none of $X_{30}$, $X_{31}$, $X_{32}$, $X_{33}$, $X_{34}$, $X_{35}$, $X_{36}$, $X_{37}$, $X_{38}$, $X_{39}$, and $X_{40}$ is C or is a substituent that contains a fatty acid. In an embodiment, is a compound of Formula I, or a pharmaceutically acceptable salt thereof, wherein none of $X_{10}$, $X_{12}$, $X_{13}$, $X_{14}$, $X_{16}$, $X_{17}$, $X_{19}$, $X_{20}$, $X_{21}$, $X_{23}$, $X_{24}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$, $X_{37}$, $X_{38}$, $X_{39}$, and $X_{40}$ is a substituent that contains a fatty acid; and none of $X_{30}$, $X_{34}$, $X_{39}$, and $X_{40}$ is C. In an embodiment is a compound of Formula I, or a pharmaceutically acceptable salt thereof, wherein none of $X_{10}$, $X_{12}$, $X_{13}$, $X_{14}$, $X_{16}$, $X_{17}$, $X_{19}$, $X_{20}$, $X_{21}$, $X_{23}$, $X_{24}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$, $X_{37}$, $X_{38}$, $X_{39}$, and $X_{40}$ is a substituent that contains a fatty acid.

As used herein "time-extension technology" means a peptide time-extension technology for example, recombinant human serum albumin ("rHSA"), peptide conjugation to a pharmaceutically acceptable polymer, such as polymeric sequence of amino acids ("XTEN"), unsulfated heparin-like carbohydrate polymer ("HEP"), hydroxyl ethyl starch ("HES"), llama heavy-chain antibody fragments ("VHH"), pegylation, Fc conjugation, bovine serum albumin ("BSA")

(Sleep, D. *Epert Opin Drug Del* (2015) 12, 793-812; Podust V N et. al. J Control. Release, 2015; ePUB; Hey, T. et. al. in: R. Kontermann (Ed.), Therapeutic Proteins: Strategies to Modulate their Plasma Half-Lives, Wiley-VCH Verlag Gmbh & Co. KGaA, Weinheim, Germany, 2012, pp 17-140; DeAngelis, P L, *Drug Dev Delivery* (2013) January, Dec. 31, 2012. In an embodiment time-extension technology is applied using a linker group. In an embodiment, the time-extension technology is applied using 0, 1, 2, or 3 amino acids as linker.

In an embodiment is a compound of Formula I, or a pharmaceutically acceptable salt thereof, without a fatty acid (i.e., a compound where none of $X_{10}$, $X_{12}$, $X_{13}$, $X_{14}$, $X_{16}$, $X_{17}$, $X_{19}$, $X_{20}$, $X_{21}$, $X_{23}$, $X_{24}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$, $X_{37}$, $X_{38}$, $X_{39}$, and $X_{40}$ is a substituent that contains a fatty acid) or time-extension technology may be administered to a patient in need thereof via transdermal or infusion methods of administration. Further, a compound of Formula I, or a pharmaceutically acceptable salt thereof, without a fatty acid may be further modified using a peptide time-extension technology for example, recombinant human serum albumin ("rHSA"), peptide conjugation to a pharmaceutically acceptable polymer, such as polymeric sequence of amino acids ("XTEN"), unsulfated heparin-like carbohydrate polymer ("HEP"), and hydroxyl ethyl starch ("HES"). In an embodiment, a time-extension technology is applied using a cysteine amino acid in a Formula I compound, or a pharmaceutically acceptable salt thereof, without a fatty acid, using procedures known to the skilled artisan. In an embodiment, a time-extension technology is applied to one amino acid in a Formula I compound, or a pharmaceutically acceptable salt thereof, without a fatty acid. In an embodiment, wherein a time-extension technology is applied to a Formula I compound, or a pharmaceutically acceptable salt thereof, without a fatty acid, $X_{17}$ is selected from the group consisting of I, K and Q. In an embodiment wherein a time-extension technology is applied to a Formula I compound, or a pharmaceutically acceptable salt thereof, without a fatty acid, $X_{30}$ is C. In an embodiment wherein a time-extension technology is applied to a Formula I compound, or a pharmaceutically acceptable salt thereof, without a fatty acid, $X_{34}$ is C. In an embodiment wherein a time-extension technology is applied to a Formula I compound, or a pharmaceutically acceptable salt thereof, without a fatty acid, $X_{39}$ is C. In an embodiment wherein a time-extension technology is applied to a Formula I compound, or a pharmaceutically acceptable salt thereof, without a fatty acid, $X_{40}$ is C.

When used herein in reference to one or more of the GIP or GLP-1 receptors, the terms "activity," "activate[s]" "activat[ing]" and the like refers to the capacity of a compound, or a pharmaceutically acceptable salt thereof, to bind to and induce a response at the receptor(s), as measured using assays known in the art, such as the in vitro assays described below.

The affinity of compounds, or a pharmaceutically acceptable salt thereof, of the present invention for each of the GIP and GLP-1 receptors may be measured using techniques known for measuring receptor binding levels in the art, including, for example those described in the examples below, and is commonly expressed as a Ki value. The activity of the compounds of the present invention at each of the receptors may also be measured using techniques known in the art, including for example the in vitro activity assays described below, and is commonly expressed as an $EC_{50}$ value, which is the concentration of compound causing half-maximal simulation in a dose response curve.

In an embodiment, a pharmaceutical composition of a compound of Formula I is suitable for administration by a parenteral route (e.g., subcutaneous, intravenous, intraperitoneal, intramuscular, or transdermal). In an embodiment, a pharmaceutical composition of a compound of Formula I is suitable for oral administration (e.g., tablet, capsule). Some pharmaceutical compositions and processes for preparing same are well known in the art. (See. e.g., Remington: The Science and Practice of Pharmacy (D. B. Troy, Editor, 21st Edition, Lippincott, Williams & Wilkins, 2006). Physiochemical properties of a peptide in addition to anatomical and physiological features of the gastrointestinal tract may provide challenges to efficient oral delivery of a peptide. In an embodiment a pharmaceutical composition for oral administration comprises of a compound of this invention, and a permeation enhancer. In an embodiment, a pharmaceutical composition for oral administration comprises a compound of Formula I or a pharmaceutically acceptable salt thereof, a permeation enharncer, and a protease inhibitor. In an embodiment, a pharmaceutical composition for oral administration comprises a compound of Formula I, or a pharmaceutically acceptable salt thereof, and a permeation enharncer, Monolithic and multi-particulate dosage forms for compounds of the present invention are contemplated. In an embodiment, a compound of Formula I is provided as a monolithic composition. A monolithic composition is intended for release of all components in a single location. A multi-particulate composition is intended to achieve fast transit from the stomach to the intestine and allow for distribution of composition components over large surface of small intestine. Concurrent release of a compound and functional excipients is desired for monolithic and multi-particulate dosage compositions. In an embodiment a monolithic composition of a compound of Formula I, or a pharmaceutically acceptable salt thereof, is formulated as an enteric capsule, enteric coated capsule or an enteric coated tablet. Such multi-particulate composition may be formulated as an enteric coated minitablets, or enteric coated granules where the coating is generally intact in the stomach at low pH and dissolves at the higher pH of the intestine. Two types of coated minitablets or coated granules may be formulated for either delivery to proximal small intestine by dissolution above pH 5.5 or to distal small intestine by dissolution above pH 7-7.2. A coating system for distal small intestinal release can also be applied to monolithic capsules or tablets if distal small intestinal delivery is desired. Minitablets may be filled into a standard uncoated capsule.

As used herein the term "permeation enhancer" means permeation enhancer that enhances oral absorption of a compound of this invention. As used herein, permeation enhancer means permeation enhancers, such as sodium decanoate, sodium taurodeoxycholate, lauroyl carnitine, dodecyl maltoside, dodecyl phosphatidylcholine, SNAC, a Rhamnolipid, and permeation enhancers reported in the literature, such as for example, Permeant inhibitor of phosphatase, PIP-250 and PIP-640. See, Pharmaceutics. 2019 January; 11(1): 41, (See Biomaterials. 2012; 33: 3464-3474), ZOT (zonula occludens toxin), ΔG (fragment of ZOT) (See Int. J. Pharm. 2009; 365, 121-130). In an embodiment, a permeation enhancer is selected from the group consisting of sodium decanoate, sodium taurodeoxycholate, and lauroyl carnitine. In an embodiment, a permeation enhancer is selected from the group consisting of C10, LC, and NaTDC. In an embodiment a permeation enhancer is C10.

As used herein the term "protease inhibitor" means a protease inhibitor that may be selected from the group consisting of protein based, peptide based, and small molecule based. Protease inhibitors are well known and may include, for example, soybean trypsin inhibitor ("SBTI"), soybean trypsin-chymotrypsin inhibitor ("SBTCI"), ecotin, sunflower trypsin inhibitor ("SFTF"), leupeptin, citric acid, ethylenediaminetetraacetic acid ("EDTA"), sodium glycocholate and 4-(2-aminoethyl)benzenesulfonyl fluoride hydrochloride ("AEBSF"). In an embodiment a protease inhibitor is selected from the group consisting of SBTI, SBTCI and SFTI. In an embodiment, a protease inhibitor is SBTI.

In an embodiment is a compound of Formula I, or a pharmaceutically acceptable salt thereof, wherein the compound is a potent GIPR/GLP-1R dual agonist that is a partial agonist on the GLP-1R as demonstrated by a Cell Membrane Guanosine 5'-(gamma-thio) Triphosphate-[$^{35}$S](GTPγS) Binding Assay, and a partial agonist on the GLP-1R as demonstrated by a β-arrestin-2 recruitment assay. In an embodiment is a compound of Formula I, or pharmaceutically acceptable salt thereof, wherein the compound stimulates GLP-1R induced activation of Gas in the GLP-1R HEK293 Cell Membrane Guanosine 5'-(gamma-thio) Triphosphate-[$^{35}$S](GTPγS) Binding Assay. In an embodiment, is a compound showing partial agonism of 75% or less in the GLP-1R HEK293 Cell Membrane Guanosine 5'-(gamma-thio) Triphosphate-[$^{35}$S] (GTPγS) Binding Assay, and 35% or less in the GLP-CHO Cell β-Arrestin.Recruitment Assay.

In an embodiment is a method for treating diabetes comprising administering an effective amount of a compound showing partial agonism of 75% or less in the GLP-1R HEK293 Cell Membrane Guanosine 5'-(gamma-thio) Triphosphate-[$^{35}$S] (GTPγS) Binding Assay, and an effective amount of a compound that is a GIP agonist. In an embodiment, the compound showing partial agonism in the GLP-1R HEK293 Cell Membrane Guanosine 5'-(gamma-thio) Triphosphate-[$^{35}$S] (GTPγS) Binding Assay is co-administered with a compound having GIP agonist activity. In an embodiment, the compound showing partial agonism in the GLP-1R HEK293 Cell Membrane Guanosine 5'-(gamma-thio) Triphosphate-[$^{35}$S] (GTPγS) Binding Assay is administered as an active agent within one week before or after a compound having GIP agonist activity. In an embodiment, a method for treating diabetes comprises administering an effective amount of a compound showing 35% or less in the GLP-CHO Cell β-Arrestin.Recruitment Assay and administering an effective amount of a compound showing partial agonism of 75% or less in the GLP-1R HEK293 Cell Membrane Guanosine 5'-(gamma-thio) Triphosphate-[$^{35}$S] (GTPγS) Binding Assay.

Compounds of the present invention may react with any of a number of inorganic and organic acids/bases to form pharmaceutically acceptable acid/base addition salts. Pharmaceutically acceptable salts and common methodology for preparing them are well known in the art. (See, e.g., P. Stahl, et al. Handbook of Pharmaceutical Salts: Properties, Selection and Use, 2nd Revised Edition (Wiley-VCH, 2011)). Pharmaceutically acceptable salts of the present invention include, but are not limited to, sodium, trifluoroacetate, hydrochloride, ammonium, and acetate salts. In an embodiment, a pharmaceutically acceptable salt of is selected from the group consisting of sodium, hydrochloride, and acetate salts.

The present invention also encompasses novel intermediates and processes useful for the synthesis of compounds of the present invention, or a pharmaceutically acceptable salt thereof. The intermediates and compounds of the present invention may be prepared by a variety of procedures known in the art. In particular, the Examples below describe a process using chemical synthesis. The specific synthetic steps for each of the routes described may be combined in different ways to prepare compounds of the present invention. The reagents and starting materials are readily available to one of ordinary skill in the art.

When used herein, the term "effective amount" refers to the amount or dose of a compound of the present invention, or a pharmaceutically acceptable salt thereof, which, upon single or multiple dose administration to the patient, provides the desired effect in the patient under diagnosis or treatment. An effective amount can be determined by a person of skill in the art using known techniques and by observing results obtained under analogous circumstances. In determining the effective amount for a subject, a number of factors are considered, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

When used herein, the term "subject in need thereof" refers to a mammal, preferably a human, with a disease or condition requiring treatment or therapy, including for example those listed in the preceding paragraphs. As used herein "EDTA" means ethylenediaminetetraacetic acid. As used herein "DMSO" means dimethyl sulfoxide. As used herein "CPM" means counts per minute. As used herein "IBMX" means 3-isobutyl-1-methylxanthine. As used herein "LC/MS" means liquid chromatography/mass spectrometry. As used herein "HTRF" means homogeneous time-resolved fluorescence. As used herein "BSA" mean bovine serum albumin.

The invention is further illustrated by the following examples, which are not to be construed as limiting.

PEPTIDE SYNTHESIS

Example 1

Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ (SEQ ID NO:10)

The structure of SEQ ID NO: 10 is depicted below using the standard single letter amino acid codes with the exception of residues Aib2, αMeF(2F)6, αMeL13, K17, Aib20, D-Glu24, and Ser39 where the structures of these amino acid residues have been expanded:

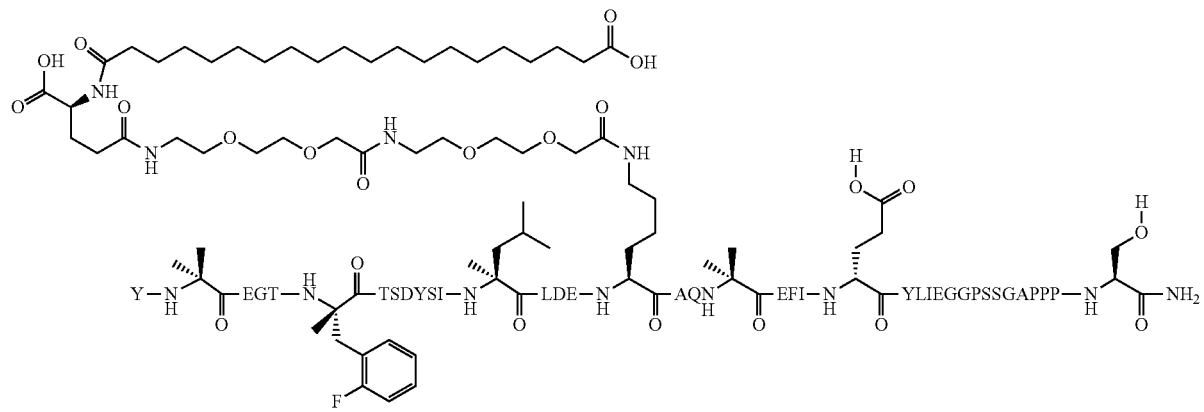

The peptide backbone of Example 1 is synthesized using Fluorenylmethyloxycarbonyl (Fmoc)/tert-Butyl (t-Bu) chemistry on a Symphony X peptide synthesizer (Gyros Protein Technologies. Tucson, Ariz.).

The resin consists of 1% DVB cross-linked polystyrene (Fmoc-Rink-MBHA Low Loading resin, 100-200 mesh, EMD Millipore) at a substitution of 0.3-0.4 meq/g. Standard side-chain protecting groups were used. Fmoc-Lys(Mtt)-OH is used for the lysine at position 17 and Boc-Tyr(tBu)-OH was used for the tyrosine at position 1. Fmoc groups are removed prior to each coupling step (2×7 minutes) using 20% piperidine in DMF. All standard amino acid couplings are performed for 1 hour to a primary amine and 3 hour to a secondary amine, using an equal molar ratio of Fmoc amino acid (0.3 mM), diisopropylcarbodiimide (0.9 mM) and Oxyma (0.9 mM), at a 9-fold molar excess over the theoretical peptide loading. Exceptions are couplings to Cα-methylated amino acids, which are coupled for 3 hours. After completion of the synthesis of the peptide backbone, the resin is thoroughly washed with DCM for 6 times to remove residual DMF. The Mtt protecting group on the lysine at position 17 is selectively removed from the peptide resin using two treatments of 300 hexafluoroisopropanol (Oakwood Chemicals) in DCM (2×40-minute treatment).

Subsequent attachment of the fatty acid-linker moiety is accomplished by coupling of 2-[2-(2-Fmoc-amino-ethoxy)-ethoxy]-acetic acid (Fmoc-AEEA-OH, ChemPep, Inc.), Fmoc-glutamic acid α-t-butyl ester (Fmoc-Glu-OtBu, Ark Pharm, Inc.), mono-OtBu-eicosanedioic acid (WuXi AppTec, Shanghai, China). 3-Fold excess of reagents (AA:PyAOP:DIPEA=1:1:1 mol/mol) are used for each coupling that is 1-hour long.

After the synthesis is complete, the peptide resin is washed with DCM, and then thoroughly air-dried. The dry resin is treated with 10 mL of cleavage cocktail (trifluoroacetic acid:water:triisopropylsilane, 95:2.5:2.5 v/v) for 2 hours at room temperature. The resin is filtered off, washed twice each with 2 mL of neat TFA, and the combined filtrates are treated with 5-fold excess volume of cold diethyl ether (−20° C.) to precipitate the crude peptide. The peptide/ether suspension is then centrifuged at 3500 rpm for 2 min to form a solid pellet, the supernatant is decanted, and the solid pellet is triturated with ether two additional times and dried in vacuo. The crude peptide is solubilized in 20% acetonitrile/20% Acetic acid/60% water and purified by RP-HPLC on a Luna 5 μm Phenyl-Hexyl preparative column (21×250 mm, Phenomenex) with linear gradients of 100% acetonitrile and 0.1% TFA/water buffer system (30-50% acetonitrile in 60 min). The purity of peptide is assessed using analytical RP-HPLC and pooling criteria is >95%. The main pool purity of compound 1 is found to be 98.0%. Subsequent lyophilization of the final main product pool yielded the lyophilized peptide TFA salt. The molecular weight is determined by LC-MS (obsd. M+3=1657.2; Calc M+3=1657.0).

Example 2

Y-Aib-EGT-αMeF(2F)-TSDYSI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ (SEQ ID NO:11)

The structure of SEQ ID NO: 11 is depicted below using the standard single letter amino acid codes with the exception of residues Aib2, αMeF(2F)6, αMeL13, Orn16, K17, Aib20 D-Glu24, and Ser39 where the structures of these amino acid residues have been expanded:

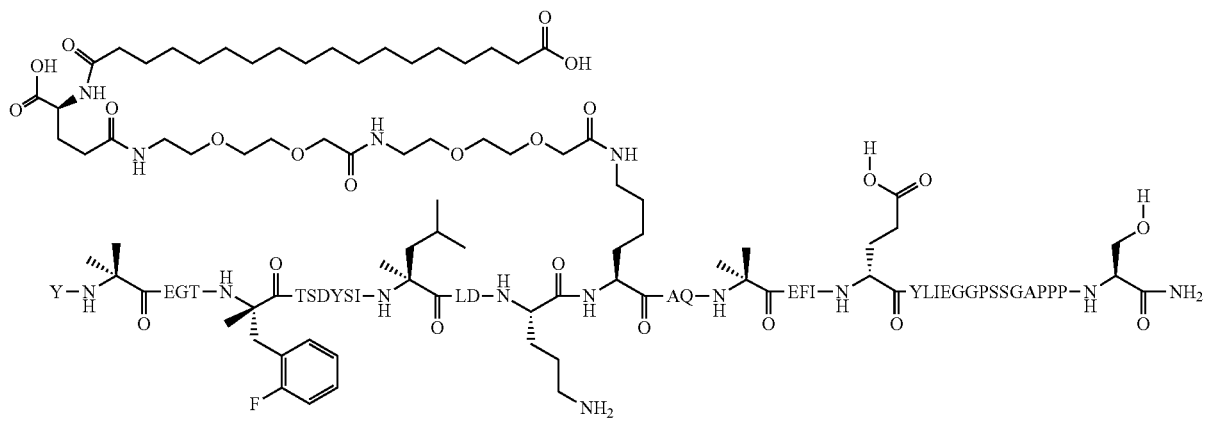

The compound according to SEQ ID NO: 11 is prepared substantially as described by the procedures of Example 1. The molecular weight is determined by LC-MS (obsd: M+3=1642.6; Calc M+3=1642.8).

Example 3

Example 3 is a compound represented by the following description:

Y-Aib-EGT-αMeF(2F)-TSDYSI-αMeL-LD-Orn-K
((2-[2-(2-Amino-ethoxy)-ethoxy]-acetyl)$_2$-(γ-Glu)-
CO—(CH$_2$)$_{18}$—CO$_2$H)AQ-Aib-EFI-(D-Glu)-
YLIEGGPSSGAPPPS-NH$_2$ (SEQ ID NO:12)

The structure of SEQ ID NO: 12 is depicted below using the standard single letter amino acid codes with the exception of residues Aib2, αMeF(2F)6, αMeL13, Orn16, K17, Aib20, D-Glu24, and Ser39, where the structures of these amino acid residues have been expanded:

The compound according to SEQ ID NO: 12 is prepared substantially as described by the procedures of Example 1. The molecular weight is determined by LC-MS (obsd: M+3=1651.8; Calc M+3=1652.2).

Example 4

Y-Aib-EGT-αMeF(2F)-TSD-4Pal-SI-αMeL-LD-
Orn-K((2-[2-(2-Amino-ethoxy)-ethoxyl]-acetyl)$_2$-(γ-
Glu)-CO—(CH$_2$)$_{16}$—CO$_2$H)AQ-Aib-EFI-(D-Glu)-
αMeY-LIEGGPSSGAPPPS-NH$_2$ (SEQ ID NO:13)

The structure of SEQ ID NO: 13 is depicted below using the standard single letter amino acid codes with the exception of residues Aib2, αMeF(2F)6, 4Pal10, αMeL13, Orn16, K17, Aib20, D-Glu24 αMeY25, and Ser39, where the structures of these amino acid residues have been expanded:

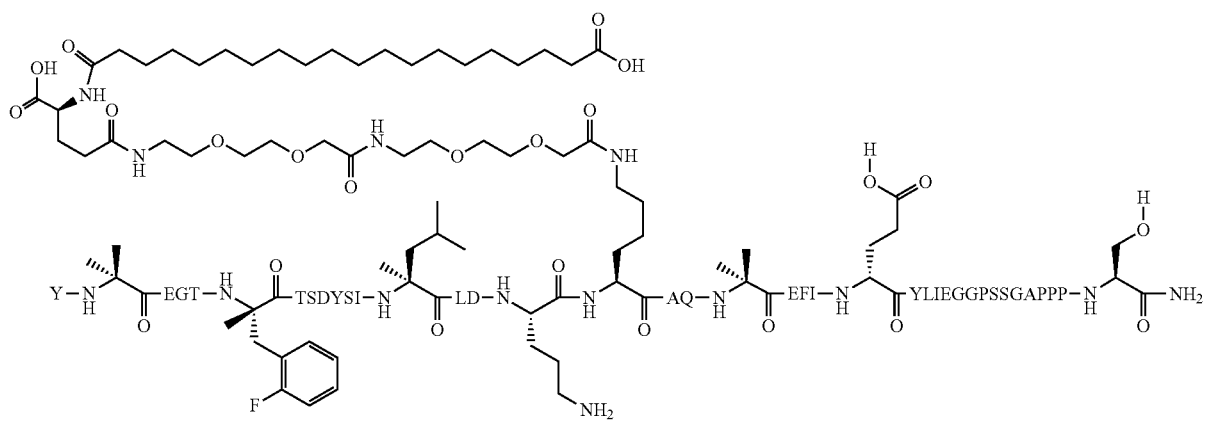

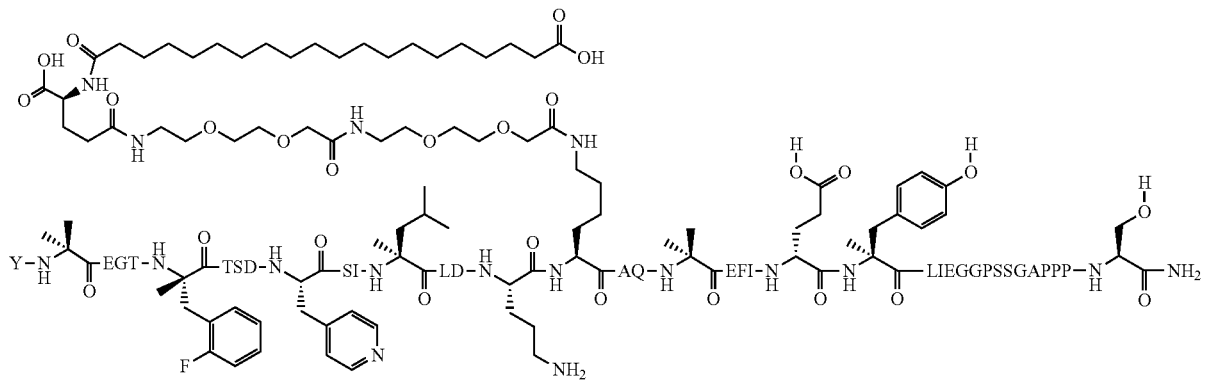

The compound according to SEQ ID NO: 13 is prepared substantially as described by the procedures of Example 1. The molecular weight is determined by LC-MS (obsd: M+3=1642.5; Calc M+3=1642.1)

Example 5

Y-Aib-EGT-αMeF(2F)-TSDVSI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-αMeY-LIEGGPSSGAPPPS-NH$_2$ (SEQ ID NO:14)

The structure of SEQ ID NO: 14 is depicted below using the standard single letter amino acid codes with the exception of residues Aib2, αMeF(2F)6, αMeL13, Orn16, K17, Aib20, D-Glu24, αMeY25, and Ser39, where the structures of these amino acid residues have been expanded:

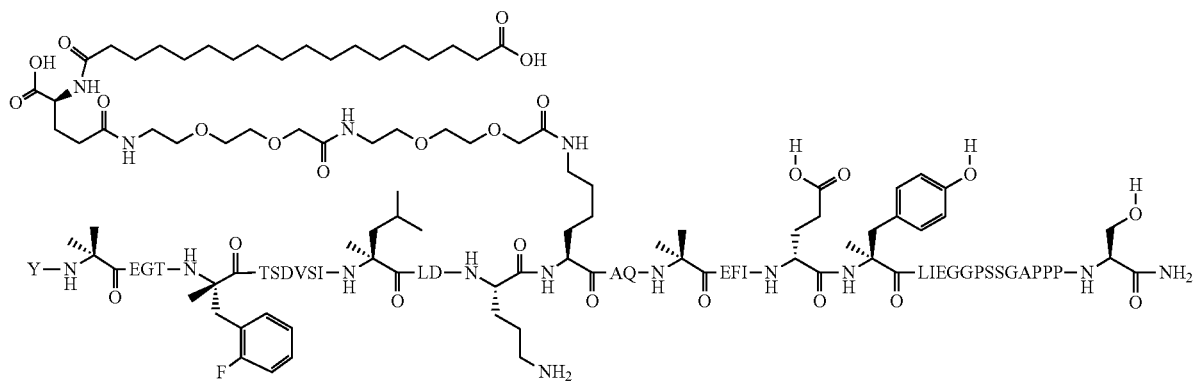

The compound according to SEQ ID NO: 14 is prepared substantially as described by the procedures of Example 1. The molecular weight is determined by LC-MS (obsd: M+3=1626.1; Calc M+3=1626.1).

Example 6 Through Example 287

The compounds according to Examples 6 (SEQ ID NO: 15) through Example 287 (SEQ ID NO:296) are prepared substantially as described by the procedures of Example 1.

| Example | Compound Name | SEQ ID NO | Calculated MW (average) | Found MW (average) |
|---|---|---|---|---|
| 6 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLLEGGPSSGAPPPS-NH$_2$ | 15 | 4863.5 | 4862.1 |
| 7 | Y-Aib-EGTFTSDYSILLDSK((2-[2-(2-Amino-ethoxy)-ethoxy]-acetyl)$_2$-(γ-Glu)-CO—(CH$_2$)$_{18}$—CO$_2$H)AQ-Aib-AFIEYLLEGGPSSGAPPPS-NH$_2$ | 16 | 4822.4 | 4821.3 |
| 8 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 17 | 4863.5 | 4863.2 |
| 9 | Y-Aib-EGTFTSDYSILLDSK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 18 | 4822.4 | 4820.7 |
| 10 | Y-Aib-EGTFTSDYSILLDSIAQ-Aib-AFIK((2-[2-(2-Amino-ethoxy)-ethoxy]-acetyl)$_2$-(γ-Glu)-CO—(CH$_2$)$_{18}$—CO$_2$H)YLLA-Aib-GPSSGAPPPS-NH$_2$ | 19 | 4776.5 | 4775.4 |
| 11 | Y-Aib-EGTFTSDYSILLDSIAQ-Aib-AFIEYLLK((2-[2-(2-Amino-ethoxy)-ethoxy]-acetyl)$_2$-(γ-Glu)-CO—(CH$_2$)$_{18}$—CO$_2$H)-Aib-GPSSGAPPPS-NH$_2$ | 20 | 4834.5 | 4834.8 |
| 12 | Y-Aib-EGTFTSDYSILLDKIAQK((2-[2-(2-Amino-ethoxy)-ethoxy]-acetyl)$_2$-(γ-Glu)-CO—(CH$_2$)$_{18}$—CO$_2$H)-AFIEYLIEGGPSSGAPPPS-NH$_2$ | 21 | 4891.6 | 4890.0 |
| 13 | Y-Aib-EGTFTSDYSILLD-Aib-IAQK((2-[2-(2-Amino-ethoxy)-ethoxy]-acetyl)$_2$-(γ-Glu)-CO—(CH$_2$)$_{18}$—CO$_2$H)-AFIEYLIEGGPSSGAPPPS-NH$_2$ | 22 | 4848.5 | 4846.8 |
| 14 | Y-Aib-EGTFTSDYSILLDKIAQK((2-[2-(2-Amino-ethoxy)-ethoxy]-acetyl)$_2$-(γ-Glu)-CO—(CH$_2$)$_{18}$—CO$_2$H)EFIQYLLE-Aib-GPSSGAPPPS-NH$_2$ | 23 | 4976.7 | 4975.5 |
| 15 | H-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLLE-Aib-GPSSGAPPPS-NH$_2$ | 24 | 4865.5 | 4863.9 |
| 16 | H-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIE-Aib-GPSSGAPPPS-NH$_2$ | 25 | 4865.5 | 4863.9 |
| 17 | H-Aib-EGTFTSDYSILLDKIAQK((2-[2-(2-Amino-ethoxy)-ethoxy]-acetyl)$_2$-(γ-Glu)-CO—(CH$_2$)$_{18}$—CO$_2$H)AFIEYLLE-Aib-GPSSG-NH$_2$ | 26 | 4444.1 | 4442.7 |
| 18 | H-Aib-EGTFTSDYSI-αMeL-LDKK(Dab-(2-[2-(2-Amino-ethoxy)-ethoxy]-acetyl)-Dab-(2-[2-(2-Amino-ethoxy)-ethoxy]-acetyl)-CO—(CH$_2$)$_{18}$—CO$_2$H)AQ-αMeK-AFIQYLLA-Aib-GPSSGAPKPS-NH$_2$ | 27 | 4979.8 | 4978.8 |
| 19 | H-Aib-EGTFTSDYSI-αMeL-LDKK(Dab-(2-[2-(2-Amino-ethoxy)-ethoxy]-acetyl)-Dab-(2-[2-(2-Amino-ethoxy)-ethoxy]-acetyl)-CO—(CH$_2$)$_{18}$—CO$_2$H)AQ-αMeK-AFIQYLLA-Aib-GPSSGAPPPS-NH$_2$ | 28 | 4948.8 | 4947.2 |
| 20 | Y-Aib-EGTFTSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 29 | 4877.5 | 4875.9 |
| 21 | Y-Aib-EGTFTSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-αMeK-AFIEYLLEGGPSSGAPPPS-NH$_2$ | 30 | 4935.6 | 4934.1 |
| 22 | Y-Aib-EGTFTSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-αMeK-AFIEYLLE-Aib-GPSSGAPPPS-NH$_2$ | 31 | 4963.6 | 4962.0 |
| 23 | Y-Aib-EGTFTSDK((2-[2-(2-Amino-ethoxy)-ethoxy]-acetyl)$_2$-(γ-Glu)-CO—(CH$_2$)$_{18}$—CO$_2$H)SILLDKIAQ-Aib-AFIEYLIEGGPSSGAPPPS-NH$_2$ | 32 | 4813.5 | 4812.9 |
| 24 | Y-Aib-EGTFTSDYK((2-[2-(2-Amino-ethoxy)-ethoxy]-acetyl)$_2$-(γ-Glu)-CO—(CH$_2$)$_{18}$—CO$_2$H)ILLDKIAQ-Aib-AFIEYLIEGGPSSGAPPPS-NH$_2$ | 33 | 4889.6 | 4888.6 |

| Example | Compound Name | SEQ ID NO | Calculated MW (average) | Found MW (average) |
|---|---|---|---|---|
| 25 | Y-Aib-EGTFTSDYSK((2-[2-(2-Amino-ethoxy)-ethoxy]-acetyl)$_2$-(γ-Glu)-CO—(CH$_2$)$_{18}$—CO$_2$H)LLDKIAQ-Aib-AFIEYLIEGGPSSGAPPPS-NH$_2$ | 34 | 4863.5 | 4862.5 |
| 26 | Y-Aib-EGTFTSDYSIK((2-[2-(2-Amino-ethoxy)-ethoxy]-acetyl)$_2$-(γ-Glu)-CO—(CH$_2$)$_{18}$—CO$_2$H)LDKIAQ-Aib-AFIEYLIEGGPSSGAPPPS-NH$_2$ | 35 | 4863.5 | N/I |
| 27 | Y-Aib-EGTFTSDYSILK((2-[2-(2-Amino-ethoxy)-ethoxy]-acetyl)$_2$-(γ-Glu)-CO—(CH$_2$)$_{18}$—CO$_2$H)DKIAQ-Aib-AFIEYLIEGGPSSGAPPPS-NH$_2$ | 36 | 4863.5 | N/I |
| 28 | Y-Aib-EGTFTSDYSILLK((2-[2-(2-Amino-ethoxy)-ethoxy]-acetyl)$_2$-(γ-Glu)-CO—(CH$_2$)$_{18}$—CO$_2$H)KIAQ-Aib-AFIEYLIEGGPSSGAPPPS-NH$_2$ | 37 | 4861.6 | N/I |
| 29 | Y-Aib-EGTFTSDYSILLDK((2-[2-(2-Amino-ethoxy)-ethoxy]-acetyl)$_2$-(γ-Glu)-CO—(CH$_2$)$_{18}$—CO$_2$H)IAQ-Aib-AFIEYLIEGGPSSGAPPPS-NH$_2$ | 38 | 4848.5 | N/I |
| 30 | Y-Aib-EGTFTSDYSILLDKIK((2-[2-(2-Amino-ethoxy)-ethoxy]-acetyl)$_2$-(γ-Glu)-CO—(CH$_2$)$_{18}$—CO$_2$H)Q-Aib-AFIEYLIEGGPSSGAPPPS-NH$_2$ | 39 | 4905.6 | N/I |
| 31 | Y-Aib-EGTFTSDYSILLDKIAK((2-[2-(2-Amino-ethoxy)-ethoxy]-acetyl)$_2$-(γ-Glu)-CO—(CH$_2$)$_{18}$—CO$_2$H)-Aib-AFIEYLIEGGPSSGAPPPS-NH$_2$ | 40 | 4848.5 | N/I |
| 32 | Y-Aib-EGTFTSDYSILLDKIAQ-Aib-K((2-[2-(2-Amino-ethoxy)-ethoxy]-acetyl)$_2$-(γ-Glu)-CO—CH$_2$)$_{18}$—CO$_2$H)FIEYLIEGGPSSGAPPPS-NH$_2$ | 41 | 4905.6 | N/I |
| 33 | Y-Aib-EGTFTSDYSILLDKIAQ-Aib-AFK((2-[2-(2-Amino-ethoxy)-ethoxy]-acetyl)$_2$-(γ-Glu)-CO—(CH$_2$)$_{18}$—CO$_2$H)EYLIEGGPSSGAPPPS-NH$_2$ | 42 | 4863.5 | N/I |
| 34 | Y-Aib-EGTFTSDYSILLDKIAQ-Aib-AFIK((2-[2-(2-Amino-ethoxy)-ethoxy]-acetyl)$_2$-(γ-Glu)-CO—(CH$_2$)$_{18}$—CO$_2$H)YLIEGGPSSGAPPPS-NH$_2$ | 43 | 4847.6 | N/I |
| 35 | Y-Aib-EGTFTSDYSILLDKIAQ-Aib-AFIEYK((2-[2-(2-Amino-ethoxy)-ethoxy]-acetyl)$_2$-(γ-Glu)-CO—(CH$_2$)$_{18}$—CO$_2$H)IEGGPSSGAPPPS-NH$_2$ | 44 | 4863.5 | N/I |
| 36 | Y-Aib-EGTFTSDYSILLDKIAQ-Aib-AFIEYLK((2-[2-(2-Amino-ethoxy)-ethoxy]-acetyl)$_2$-(γ-Glu)-CO—(CH$_2$)$_{18}$—CO$_2$H)EGGPSSGAPPPS-NH$_2$ | 45 | 4863.5 | N/I |
| 37 | Y-Aib-EGTFTSDYSILLDKIAQ-Aib-AFIEYLIK((2-[2-(2-Amino-ethoxy)-ethoxy]-acetyl)$_2$-(γ-Glu)-CO—(CH$_2$)$_{18}$—CO$_2$H)GGPSSGAPPPS-NH$_2$ | 46 | 4847.6 | N/I |
| 38 | Y-Aib-EGTFTSDYSILLDKIAQ-Aib-AFIEYLIEK((2-[2-(2-Amino-ethoxy)-ethoxy]-acetyl)$_2$-(γ-Glu)-CO—(CH$_2$)$_{18}$—CO$_2$H)GPSSGAPPPS-NH$_2$ | 47 | 4919.6 | N/I |
| 39 | Y-Aib-EGTFTSDYSILLDKIAQ-Aib-AFIEYLIEGK((2-[2-(2-Amino-ethoxy)-ethoxy]-acetyl)$_2$-(γ-Glu)-CO—(CH$_2$)$_{18}$—CO$_2$H)PSSGAPPPS-NH$_2$ | 48 | 4919.6 | N/I |
| 40 | Y-Aib-EGTFTSDYSILLDKIAQ-Aib-AFIEYLIEGGK((2-[2-(2-Amino-ethoxy)-ethoxy]-acetyl)$_2$-(γ-Glu)-CO—(CH$_2$)$_{18}$—CO$_2$H)SSGAPPPS-NH$_2$ | 49 | 4879.5 | N/I |
| 41 | Y-Aib-EGTFTSDYSILLDKIAQ-Aib-AFIEYLIEGGPK((2-[2-(2-Amino-ethoxy)-ethoxy]-acetyl)$_2$-(γ-Glu)-CO—(CH$_2$)$_{18}$—CO$_2$H)SGAPPPS-NH$_2$ | 50 | 4889.6 | N/I |
| 42 | Y-Aib-EGTFTSDYSILLDKIAQ-Aib-AFIEYLIEGGPSK((2-[2-(2-Amino-ethoxy)-ethoxy]-acetyl)$_2$-(γ-Glu)-CO—(CH$_2$)$_{18}$—CO$_2$H)GAPPPS-NH$_2$ | 51 | 4889.6 | N/I |

| Example | Compound Name | SEQ ID NO | Calculated MW (average) | Found MW (average) |
|---|---|---|---|---|
| 43 | Y-Aib-EGTFTSDYSILLDKIAQ-Aib-AFIEYLIEGGPSSK((2-[2-(2-Amino-ethoxy)-ethoxy]-acetyl)$_2$-(γ-Glu)-CO—(CH$_2$)$_{18}$—CO$_2$H)APPPS-NH$_2$ | 52 | 4919.6 | N/I |
| 44 | Y-Aib-EGTFTSDYSILLDKIAQ-Aib-AFIEYLIEGGPSSGK((2-[2-(2-Amino-ethoxy)-ethoxy]-acetyl)$_2$-(γ-Glu)-CO—(CH$_2$)$_{18}$—CO$_2$H)PPPS-NH$_2$ | 53 | 4905.6 | N/I |
| 45 | Y-Aib-EGTFTSDYSILLDKIAQ-Aib-AFIEYLIEGGPSSGAK((2-[2-(2-Amino-ethoxy)-ethoxy]-acetyl)$_2$-(γ-Glu)-CO—(CH$_2$)$_{18}$—CO$_2$H)PPS-NH$_2$ | 54 | 4879.5 | N/I |
| 46 | Y-Aib-EGTFTSDYSILLDKIAQ-Aib-AFIEYLIEGGPSSGAPK((2-[2-(2-Amino-ethoxy)-ethoxy]-acetyl)$_2$-(γ-Glu)-CO—(CH$_2$)$_{18}$—CO$_2$H)PS-NH$_2$ | 55 | 4879.5 | N/I |
| 47 | Y-Aib-EGTFTSDYSILLDKIAQ-Aib-AFIEYLIEGGPSSGAPPK((2-[2-(2-Amino-ethoxy)-ethoxy]-acetyl)$_2$-(γ-Glu)-CO—(CH$_2$)$_{18}$—CO$_2$H)S—NH$_2$ | 56 | 4879.5 | N/I |
| 48 | Y-Aib-EGTFTSDYSILLDKIAQ-Aib-AFIEYLIEGGPSSGAPPPK((2-[2-(2-Amino-ethoxy)-ethoxy]-acetyl)$_2$-(γ-Glu)-CO—(CH$_2$)$_{18}$—CO$_2$H)—NH$_2$ | 57 | 4889.6 | N/I |
| 49 | Y-Aib-EGTFTSDYSILLDKIAQ-Aib-AFIEYLIEGGPSSGAPPPSK((2-[2-(2-Amino-ethoxy)-ethoxy]-acetyl)$_2$-(γ-Glu)-CO—(CH$_2$)$_{18}$—CO$_2$H)—NH$_2$ | 58 | 4976.7 | N/I |
| 50 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSG-NH$_2$ | 59 | 4414.0 | N/I |
| 51 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 60 | 4085.7 | N/I |
| 52 | Y-Aib-EGTFTSDYSI-αMeL-LDSK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 61 | 4836.4 | N/I |
| 53 | H-Aib-EGTFTSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 62 | 4851.5 | N/I |
| 54 | H-Aib-EGTFTSDYSI-αMeL-LDKK((2-[2-(2-Amino-ethoxy)-ethoxy]-acetyl)$_2$-(γ-Glu)-CO—(CH$_2$)$_{18}$—CO$_2$H)AQHAFIEYLIEGGPSSGAPPPS-NH$_2$ | 63 | 4903.5 | N/I |
| 55 | H-Aib-EGTFTSDYSI-αMeL-LDEK((2-[2-(2-Amino-ethoxy)-ethoxy]-acetyl)$_2$-(γ-Glu)-CO—(CH$_2$)$_{18}$—CO$_2$H)AQHAFIEYLIEGGPSSGAPPPS-NH$_2$ | 64 | 4904.5 | N/I |
| 56 | Y-Aib-EGTFTSDYSI-αMeL-LDEK((2-[2-(2-Amino-ethoxy)-ethoxy]-acetyl)$_2$-(γ-Glu)-CO—(CH$_2$)$_{18}$—CO$_2$H)AQHAFIEYLIEGGPSSGAPPPS-NH$_2$ | 65 | 4930.5 | N/I |
| 57 | Y-Aib-EGT-αMeF-TSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 66 | 4877.5 | N/I |
| 58 | Y-Aib-EGTFTSDYSSLLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 67 | 4837.4 | N/I |
| 59 | Y-Aib-EGTFTSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 68 | 4878.5 | N/I |
| 60 | Y-Aib-EGTFTSDYSI-αMeL-LD-Aib-K((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 69 | 4834.5 | N/I |
| 61 | Y-Aib-EGTFTSDYSI-αMeL-LDSK((2-[2-(2-Amino-ethoxy)-ethoxy]-acetyl)$_2$-(γ-Glu)-CO—(CH$_2$)$_{18}$—CO$_2$H)AQ-Aib-AFIEYLLEGGPSSGAPPPS-NH$_2$ | 70 | 4836.4 | N/I |

| Example | Compound Name | SEQ ID NO | Calculated MW (average) | Found MW (average) |
|---|---|---|---|---|
| 62 | Y-Aib-EGTFTSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 71 | 4099.7 | N/I |
| 63 | Y-Aib-EGTFTSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 72 | 4100.6 | N/I |
| 64 | Y-Aib-EGTFTSDYSI-αMeL-LDSK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 73 | 4058.6 | N/I |
| 65 | Y-Aib-EGTFTSDYSI-αMeL-LDTK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 74 | 4072.6 | N/I |
| 66 | Y-Aib-EGTFTSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLLEGGPSSGAPPPS-NH$_2$ | 75 | 4878.5 | N/I |
| 67 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-A-αMeF-IEYLIEGGPSSGAPPPS-NH$_2$ | 76 | 4877.5 | N/I |
| 68 | Y-Aib-EGTFTSDY-αMeS-ILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 77 | 4877.5 | N/I |
| 69 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 78 | 4891.6 | N/I |
| 70 | Y-Aib-EGTFTSDK((2-[2-(2-Amino-ethoxy)-ethoxy]-acetyl)$_2$-(γ-Glu)-CO—(CH$_2$)$_{18}$—CO$_2$H)SILLDKIAQ-Aib-AFIEYLIEGG-NH$_2$ | 79 | 4035.7 | N/I |
| 71 | Y-Aib-EGTFTSDYSILK((2-[2-(2-Amino-ethoxy)-ethoxy]-acetyl)$_2$-(γ-Glu)-CO—(CH$_2$)$_{18}$—CO$_2$H)DKIAQ-Aib-AFIEYLIEGG-NH$_2$ | 80 | 4085.7 | N/I |
| 72 | Y-Aib-EGTFTSDYSILLDKIAQ-Aib-K((2-[2-(2-Amino-ethoxy)-ethoxy]-acetyl)$_2$-(γ-Glu)-CO—(CH$_2$)$_{18}$—CO$_2$H)FIEYLIEGG-NH$_2$ | 81 | 4127.8 | N/I |
| 73 | Y-Aib-EGTFTSDYSILLDKIAQ-Aib-AFIEYLIK((2-[2-(2-Amino-ethoxy)-ethoxy]-acetyl)$_2$-(γ-Glu)-CO—(CH$_2$)$_{18}$—CO$_2$H)GG-NH$_2$ | 82 | 4069.7 | N/I |
| 74 | Y-Aib-EGTFTSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-A-αMeF-IEYLIEGGPSSGAPPPS-NH$_2$ | 83 | 4891.6 | N/I |
| 75 | Y-Aib-EGTFTSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-AFIEY-αMeL-IEGGPSSGAPPPS-NH$_2$ | 84 | 4891.6 | N/I |
| 76 | Y-Aib-EGT-aMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-A-αMeF-IEYLIEGGPSSGAPPPS-NH$_2$ | 85 | 4905.6 | N/I |
| 77 | Y-Aib-EGTFTSDYSILLKIAQ-Aib-AFIEYLIEGGPSSGAPPK((2-[2-(2-Amino-ethoxy)-ethoxy]-acetyl)$_2$-(γ-Glu)-CO—(CH$_2$)$_{18}$—CO$_2$H)S—NH$_2$ | 86 | 4764.5 | N/I |
| 78 | (D-Tyr)-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 87 | 4863.5 | N/I |
| 79 | Ac-(D-Tyr)-AEGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 88 | 4891.5 | N/I |
| 80 | Y-(D-Ala)-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 89 | 4849.5 | N/I |
| 81 | Y-Aib-EGTFTSDY-(D-Ser)-ILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 90 | 4863.5 | N/I |

| Example | Compound Name | SEQ ID NO | Calculated MW (average) | Found MW (average) |
|---|---|---|---|---|
| 82 | Y-Aib-EGTFTSDYS-(D-Ile)-LLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 91 | 4863.5 | N/I |
| 83 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLI-(D-Glu)-GGPSSGAPPPS-NH$_2$ | 92 | 4863.5 | N/I |
| 84 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFI-(D-Glu)-YLIEGGPSSGAPPPS-NH$_2$ | 93 | 4863.5 | N/I |
| 85 | Y-Aib-EGTFTSDASILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 94 | 4771.4 | N/I |
| 86 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEAGPSSGAPPPS-NH$_2$ | 95 | 4877.5 | N/I |
| 87 | Y-αMePro-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 96 | 4889.5 | N/I |
| 88 | Y-Pro-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 97 | 4875.5 | N/I |
| 89 | Y-Aib-Aad-GTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 98 | 4877.5 | N/I |
| 90 | Y-Aib-NGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 99 | 4848.5 | N/I |
| 91 | Y-Aib-(γ-Glu)-GTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 100 | 4863.5 | N/I |
| 92 | Y-Aib-EGT-αMeF-TSDK((2-[2-(2-Amino-ethoxy)-ethoxy]-acetyl)$_2$-(γ-Glu)-CO—(CH$_2$)$_{18}$—CO$_2$H)SILLDKIAQ-Aib-AFIEYLIEGG-NH$_2$ | 101 | 4049.7 | N/I |
| 93 | Y-Aib-EGT-αMeF-TSDYSILK((2-[2-(2-Amino-ethoxy)-ethoxy]-acetyl)$_2$-(γ-Glu)-CO—(CH$_2$)$_{18}$—CO$_2$H)DKIAQ-Aib-AFIEYLIEGG-NH$_2$ | 102 | 4099.7 | N/I |
| 94 | Y-Aib-EGT-αMeF-TSDYSILLDKIAQ-Aib-K((2-[2-(2-Amino-ethoxy)-ethoxy]-acetyl)$_2$-(γ-Glu)-CO—(CH$_2$)$_{18}$—CO$_2$H)FIEYLIEGG-NH$_2$ | 103 | 4141.8 | N/I |
| 95 | Y-Aib-EGT-αMeF-TSDYSILLDKIAQ-Aib-AFIEYLIK((2-[2-(2-Amino-ethoxy)-ethoxy]-acetyl)$_2$-(γ-Glu)-CO—(CH$_2$)$_{18}$—CO$_2$H)GG-NH$_2$ | 104 | 4083.7 | N/I |
| 96 | Y-Aib-EGTFTSDK((2-[2-(2-Amino-ethoxy)-ethoxy]-acetyl)$_2$-(γ-Glu)-CO—(CH$_2$)$_{18}$—CO$_2$H)SI-αMeL-LDKIAQ-Aib-AFIEYLIEGG-NH$_2$ | 105 | 4049.7 | N/I |
| 97 | Y-Aib-EGTFTSDYSI-αMeL-LDKIAQ-Aib-AFIEYLIK((2-[2-(2-Amino-ethoxy)-ethoxy]-acetyl)$_2$-(γ-Glu)-CO—(CH$_2$)$_{18}$—CO$_2$H)GG-NH$_2$ | 106 | 4083.7 | N/I |
| 98 | Y-Aib-EGT-αMeF-TSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 107 | 4099.7 | N/I |
| 99 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 108 | 4113.7 | N/I |
| 100 | Y-Aib-EGT-αMeF-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 109 | 4114.7 | N/I |

| Example | Compound Name | SEQ ID NO | Calculated MW (average) | Found MW (average) |
|---|---|---|---|---|
| 101 | Y-Aib-EGT-αMeF(2F)-TSDYSI-Aib-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 110 | 4090.6 | N/I |
| 102 | Y-Aib-EGT-αMeF-TSDYSI-Aib-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGG-NH$_2$ | 111 | 4072.6 | N/I |
| 103 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGG-NH$_2$ | 112 | 4190.7 | N/I |
| 104 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{16}$—CO$_2$H)AQ-Aib-EFIEYLIEGG-NH$_2$ | 113 | 4162.6 | N/I |
| 105 | DesHis-ψ[NHCO]-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 114 | 4822.5 | N/I |
| 106 | DesHis-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 115 | 4822.5 | N/I |
| 107 | DesTyr-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 116 | 4848.5 | N/I |
| 108 | Y-Aib-EGTFTSDYSILLDKK((2-[2-(2-Amino-ethoxy)-ethoxy]-acetyl)-AOC-(γ-Glu)-CO—(CH$_2$)$_{18}$—CO$_2$H)AQ-Aib-AFIEYLIEGGPSSGAPPPS-NH$_2$ | 117 | 4859.6 | N/I |
| 109 | Y-Aib-EGTFTSDYSILLDKK(AOC-(2-[2-(2-Amino-ethoxy)-ethoxy]-acetyl)-(γ-Glu)-CO—(CH$_2$)$_{18}$—CO$_2$H)AQ-Aib-AFIEYLIEGGPSSGAPPPS-NH2 | 118 | 4859.6 | N/I |
| 110 | Y-Aib-EGTFTSDYSILLDKK((2-[2-(2-Amino-ethoxy)-ethoxy]-acetyl)-(γ-Glu)-(Trx)-CO—(CH$_2$)$_{18}$—CO$_2$H)AQ-Aib-AFIEYLIEGGPSSGAPPPS-NH$_2$ | 119 | | N/I |
| 111 | Y-Aib-EGTFTSDYSILLDKK((2-[2-(2-Amino-ethoxy)-ethoxy]-acetyl)-(Trx)-(γ-Glu)-CO—(CH$_2$)$_{18}$—CO$_2$H)AQ-Aib-AFIEYLIEGGPSSGAPPPS-NH$_2$ | 120 | | N/I |
| 112 | Y-Aib-EGTFTSDYSILLDKK((2-[2-(2-Amino-ethoxy)-ethoxy]-acetyl)-(εK)-(γ-Glu)-CO—(CH$_2$)$_{18}$—CO$_2$H)AQ-Aib-AFIEYLIEGGPSSGAPPPS-NH$_2$ | 121 | 4846.5 | N/I |
| 113 | Y-Aib-EGTFTSDYSILLDKK((2-[2-(2-Amino-ethoxy)-ethoxy]-acetyl)$_2$-(εK)-CO—(CH$_2$)$_{18}$—CO$_2$H)AQ-Aib-AFIEYLIEGGPSSGAPPPS-NH$_2$ | 122 | 4862.6 | N/I |
| 114 | Y-Aib-EGTFTSDYSILLDKK((2-[2-(2-Amino-ethoxy)-ethoxy]-acetyl)-(εK)-(εK)-CO—(CH$_2$)$_{18}$—CO$_2$H)AQ-Aib-AFIEYLIEGGPSSGAPPPS-NH$_2$ | 123 | 4845.6 | N/I |
| 115 | Y-Aib-EGT-αMeF-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 124 | 4892.5 | N/I |
| 116 | Y-Aib-EGT-αMeF-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 125 | 4950.5 | N/I |
| 117 | Y-Aib-EGT-αMeF-TSDYSI-Aib-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 126 | 4850.4 | N/I |
| 118 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 127 | 4968.5 | N/I |

-continued

| Example | Compound Name | SEQ ID NO | Calculated MW (average) | Found MW (average) |
|---|---|---|---|---|
| 119 | F-Aib-EGT-αMeF-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 128 | 4876.5 | N/I |
| 120 | Y-Aib-cTA-GT-αMeF-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 129 | 4902.5 | N/I |
| 121 | Y-Aib-EGT-αMeF-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQQAFIEYLIEGGPSSGAPPPS-NH$_2$ | 130 | 4935.5 | N/I |
| 122 | Y-Aib-EGT-αMeF-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQQAFIEYLIE-Aib-GPSSGAPPPS-NH$_2$ | 131 | 4963.6 | N/I |
| 123 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSG-NH$_2$ | 132 | 4500.1 | N/I |
| 124 | Y-Aib-EGT-αMeF-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSG-NH$_2$ | 133 | 4501.0 | N/I |
| 125 | Y-Aib-EGT-αMeF-TSDYSI-αMeL-LDKK((2-[2-(2-Amino-ethoxy)-ethoxy]-acetyl)$_2$-(γ-Glu)$_2$-CO—(CH$_2$)$_{18}$—CO$_2$H)AQ-Aib-AFIEYLIEGGPSSGAPPPS-NH$_2$ | 134 | 5020.7 | N/I |
| 126 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEAGPSSGAPPPS-NH$_2$ | 135 | 4905.6 | N/I |
| 127 | Y-Aib-EGT-αMeF-TSDISILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 136 | 4827.5 | N/I |
| 128 | Y-Aib-EGT-αMeF-TSDHSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 137 | 4851.5 | N/I |
| 129 | Y-Aib-EGT-αMeF-TSDLSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 138 | 4827.5 | N/I |
| 130 | Y-Aib-EGT-αMeF-TSDESILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 139 | 4843.5 | N/I |
| 131 | Y-Aib-EGT-αMeF-TSD-αMeF-SILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 140 | 4875.6 | N/I |
| 132 | Y-Aib-EGT-αMeF-TSD-3Pal-SILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 141 | 4862.5 | N/I |
| 133 | DesTyr-Aib-EGT-αMeF-TSDYSI-Aib-LDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 142 | 4835.4 | N/I |
| 134 | DesTyr-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 143 | 4953.5 | N/I |
| 135 | H-Aib-NGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 144 | 4822.5 | N/I |
| 136 | Y-Aib-EGTFTSDASILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEAGPSSGAPPPS-NH$_2$ | 145 | 4785.4 | N/I |

| Example | Compound Name | SEQ ID NO | Calculated MW (average) | Found MW (average) |
|---|---|---|---|---|
| 137 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-Aad-FIEYLIEGGPSSGAPPPS-NH$_2$ | 146 | 4963.6 | N/I |
| 138 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-SFIEYLIEGGPSSGAPPPS-NH$_2$ | 147 | 4907.6 | N/I |
| 139 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-TFIEYLIEGGPSSGAPPPS-NH$_2$ | 148 | 4921.6 | N/I |
| 140 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-DFIEYLIEGGPSSGAPPPS-NH$_2$ | 149 | 4935.6 | N/I |
| 141 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-IFIEYLIEGGPSSGAPPPS-NH$_2$ | 150 | 4933.6 | N/I |
| 142 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-HFIEYLIEGGPSSGAPPPS-NH$_2$ | 151 | 4957.6 | N/I |
| 143 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-Aib-FIEYLIEGGPSSGAPPPS-NH$_2$ | 152 | 4905.6 | N/I |
| 144 | Y-Aib-EGT-αMeF-TSDYSI-αMeL-LDKK((2-[2-(2-Amino-ethoxy)-ethoxy]-acetyl)$_2$-(γ-Glu)-CO—(CH$_2$)$_{18}$—CO$_2$H)AQH-Aib-FIEYLIEGGPSSGAPPPS-NH$_2$ | 153 | 4957.6 | N/I |
| 145 | Y-Aib-EGT-αMeF-TSDASI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 154 | 4799.5 | N/I |
| 146 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIQYLIEGGPSSGAPPPS-NH$_2$ | 155 | 4967.5 | N/I |
| 147 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-Aad-YLIEGGPSSGAPPPS-NH$_2$ | 156 | 4982.6 | N/I |
| 148 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIAYLIEGGPSSGAPPPS-NH$_2$ | 157 | 4910.5 | N/I |
| 149 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIVYLIEGGPSSGAPPPS-NH$_2$ | 158 | 4938.5 | N/I |
| 150 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFISYLIEGGPSSGAPPPS-NH$_2$ | 159 | 4926.5 | N/I |
| 151 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIPYLIEGGPSSGAPPPS-NH$_2$ | 160 | 4936.5 | N/I |
| 152 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-Aib-YLIEGGPSSGAPPPS-NH$_2$ | 161 | 4924.5 | N/I |
| 153 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIHYLIEGGPSSGAPPPS-NH$_2$ | 162 | 4976.6 | N/I |
| 154 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 163 | 4942.5 | N/I |

| Example | Compound Name | SEQ ID NO | Calculated MW (average) | Found MW (average) |
|---|---|---|---|---|
| 155 | Y-Aib-EGT-αMeF(2F)-TSD-cTA-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 164 | 4944.5 | N/I |
| 156 | Y-Aib-EGT-αMeF(2F)-TSD-2Pal-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 165 | 4953.5 | N/I |
| 157 | Y-Aib-EGT-αMeF(2F)-TSD-3Pal-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 166 | 4953.5 | N/I |
| 158 | Y-Aib-EGT-αMeF(2F)-TSD-4Pal-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 167 | 4953.5 | N/I |
| 159 | Y-Aib-EGT-αMeF(2F)-TSD-αMeF-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 168 | 4938.5 | N/I |
| 160 | Y-Aib-EGT-αMeF(2F)-TSD-Aib-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-YLIEGGPSSGAPPPS-NH$_2$ | 169 | 4862.4 | N/I |
| 161 | Y-Aib-EGT-αMeF(2F)-TSDHSI-αMeL-LDEK((2-[2-(2-Amino-ethoxy)-ethoxy]-acetyl)$_2$-(γ-Glu)$_2$-CO—(CH$_2$)$_{18}$—CO$_2$H)AQ-Aib-TFI-(D-Glu)-YLIEGGPSSG-NH$_2$ | 170 | 4594.1 | N/I |
| 162 | Y-Aib-EGT-αMeF(2F)-TSDHSI-αMeL-LDEK((2-[2-(2-Amino-ethoxy)-ethoxy]-acetyl)$_2$-(γ-Glu)$_2$-CO—(CH$_2$)$_{18}$—CO$_2$H)AQ-Aib-TFI-(D-Glu)-HLIEGGPSSG-NH$_2$ | 171 | 4568.1 | N/I |
| 163 | H-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFIEYLIEGGPSSGAPPPS-NH$_2$ | 172 | 4942.5 | N/I |
| 164 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-YLI-(D-Glu)-GGPSSGAPPPS-NH$_2$ | 173 | 4914.5 | N/I |
| 165 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-αMeF-LI-(D-Glu)-GGPSSGAPPPS-NH$_2$ | 174 | 4912.5 | N/I |
| 166 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-YLIEGG-NH$_2$ | 175 | 4136.7 | N/I |
| 167 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-YLIEGGPSSG-NH$_2$ | 176 | 4465.0 | N/I |
| 168 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-YLIEGGPSSGAPPPS-NH$_2$ | 177 | 4914.5 | N/I |
| 169 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{16}$—CO$_2$H)AQ-Aib-TFI-(D-Glu)-YLIEGGPSSGAPPPS-NH$_2$ | 178 | 4886.4 | N/I |
| 170 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{14}$—CO$_2$H)AQ-Aib-TFI-(D-Glu)-YLIEGGPSSGAPPPS-NH$_2$ | 179 | 4858.4 | N/I |
| 171 | Y-Aib-EGT-αMeF(2F)-TSDHSI-αMeL-LD-Orn-K((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-YLIEGGPSSGAPPPS-NH$_2$ | 180 | 4899.5 | N/I |
| 172 | Y-Aib-EGT-αMeF(2F)-TSDHSI-αMeL-LD-Dab-K((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-YLIEGGPSSGAPPPS-NH$_2$ | 181 | 4885.5 | N/I |

-continued

| Example | Compound Name | SEQ ID NO | Calculated MW (average) | Found MW (average) |
|---|---|---|---|---|
| 173 | Y-Aib-EGT-αMeF(2F)-TSDHSI-αMeL-LD-Dap-K((2-[2-(2-Amino-ethoxy)-ethoxy]-acetyl)$_2$-(γ-Glu)-CO—(CH$_2$)$_{18}$—CO$_2$H)AQ-Aib-TFI-(D-Glu)-YLIEGGPSSGAPPPS-NH$_2$ | 182 | 4871.5 | N/I |
| 174 | Y-Aib-EGT-αMeF(2F)-TSDHSI-αMeL-LDEK((2-[2-(2-Amino-ethoxy)-ethoxy]-acetyl)$_2$-CO—(CH$_2$)$_{18}$—CO$_2$H)AQ-Aib-TFI-(D-Glu)-YLIEGGPSSGAPPPS-NH$_2$ | 183 | 4785.4 | N/I |
| 175 | Y-Aib-EGT-αMeF(2F)-TSDHSI-αMeL-LDEK((2-[2-(2-Amino-ethoxy)-ethoxy]-acetyl)$_2$-(εK)-CO—(CH$_2$)$_{18}$—CO$_2$H)AQ-Aib-TFI-(D-Glu)-YLIEGGPSSGAPPPS-NH$_2$ | 184 | 4913.5 | N/I |
| 176 | Y-Aib-EGT-αMeF(2F)-TSDHSI-αMeL-LDEK((2-[2-(2-Amino-ethoxy)-ethoxy]-acetyl)$_2$-(εK)-CO—(CH$_2$)$_{16}$—CO$_2$H)AQ-Aib-TFI-(D-Glu)-YLIEGGPSSGAPPPS-NH$_2$ | 185 | 4885.5 | N/I |
| 177 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{16}$—CO$_2$H)AQ-Aib-HFI-(D-Glu)-YLIEGGPSSGAPPPS-NH$_2$ | 186 | 4922.5 | N/I |
| 178 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{14}$—CO$_2$H)AQ-Aib-HFI-(D-Glu)-YLIEGGPSSGAPPPS-NH$_2$ | 187 | 4894.4 | N/I |
| 179 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{16}$—CO$_2$H)AQ-Aib-HFI-(D-Glu)-YLIEGGPSSG-NH$_2$ | 188 | 4473.0 | N/I |
| 180 | Y-Aib-EGT-αMeF(2F)-TSDHSI-αMeL-LDEK((2-[2-(2-Amino-ethoxy)-ethoxy]-acetyl)$_2$-(γ-Glu)-CO—(CH$_2$)$_{16}$—CO$_2$H)AQ-Aib-HFI-(D-Glu)-YLIEGG-NH$_2$ | 189 | 4144.6 | N/I |
| 181 | Y-Aib-EGT-αMeF(2F)-TSD-3Pal-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 190 | 4953.5 | N/I |
| 182 | Y-Aib-EGT-αMeF(2F)-TSD-4Pal-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 191 | 4953.5 | N/I |
| 183 | Y-Aib-EGT-αMeF(2F)-TSDLSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 192 | 4918.5 | N/I |
| 184 | Y-Aib-EGT-αMeF(2F)-TSD-(D-Tyr)-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 193 | 4968.5 | N/I |
| 185 | Y-Aib-EGT-αMeF(2F)-TSD-(D-His)-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 194 | 4942.5 | N/I |
| 186 | Y-Aib-EGT-αMeF(2F)-TSD-αMeY-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 195 | 4982.6 | N/I |
| 187 | Y-Aib-EGT-αMeF(2F)-TSDQSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 196 | 4933.5 | N/I |
| 188 | Y-Aib-EGT-αMeF(2F)-TSD-3Pal-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-Aib-YLIEGGPSSGAPPPS-NH$_2$ | 197 | 4909.5 | N/I |
| 189 | Y-Aib-EGT-αMeF(2F)-TSD-4Pal-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-Aib-YLIEGGPSSGAPPPS-NH$_2$ | 198 | 4909.5 | N/I |
| 190 | H-Aib-EGT-αMeF(2F)-TSD-3Pal-SI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 199 | 4927.5 | N/I |

| Example | Compound Name | SEQ ID NO | Calculated MW (average) | Found MW (average) |
|---|---|---|---|---|
| 191 | Y-Aib-EGT-αMeF(2F)-TSDVSI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 200 | 4904.5 | N/I |
| 192 | Y-Aib-EGT-αMeF(2F)-TSDASI-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 201 | 4876.4 | N/I |
| 193 | Y-αMePro-EGTFTSDYSILLDEK((2-[2-(2-Amino-ethoxy)-ethoxy]-acetyl)$_2$-(γ-Glu)-CO—(CH$_2$)$_{18}$—CO$_2$H)AQQAFIEYLIEGGPSSGAPPPS-NH$_2$ | 202 | 4933.5 | N/I |
| 194 | Y-αMePro-EGTFTSDYSILLDEK((2-[2-(2-Amino-ethoxy)-ethoxy]-acetyl)$_2$-(γ-Glu)-CO—(CH$_2$)$_{18}$—CO$_2$H)AQHAFIEYLIEGGPSSGAPPPS-NH$_2$ | 203 | 4942.5 | N/I |
| 195 | Y-αMePro-EGTFTSDYSILLDRK((2-[2-(2-Amino-ethoxy)-ethoxy]-acetyl)$_2$-(γ-Glu)-CO—(CH$_2$)$_{18}$—CO$_2$H)AQQAFIEYLIEGGPSSGAPPPS-NH$_2$ | 204 | 4960.6 | N/I |
| 196 | Y-αMePro-EGTFTSDYSILLDRK((2-[2-(2-Amino-ethoxy)-ethoxy]-acetyl)$_2$-(γ-Glu)-CO—(CH$_2$)$_{18}$—CO$_2$H)AQHAFIEYLIEGGPSSGAPPPS-NH$_2$ | 205 | 4969.6 | N/I |
| 197 | Y-αMePro-EGTFTSDYSILLDEK((2-[2-(2-Amino-ethoxy)-ethoxy]-acetyl)$_2$-(γ-Glu)-CO—(CH$_2$)$_{16}$—CO$_2$H)AQQAFIEYLIEGGPSSG-NH$_2$ | 206 | 4456.0 | N/I |
| 198 | (D-Tyr)-αMePro-EGTFTSDYSILLDEK((2-[2-(2-Amino-ethoxy)-ethoxy]-acetyl)$_2$-(γ-Glu)-CO—(CH$_2$)$_{16}$—CO$_2$H)AQQAFIEYLIEGGPSSG-NH$_2$ | 207 | 4456.0 | N/I |
| 199 | DesTyr-Aib-EGTFTSDYSILLDEK((2-[2-(2-Amino-ethoxy)-ethoxy]-acetyl)$_2$-(γ-Glu)-CO—(CH$_2$)$_{18}$—CO$_2$H)AQQAFIEYLIEGGPSSGAPPPS-NH$_2$ | 208 | 4892.5 | N/I |
| 200 | DesTyr-AEGTFTSDYSILLDEK((2-[2-(2-Amino-ethoxy)-ethoxy]-acetyl)$_2$-(γ-Glu)-CO—(CH$_2$)$_{18}$—CO$_2$H)AQQAFIEYLIEGGPSSGAPPPS-NH$_2$ | 209 | 4878.4 | N/I |
| 201 | DesHis-αMePro-EGTFTSDYSILLDEK((2-[2-(2-Amino-ethoxy)-ethoxy]-acetyl)$_2$-(γ-Glu)-CO—(CH$_2$)$_{18}$—CO$_2$H)AQQAFIEYLIEGGPSSGAPPPS-NH$_2$ | 210 | 4892.5 | N/I |
| 202 | Y-Aib-EGT-αMeF(2F)-TSD-4Pal-SI-αMeL-LDKK((2-[2-(2-Amino-ethoxy)-ethoxy]-acetyl)-(γ-Glu)-(2-[2-(2-Amino-ethoxy)-ethoxy]-acetyl)-CO—(CH$_2$)$_{18}$—CO$_2$H)AQ-Aib-EFI-(D-Glu)-YLIEGGPSSGAPPPS-NH$_2$ | 211 | 4938.6 | N/I |
| 203 | Y-Aib-EGT-αMeF(2F)-TSD-4Pal-SI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 212 | 4952.6 | N/I |
| 204 | Y-Aib-EGT-αMeF(2F)-TSD-4Pal-SI-αMeL-LDEK((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 213 | 4924.5 | N/I |
| 205 | Y-Aib-EGT-αMeF(2F)-TSD-4Pal-SI-αMeL-LDEK((2-[2-(2-Amino-ethoxy)-ethoxy]-acetyl)$_2$-CO—(CH$_2$)$_{16}$—CO$_2$H)AQ-Aib-EFI-(D-Glu)-YLIEGGPSSGAPPPS-NH$_2$ | 214 | 4795.4 | N/I |
| 206 | Y-Aib-EGT-αMeF(2F)-TSD-4Pal-SI-αMeL-LDEK((2-[2-(2-Amino-ethoxy)-ethoxy]-acetyl)$_2$-CO—(CH$_2$)$_{18}$—CO$_2$H)AQ-Aib-EFI-(D-Glu)-YLIEGGPSSGAPPPS-NH$_2$ | 215 | 4823.5 | N/I |
| 207 | Y-Aib-EGT-αMeF(2F)-TSD-4Pal-SI-αMeL-LDEK((2-[2-(2-Amino-ethoxy)-ethoxy]-acetyl)$_2$-(εK)-CO—(CH$_2$)$_{18}$—CO$_2$H)AQ-Aib-EFI-(D-Glu)-YLIEGGPSSGAPPPS-NH$_2$ | 216 | 4923.6 | N/I |
| 208 | Y-Aib-EGT-αMeF(2F)-TSDYSI-αMeL-LDEK((2-[2-(2-Amino-ethoxy)-ethoxy]-acetyl)$_2$-(γ-Glu)-CO—(CH$_2$)$_{14}$—CO$_2$H)AQ-Aib-EFI-(D-Glu)-YLIEGGPSSGAPPPS-NH$_2$ | 217 | 4912.4 | N/I |
| 209 | Y-Aib-EGT-αMeF(2F)-TSDYSI-αMeL-LD-Dab-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 218 | 4911.4 | N/I |
| 210 | Y-Aib-EGT-αMeF(2F)-TSDYSI-αMeL-LD-Dap-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 219 | 4897.5 | N/I |

-continued

| Example | Compound Name | SEQ ID NO | Calculated MW (average) | Found MW (average) |
|---|---|---|---|---|
| 211 | Y-Aib-EGT-αMeF(2F)-TSDYSI-αMeL-LDKK((2-[2-(2-Amino-ethoxy)-ethoxy]-acetyl)-(γ-Glu)-(2-[2-(2-Amino-ethoxy)-ethoxy]-acetyl)-CO—$(CH_2)_{18}$—$CO_2H$)AQ-Aib-EFI-(D-Glu)-YLIEGGPSSGAPPPS-$NH_2$ | 220 | 4953.6 | N/I |
| 212 | Y-Aib-EGT-αMeF(2F)-TSDYSI-αMeL-LDKK((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-YLIEGGPSSGAPPPS-$NH_2$ | 221 | 4967.5 | N/I |
| 213 | Y-Aib-EGT-αMeF-TSDYSI-αMeL-LDEK((2-[2-(2-Amino-ethoxy)-ethoxy]-acetyl)$_2$-(γ-Glu)-CO—$(CH_2)_{16}$—$CO_2H$)AQ-Aib-EFI-(D-Glu)-YLIEGGPSSGAPPPS-$NH_2$ | 222 | 4922.4 | N/I |
| 214 | Y-Aib-EGT-αMeF(2F)-TSDYSI-αMeL-LDEK((2-[2-(2-Amino-ethoxy)-ethoxy]-acetyl)$_2$-CO—$(CH_2)_{16}$—$CO_2H$)AQ-Aib-EFI-(D-Glu)-YLIEGGPSSGAPPPS-$NH_2$ | 223 | 4811.4 | N/I |
| 215 | Y-Aib-EGT-αMeF(2F)-TSDYSI-αMeL-LDEK((2-[2-(2-Amino-ethoxy)-ethoxy]-acetyl)$_2$-CO—$(CH_2)_{18}$—$CO_2H$)AQ-Aib-EFI-(D-Glu)-YLIEGGPSSGAPPPS-$NH_2$ | 224 | 4839.4 | N/I |
| 216 | Y-Aib-EGT-αMeF(2F)-TSDYSI-αMeL-LDEK((2-[2-(2-Amino-ethoxy)-ethoxy]-acetyl)$_2$-(εK)-CO—$(CH_2)_{18}$—$CO_2H$)AQ-Aib-EFI-(D-Glu)-YLIEGGPSSGAPPPS-$NH_2$ | 225 | 4967.5 | N/I |
| 217 | Y-Aib-EGT-αMeF(2F)-TSDYSI-αMeL-LD-Dab-K((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-YLIEGGPSSGAPPPS-$NH_2$ | 226 | 4939.5 | N/I |
| 218 | Y-Aib-EGT-αMeF(2F)-TSDYSI-αMeL-LD-Dap-K((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-YLIEGGPSSGAPPPS-$NH_2$ | 227 | 4925.5 | N/I |
| 219 | Y-Aib-EGT-αMeF(2F)-TSDYSI-αMeL-LDEK((2-[2-(2-Amino-ethoxy)-ethoxy]-acetyl)$_2$-(γ-Glu)-CO—$(CH_2)_{16}$—$CO_2H$)AQ-Aib-EFI-(D-Glu)-YLIEGGPSSG-$NH_2$ | 228 | 4491.0 | N/I |
| 220 | Y-Aib-EGT-αMeF(2F)-TSDYSI-αMeL-LDEK((2-[2-(2-Amino-ethoxy)-ethoxy]-acetyl)$_2$-(γ-Glu)-CO—$(CH_2)_{16}$—$CO_2H$)AQ-Aib-EFI-(D-Glu)-YLIEGG-$NH_2$ | 229 | 4162.6 | N/I |
| 221 | Y-Aib-EGT-αMeF(2F)-TSDYSI-αMeL-LDEK((2-[2-(2-Amino-ethoxy)-ethoxy]-acetyl)$_2$-(γ-Glu)-CO—$(CH_2)_{16}$—$CO_2H$)AQ-Aib-EFI-(D-Glu)-YLIEGGPSSGAPPPS-$NH_2$ | 230 | 4940.5 | N/I |
| 222 | Y-Aib-EGT-αMeF(2F)-TSDYSI-αMeL-LDEK((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-αMeY-LIEGGPSSGAPPPS-$NH_2$ | 231 | 4982.6 | N/I |
| 223 | Y-Aib-EGT-αMeF(2F)-TSDYSI-αMeL-LDEK((2-[2-(2-Amino-ethoxy)-ethoxy]-acetyl)$_2$-(γ-Glu)-CO—$(CH_2)_{18}$—$CO_2H$)AQ-Aib-EFIE-αMeY-LIEGGPSSGAPPPS-$NH_2$ | 232 | 4982.6 | N/I |
| 224 | Y-Aib-EGT-αMeF(2F)-TSDYSI-Aib-LDEK((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-YLIEGGPSSGAPPPS-$NH_2$ | 233 | 4926.4 | N/I |
| 225 | Y-Aib-EGT-αMeF-TSDYSI-Aib-LDEK((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-YLIEGGPSSGAPPPS-$NH_2$ | 234 | 4908.5 | N/I |
| 226 | Y-Aib-EGT-αMeF(2F)-TSDYSILLDEK((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-YLIEGGPSSGAPPPS-$NH_2$ | 235 | 4954.5 | N/I |
| 227 | Y-Aib-EGT-αMeF-TSDYSI-αMeL-LDEK((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-YLIEGGPSSGAPPPS-$NH_2$ | 236 | 4950.5 | N/I |
| 228 | Y-Aib-EGT-αMeF-TSDYSI-αMeL-LDKK((2-[2-(2-Amino-ethoxy)-ethoxy]-acetyl)$_2$-(γ-Glu)-CO—$(CH_2)_{18}$—$CO_2H$)AQ-Aib-EFI-(D-Glu)-YLIEGGPSSG-$NH_2$ | 237 | 4500.1 | N/I |

| Example | Compound Name | SEQ ID NO | Calculated MW (average) | Found MW (average) |
|---|---|---|---|---|
| 229 | Y-Aib-EGT-αMeF(2F)-TSDYS-αMeL-LDEK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 238 | 4855.4 | N/I |
| 230 | Y-Aib-EGT-αMeF(2F)-TSDYSI-αMeL-LDHK((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 239 | 4976.6 | N/I |
| 231 | Y-Aib-EGT-αMeF(2F)-TSDYSI-αMeL-LDKK((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 240 | 4939.5 | N/I |
| 232 | Y-Aib-EGT-αMeF(2F)-TSD-4Pal-SI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 241 | 4910.5 | N/I |
| 233 | Y-Aib-EGT-αMeF(2F)-TSD-4Pal-SI-αMeL-LD-Dab-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 242 | 4896.5 | N/I |
| 234 | Y-Aib-EGT-αMeF(2F)-TSD-4Pal-SILLD-Dab-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 243 | 4882.4 | N/I |
| 235 | Y-Aib-EGT-αMeF-TSD-4Pal-SI-αMeL-LD-Dab-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 244 | 4878.5 | N/I |
| 236 | Y-Aib-EGT-αMeF(2F)-TSDYSI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-αMeY-LIEGGPSSGAPPPS-NH$_2$ | 245 | 4939.5 | N/I |
| 237 | Y-Aib-EGT-αMeF(2F)-TSDASI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-αMeY-LIEGGPSSGAPPPS-NH$_2$ | 246 | 4847.4 | N/I |
| 238 | Y-Aib-EGT-αMeF(2F)-TSDLSI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-αMeY-LIEGGPSSGAPPPS-NH$_2$ | 247 | 4889.5 | N/I |
| 239 | Y-Aib-EGT-αMeF(2F)-TSD-4Pal-SI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-TFI-(D-Glu)-αMeY-LIEGGPSSGAPPPS-NH$_2$ | 248 | 4896.5 | N/I |
| 240 | Y-Aib-EGT-αMeF(2F)-TSD-4Pal-SI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-AFI-(D-Glu)-αMeY-LIEGGPSSGAPPPS-NH$_2$ | 249 | 4866.5 | N/I |
| 241 | Y-Aib-EGT-αMeF(2F)-TSDVSI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-TFI-(D-Glu)-αMeY-LIEGGPSSGAPPPS-NH$_2$ | 250 | N/I | N/I |
| 242 | Y-Aib-EGT-αMeF(2F)-TSDVSI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-AFI-(D-Glu)-αMeY-LIEGGPSSGAPPPS-NH$_2$ | 251 | N/I | N/I |
| 243 | Y-Aib-EGT-αMeF(2F)-TSDLSI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-TFI-(D-Glu)-αMeY-LIEGGPSSGAPPPS-NH$_2$ | 252 | N/I | N/I |
| 244 | Y-Aib-EGT-αMeF(2F)-TSDLSI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-AFI-(D-Glu)-αMeY-LIEGGPSSGAPPPS-NH$_2$ | 253 | N/I | N/I |

| Example | Compound Name | SEQ ID NO | Calculated MW (average) | Found MW (average) |
|---|---|---|---|---|
| 245 | Y-Aib-EGT-αMeF(2F)-TSDASI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-TFI-(D-Glu)-αMeY-LIEGGPSSGAPPPS-NH$_2$ | 254 | N/I | N/I |
| 246 | Y-Aib-EGT-αMeF(2F)-TSDASI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-AFI-(D-Glu)-αMeY-LIEGGPSSGAPPPS-NH$_2$ | 255 | N/I | N/I |
| 247 | Y-Aib-EGT-αMeF(2F)-TSDYSI-Aib-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 256 | 4883.4 | N/I |
| 248 | Y-Aib-EGT-αMeF(2F)-TSDYSILLD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 257 | 4911.5 | N/I |
| 249 | Y-Aib-EGT-αMeF(2F)-TSDYSI-Nle-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-YLIEGGPSSGAPPPS-NH$_2$ | 258 | 4911.5 | N/I |
| 250 | Y-Aib-EGT-αMeF(2F)-TSDYSI-Aib-LD-Orn-K((2-[2-(2-Amino-ethoxy)-ethoxy]-acetyl)$_2$-(γ-Glu)-CO—(CH$_2$)$_{18}$—CO$_2$H)AQ-Aib-EFI-(D-Glu)-YLIEGGPSSGAPPPS-NH$_2$ | 259 | 4911.5 | N/I |
| 251 | Y-Aib-EGT-αMeF(2F)-TSD-4Pal-SI-αMeL-LD-Orn-K((2-[2-(2-Amino-ethoxy)-ethoxy]-acetyl)$_2$-(εK)-CO—(CH$_2$)$_{18}$—CO$_2$H)AQ-Aib-AFI-(D-Glu)-αMeY-LIEGGPSSGAPPPS-NH$_2$ | 260 | 4893.6 | N/I |
| 252 | Y-Aib-EGT-αMeF(2F)-TSD-4Pal-SI-αMeL-LD-Orn-K((2-[2-(2-Amino-ethoxy)-ethoxy]-acetyl)$_2$-(εK)-CO—(CH$_2$)$_{18}$—CO$_2$H)AQ-Aib-AFI-(D-Glu)-αMeY-LIAGGPSSGAPPPS-NH$_2$ | 261 | 4835.6 | N/I |
| 253 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQAAFIEYLIEGGPSSGAPPPS-NH$_2$ | 262 | 4849.5 | N/I |
| 254 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQQAFIEYLIEGGPSSGAPPPS-NH$_2$ | 263 | 4906.5 | N/I |
| 255 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQHAFIEYLIEGGPSSGAPPPS-NH$_2$ | 264 | 4915.5 | N/I |
| 256 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQKAFIEYLIEGGPSSGAPPPS-NH$_2$ | 265 | 4906.6 | N/I |
| 257 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQRAFIEYLIEGGPSSGAPPPS-NH$_2$ | 266 | 4934.6 | N/I |
| 258 | Y-Aib-EGTFTSDYSILLDEK((2-[2-(2-Amino-ethoxy)-ethoxy]-acetyl)$_2$-(γ-Glu)-CO—(CH$_2$)$_{18}$—CO$_2$H)AQKAFIEYLIEGGPSSGAPPPS-NH$_2$ | 267 | 4907.5 | N/I |
| 259 | Y-Aib-EGTFTSDYSILLDEK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 268 | 4864.4 | N/I |
| 260 | Y-Aib-EGTFTSDHSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIEGGPSSGAPPPS-NH$_2$ | 269 | 4837.5 | N/I |
| 261 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQEAFIEYLIEGGPSSGAPPPS-NH$_2$ | 270 | 4907.5 | N/I |
| 262 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQTAFIEYLIEGGPSSGAPPPS-NH$_2$ | 271 | 4879.5 | N/I |
| 263 | Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQSAFIEYLIEGGPSSGAPPPS-NH$_2$ | 272 | 4865.5 | N/I |
| 264 | Y-Aib-EGT-αMeF(2F)-TSD-4Pal-SI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-αMeY-LIEGGPSSG-NH$_2$ | 273 | 4475.0 | N/I |

| Example | Compound Name | SEQ ID NO | Calculated MW (average) | Found MW (average) |
|---|---|---|---|---|
| 265 | Y-Aib-EGT-αMeF(2F)-TSD-4Pal-SI-αMeL-LD-Orn-K((2-[2-(2-Amino-ethoxy)-ethoxy]-acetyl)$_2$-(γ-Glu)-CO—(CH$_2$)$_{16}$—CO$_2$H)AQ-Aib-EFI-(D-Glu)-αMeY-LIEGG-NH$_2$ | 274 | 4146.7 | N/I |
| 266 | Y-Aib-EGTFTSDYSILLDKK((2-[2-(2-Amino-ethoxy)-ethoxy]-acetyl)$_2$-(γ-Glu)-CO—(CH$_2$)$_{16}$—CO$_2$H)AQ-Aib-AFIEYLIEGGPSSG-NH$_2$ | 275 | 4385.94 | 4386.6 |
| 267 | Y-Aib-EGTFTSDYSILLDKK((2-[2-(2-Amino-ethoxy)-ethoxy]-acetyl)$_2$-(γ-Glu)-CO—(CH$_2$)$_{16}$—CO$_2$H)AQ-Aib-AFIEYLIEGG-NH$_2$ | 276 | 4057.62 | N/I |
| 268 | Y-Aib-EGTFTSDYSILLDEK((2-[2-(2-Amino-ethoxy)-ethoxy]-acetyl)$_2$-(γ-Glu)-CO—(CH$_2$)$_{16}$—CO$_2$H)AQ-Aib-AFIEYLIEGGPSSG-NH$_2$ | 277 | 4386.88 | N/I |
| 269 | Y-Aib-EGTFTSDYSILLDEK((2-[2-(2-Amino-ethoxy)-ethoxy]-acetyl)$_2$-(γ-Glu)-CO—(CH$_2$)$_{16}$—CO$_2$H)AQ-Aib-AFIEYLIEGG-NH$_2$ | 278 | 4058.56 | N/I |
| 270 | Y-Aib-EGTFTSDYSILLDKK((2-[2-(2-Amino-ethoxy)-ethoxy]-acetyl)$_2$-(γ-Glu)-CO—(CH$_2$)$_{16}$—CO$_2$H)AQ-Aib-EFIEYLIEGGPSSG-NH$_2$ | 279 | 4443.98 | N/I |
| 271 | Y-Aib-EGTFTSDYSILLDKK((2-[2-(2-Amino-ethoxy)-ethoxy]-acetyl)$_2$-(γ-Glu)-CO—(CH$_2$)$_{16}$—CO$_2$H)AQ-Aib-EFIEYLIEGG-NH$_2$ | 280 | 4115.66 | N/I |
| 272 | Y-Aib-EGTFTSDYSILLDKK((2-[2-(2-Amino-ethoxy)-ethoxy]-acetyl)$_2$-(γ-Glu)-CO—(CH$_2$)$_{16}$—CO$_2$H)AQ-Aib-AFIEYLIAGGPSSG-NH$_2$ | 281 | 4327.91 | 4327.8 |
| 273 | Y-Aib-EGTFTSDYSILLDKK((2-[2-(2-Amino-ethoxy)-ethoxy]-acetyl)$_2$-(γ-Glu)-CO—(CH$_2$)$_{16}$—CO$_2$H)AQ-Aib-AFIEYLIAGG-NH$_2$ | 282 | 3999.58 | N/I |
| 274 | Y-Aib-EGTFTSDYSILLDKK((2-[2-(2-Amino-ethoxy)-ethoxy]-acetyl)$_2$-(γ-Glu)-CO—(CH$_2$)$_{16}$—CO$_2$H)AQPAFIEYLIEGGPSSG-NH$_2$ | 283 | 4397.95 | N/I |
| 275 | Y-Aib-EGTFTSDYSILLDKK((2-[2-(2-Amino-ethoxy)-ethoxy]-acetyl)$_2$-(γ-Glu)-CO—(CH$_2$)$_{16}$—CO$_2$H)AQPAFIEYLIEGG-NH$_2$ | 284 | 4069.63 | N/I |
| 276 | Y-Aib-EGT-αMeF(2F)-TSDYSI-αMeL-LDEKAQ-Aib-EFI-(D-Glu)-YLIEGGPSSGAPPPS-NH$_2$ | 285 | 4224.59 | N/I |
| 277 | Y-Aib-EGT-αMeF(2F)-TSDYSI-αMeL-LDEQAQ-Aib-EFI-(D-Glu)-YLIEGGPSSGAPPPS-NH$_2$ | 286 | 4224.55 | N/I |
| 278 | Y-Aib-EGT-αMeF(2F)-TSDYSI-αMeL-LDEKAQ-Aib-EFI-(D-Glu)-YLIEGGPSSGAPPPSC-NH$_2$ | 287 | 4327.74 | N/I |
| 279 | Y-Aib-EGT-αMeF(2F)-TSDYSI-αMeL-LDEQAQ-Aib-EFI-(D-Glu)-YLIEGGPSSGAPPPSC-NH$_2$ | 288 | 4327.69 | N/I |
| 280 | Y-Aib-EGT-αMeF(2F)-TSDYSI-αMeL-LD-Orn-KAQ-Aib-EFI-(D-Glu)-YLIEGGPSSGAPPPS-NH$_2$ | 289 | 4210.61 | N/I |
| 281 | Y-Aib-EGT-αMeF(2F)-TSDYSI-αMeL-LD-Orn-QAQ-Aib-EFI-(D-Glu)-YLIEGGPSSGAPPPS-NH$_2$ | 290 | 4209.58 | N/I |
| 282 | Y-Aib-EGT-αMeF(2F)-TSDYSI-αMeL-LD-Orn-KAQ-Aib-EFI-(D-Glu)-YLIEGGPSSGAPPPSC-NH$_2$ | 291 | 4312.77 | N/I |
| 283 | Y-Aib-EGT-αMeF(2F)-TSDYSI-αMeL-LD-Orn-QAQ-Aib-EFI-(D-Glu)-YLIEGGPSSGAPPPSC-NH$_2$ | 292 | 4312.73 | N/I |
| 284 | Y-Aib-EGT-αMeF(2F)-TSD-4Pal-SI-αMeL-LD-Orn-KAQ-Aib-EFI-(D-Glu)-αMeY-LIEGGPSSGAPPPS-NH$_2$ | 293 | 4208.64 | N/I |

| Example | Compound Name | SEQ ID NO | Calculated MW (average) | Found MW (average) |
|---|---|---|---|---|
| 285 | Y-Aib-EGT-αMeF(2F)-TSD-4Pal-SI-αMeL-LD-Orn-QAQ-Aib-EFI-(D-Glu)-αMeY-LIEGGPSSGAPPPS-NH$_2$ | 294 | 4208.6 | N/I |
| 286 | Y-Aib-EGT-αMeF(2F)-TSD-4Pal-SI-αMeL-LD-Orn-KAQ-Aib-EFI-(D-Glu)-αMeY-LIEGGPSSGAPPPSC-NH$_2$ | 295 | 4311.78 | N/I |
| 287 | Y-Aib-EGT-αMeF(2F)-TSD-4Pal-SI-αMeL-LD-Orn-QAQ-Aib-EFI-(D-Glu)-αMeY-LIEGGPSSGAPPPSC-NH$_2$ | 296 | 4311.74 | N/I |

N/I means Not Included

Example 288

Y-Aib-EGTFTSDYSILLDKK((2-[2-(2-Amino-ethoxy)-ethoxy]-acetyl)$_2$-(γ-Glu)-CO—(CH$_2$)$_{18}$—CO$_2$H)AQ-Aib-AFIEYLIAGGPSSGAPPPS-NH$_2$ (SEQ ID NO:303)

The structure of SEQ ID NO:303 is depicted below using the standard single letter amino acid codes with the exception of residues Aib2, K17, Aib20, and Ser39, where the structures of these amino acid residues have been expanded:

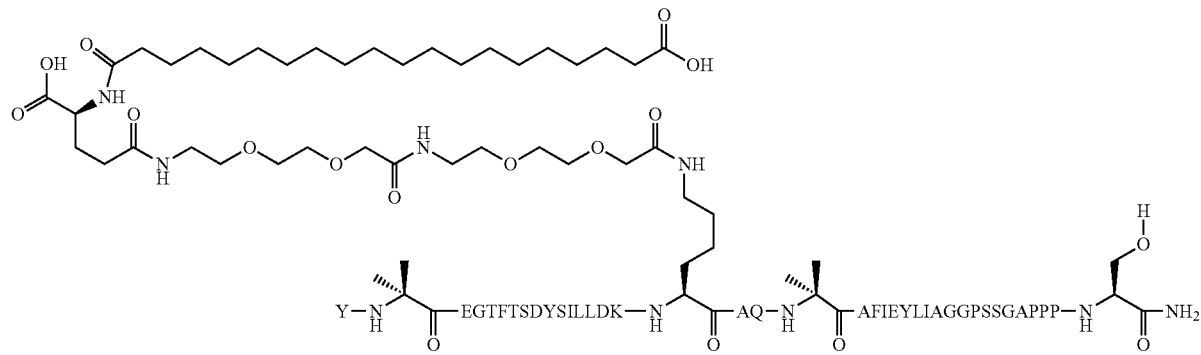

The compound according to SEQ ID NO:303 is prepared substantially as described by the procedures of Example 1. The molecular weight is determined by LC-MS (obsd: M+3 10=1602.5; Calc M+3=1602.8).

Example 289

Y-Aib-EGTFTSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-EFIEY-LIAGGPSSGAPPPS-NH$_2$ (SEQ ID NO:304)

The structure of SEQ ID NO:304 is depicted below using the standard single letter amino acid codes with the exception of residues Aib2, αMeL13, K17, Aib20, and Ser39, where the structures of these amino acid residues have been expanded:

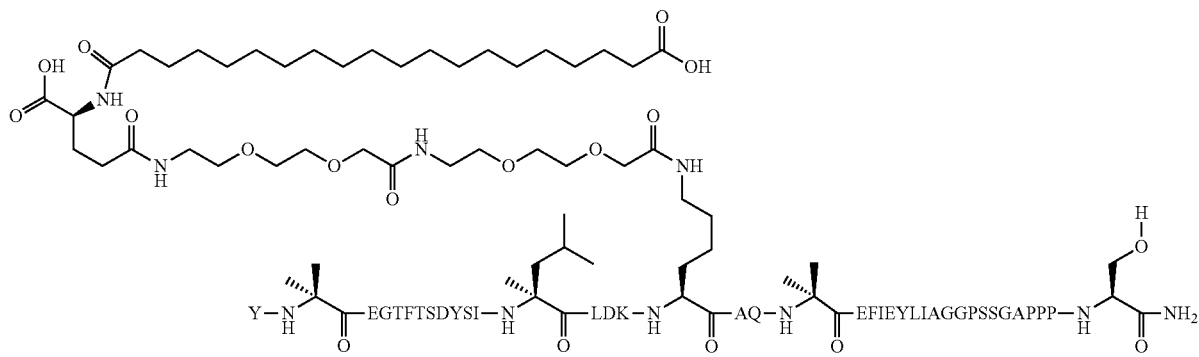

The compound according to SEQ ID NO:304 is prepared substantially as described by the procedures of Example 1. The molecular weight is determined by LC-MS (obsd: M+3=1626.8; Calc M+3=1626.8).

Example 290

(D-Tyr)-Aib-EGTFTSDYSI-αMeL-LDKK((2-[2-(2-Amino-ethoxy)-ethoxy]-acetyl)₂-(γ-Glu)-CO—(CH₂)₁₈—CO₂H)AQ-Aib-EFIEY-LIAGGPSSGAPPPS-NH₂ (SEQ ID NO:305)

The structure of SEQ ID NO:305 is depicted below using the standard single letter amino acid codes with the exception of residues D-Tyr1, Aib2, αMeL13, K17, Aib20, and Ser39, where the structures of these amino acid residues have been expanded:

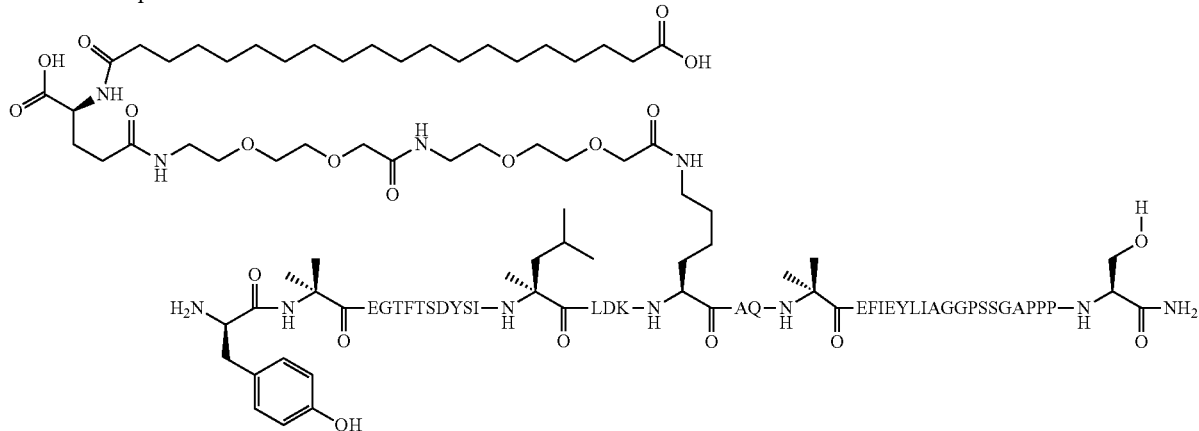

The compound according to SEQ ID NO:305 is prepared substantially as described by the procedures of Example 1. The molecular weight is determined by LC-MS (obsd: M+3=1626.6; Calc M+3=1626.8).

Example 291

(D-Tyr)-Aib-EGTFTSDYSI-αMeL-LD-Orn-K((2-[2-(2-Amino-ethoxy)-ethoxy]-acetyl)₂-(γ-Glu)-CO—(CH₂)₁₈—CO₂H)AQ-Aib-AFI-(D-Glu)-YLIAGGPSSGAPPPS-NH₂ (SEQ ID NO:306)

The structure of SEQ ID NO:306 is depicted below using the standard single letter amino acid codes with the exception of residues D-Tyr1, Aib2, αMeL13, Orn16, K17, Aib20, D-Glu24, and Ser39, where the structures of these amino acid residues have been expanded:

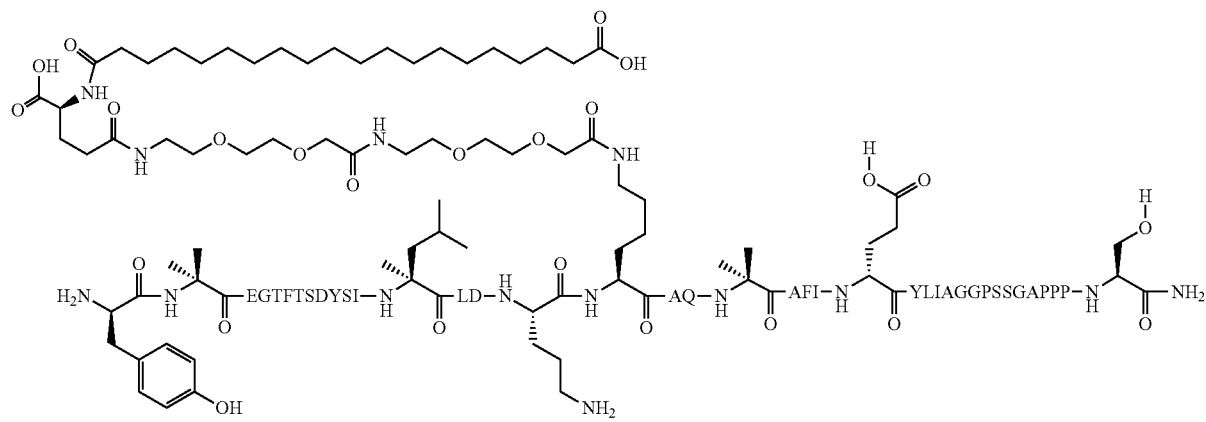

The compound according to SEQ ID NO:306 is prepared substantially as described by the procedures of Example 1. The molecular weight is determined by LC-MS (obsd: M+3=1602.4; Calc M+3=1602.8).

Example 292

(D-Tyr)-Aib-EGTFTSDYSI-αMeL-LDKK((2-[2-(2-Amino-ethoxy)-ethoxy]-acetyl)$_2$-(γ-Glu)-CO—(CH$_2$)$_{18}$—CO$_2$H)AQ-Aib-EFIE-αMeY-LI-AGGPSSGAPPPS-NH$_2$ (SEQ ID NO:307)

The structure of SEQ ID NO:307 is depicted below using the standard single letter amino acid codes with the exception of residues D-Tyr1, Aib2, αMeL13, K17, Aib20, αMeY25, and Ser39, where the structures of these amino acid residues have been expanded:

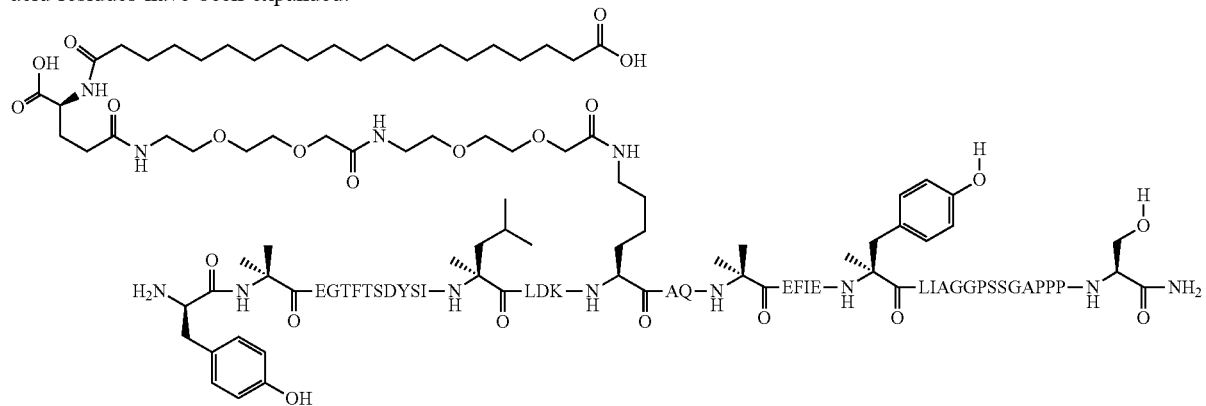

The compound according to SEQ ID NO:307 is prepared substantially as described by the procedures of Example 1. The molecular weight is determined by LC-MS (obsd: M+3=1631.3; Calc M+3=1631.5).

Example 293

(D-Tyr)-Aib-EGTFTSDYSI-αMeL-LD-Orn-K((2-[2-(2-Amino-ethoxy)-ethoxy]-acetyl)$_2$-(γ-Glu)-CO—(CH$_2$)$_{18}$—CO$_2$H)AQ-Aib-EFIE-αMeY-LI-AGGPSSGAPPPS-NH$_2$ (SEQ ID NO:308)

The structure of SEQ ID NO:308 is depicted below using the standard single letter amino acid codes with the exception of residues D-Tyr1, Aib2, αMeL13, Orn16, K17, Aib20, αMeY25, and Ser39, where the structures of these amino acid residues have been expanded:

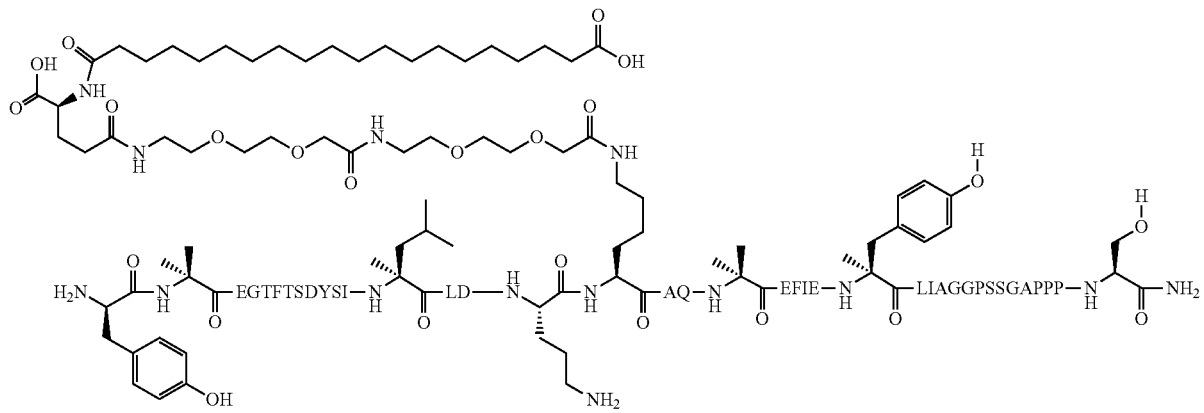

The compound according to SEQ ID NO:308 is prepared substantially as described by the procedures of Example 1. The molecular weight is determined by LC-MS (obsd: M+3=1626.5; Calc M+3=1626.8).

Example 294 Through Example 381

The compounds according to Examples 294 (SEQ ID NO:309) through Example 381 (SEQ ID NO:396) are prepared substantially as described by the procedures of Example 1.

| Example | Compound Name | SEQ ID NO | Calculated MW (average) | Found MW (average) |
|---|---|---|---|---|
| 294 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQQAFIEYLIEGG-NH$_2$ | 309 | 4100.6 | N/I |
| 295 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQHAFIEYLIEGG-NH$_2$ | 310 | 4109.7 | N/I |
| 296 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQKAFIEYLIEGGPSSG-NH$_2$ | 311 | 4429.0 | N/I |
| 297 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQ-Aib-EFIEYLIAGG-NH$_2$ | 312 | 4057.6 | N/I |
| 298 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQ-Aib-AFVEYLIEGGPSSG-NH$_2$ | 313 | 4313.9 | N/I |
| 299 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQ-Aib-AFLEYLIEGGPSSG-NH$_2$ | 314 | 4385.9 | N/I |
| 300 | Y-Aib-EGTFTSDYSI-αMeL-LDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSG-NH$_2$ | 315 | 4400.0 | N/I |
| 301 | Y-Aib-EGT-αMeF-TSDYSILLDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSG-NH$_2$ | 316 | 4400.0 | 4399.2 |
| 302 | Y-Aib-EGT-αMeF(2F)-TSDYSILLDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSG-NH$_2$ | 317 | 4418.0 | N/I |
| 303 | Y-Aib-EGTFTSDYSI-αMeL-LDEK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSG-NH$_2$ | 318 | 4400.9 | 4400.7 |
| 304 | Y-Aib-EGTFTSDYSI-αMeL-LDKK((2-[2-(2-Amino-ethoxy)-ethoxy]-acetyl)$_2$-(γ-Glu)-CO-(CH$_2$)$_{16}$-CO$_2$H)AQ-Aib-EFIEYLIEGGPSSG-NH$_2$ | 319 | 4458.0 | N/I |
| 305 | Y-Aib-EGTFTSDYSI-αMeL-LDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSG-NH$_2$ | 320 | 4341.9 | N/I |
| 306 | Y-Aib-EGTFTSDYSI-αMeL-LDKK((2-[2-(2-Amino-ethoxy)-ethoxy]-acetyl)$_2$-(γ-Glu)-CO-(CH$_2$)$_{16}$-CO$_2$H)AQ-Aib-EFIEYLIAGGPSSG-NH$_2$ | 321 | 4400.0 | N/I |
| 307 | Y-Aib-EGT-αMeF-TSDYSILLDEK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSG-NH$_2$ | 322 | 4400.9 | N/I |
| 308 | Y-Aib-EGT-αMeF-TSDYSILLDKK((2-[2-(2-Amino-ethoxy)-ethoxy]-acetyl)$_2$-(γ-Glu)-CO-(CH$_2$)$_{16}$-CO$_2$H)AQ-Aib-EFIEYLIEGGPSSG-NH$_2$ | 323 | 4458.0 | N/I |
| 309 | Y-Aib-EGT-αMeF-TSDYSILLDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIAGGPSSG-NH$_2$ | 324 | 4341.9 | N/I |
| 310 | Y-Aib-EGT-αMeF-TSDYSILLDKK((2-[2-(2-Amino-ethoxy)-ethoxy]-acetyl)$_2$-(γ-Glu)-CO-(CH$_2$)$_{16}$-CO$_2$H)AQ-Aib-EFIEYLIAGGPSSG-NH$_2$ | 325 | 4400.0 | N/I |
| 311 | Y-Aib-EGT-αMeF(2F)-TSDYSILLDEK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSG-NH$_2$ | 326 | 4418.9 | N/I |
| 312 | Y-Aib-EGT-αMeF(2F)-TSDYSILLDKK((2-[2-(2-Amino-ethoxy)-ethoxy]-acetyl)$_2$-(γ-Glu)-CO-(CH$_2$)$_{16}$-CO$_2$H)AQ-Aib-EFIEYLIEGGPSSG-NH$_2$ | 327 | 4476.0 | N/I |

| Example | Compound Name | SEQ ID NO | Calculated MW (average) | Found MW (average) |
|---|---|---|---|---|
| 313 | Y-Aib-EGT-αMeF(2F)-TSDYSILLDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIAGGPSSG-NH$_2$ | 328 | 4359.9 | N/I |
| 314 | Y-Aib-EGT-αMeF(2F)-TSDYSILLDKK((2-[2-(2-Amino-ethoxy)-ethoxy]-acetyl)$_2$-(γ-Glu)-CO-(CH$_2$)$_{16}$-CO$_2$H)AQ-Aib-EFIEYLIAGGPSSG-NH$_2$ | 329 | 4418.0 | N/I |
| 315 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSGAPPPS-NH$_2$ | 330 | 4835.5 | N/I |
| 316 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIAGGPSSGAPPPS-NH$_2$ | 331 | 4777.4 | 4777.2 |
| 317 | Y-Aib-EGTFTSDYSILLDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSG-NH$_2$ | 332 | 4356.0 | N/I |
| 318 | Y-Aib-EGTFTSDYSILLDKK((2-[2-(2-Amino-ethoxy)-ethoxy]-acetyl)$_2$-(γ-Glu)-CO-(CH$_2$)$_{18}$-CO$_2$H)AQ-Aib-EFIEYLIAGGPSSG-NH$_2$ | 333 | 4414.0 | N/I |
| 319 | Y-Aib-EGTFTSDYSILLDKK((2-[2-(2-Amino-ethoxy)-ethoxy]-acetyl)$_2$-(γ-Glu)-CO-(CH$_2$)$_{18}$-CO$_2$H)AQ-Aib-EFIEYLIAGGPSSGAPPPS-NH$_2$ | 334 | 4863.5 | N/I |
| 320 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQ-Aib-DFIEYLIEGGPSSG-NH$_2$ | 335 | 4430.0 | N/I |
| 321 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQ-Aib-TFIEYLIEGGPSSG-NH$_2$ | 336 | 4416.0 | N/I |
| 322 | Y-Aib-EGTFTSDYSILLDKK((2-[2-(2-Amino-ethoxy)-ethoxy]-acetyl)$_2$-(γ-Glu)-CO-(CH$_2$)$_{16}$-CO$_2$H)AQ-Aib-HFIEYLIEGGPSSG-NH$_2$ | 337 | 4452.0 | N/I |
| 323 | Y-Aib-EGTFTSDYSI-αMeL-LDEK((2-[2-(2-Amino-ethoxy)-ethoxy]-acetyl)$_2$-(γ-Glu)-CO-(CH$_2$)$_{16}$-CO$_2$H)AQ-Aib-AFIEYLIEGGPSSGAPPPS-NH$_2$ | 338 | 4850.4 | N/I |
| 324 | Y-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 339 | 4819.5 | N/I |
| 325 | Y-Aib-EGT-αMeF(2F)-TSDYSILLDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIEGGPSSGAPPPS-NH$_2$ | 340 | 4895.5 | N/I |
| 326 | F-Aib-EGTFTSDYSILLDKK((2-[2-(2-Amino-ethoxy)-ethoxy]-acetyl)$_2$-(γ-Glu)-CO-(CH$_2$)$_{18}$-CO$_2$H)AQ-Aib-EFIEYLIEGGPSSGAPPPS-NH$_2$ | 341 | 4847.5 | N/I |
| 327 | F-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-EFIEYLIEGGPSSGAPPPS-NH$_2$ | 342 | 4861.5 | N/I |
| 328 | F-Aib-EGTFTSDYSI-αMeL-LDKK((2-[2-(2-Amino-ethoxy)-ethoxy]-acetyl)$_2$-(γ-Glu)-CO-(CH$_2$)$_{16}$-CO$_2$H)AQ-Aib-AFIEYLIEAGPSSGAPPPS-NH$_2$ | 343 | 4847.5 | N/I |
| 329 | (D-Tyr)-Aib-EGT-αMeF-TSDYSILLDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIEGGPSSGAPPPS-NH$_2$ | 344 | 4877.5 | N/I |
| 330 | Y-Aib-EGTFTSDYSILLDEK((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 345 | 4806.4 | 4805.4 |
| 331 | Y-Aib-EGTFTSDYSI-αMeL-LDEK((2-[2-(2-Amino-ethoxy)-ethoxy]-acetyl)$_2$-(γ-Glu)-CO-(CH$_2$)$_{18}$-CO$_2$H)AQ-Aib-EFIEYLIEGGPSSGAPPPS-NH$_2$ | 346 | 4878.5 | N/I |
| 332 | Y-Aib-EGTFTSDYSI-αMeL-LDEK((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 347 | 4820.4 | N/I |
| 333 | Y-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-EFIEYLIEGGPSSGAPPPS-NH$_2$ | 348 | 4935.6 | N/I |
| 334 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIEGGPSSGAPPPS-NH$_2$ | 349 | 4877.5 | N/I |
| 335 | (D-Tyr)-Aib-EGT-αMeF-TSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIEGGPSSGAPPPS-NH$_2$ | 350 | 4891.6 | N/I |
| 336 | (D-Tyr)-Aib-EGT-αMeF(2F)-TSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIEGGPSSGAPPPS-NH$_2$ | 351 | 4909.5 | N/I |
| 337 | F-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 352 | 4803.5 | N/I |
| 338 | F-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-EFIEYLIAGGPSSGAPPPS-NH$_2$ | 353 | 4861.5 | N/I |
| 339 | Y-Aib-EGTFTSDYSI-αMeL-LDKK((2-[2-(2-Amino-ethoxy)-ethoxy]-acetyl)-(γ-Glu)-CO-(CH$_2$)$_{18}$-CO$_2$H)AQ-Aib-EFIEYLIAGGPSSGAPPPS-NH$_2$ | 354 | 4732.4 | 4732.2 |
| 340 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 355 | 4819.5 | 4818.8 |
| 341 | (D-Tyr)-Aib-EGTFTSDYSI-αMeL-LDEK((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 356 | 4820.4 | N/I |
| 342 | (D-Tyr)-Aib-EGTFTSDYSI-αMeL-LDEK((2-[2-(2-Amino-ethoxy)-ethoxy]-acetyl)$_2$-(γ-Glu)-CO-(CH$_2$)$_{18}$-CO$_2$H)AQ-Aib-EFIEYLIAGGPSSGAPPPS-NH$_2$ | 357 | 4878.5 | N/I |
| 343 | Y-Aib-EGTFTSDYSI-αMeL-LDEK((2-[2-(2-Amino-ethoxy)-ethoxy]-acetyl)$_2$-(γ-Glu)-CO-(CH$_2$)$_{18}$-CO$_2$H)AQ-Aib-AFI-(D-Glu)-YLIAGGPSSGAPPPS-NH$_2$ | 358 | 4820.4 | N/I |
| 344 | Y-Aib-EGTFTSDYSI-αMeL-LDEK((2-[2-(2-Amino-ethoxy)-ethoxy]-acetyl)$_2$-(γ-Glu)-CO-(CH$_2$)$_{18}$-CO$_2$H)AQ-Aib-DFIEYLIAGGPSSGAPPPS-NH$_2$ | 359 | 4864.4 | N/I |

| Example | Compound Name | SEQ ID NO | Calculated MW (average) | Found MW (average) |
|---|---|---|---|---|
| 345 | (D-Tyr)-Aib-EGT-αMeF-TSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-EFIEYLIAGGPSSGAPPPS-NH$_2$ | 360 | 4891.6 | N/I |
| 346 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 361 | 4805.5 | 4804.8 |
| 347 | (D-Tyr)-Aib-EGTFTSDYSI-αMeL-LD-Dab-K((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 362 | 4791.4 | N/I |
| 348 | (D-Tyr)-Aib-EGTFTSDYSI-αMeL-LD-Dap-K((2-[2-(2-Amino-ethoxy)-ethoxy]-acetyl)$_2$-(γ-Glu)-CO-(CH$_2$)$_{18}$-CO$_2$H)AQ-Aib-AFIEYLIAGGPSSGAPPPS-NH$_2$ | 363 | 4807.5 | N/I |
| 349 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-EFIEYLIAGGPSSGAPPPS-NH$_2$ | 364 | 4863.5 | 4862.7 |
| 350 | (D-Tyr)-Aib-EGTFTSDYSI-αMeL-LD-Dab-K((2-[2-(2-Amino-ethoxy)-ethoxy]-acetyl)$_2$-(γ-Glu)-CO-(CH$_2$)$_{18}$-CO$_2$H)AQ-Aib-EFIEYLIAGGPSSGAPPPS-NH$_2$ | 365 | 4849.5 | N/I |
| 351 | (D-Tyr)-Aib-EGTFTSDYSI-αMeL-LD-Dap-K((2-[2-(2-Amino-ethoxy)-ethoxy]-acetyl)$_2$-(γ-Glu)-CO-(CH$_2$)$_{18}$-CO$_2$H)AQ-Aib-EFIEYLIAGGPSSGAPPPS-NH$_2$ | 366 | 4835.5 | N/I |
| 352 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFI-(D-Glu)-YLIAGGPSSGAPPPS-NH$_2$ | 367 | 4819.5 | N/I |
| 353 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-EFI-(D-Glu)-YLIEGGPSSGAPPPS-NH$_2$ | 368 | 4935.6 | N/I |
| 354 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-EFI-(D-Glu)-YLIAGGPSSGAPPPS-NH$_2$ | 369 | 4863.5 | N/I |
| 355 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-EFI-(D-Glu)-YLIEGGPSSGAPPPS-NH$_2$ | 370 | 4921.5 | N/I |
| 356 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFI-(D-Glu)-YLIEGGPSSGAPPPS-NH$_2$ | 371 | 4877.5 | N/I |
| 357 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-AFI-(D-Glu)-YLIEGGPSSGAPPPS-NH$_2$ | 372 | 4863.5 | N/I |
| 358 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-AFVEYLIAGGPSSGAPPPS-NH$_2$ | 373 | 4791.4 | N/I |
| 359 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-EFVEYLIAGGPSSGAPPPS-NH$_2$ | 374 | 4849.5 | N/I |
| 360 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-AFVEYLIEGGPSSGAPPPS-NH$_2$ | 375 | 4849.5 | N/I |
| 361 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFV-(D-Glu)-YLIAGGPSSGAPPPS-NH$_2$ | 376 | 4805.5 | N/I |
| 362 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-AFV-(D-Glu)-YLIAGGPSSGAPPPS-NH$_2$ | 377 | 4791.4 | N/I |
| 363 | (D-Tyr)-Aib-EGTFTSDYSI-αMeL-LD-Orn-K((2-[2-(2-Amino-ethoxy)-ethoxy]-acetyl)$_2$-(D-(γ-Glu)-CO-(CH$_2$)$_{16}$-CO$_2$H)AQ-Aib-AFI-Glu)-YLIAGGPSSGAPPPS-NH$_2$ | 378 | 4777.4 | N/I |
| 364 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{16}$-CO$_2$H)AQ-Aib-AFV-(D-Glu)-YLIAGGPSSGAPPPS-NH$_2$ | 379 | 4763.4 | N/I |
| 365 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-AFIE-αMeY-LIAGGPSSGAPPPS-NH$_2$ | 380 | 4833.5 | 4832.4 |
| 366 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-AFIE-αMeY-LIAGGPSSGAPPPS-NH$_2$ | 381 | 4819.5 | 4818.3 |
| 367 | Y-Aib-EGTFTSDYSI-αMeL-LDKK((2[2-(2-Amino-ethoxy)-ethoxy]-acetyl)$_2$-(γ-Glu)-CO-(CH$_2$)$_{18}$-CO$_2$H)AQ-Aib-EFIE-αMeY-LIAGGPSSGAPPPS-NH$_2$ | 382 | 4891.6 | N/I |
| 368 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{16}$-CO$_2$H)AQ-Aib-EFIEYLIAGGPSSGAPPPS-NH$_2$ | 383 | 4835.5 | N/I |
| 369 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-DFIEYLIAGGPSSGAPPPS-NH$_2$ | 384 | 4849.5 | N/I |
| 370 | (D-Tyr)-Aib-EGTFTSDYSI-αMeL-LD-Orn-K((2-[2-(2-Amino-ethoxy)-ethoxy]-acetyl)$_2$-(c-Glu)-CO-(CH$_2$)$_{18}$-CO$_2$H)AQ-Aib-EFIEYLIAGGPSSG-NH$_2$ | 385 | 4414.0 | N/I |
| 371 | (D-Tyr)-Aib-EGTFTSDYSI-αMeL-LD-Orn-K((2-[2-(2-Amino-ethoxy)-ethoxy]-acetyl)-(γ-Glu)-CO-(CH$_2$)$_{18}$-CO$_2$H)AQ-Aib-EFIEYLIAGGPSSGAPPPS-NH$_2$ | 386 | 4718.3 | N/I |
| 372 | (D-Tyr)-Aib-EGTFTSDYSI-αMeL-LDKK((2-[2-(2-Amino-ethoxy)-ethoxy]-acetyl)-(γ-Glu)-CO-(CH$_2$)$_{18}$-CO$_2$H)AQ-Aib-EFIE-αMeY-LIAGGPSSGAPPPS-NH$_2$ | 387 | 4746.4 | N/I |
| 373 | (D-Tyr)-Aib-EGTFTSDYSI-αMeL-LDKK((2-[2-(2-Amino-ethoxy)-ethoxy]-acetyl)-(γ-Glu)-CO-(CH$_2$)$_{18}$-CO$_2$H)AQ-Aib-AFIE-αMeY-LIAGGPSSGAPPPS-NH$_2$ | 388 | 4688.3 | N/I |

-continued

| Example | Compound Name | SEQ ID NO | Calculated MW (average) | Found MW (average) |
|---|---|---|---|---|
| 374 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{16}$-CO$_2$H)AQ-Aib-EFIE-αMeY-LIAGGPSSGAPPPS-NH$_2$ | 389 | 4863.5 | N/I |
| 375 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{16}$-CO$_2$H)AQ-Aib-EFIE-αMeY-LIAGGPSSGAPPPS-NH$_2$ | 390 | 4849.5 | N/I |
| 376 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{16}$-CO$_2$H)AQ-Aib-AFIE-αMeY-LIAGGPSSGAPPPS-NH$_2$ | 391 | 4805.5 | N/I |
| 377 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{16}$-CO$_2$H)AQ-Aib-AFIE-αMeY-LIAGGPSSGAPPPS-NH$_2$ | 392 | 4791.4 | 4790.7 |
| 378 | (D-Tyr)-Aib-EGTFTSDYSI-αMeL-LDKK((2-[2-(2-Amino-ethoxy)-ethoxy]-acetyl)-(γ-Glu)-CO-(CH$_2$)$_{18}$-CO$_2$H)AQ-Aib-EFIEYLIAGGPSSGAPPPS-NH$_2$ | 393 | 4732.4 | N/I |
| 379 | (D-Tyr)-Aib-EGTFTSDYSI-αMeL-LDKK((2-[2-(2-Amino-ethoxy)-ethoxy]-acetyl)$_2$-(γ-Glu)-CO-(CH$_2$)$_{18}$-CO$_2$H)AQ-Aib-EFIE-αMeY-LIEGGPSSGAPPPS-NH$_2$ | 394 | 4949.5 | N/I |
| 380 | (D-Tyr)-Aib-EGTFTSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-EFIE-αMeY-LIEGGPSSGAPPPS-NH$_2$ | 395 | 4935.5 | N/I |
| 381 | (D-Tyr)-Aib-EGTFTSDYSI-αMeL-LDEK((2-[2-(2-Amino-ethoxy)-ethoxy]-acetyl)$_2$-(γ-Glu)-CO-(CH$_2$)$_{18}$-CO$_2$H)AQ-Aib-AFIE-αMeY-LIAGGPSSGAPPPS-NH$_2$ | 396 | 4934.4 | N/I |

N/I means Not Included

Binding Assays

Glucagon (referred to as Gcg) is a Reference Standard prepared at Eli Lilly and Company. GLP-1, 7-36-NH$_2$ (referred to as GLP-1) is obtained from CPC Scientific (Sunnyvale, Calif., 97.2% purity, 100 µM aliquots in 100% DMSO). GIP 1-42 (referred to as GIP) is prepared at Lilly Research Laboratories using peptide synthesis and HPLC chromatography as described above (>80% purity, 100 µM aliquots in 100% DMSO). [$^{125}$I]-radiolabeled Gcg, GLP-1, or GIP is prepared using [$^{125}$I]-lactoperoxidase and obtained from Perkin Elmer (Boston, Mass.).

Stably transfected cell lines are prepared by subcloning receptor cDNA into a pcDNA3 expression plasmid and transfected into human embryonic kidney (HEK) 293 (hGcgR and hGLP-1R) or Chinese Hamster Ovary (CHO) (hGIPR) cells followed by selection with Geneticin (hGLP-1R and hGIPR) or hygromycin B (hGcgR).

Two methods are used for the preparation of crude cell membranes.

Method 1:

Frozen cell pellets are lysed on ice in hypotonic buffer containing 50 mM Tris HCl, pH 7.5, and Roche Complete™ Protease Inhibitors with EDTA. The cell suspension is disrupted using a glass Potter-Elvehjem homogenizer fitted with a Teflon® pestle for 25 strokes. The homogenate is centrifuged at 4° C. at 1100×g for 10 minutes. The supernatant is collected and stored on ice while the pellets are resuspended in homogenization buffer and rehomogenized as described above. The homogenate is centrifuged at 1100×g for 10 minutes. The second supernatant is combined with the first supernatant and centrifuged at 35000×g for 1 hour at 4° C. The resulting membrane pellet is resuspended in homogenization buffer containing protease inhibitors at approximately 1 to 3 mg/mL, quick frozen in liquid nitrogen and stored as aliquots in a −80° C. freezer until use.

Method 2:

Frozen cell pellets are lysed on ice in hypotonic buffer containing 50 mM Tris HCl, pH 7.5, 1 mM MgCl$_2$, Roche Complete™ EDTA-free Protease Inhibitors and 25 units/ml DNAse I (Invitrogen). The cell suspension is disrupted using a glass Potter-Elvehjem homogenizer fitted with a Teflon® pestle for 20 to 25 strokes. The homogenate is centrifuged at 4° C. at 1800×g for 15 minutes. The supernatant is collected and stored on ice while the pellets are resuspended in homogenization buffer (without DNAse I) and rehomogenized as described above. The homogenate is centrifuged at 1800×g for 15 minutes. The second supernatant is combined with the first supernatant and centrifuged an additional time at 1800×g for 15 minutes. The overall supernatant is then centrifuged at 25000×g for 30 minutes at 4° C. The resulting membrane pellet is resuspended in homogenization buffer (without DNAse I) containing protease inhibitors at approximately 1 to 3 mg/mL and stored as aliquots in a −80° C. freezer until use.

Binding Determination Methods

The equilibrium binding dissociation constants ($K_d$) for the various receptor/radioligand interactions are determined from homologous competition binding analysis instead of saturation binding due to high propanol content in the [$^{125}$I] stock material. The $K_d$ values determined for the receptor preparations were as follows: hGcgR (3.9 nM), hGLP-1R (1.2 nM) and hGIPR (0.14 nM).

[$^{125}$I]-Glucagon Binding

The human Gcg receptor binding assays are performed using a Scintillation Proximity Assay (SPA) format with wheat germ agglutinin (WGA) beads (Perkin Elmer). The binding buffer contains 25 mM 4-(2-hydroxyethyl)-1-piperazineethanesulfonic acid (HEPES), pH 7.4, 2.5 mM CaCl$_2$, 1 mM MgCl$_2$, 0.1% (w/v) bacitracin (Research Products), 0.003% (w/v) Polyoxyethylenesorbitan monolaurate (TWEEN®-20), and Roche Complete™ Protease Inhibitors without EDTA. Peptides and Gcg are thawed and 3-fold serially diluted in 100%/DMSO (10 point concentration response curves). Next, 5 µL serially diluted compound or DMSO is transferred into Corning® 3632 clear bottom assay plates containing 45 µL assay binding buffer or unlabeled Gcg control (non-specific binding or NSB, at 1 µM final). Then, 50 µL [$^{125}$I]-Gcg (0.15 nM final), 50 µL human GcgR membranes (1.5 µg/well) and 50 µL of WGA SPA beads (80 to 150 µg/well) are added with a Biotek Multiflo dispenser. Plates are sealed and mixed on a plate shaker (setting 6) for 1 minute and read with a PerkinElmer Trilux MicroBeta® scintillation counter after 12 hours of incubation/settling time at room temperature. Final assay concentration ranges for peptides tested in response curves is typically 1150 nM to 0.058 nM and for the control Gcg from 1000 nM to 0.05 nM.

[$^{125}$I]-GLP-1 Binding

The human GLP-1 receptor binding assay is performed using an SPA format with WGA beads. The binding buffer contains 25 mM HEPES, pH 7.4, 2.5 mM CaCl$_2$, 1 mM MgCl$_2$, 0.1% (w/v) bacitracin, 0.003% (w/v) TWEEN®-20, and Roche Complete™ Protease Inhibitors without EDTA.

Peptides and GLP-1 are thawed and 3-fold serially diluted in 100% DMSO (10 point concentration response curves). Next, 5 μL serially diluted compound or DMSO is transferred into Corning® 3632 clear bottom assay plates containing 45 μL assay binding buffer or unlabeled GLP-1 control (non-specific binding or NSB, at 0.25 μM final). Then, 50 μL [$^{125}$I]-GLP-1 (0.15 nM final), 50 μL human GLP-1R membranes (0.5 μg/well and 50 μL of WGA SPA beads (100 to 150 μg/well) are added with a Biotek Multiflo dispenser. Plates are sealed and mixed on a plate shaker (setting 6) for 1 minute and read with a PerkinElmer Trilux MicroBeta® scintillation counter after 5 to 12 hours of incubation/settling time at room temperature. Final assay concentration ranges for peptides tested in response curves are typically 1150 nM to 0.058 nM and for the control GLP-1, 250 nM to 0.013 nM.

[125I]-GIP Binding

The human GIP receptor binding assay is performed using an SPA format with WGA beads. The binding buffer contains 25 mM HEPES, pH 7.4, 2.5 mM CaCl$_2$, 1 mM MgCl$_2$, 0.1% (w/v) bacitracin, 0.003% (w/v) TWEEN®-20, and Roche Complete™ Protease Inhibitors without EDTA. Peptides and GIP are thawed and 3 fold serially diluted in 100% DMSO (10 point concentration response curves). Next, 5 μL serially diluted compound or DMSO is transferred into Corning® 3632 clear bottom assay plates containing 45 μL assay binding buffer or unlabeled GIP control (non-specific binding or NSB, at 0.25 μM final). Then, 50 μL [$^{125}$I]-GIP (0.075-0.15 nM final), 50 μL human GIPR membranes (3 μg/well) and 50 μL of WGA SPA beads (100 to 150 μg/well) are added with a Biotek Multiflo dispenser. Plates are sealed and mixed on a plate shaker (setting 6) for 1 minute and read with a PerkinElmer Trilux MicroBeta® scintillation counter after 2.5 to 12 hours of incubation/settling time at room temperature. Final assay concentration ranges for peptides tested in response curves is typically 1150 to 0.058 nM or 115 nM to 0.0058 nM and for the control GIP, 250 nM to 0.013 nM.

Binding Assay Data Analysis

Raw CPM data for concentration curves of peptides, Gcg, GLP-1, or GIP are converted to percent inhibition by subtracting nonspecific binding (binding in the presence of excess unlabeled Gcg, GLP-1, or GIP, respectively) from the individual CPM values and dividing by the total binding signal, also corrected by subtracting nonspecific binding. Data are analyzed using four-parameter (curve maximum, curve minimum, IC$_{50}$, Hill slope) nonlinear regression routines (Genedata Screener, version 12.0.4, Genedata AG, Basal, Switzerland). The affinity constant (K$_i$) is calculated from the absolute IC$_{50}$ value based upon the equation K$_i$=IC$_{50}$/(1+D/K$_d$) where D is the concentration of radioligand used in the experiment, IC$_{50}$ is the concentration causing 50% inhibition of binding and K$_d$ is the equilibrium binding dissociation constant of the radioligand (described above). Values for K$_i$ are reported as the geometric mean, with error expressed as the standard error of the mean (SEM) and n is equal to the number of independent replicates (determined in assays performed on different days). Geometric Means are calculated as follows:

$$\text{Geometric Mean} = 10^{(\text{Arithmetic Mean of Log Ki Values})}$$

The Ki Ratio (Ki for native control peptide/Ki for test compound) at each receptor and each species is calculated. The Ki Ratio is a rapid indication of the apparent affinity of a peptide compared to the native control peptide. A Ki Ratio <1 indicates that the test peptide has a lower affinity (higher Ki value) for the receptor than the native peptide, whereas a Ki Ratio >1 indicates that the test peptide has a higher affinity (lower Ki value) for the receptor than the native peptide.

n=1/x means that only one value out of the total number of replicates (x) is used to express the mean. SEM is only calculated when n=2 or greater non-qualified results exist. Means are expressed as GeoMetric means with the standard error of the mean (SEM) and the number of replicates (n) indicated in parenthesis.

TABLE 1

In vitro Binding Affinity (K$_i$) of indicated Examples and comparator molecules for human GLP-1R, GcgR and GIPR.

| Example or comparator | hGLcgR Ki, nM (SEM, n) | hGIPR Ki, nM (SEM, n) | hGLP1R Ki, (nM) (SEM, n) |
|---|---|---|---|
| hGcg | 3.65 (0.26, n = 10) | | |
| hGIP amide | | 0.0922 (0.0085, n = 11) | |
| hGLP-1 amide | | | 0.614 (0.066, n = 12) |
| 1 | 207 (13.8, n = 5) | 0.0546 (0.0120, n = 5) | 6.67 (1.25, n = 6) |
| 2 | 361 (55.1, n = 5) | 0.0600 (0.0150, n = 5) | 2.35 (0.220, n = 5) |
| 3 | 242 (56.2, n = 6) | 0.0458 (0.00357, n = 6) | 2.23 (0.366, n = 6) |
| 4 | 686 (n = ⅕) | 0.0528 (0.00647, n = 5) | 1.63 (0.260, n = 5) |
| 5 | 519 (109, n = 4) | 0.0611 (0.00592, n = 4) | 0.902 (0.114, n = 4) |
| 6 | 55.8 (10.2, n = 2) | 0.0835 (0.00437, n = 2) | 6.71 (1.25, n = 2) |
| 7 | 198 | 0.252 | 43.3 |
| 8 | 206 (25.7, n = 2) | 0.0772 (0.0155, n = 2) | 2.84 (0.753, n = 2) |
| 9 | 375 (87.5, n = 2) | 0.127 (0.0118, n = 2) | 14.9 (2.15, n = 2) |
| 10 | 226 (67.4, n = 2) | 0.109 (0.0927, n = 2) | 9.33 (1.49, n = 2) |
| 11 | 174 (25.3, n = 2) | 0.226 (0.0728, n = 2) | 15.7 (4.37, n = 2) |
| 12 | 684 (141, n = 2) | 0.167 (0.0853, n = 2) | 12.9 (2.71, n = 2) |
| 13 | >1060 (n = ½) | 0.296 (0.0291, n = 2) | 31.1 (11.9, n = 2) |
| 14 | 160 | 0.0494 | 29.6 |
| 15 | 130 | 0.284 | 2.19 |
| 16 | 371 | 0.0841 | 2.78 |
| 17 | 261 (115, n = 2) | 0.606 (0.363, n = 2) | 7.63 (2.47, n = 2) |
| 18 | 50.1 | 0.0798 | 0.319 |
| 19 | 60.5 | 0.0518 | 0.24 |
| 20 | 228 (65.3, n = 2) | 0.0849 (0.0168, n = 2) | 3.30 (1.01, n = 2) |
| 21 | 149 | 0.529 | 14.5 |
| 22 | 53.4 | 0.624 | 23.1 |
| 23 | >1010 | 0.258 | 6.32 |
| 24 | 49.8 | 0.232 | 5.04 |
| 25 | 81.1 | 0.179 | 4.8 |
| 26 | >960 | 0.176 | 4.22 |
| 27 | 315 | 0.103 | 3.68 |
| 28 | >902 | 0.24 | 21.1 |
| 29 | 132 | 0.377 | 8 |
| 30 | 123 | 0.151 | 6.2 |
| 31 | 290 | 0.0275 | 6.58 |
| 32 | 44.7 | 0.0205 | 3.96 |
| 33 | >979 | 6.4 | 361 |
| 34 | 134 | 0.0467 | 3.41 |
| 35 | >964 | 0.0358 | 54.6 |
| 36 | 413 | 0.141 | 16.4 |
| 37 | 255 | 0.0523 | 3.84 |
| 38 | >974 | 0.104 | 31.3 |
| 39 | 161 | 0.0499 | 16.8 |
| 40 | 150 | 0.0345 | 7.56 |
| 41 | 165 | 0.0551 | 13.4 |

TABLE 1-continued

In vitro Binding Affinity ($K_i$) of indicated Examples and comparator molecules for human GLP-1R, GcgR and GIPR.

| Example or comparator | hGLcgR Ki, nM (SEM, n) | hGIPR Ki, nM (SEM, n) | hGLP1R Ki, (nM) (SEM, n) |
|---|---|---|---|
| 42 | 160 | 0.0514 | 13.2 |
| 43 | 134 | 0.101 | 11.8 |
| 44 | 121 | 0.0516 | 10.6 |
| 45 | 11.1 | 0.0463 | 5.65 |
| 46 | 133 | 0.0852 | 13.4 |
| 48 | 111 | 0.074 | 15.7 |
| 49 | 236 | 0.087 | 12.3 |
| 50 | 220 (61.2, n = 2) | 0.0568 (0.00744, n = 2) | 4.71 (1.22, n = 2) |
| 51 | 195 (65.9, n = 2) | 0.0620 (0.0131, n = 2) | 5.62 (0.658, n = 2) |
| 52 | >1100 | 0.0342 | 5.81 |
| 53 | 216 | 0.188 | 1.23 |
| 54 | 333 | 0.965 | 1.66 |
| 55 | >1100 | 6.24 | 7.29 |
| 56 | >1060 | 0.148 | 10.3 |
| 57 | 26.1 (4.31, n = 2) | 0.0583 (0.0131, n = 2) | 3.00 (0.293, n = 2) |
| 58 | 339 | 0.105 | 2.77 |
| 59 | 292 (11.8, n = 2) | 0.136 (0.00422, n = 2) | 8.20 (4.13, n = 2) |
| 60 | 237 | 0.0655 | 9.55 |
| 61 | 110 | 0.102 | 11.1 |
| 62 | 168 | 0.0545 | 2.03 |
| 63 | 273 | 0.141 | 7.79 |
| 64 | 260 | 0.0866 | 4.86 |
| 65 | 194 | 0.0643 | 4.53 |
| 66 | 93.7 | 0.106 | 7.53 |
| 67 | 270 | 0.061 | 10.2 |
| 68 | 99.2 | 0.0243 | 1.58 |
| 69 | 22.1 (4.18, n = 3) | 0.0300 (0.00657, n = 3) | 1.22 (0.353, n = 3) |
| 74 | 69.8 | 0.0279 | 5.99 |
| 75 | 283 | 0.103 | 24.4 |
| 76 | 14.4 | 0.0659 | 2.64 |
| 78 | 215 (66.2, n = 3) | 0.163 (0.0356, n = 2) | 3.94 (1.21, n = 2) |
| 79 | 429 (n = ½) | 0.0313 | 2.69 |
| 80 | 347 (n = ½) | 0.0931 | 2.16 |
| 81 | 344 | 0.198 | 2.88 |
| 82 | >1060 | 14.9 | 6.82 |
| 83 | 320 | 0.142 | 7.1 |
| 84 | >1100 | 0.143 | 10.2 |
| 85 | >894 (n = ½) | 0.621 | 1.87 |
| 86 | >1060 | 0.0401 | 3.74 |
| 87 | 278 (n = ½) | 0.0340 (0.00150, n = 2) | 1.79 (0.417, n = 2) |
| 88 | 545 (57.8, n = 2) | 0.0717 | 4.24 |
| 89 | 324 (22.9, n = 2) | 0.045 | 2.64 |
| 90 | 245 (7.55, n = 2) | 0.0472 | 4.76 |
| 91 | 540 | 1.8 | 5.23 |
| 93 | 15.7 | 0.0859 | 1.89 |
| 99 | 23.6 | 0.027 | 1.15 |
| 100 | 44 | 0.115 | 4.13 |
| 101 | 117 | 0.0953 | 8.1 |
| 103 | 40.3 | 0.0645 | 6.68 |
| 104 | 123 (17.1, n = 5) | 0.0565 (0.0153, n = 5) | 3.91 (0.955, n = 5) |
| 105 | 20.4 | 0.119 | 0.871 |
| 106 | 515 | 0.179 | 1.2 |
| 107 | 303 | 0.0425 | 0.867 |
| 108 | 171 | 0.0732 | 3 |
| 109 | 43.1 | 0.0279 | 1.34 |
| 110 | 73.9 | 0.0395 | 4.38 |
| 115 | 9.89 | 0.0302 | 3.43 |
| 116 | 137 (13.9, n = 2) | 0.0597 (0.0486, n = 2) | 6.80 (1.85, n = 2) |
| 117 | 192 (14.6, n = 3) | 0.0497 (0.0111, n = 3) | 6.96 (1.95, n = 3) |
| 118 | 53.0 (7.07, n = 3) | 0.0859 (0.00402, n = 3) | 6.10 (0.870, n = 3) |
| 119 | 30.6 | 0.0925 | 9.87 |
| 120 | 93.6 | 0.11 | 11.7 |
| 121 | 51.9 | 0.177 | 3.16 |
| 122 | 43.3 (8.07, n = 2) | 0.190 (0.0189, n = 2) | 3.36 (0.799, n = 2) |
| 123 | 80.1 (11.7, n = 6) | 0.0469 (0.00804, n = 6) | 1.31 (0.197, n = 6) |
| 124 | 41.5 (9.39, n = 2) | 0.0424 (0.00200, n = 2) | 4.87 (0.277, n = 2) |
| 125 | 54.4 (0.365, n = 2) | 0.0624 (0.0117, n = 2) | 3.19 (0.123, n = 2) |
| 126 | 101 (11.5, n = 2) | 0.0644 (0.0267, n = 2) | 1.46 (0.299, n = 2) |
| 127 | 43.6 | 0.126 | 1.86 |
| 128 | 433 (203, n = 2) | 0.0625 (0.0355, n = 2) | 1.88 (0.296, n = 2) |
| 129 | 14.9 | 0.0278 | 1 |
| 130 | >1060 | 0.177 | 3.66 |
| 133 | 216 | 0.157 | 11.4 (2.31, n = 2) |
| 134 | 60.5 | 0.14 | 12.7 (0.947, n = 2) |
| 135 | 454 | 0.161 | 3.01 |
| 137 | 98.1 (14.8, n = 3) | 0.0373 (0.00200, n = 3) | 1.24 (0.341, n = 3) |
| 138 | 61.2 (4.65, n = 2) | 0.0295 (0.00145, n = 2) | 0.926 (0.201, n = 2) |
| 139 | 105 (6.68, n = 2) | 0.0360 (0.00446, n = 2) | 1.25 (0.0904, n = 2) |
| 140 | 175 (40.1, n = 3) | 0.0474 (0.00461, n = 3) | 1.46 (0.0630, n = 3) |
| 142 | 53.1 (1.60, n = 2) | 0.0275 (0.00210, n = 2) | 1.06 (0.300, n = 2) |
| 143 | 65.5 | 0.0304 | 1.15 |
| 144 | 77 | 0.0341 | 1.78 |
| 145 | 158 | 0.0652 | 2.22 |
| 147 | 64.9 (19.9, n = 2) | 0.0981 (0.0285, n = 2) | 4.47 (0.742, n = 2) |
| 149 | 127 | 0.0708 | 26.1 |
| 150 | 63.2 | 0.0649 | 30.5 |
| 152 | 93.4 | 0.117 | 48 |
| 153 | 43.8 | 0.0578 | 22.2 |
| 154 | 762 (51.7, n = 3) | 0.0610 (0.00457, n = 3) | 5.64 (2.52, n = 3) |
| 157 | 179 (82.9, n = 3) | 0.0937 (0.0160, n = 3) | 8.97 (2.28, n = 3) |
| 158 | 285 (17.4, n = 2) | 0.114 (0.0193, n = 2) | 11.8 (5.32, n = 2) |
| 160 | >1060 (n = ½) | 5.98 (1.46, n = 2) | 14.4 (3.72, n = 2) |
| 163 | 117 | 0.116 | 10.8 |
| 181 | 413 (132, n = 2) | 0.145 (0.0856, n = 2) | 7.28 (0.798, n = 2) |
| 182 | 565 (335, n = 2) | 0.0669 (0.0311, n = 2) | 4.64 (0.655, n = 2) |
| 183 | 304 (128, n = 2) | 0.0869 (0.0118, n = 2) | 4.11 (0.369, n = 2) |
| 189 | 146 (7.81, n = 2) | 0.128 (0.0817, n = 2) | 8.81 (0.434, n = 2) |
| 191 | 348 (54.7, n = 2) | 0.144 (0.0676, n = 2) | 4.52 (1.95, n = 2) |
| 192 | >1110 (n = ½) | 0.118 (0.108, n = 2) | 2.89 (0.516, n = 2) |
| 202 | 394 | 0.0579 | 5.38 |
| 203 | 845 (n = ½) | 0.0337 (0.00260, n = 2) | 3.90 (1.10, n = 2) |
| 204 | >1150 | 0.0704 | 1.9 |
| 205 | 438 | 0.0367 | 3.05 |
| 206 | 176 (126, n = 2) | 0.0814 (0.00608, n = 2) | 5.27 (0.359, n = 2) |
| 207 | 74.2 | 0.0786 | 1.37 |

TABLE 1-continued

In vitro Binding Affinity ($K_i$) of indicated Examples and comparator molecules for human GLP-1R, GcgR and GIPR.

| Example or comparator | hGLcgR Ki, nM (SEM, n) | hGIPR Ki, nM (SEM, n) | hGLP1R Ki, (nM) (SEM, n) |
|---|---|---|---|
| 208 | >1060 | 0.0537 | 2.13 |
| 209 | >1060 (n = ½) | 0.0664 (0.0267, n = 2) | 1.43 (0.466, n = 2) |
| 210 | >1010 | 0.0399 | 1.58 |
| 211 | 131 | 0.0243 | 2.64 |
| 212 | 205 (1.77, n = 2) | 0.0978 (0.0730, n = 2) | 2.76 (0.561, n = 2) |
| 213 | 544 | 0.365 | 2.75 |
| 214 | 126 | 0.0304 | 1.99 |
| 215 | 75.2 | 0.0666 | 6.85 |
| 216 | 45.2 | 0.0559 | 2.34 |
| 217 | 516 | 0.0376 | 2.02 |
| 218 | 270 | 0.0593 | 2.54 |
| 219 | 373 | 0.0689 | 2.01 |
| 220 | 377 | 0.0919 | 2.71 |
| 221 | 154 (n = ½) | 0.0414 (0.00291, n = 2) | 1.77 (0.900, n = 2) |
| 222 | 71.3 (11.9, n = 2) | 0.0495 (0.0210, n = 2) | 3.59 (0.660, n = 2) |
| 223 | 46.5 | 0.0921 | 5.62 |
| 224 | 627 (267, n = 2) | 0.0482 (0.0174, n = 2) | 6.86 (1.85, n = 2) |
| 225 | 714 (n = ½) | 0.0622 (0.0208, n = 2) | 8.79 (4.24, n = 2) |
| 226 | 200 | 0.0254 | 4.1 |
| 227 | 113 | 0.0146 | 2.01 |
| 228 | 182 | 0.028 | 2.43 |
| 229 | >1100 | 2.47 | 36.2 |
| 230 | 494 | 0.042 | 4.68 |
| 231 | 440 | 0.0394 | 3.03 |
| 232 | >1150 | 0.0544 | 5.62 |
| 233 | >1150 | 0.0445 | 5.99 |
| 234 | >1100 | 0.0563 | 10.9 |
| 235 | >1200 | 0.0581 | 7.65 |
| 236 | 200 (15.1, n = 2) | 0.0425 (0.00194, n = 2) | 1.05 (0.173, n = 2) |
| 237 | >1060 | 0.131 | 1.04 |
| 238 | 230 | 0.0403 | 0.548 |
| 239 | 596 (215, n = 3) | 0.101 (0.0172, n = 3) | 2.71 (0.0420, n = 3) |
| 240 | 204 | 0.0284 | 0.552 |
| 241 | 167 (45.6, n = 2) | 0.0420 (0.0118, n = 2) | 0.799 (0.401, n = 2) |
| 242 | 95.9 (14.1, n = 2) | 0.0604 (0.00642, n = 2) | 0.853 (0.0475, n = 2) |
| 243 | 145 (5.05, n = 2) | 0.0325 (0.00840, n = 2) | 0.670 (0.0478, n = 2) |
| 244 | 87.8 (2.39, n = 2) | 0.0308 (0.0150, n = 2) | 0.820 (0.141, n = 2) |
| 246 | >1010 (n = ⅓) | 0.0509 (0.0147, n = 3) | 0.812 (0.0900, n = 3) |
| 247 | >1100 | >55.1 | 4.39 |
| 248 | >1050 | 0.0397 | 2.4 |
| 249 | >1000 | 0.0394 | 2.35 |
| 250 | 198 | 0.0171 | 1.72 |
| 251 | 21.2 | 0.0249 | 1.09 |
| 252 | 26 | 0.00971 | 0.383 |
| 253 | >912 | 0.138 | 2.57 |
| 254 | 148 | 0.108 | 2.58 |
| 255 | 257 | 0.0772 | 2.58 |
| 264 | 388 | 0.015 | 0.412 |
| 265 | 567 | 0.0224 | 0.537 |
| 266 | 193 (28.2, n = 2) | 0.0666 (0.0189, n = 2) | 2.01 (0.256, n = 2) |
| 267 | 349 (178, n = 2) | 0.0628 (0.00765, n = 2) | 1.57 (0.109, n = 2) |
| 268 | >1190 | 0.0814 | 3.98 |
| 269 | >1100 | 0.152 | 7.1 |
| 270 | >1190 | 0.117 | 8.27 |
| 271 | >1150 | 0.107 | 5.09 |
| 272 | 550 (243, n = 2) | 0.0353 (0.00276, n = 2) | 1.22 (0.291, n = 2) |
| 273 | 724 | 0.0698 | 1.13 |
| 288 | 345 | 0.0580 | 1.60 |
| | (35.7, n = 3) | (0.0105, n = 3) | (0.866, n = 3) |
| 289 | >1050 (n = ⅓) | 0.0457 (0.0220, n = 3) | 2.63 (1.74, n = 3) |
| 290 | 308 (n = ⅓) | 0.0617 (0.0115, n = 3) | 2.44 (0.162, n = 3) |
| 291 | >872 (n = ½) | 0.129 (0.0346, n = 3) | 3.16 (0.270, n = 3) |
| 292 | 595 | 0.0547 | 1.19 |
| 293 | 668 | 0.0775 | 1.64 |
| 294 | 629 | 0.205 | 2.92 |
| 295 | >1000 | 0.181 | 4.12 |
| 296 | >1000 | 0.444 | 3.33 |
| 297 | >1240 | 0.0958 | 2.98 |
| 298 | >1370 | 0.0578 | 3.03 |
| 299 | >1040 | 0.734 | 54.3 |
| 300 | 251 | 0.0504 | 2.13 |
| 301 | 44.4 (6.17, n = 3) | 0.0273 (0.00127, n = 3) | 0.875 (0.0889, n = 3) |
| 302 | 18.5 | 0.0289 | 0.617 |
| 303 | 502 (189, n = 3) | 0.0580 (0.0151, n = 3) | 3.69 (1.86, n = 3) |
| 304 | >855 | 0.0499 | 4.44 |
| 305 | 352 (30.8, n = 2) | 0.0250 (0.00586, n = 2) | 0.830 (0.481, n = 2) |
| 306 | >1040 | 0.0349 | 2.86 |
| 307 | 117 | 0.0773 | 5.1 |
| 308 | 94.2 | 0.0288 | 1.01 |
| 309 | 64.1 | 0.0264 | 1.04 |
| 310 | 174 (8.97, n = 2) | 0.0315 (0.00162, n = 2) | 1.70 (0.144, n = 2) |
| 311 | 115 | 0.0497 | 11.5 |
| 312 | 106 | 0.0348 | 1.63 |
| 313 | 27.6 | 0.0261 | 0.815 |
| 314 | 116 | 0.027 | 0.717 |
| 315 | 539 | 0.0677 | 2.28 |
| 316 | 654 (76.5, n = 3) | 0.0418 (0.00224, n = 3) | 0.957 (0.180, n = 3) |
| 317 | 253 | 0.0215 | 2.63 |
| 318 | 730 (n = ½) | 0.0452 (0.00883, n = 2) | 7.52 (0.256, n = 2) |
| 319 | >984 | 0.0349 | 3.61 |
| 320 | >1040 | 0.136 | 5.17 |
| 321 | 770 | 0.064 | 4.2 |
| 322 | 1030 | 0.175 | 2.31 |
| 323 | 300 | 0.0516 | 1.65 |
| 324 | 449 | 0.0278 | 0.609 |
| 325 | 13 | 0.0209 | 0.475 |
| 326 | 207 | 0.251 | 2.92 |
| 327 | 114 (8.53, n = 2) | 0.0667 (0.0211, n = 2) | 2.10 (0.287, n = 2) |
| 328 | >1450 (n = ½) | 0.136 (0.0602, n = 2) | 3.98 (0.339, n = 2) |
| 329 | 17.0 (2.51, n = 2) | 0.0439 (0.0105, n = 2) | 3.28 (0.327, n = 2) |
| 330 | >1050 | 0.114 | 12.7 |
| 331 | >969 (n = ½) | 0.0851 (0.00508, n = 2) | 11.4 (0.160, n = 2) |
| 332 | 397 (272, n = 2) | 0.0497 (0.00681, n = 2) | 7.87 (0.333, n = 2) |
| 333 | 578 (68.8, n = 2) | 0.0634 (0.00255, n = 2) | 4.25 (0.180, n = 2) |
| 334 | 192 | 0.0646 | 2.17 |
| 335 | 27.1 | 0.0444 | 2.54 |
| 336 | 17.1 | 0.0277 | 2.44 |
| 337 | 335 | 0.0363 | 1.61 |
| 338 | >1060 | 0.0831 | 3.23 |
| 339 | 873 (19.4, n = 2) | 0.0388 (0.0198, n = 2) | 2.69 (0.218, n = 2) |
| 340 | 250 (60.8, n = 2) | 0.0507 (0.0177, n = 2) | 2.08 (0.0742, n = 2) |
| 341 | 39.7 | 0.0559 | 6.49 |
| 342 | >1000 | 0.129 | 15.4 |

TABLE 1-continued

In vitro Binding Affinity ($K_i$) of indicated Examples and comparator molecules for human GLP-1R, GcgR and GIPR.

| Example or comparator | hGLcgR Ki, nM (SEM, n) | hGIPR Ki, nM (SEM, n) | hGLP1R Ki, (nM) (SEM, n) |
|---|---|---|---|
| 343 | >1070 | 0.0374 | 13.3 |
| 344 | >1080 | 0.0507 | 14.8 |
| 346 | 310 (26.0, n = 3) | 0.0559 (0.0248, n = 2) | 1.67 (0.911, n = 2) |
| 349 | >1060 (n = ⅓) | 0.0800 (0.0215, n = 3) | 1.72 (0.0730, n = 3) |
| 352 | >1030 (n = ½) | 0.0726 (0.00687, n = 3) | 3.03 (0.673, n = 3) |
| 354 | >953 (n = ½) | 0.175 (0.0209, n = 2) | 7.85 (0.190, n = 2) |
| 356 | >1010 | 0.350 (0.0397, n = 2) | 10.3 (1.53, n = 2) |
| 357 | >977 | 0.316 (0.0233, n = 2) | 7.02 (1.19, n = 2) |
| 358 | 915 (n = ½) | 0.0636 (0.00684, n = 3) | 1.37 (0.189, n = 3) |
| 359 | >982 (n = ½) | 0.0874 (0.0159, n = 3) | 2.59 (0.833, n = 3) |
| 360 | 485 | 0.128 (0.00895, n = 2) | 1.74 (0.0269, n = 2) |
| 362 | >1050 | 0.337 (0.00484, n = 2) | 6.95 (0.446, n = 2) |
| 363 | >1020 (n = ½) | 0.170 (0.0113, n = 3) | 3.89 (0.864, n = 3) |
| 364 | >1150 (n = ½) | 0.672 (0.0431, n = 3) | 17.2 (2.26, n = 3) |
| 367 | 777 | 0.0282 | 0.809 |

Functional Activity (With BSA)

Functional activity is determined in hGLP-1R, hGcgR and hGIP-R expressing HEK-293 clonal cell lines. Each receptor over-expressing cell line is treated with peptide (20 point CRC, 2.75-fold Labcyte Echo direct dilution) in DMEM (Gibco Cat #31053) supplemented with 1× GlutaMAX™ supplement (L-alanyl-L-glutamine dipeptide Gibco®), 0.25% FBS (Fetal Bovine Serum), 0.05% fraction V BSA (Bovine Serum Albumin), 250 μM 3-isobutyl-1-methylxanthine (IBMX) and 20 mM 4-(2-hydroxyethyl)-1-piperazineethanesulfonic acid (HEPES) in a 20 μl assay volume.

After 60-minute incubation at room temperature, the resulting increase in intracellular cAMP is quantitatively determined using the CisBio cAMP Dynamic 2 homogeneous time-resolved fluorescence (HTRF) Assay Kit. The cAMP levels within the cell are detected by adding the cAMP-d2 conjugate in cell lysis buffer followed by the antibody anti-cAMP-Eu$^{3+}$-Cryptate, also in cell lysis buffer. The resulting competitive assay is incubated for at least 60 minutes at room temperature and then detected using an instrument with excitation at 320 nm and emission at 665 nm and 620 nm. Envision units (emission at 665 nm/620 nm*10,000) are inversely proportional to the amount of cAMP present and are converted to nM cAMP per well using a cAMP standard curve.

The amount of cAMP generated (nM) in each well is converted to a percent of the maximal response observed with either human GLP-1(7-36)NH$_2$, human Gcg, or human GIP(1-42)NH$_2$. A relative $EC_{50}$ value is derived by non-linear regression analysis using the percent maximal response vs. the concentration of peptide added, fitted to a four-parameter logistic equation.

$EC_{50}$ determination of human GLP-1(7-36)NH$_2$ at human GLP-1R, human Gcg at human GcgR, and human GIP(1-42)NH$_2$ at human GIP-R: the peptide concentration ranges were 448 pM to 99.5 nM. $EC_{50}$ determination of Examples at human GLP-1R, human GcgR, and human GIP-R: the peptide concentration ranges are 51.5 fM to 11.4 μM.

TABLE 2

Functional cAMP Potency ($EC_{50}$) for Example and comparator peptides (hGcg, hGIP amide, and hGLP-1 amide) in the presence of FBS.

| Example or comparator | cAMP $EC_{50}$, nM (SEM, n) | | |
|---|---|---|---|
| | GcgR | GIPR | GLP-1R |
| hGcg | 0.0125 ± 0.0011 (n = 12) | | |
| hGIP amide | | 0.0979 (0.0088, n = 12) | |
| hGLP-1 amide | | | 0.0424 (0.0043, n = 12) |
| Example 1 | >11400 (n = 1/9) | 38.5 (20.2, n = 12) | 53.3 (21.4, n = 12) |
| Example 2 | >10900 (n = 1/12) | 2.64 (0.696, n = 12) | 6.52 (1.76, n = 11) |
| Example 3 | >10900 (n = 1/7) | 9.24 (2.23, n = 7) | 19.4 (7.02, n = 7) |
| Example 4 | >10900 (n = 1/5) | 1.03 (0.181, n = 5) | 2.02 (0.596, n = 4) |
| Example 5 | >10900 | 1.98 | 1.61 | cAMP Pharmacological Functional Assay in Presence of Casein

An additional set of cAMP assays are conducted in HEK293 cells expressing the human GLP-1 receptor (GLP-1R), gastric inhibitory peptide receptor (GIPR), Glucagon receptor (GcgR). Pharmacological activity of the hGLP1R/GIPR peptides are determined in HEK293 cells stably expressing the human GLP-1 receptor (GLP-1R), gastric inhibitory peptide receptor (GIPR), or GLP-2 receptor (GLP-2R). Each receptor over-expressing cell line (20 μl) is treated with the test peptide in DMEM (Gibco Cat #31053) supplemented with 0.1% Casein (Sigma Cat #C4765), 250 μM IBMX, 1× GlutaMAX™ (Gibco Cat #35050), and 20 mM HEPES (HyClone Cat #SH30237.01) in a 20 μl assay volume. After 60 minute incubation at room temperature, the resulting increase in intracellular cAMP is quantitatively determined using the CisBio cAMP Dynamic 2 HTRF Assay Kit (62AM4PEJ). The Lysis buffer containing cAMP-d2 conjugate (20 μl) and the antibody anti-cAMP-Eu3+-Cryptate (20 μl) are then added to determine the cAMP level. After 1 h-incubation at room temperature, HTRF signal is detected with an Envision 2104 plate reader (PerkinElmer). Fluorescent emission at 620 nm and at 665 nm is measured and the ratio between 620 nm and at 665 nm is calculated and then are converted to nM cAMP per well using a cAMP standard curve. Dose response curves of compounds are plotted as the percentage of stimulation normalized to minimum (buffer only) and maximum (maximum concentration of each control ligand) values and analyzed using a four parameter non-liner regression fit with a variable slope (Genedata Screener 13). EC50 is the concentration of compound causing half-maximal simulation in a dose response curve. A relative $EC_{50}$ value is derived by non-linear regression analysis using the percent maximal response vs. the concentration of peptide added, fitted to a four-parameter logistic equation.

Using Homogeneous Time Resolved Fluorescence methods, assays are conducted to determine the intrinsic potency of Example and comparator molecules performed in the presence of casein (instead of serum albumin) as a nonspecific blocker, which does not interact with the fatty acid moieties of the analyzed molecules.

Intracellular cAMP levels are determined by extrapolation using a standard curve. Dose response curves of compounds are plotted as the percentage of stimulation normalized to minimum (buffer only) and maximum (maximum concentration of each control ligand) values and analyzed using a four parameter non-linear regression fit with a variable slope (Genedata Screener 13). $EC_{50}$ is the concentration of compound causing half-maximal simulation in a dose response curve. Each relative EC50 value for the Geometric mean calculation is determined from a curve fitting.

Concentration response curves of compounds are plotted as the percentage of stimulation normalized to minimum (buffer only) and maximum (maximum concentration of each control ligand) values and analyzed using a four parameter non-liner regression fit with a variable slope (Genedata Screener 13). EC50 is the concentration of compound causing half-maximal simulation in a dose response curve.

The $EC_{50}$ summary statistics are computed as follows:

Geometric mean:

GM=10^(arithmetic mean of $\log_{10}$ transformed $EC_{50}$ values).

The standard error of the mean is reported:

SEM=geometric mean×(standard deviation of $\log_{10}$ transformed $EC_{50}$ values/square root of the # of runs)×$\log_e$ of 10.

The log transform accounts for the $EC_{50}$ values falling on a multiplicative, rather than an arithmetic scale.

Each day, the assay is run, the test peptides are run plus the native ligands GIP and GLP-1, buffer only as baseline (minimum) and the highest concentration of the respective GIP and GLP-1 standard is used as maximum for calculations. For illustration, as shown by Example 1, the test peptide is tested in 8 runs of the assay. For avoidance of doubt, hGIP amide and hGLP-1 amide EC50 in Table 3 are illustrative of geometric mean values from a series of 18 assay values, and values will vary each day compared to the zero buffer. Accordingly, each Example will use the geometric mean of those values to normalize the Example assay runs.

TABLE 3

Functional activation of hGLP-1R, hGIPR, hGcgR in the presence of 0.1% Casein.

| Example or comparator | hGIPR cAMP Rel $EC_{50}$ nM (SEM, n) | hGIPR cAMP $EC_{50}$ ratio (SEM, n) | hGLP1R cAMP Rel $EC_{50}$ nM (SEM, n) | hGLP1R cAMP $EC_{50}$ ratio (SEM, n) |
|---|---|---|---|---|
| hGIP amide | 0.170 (0.012, n = 18) | | | |
| hGLP-1 amide | | | 0.0396 (0.0030, n = 16) | |
| 1 | 0.0356 (0.00576, n = 8) | 4.65 (0.514, n = 8) | 0.0410 (0.00720, n = 7) | 1.12 (0.0949, n = 7) |
| 2 | 0.0339 (0.00650, n = 5) | 5.89 (1.10, n = 5) | 0.0441 (0.00670, n = 5) | 0.888 (0.0993, n = 5) |
| 3 | 0.0411 (0.00541, n = 5) | 4.51 (0.355, n = 5) | 0.0338 (0.00156, n = 4) | 1.25 (0.0916, n = 4) |
| 4 | 0.0272 (0.00358, n = 6) | 5.95 (0.466, n = 6) | 0.0297 (0.00319, n = 6) | 1.41 (0.241, n = 6) |
| 5 | 0.0309 (0.00402, n = 5) | 6.27 (0.808, n = 5) | 0.0164 (0.00219, n = 5) | 2.69 (0.547, n = 5) |
| 6 | 0.0899 (0.0196, n = 2) | 2.09 (0.301, n = 2) | 0.374 (0.0100, n = 2) | 0.185 (0.00340, n = 2) |
| 7 | 0.461 | 0.317 | 0.470 (0.0988, n = 2) | 0.130 (0.0215, n = 2) |
| 8 | 0.0848 (0.00744, n = 6) | 1.97 (0.170, n = 6) | 0.148 (0.00926, n = 6) | 0.419 (0.0352, n = 6) |
| 9 | 0.210 (0.0335, n = 6) | 0.768 (0.122, n = 6) | 0.194 (0.0284, n = 6) | 0.314 (0.0384, n = 6) |
| 10 | 1.28 (0.270, n = 2) | 0.151 (0.0416, n = 2) | 7.64 (0.786, n = 2) | 0.00912 (0.000859, n = 2) |
| 11 | 0.486 (0.108, n = 2) | 0.399 (0.114, n = 2) | 6.89 (2.68, n = 3) | 0.0111 (0.00387, n = 3) |
| 12 | 0.300 (0.0827, n = 2) | 0.659 (0.221, n = 2) | 1.15 (0.00296, n = 2) | 0.0603 (0.000359, n = 2) |
| 13 | 1.05 (0.236, n = 2) | 0.180 (0.0272, n = 2) | 5.39 (1.35, n = 2) | 0.0133 (0.00338, n = 2) |
| 14 | 0.284 (0.0828, n = 2) | 0.545 (0.161, n = 2) | 1.87 (0.534, n = 2) | 0.0306 (0.00519, n = 2) |
| 15 | 0.613 (0.141, n = 2) | 0.273 (0.00678, n = 2) | 0.0336 (0.0000222, n = 2) | 1.65 (0.0634, n = 2) |
| 16 | 0.975 (0.241, n = 2) | 0.157 (0.0401, n = 2) | 0.0437 (0.00494, n = 4) | 1.43 (0.260, n = 3) |
| 17 | 5.81 (0.758, n = 2) | 0.0257 (0.00368, n = 2) | 0.152 (0.0166, n = 2) | 0.398 (0.0260, n = 2) |
| 18 | 0.610 (0.200, n = 2) | 0.275 (0.0204, n = 2) | 0.0945 (0.00823, n = 2) | 0.589 (0.0732, n = 2) |
| 19 | 0.386 (0.0583, n = 2) | 0.436 (0.0449, n = 2) | 0.104 (0.00342, n = 2) | 0.532 (0.0375, n = 2) |
| 20 | 0.0556 (0.00518, n = 5) | 2.81 (0.293, n = 5) | 0.117 (0.0121, n = 8) | 0.577 (0.0706, n = 8) |
| 21 | 0.0748 (0.00682, n = 8) | 1.95 (0.145, n = 8) | 0.160 (0.00495, n = 7) | 0.402 (0.0178, n = 7) |
| 22 | 0.0842 (0.0103, n = 4) | 1.86 (0.109, n = 4) | 0.206 (0.0172, n = 5) | 0.290 (0.0233, n = 5) |
| 23 | 0.204 (0.0160, n = 5) | 0.754 (0.0348, n = 5) | 0.190 (0.00766, n = 7) | 0.342 (0.0255, n = 7) |
| 24 | 0.762 (0.206, n = 2) | 0.228 (0.0443, n = 2) | 13.0 (n = ½) | 0.00416 (n = ½) |
| 25 | 0.230 (0.0191, n = 6) | 0.636 (0.0564, n = 6) | 0.356 (0.0415, n = 6) | 0.197 (0.0287, n = 6) |
| 26 | 0.251 (0.0264, n = 6) | 0.585 (0.0531, n = 6) | 0.293 (0.0442, n = 5) | 0.238 (0.0309, n = 5) |
| 27 | 0.0789 (0.00792, n = 6) | 1.90 (0.295, n = 6) | 0.557 (0.0717, n = 5) | 0.123 (0.0102, n = 5) |
| 28 | 1.66 (0.257, n = 2) | 0.106 (0.0238, n = 2) | 32.7 (n = ½) | 0.00166 (n = ½) |
| 29 | 0.320 (0.0548, n = 2) | 0.536 (0.0522, n = 2) | 0.999 (0.336, n = 2) | 0.0671 (0.0283, n = 2) |

TABLE 3-continued

Functional activation of hGLP-1R, hGIPR, hGcgR in the presence of 0.1% Casein.

| Example or comparator | hGIPR cAMP Rel EC$_{50}$ nM (SEM, n) | hGIPR cAMP EC$_{50}$ ratio (SEM, n) | hGLP1R cAMP Rel EC$_{50}$ nM (SEM, n) | hGLP1R cAMP EC$_{50}$ ratio (SEM, n) |
|---|---|---|---|---|
| 30 | 0.114 (0.00650, n = 2) | 1.50 (0.0246, n = 2) | 1.84 (0.280, n = 2) | 0.0331 (0.00127, n = 2) |
| 31 | 0.388 (0.0773, n = 2) | 0.456 (0.121, n = 2) | 0.891 (0.147, n = 2) | 0.0708 (0.0192, n = 2) |
| 32 | 0.179 (0.0200, n = 5) | 0.840 (0.0750, n = 5) | 0.498 (0.0124, n = 5) | 0.136 (0.00728, n = 5) |
| 33 | 63.3 (6.65, n = 2) | 0.00222 (0.000125, n = 2) | 251 (n = ½) | 0.000256 (n = ½) |
| 34 | 0.360 (0.0200, n = 2) | 0.393 (0.00105, n = 2) | 1.56 (0.132, n = 2) | 0.0392 (0.00119, n = 2) |
| 35 | 0.0905 (0.00717, n = 2) | 1.58 (0.215, n = 2) | 8.38 (0.707, n = 2) | 0.00728 (0.000221, n = 2) |
| 36 | 0.309 (0.0126, n = 2) | 0.458 (0.00789, n = 2) | 2.29 (0.390, n = 2) | 0.0268 (0.00309, n = 2) |
| 37 | 0.269 (0.0546, n = 2) | 0.532 (0.0765, n = 2) | 1.15 (0.216, n = 2) | 0.0533 (0.00707, n = 2) |
| 38 | 0.147 (0.0217, n = 2) | 0.967 (0.0861, n = 2) | 2.82 (0.0832, n = 2) | 0.0217 (0.00181, n = 2) |
| 39 | 0.133 (0.0242, n = 2) | 1.07 (0.132, n = 2) | 1.92 (0.447, n = 2) | 0.0323 (0.00571, n = 2) |
| 40 | 0.136 (0.0164, n = 2) | 1.06 (0.188, n = 2) | 0.746 (0.118, n = 2) | 0.0801 (0.0105, n = 2) |
| 41 | 0.229 (0.0451, n = 2) | 0.637 (0.159, n = 2) | 0.960 (0.0203, n = 2) | 0.0637 (0.00478, n = 2) |
| 42 | 0.161 (0.00967, n = 2) | 0.897 (0.149, n = 2) | 1.45 (0.328, n = 2) | 0.0471 (0.0107, n = 2) |
| 43 | 0.112 (0.0129, n = 2) | 1.28 (0.0105, n = 2) | 0.862 (0.0963, n = 2) | 0.0777 (0.00826, n = 2) |
| 44 | 0.128 (0.0118, n = 2) | 1.11 (0.0174, n = 2) | 0.752 (0.201, n = 2) | 0.0918 (0.0245, n = 2) |
| 45 | 0.106 (0.0158, n = 2) | 1.75 (0.164, n = 2) | 1.03 (0.194, n = 2) | 0.0569 (0.00591, n = 2) |
| 46 | 0.172 (0.0231, n = 2) | 0.828 (0.0222, n = 2) | 0.687 (0.0147, n = 2) | 0.0969 (0.00159, n = 2) |
| 47 | 0.287 (0.0529, n = 2) | 0.654 (0.0819, n = 2) | 0.702 (0.197, n = 2) | 0.0890 (0.0310, n = 2) |
| 48 | 0.168 (0.0126, n = 2) | 0.863 (0.156, n = 2) | 0.691 (0.0491, n = 2) | 0.0966 (0.00733, n = 2) |
| 49 | 0.0868 (0.0288, n = 2) | 1.69 (0.372, n = 2) | 0.597 (0.0314, n = 2) | 0.112 (0.00642, n = 2) |
| 50 | 0.0794 (0.0104, n = 5) | 1.96 (0.179, n = 5) | 0.0961 (0.00519, n = 7) | 0.675 (0.0492, n = 7) |
| 51 | 0.0960 (0.0106, n = 7) | 1.69 (0.201, n = 7) | 0.153 (0.0110, n = 7) | 0.426 (0.0376, n = 7) |
| 52 | 0.0997 (0.0119, n = 6) | 1.40 (0.154, n = 6) | 0.132 (0.0143, n = 5) | 0.514 (0.0413, n = 5) |
| 53 | 0.628 (0.161, n = 2) | 0.287 (0.0912, n = 2) | 0.0339 (0.000266, n = 2) | 1.80 (0.190, n = 2) |
| 54 | 1.57 (0.144, n = 2) | 0.110 (0.0181, n = 2) | 0.0242 (0.00711, n = 2) | 2.55 (0.456, n = 2) |
| 55 | 5.45 (n = ½) | <0.00159 | 0.0286 (0.000346, n = 2) | 2.33 (0.0282, n = 2) |
| 56 | 0.167 (0.0132, n = 2) | 1.02 (0.00567, n = 2) | 0.136 (0.00964, n = 2) | 0.491 (0.0347, n = 2) |
| 57 | 0.0849 (0.0107, n = 6) | 1.74 (0.148, n = 6) | 0.0668 (0.00654, n = 7) | 0.996 (0.0730, n = 7) |
| 58 | 0.266 (0.0307, n = 5) | 0.522 (0.0439, n = 5) | 0.180 (0.0151, n = 5) | 0.378 (0.0347, n = 5) |
| 59 | 0.0922 (0.0134, n = 5) | 1.54 (0.186, n = 5) | 0.0840 (0.00742, n = 5) | 0.812 (0.0816, n = 5) |
| 60 | 0.135 (0.0107, n = 2) | 1.06 (0.0296, n = 2) | 0.287 (0.0377, n = 3) | 0.237 (0.0270, n = 3) |
| 61 | 0.0739 (0.0140, n = 2) | 1.94 (0.158, n = 2) | 0.371 (0.0664, n = 3) | 0.187 (0.0341, n = 3) |
| 62 | 0.0601 (0.00469, n = 5) | 2.33 (0.234, n = 5) | 0.159 (0.0151, n = 5) | 0.463 (0.0644, n = 5) |
| 63 | 0.0925 (0.0106, n = 7) | 1.58 (0.156, n = 7) | 0.190 (0.0195, n = 5) | 0.386 (0.0466, n = 5) |
| 64 | 0.0916 (0.0104, n = 6) | 1.57 (0.192, n = 6) | 0.172 (0.0184, n = 5) | 0.429 (0.0598, n = 5) |
| 65 | 0.143 (0.0264, n = 2) | 1.04 (0.295, n = 2) | 0.289 (0.0215, n = 3) | 0.233 (0.0144, n = 3) |
| 66 | 0.0743 (0.00740, n = 5) | 1.89 (0.209, n = 5) | 0.285 (0.0291, n = 5) | 0.255 (0.0245, n = 5) |
| 67 | 0.0913 (0.00577, n = 2) | 1.61 (0.0648, n = 2) | 0.447 (0.0958, n = 2) | 0.123 (0.0314, n = 2) |
| 68 | 0.0881 (0.00725, n = 2) | 1.67 (0.0990, n = 2) | 0.153 (0.0169, n = 2) | 0.354 (0.0550, n = 2) |
| 69 | 0.0712 (0.0156, n = 4) | 2.73 (0.431, n = 3) | 0.0844 (0.00548, n = 4) | 0.850 (0.0870, n = 4) |
| 70 | 0.480 (0.0706, n = 2) | 0.351 (0.0135, n = 2) | 0.283 (0.0281, n = 3) | 0.207 (0.0330, n = 3) |
| 71 | 0.166 (0.0417, n = 2) | 1.02 (0.0668, n = 2) | 1.02 (0.227, n = 3) | 0.0604 (0.0170, n = 3) |
| 72 | 0.252 (0.0456, n = 2) | 0.715 (0.251, n = 2) | 0.906 (0.127, n = 3) | 0.0645 (0.0103, n = 3) |
| 73 | 0.979 (0.317, n = 2) | 0.174 (0.0239, n = 2) | 2.55 (0.337, n = 3) | 0.0225 (0.00178, n = 3) |
| 74 | 0.0866 (0.00653, n = 2) | 1.70 (0.166, n = 2) | 0.467 (0.00217, n = 2) | 0.115 (0.00580, n = 2) |
| 75 | 0.214 (0.0234, n = 2) | 0.690 (0.0905, n = 2) | 1.49 (0.00142, n = 2) | 0.0359 (0.00168, n = 2) |
| 76 | 0.124 (0.000853, n = 2) | 1.24 (0.0255, n = 2) | 0.125 (0.00942, n = 2) | 0.630 (0.0992, n = 2) |

TABLE 3-continued

Functional activation of hGLP-1R, hGIPR, hGcgR in the presence of 0.1% Casein.

| Example or comparator | hGIPR cAMP Rel EC$_{50}$ nM (SEM, n) | hGIPR cAMP EC$_{50}$ ratio (SEM, n) | hGLP1R cAMP Rel EC$_{50}$ nM (SEM, n) | hGLP1R cAMP EC$_{50}$ ratio (SEM, n) |
|---|---|---|---|---|
| 77 | 135 (22.8, n = 2) | 0.00102 (0.000331, n = 2) | >2000 (n = ½) | <0.0000325 (n = ½) |
| 78 | 0.532 (0.120, n = 2) | 0.293 (0.0571, n = 2) | 0.544 (0.0263, n = 2) | 0.143 (0.00495, n = 2) |
| 79 | 0.0732 (0.0127, n = 2) | 2.11 (0.305, n = 2) | 2.02 (0.562, n = 2) | 0.0410 (0.0142, n = 2) |
| 80 | 0.140 (0.0130, n = 2) | 1.09 (0.0709, n = 2) | 0.351 (0.0522, n = 2) | 0.227 (0.0516, n = 2) |
| 81 | 0.428 (0.0445, n = 2) | 0.373 (0.0131, n = 2) | 1.29 (0.00950, n = 2) | 0.0630 (0.00192, n = 2) |
| 82 | 24.3 (8.06, n = 2) | 0.00679 (0.00175, n = 2) | 26.1 (6.81, n = 2) | 0.00325 (0.000941, n = 2) |
| 83 | 0.182 (0.0176, n = 2) | 0.804 (0.0637, n = 2) | 0.387 (0.0648, n = 2) | 0.166 (0.0265, n = 2) |
| 84 | 0.0915 (0.00451, n = 2) | 1.59 (0.0514, n = 2) | 0.374 (0.0762, n = 2) | 0.173 (0.0337, n = 2) |
| 85 | 1.67 (0.143, n = 2) | 0.111 (0.00296, n = 2) | 0.0518 (0.00318, n = 2) | 1.13 (0.0246, n = 2) |
| 86 | 0.0452 (0.00765, n = 2) | 3.29 (0.605, n = 2) | 0.271 (0.0756, n = 2) | 0.243 (0.0647, n = 2) |
| 87 | 0.0945 (0.0277, n = 2) | 1.1 | 0.0801 | 0.786 |
| 88 | 0.475 (0.00187, n = 2) | 0.392 (0.0215, n = 2) | 0.640 (0.00544, n = 2) | 0.0918 (0.00840, n = 2) |
| 89 | 0.119 (0.0150, n = 2) | 1.57 (0.107, n = 2) | 0.335 (0.00771, n = 2) | 0.175 (0.0105, n = 2) |
| 90 | 0.0361 (0.000915, n = 2) | 5.17 (0.434, n = 2) | 0.532 (0.0564, n = 2) | 0.110 (0.00250, n = 2) |
| 91 | 19.2 (n = ½) | 0.0103 (n = ½) | >5000 (n = ½) | <0.0000108 (n = ½) |
| 92 | 0.338 | 0.546 | 0.257 | 0.258 |
| 93 | 0.185 (0.0241, n = 2) | 0.956 (0.292, n = 2) | 0.115 (0.0143, n = 3) | 0.498 (0.0199, n = 3) |
| 94 | 0.425 | 0.434 | 0.338 | 0.196 |
| 95 | 1.17 (0.0326, n = 2) | 0.145 (0.0227, n = 2) | 1.01 (0.229, n = 3) | 0.0576 (0.00824, n = 3) |
| 96 | 0.712 (0.0736, n = 2) | 0.238 (0.0195, n = 2) | 0.590 (0.0509, n = 3) | 0.0977 (0.0101, n = 3) |
| 97 | 1.85 (0.214, n = 2) | 0.0953 (0.0278, n = 2) | 2.18 (0.347, n = 3) | 0.0268 (0.00442, n = 3) |
| 98 | 0.0718 | 2.43 | 0.157 | 0.384 |
| 99 | 0.0643 (0.0120, n = 5) | 2.27 (0.208, n = 5) | 0.0986 (0.0104, n = 4) | 0.629 (0.0938, n = 4) |
| 100 | 0.120 (0.0169, n = 2) | 1.48 (0.191, n = 2) | 0.0790 (0.00439, n = 2) | 0.724 (0.0809, n = 2) |
| 101 | 0.0704 (0.00913, n = 5) | 2.07 (0.138, n = 5) | 0.0579 (0.00589, n = 4) | 1.06 (0.131, n = 4) |
| 102 | 0.178 | 0.983 | 0.0628 (0.00458, n = 2) | 0.913 (0.118, n = 2) |
| 103 | 0.0693 (0.0165, n = 4) | 2.01 (0.183, n = 4) | 0.101 (0.0132, n = 3) | 0.655 (0.108, n = 3) |
| 104 | 0.0323 (0.00474, n = 8) | 4.93 (0.595, n = 8) | 0.0248 (0.00679, n = 6) | 1.85 (0.242, n = 6) |
| 105 | 1.85 (0.133, n = 2) | 0.101 (0.00134, n = 2) | 0.0401 (0.00740, n = 2) | 1.51 (0.396, n = 2) |
| 106 | 6.54 (n = ½) | 0.0302 (n = ½) | 0.0413 (0.000823, n = 2) | 1.42 (0.0898, n = 2) |
| 107 | 0.241 (0.0209, n = 5) | 0.747 (0.0859, n = 5) | 0.0539 (0.00678, n = 5) | 1.10 (0.128, n = 5) |
| 108 | 0.0885 (0.00413, n = 2) | 2.19 (0.0798, n = 2) | 0.294 (0.0441, n = 2) | 0.218 (0.0253, n = 2) |
| 109 | 0.109 (0.0252, n = 2) | 1.83 (0.397, n = 2) | 0.350 (0.0142, n = 2) | 0.182 (0.0134, n = 2) |
| 110 | 0.218 (0.0657, n = 2) | 0.929 (0.263, n = 2) | 0.179 (0.0168, n = 2) | 0.358 (0.0452, n = 2) |
| 111 | 0.141 (0.0253, n = 2) | 1.1 | 0.308 (0.0144, n = 2) | 0.209 (0.0151, n = 2) |
| 112 | 0.124 (0.00217, n = 2) | 1.53 | 0.160 (0.0115, n = 2) | 0.402 (0.0185, n = 2) |
| 113 | 0.166 (0.0364, n = 2) | 1.39 | 0.233 (0.0133, n = 2) | 0.275 (0.0228, n = 2) |
| 114 | 0.133 (0.0220, n = 2) | 1.65 | 0.267 | 0.234 |
| 115 | 0.102 (0.0163, n = 5) | 1.85 (0.319, n = 5) | 0.0880 (0.00660, n = 4) | 0.743 (0.0516, n = 4) |
| 116 | 0.0867 (0.0141, n = 5) | 2.13 (0.255, n = 5) | 0.0703 (0.0111, n = 4) | 0.956 (0.147, n = 4) |
| 117 | 0.0648 (0.00602, n = 7) | 2.44 (0.263, n = 6) | 0.0615 (0.00275, n = 7) | 0.998 (0.0681, n = 7) |
| 118 | 0.0538 (0.00395, n = 7) | 3.42 (0.247, n = 6) | 0.0588 (0.00577, n = 6) | 1.13 (0.115, n = 6) |
| 119 | 0.216 (0.0107, n = 2) | 0.901 (0.0541, n = 2) | 0.0913 (0.00729, n = 2) | 0.702 (0.0788, n = 2) |
| 120 | 0.122 (0.0397, n = 2) | 1.67 (0.509, n = 2) | 0.201 (0.0318, n = 2) | 0.319 (0.0398, n = 2) |
| 121 | 0.0760 (0.0189, n = 2) | 1.44 | 0.0849 (0.0136, n = 2) | 0.760 (0.128, n = 2) |
| 122 | 0.0923 (0.0122, n = 2) | 1.73 (0.399, n = 2) | 0.0760 (0.0221, n = 2) | 0.856 (0.223, n = 2) |
| 123 | 0.0423 (0.00604, n = 8) | 4.04 (0.586, n = 8) | 0.0344 (0.00562, n = 5) | 1.58 (0.180, n = 5) |
| 124 | 0.0762 (0.00816, n = 4) | 2.18 (0.283, n = 4) | 0.0475 (0.00318, n = 4) | 1.29 (0.0473, n = 4) |
| 125 | 0.0381 (0.00482, n = 5) | 3.79 (0.152, n = 5) | 0.0478 (0.00569, n = 4) | 1.31 (0.229, n = 4) |
| 126 | 0.0685 (0.00653, n = 4) | 2.53 (0.361, n = 3) | 0.0715 (0.00249, n = 4) | 0.869 (0.0332, n = 4) |

TABLE 3-continued

Functional activation of hGLP-1R, hGIPR, hGcgR in the presence of 0.1% Casein.

| Example or comparator | hGIPR cAMP Rel EC$_{50}$ nM (SEM, n) | hGIPR cAMP EC$_{50}$ ratio (SEM, n) | hGLP1R cAMP Rel EC$_{50}$ nM (SEM, n) | hGLP1R cAMP EC$_{50}$ ratio (SEM, n) |
|---|---|---|---|---|
| 127 | 0.158 (0.0401, n = 2) | 0.917 | 0.145 (0.00951, n = 2) | 0.443 (0.0176, n = 2) |
| 128 | 0.0694 (0.00856, n = 4) | 2.46 (0.344, n = 3) | 0.0924 (0.0147, n = 4) | 0.700 (0.119, n = 4) |
| 129 | 0.106 (0.00707, n = 2) | 1.88 | 0.121 (0.0220, n = 2) | 0.543 (0.112, n = 2) |
| 130 | 1.55 | 0.116 | 0.368 | 0.182 |
| 131 | 0.183 | 1.03 | 0.156 | 0.425 |
| 132 | 0.0657 | 2.88 | 0.26 | 0.255 |
| 133 | 0.0879 (0.0298, n = 2) | 1.89 (1.13, n = 2) | 0.0436 | 1.52 |
| 134 | 0.104 (0.00639, n = 2) | 1.43 (0.244, n = 2) | 0.0654 (0.00394, n = 2) | 0.942 (0.00985, n = 2) |
| 135 | 0.373 | 0.482 | 0.131 | 0.509 |
| 136 | 3.39 | 0.0544 | 0.06 | 1.1 |
| 137 | 0.0333 (0.00461, n = 8) | 4.47 (0.381, n = 8) | 0.0397 (0.00540, n = 5) | 1.25 (0.114, n = 5) |
| 138 | 0.0581 (0.00498, n = 3) | 2.18 (0.423, n = 3) | 0.0471 (0.00784, n = 3) | 1.12 (0.105, n = 3) |
| 139 | 0.0370 (0.00460, n = 5) | 3.61 (0.444, n = 5) | 0.0417 (0.00760, n = 5) | 1.13 (0.105, n = 5) |
| 140 | 0.0349 (0.00428, n = 5) | 3.76 (0.415, n = 5) | 0.0424 (0.00487, n = 5) | 1.16 (0.0926, n = 5) |
| 141 | 0.2 | 0.538 | 0.0975 | 0.414 |
| 142 | 0.0489 (0.00436, n = 2) | 2.84 (0.637, n = 2) | 0.0426 (0.00626, n = 2) | 1.22 (0.0942, n = 2) |
| 143 | 0.0515 (0.0105, n = 2) | 2.78 (0.920, n = 2) | 0.0745 (0.0109, n = 2) | 0.714 (0.152, n = 2) |
| 144 | 0.0375 (0.00249, n = 3) | 3.60 (0.373, n = 3) | 0.0608 (0.00352, n = 3) | 0.851 (0.0845, n = 3) |
| 145 | 0.0514 (0.0124, n = 3) | 2.46 (0.300, n = 3) | 0.0427 (0.00108, n = 2) | 1.22 (0.116, n = 2) |
| 146 | 0.0583 | 1.98 | 0.0604 | 0.951 |
| 147 | 0.0304 (0.00146, n = 3) | 4.14 (0.241, n = 3) | 0.0527 (0.00623, n = 3) | 1.13 (0.117, n = 3) |
| 148 | 0.0430 (0.00713, n = 3) | 2.70 (0.462, n = 3) | 0.0626 (0.00751, n = 3) | 0.859 (0.167, n = 3) |
| 149 | 0.0711 (0.0109, n = 2) | 1.82 (0.0572, n = 2) | 0.0916 (0.0149, n = 2) | 0.484 (0.0343, n = 2) |
| 150 | 0.0511 (0.00569, n = 2) | 2.64 (0.761, n = 2) | 0.0575 (0.00855, n = 2) | 0.790 (0.186, n = 2) |
| 151 | 0.41 | 0.262 | 1.60 (0.338, n = 2) | 0.0278 (0.00331, n = 2) |
| 152 | 0.0504 (0.00566, n = 2) | 2.57 (0.188, n = 2) | 0.0915 (0.0128, n = 2) | 0.484 (0.0236, n = 2) |
| 153 | 0.0634 | 1.7 | 0.0904 (0.0113, n = 2) | 0.501 (0.107, n = 2) |
| 154 | 0.0266 (0.00348, n = 7) | 5.90 (0.513, n = 7) | 0.0393 (0.00511, n = 5) | 1.23 (0.117, n = 5) |
| 155 | 0.266 | 0.584 | 0.495 | 0.0978 |
| 156 | >30.0 | <0.00519 | 0.638 | 0.0759 |
| 157 | 0.0453 (0.00495, n = 6) | 3.15 (0.444, n = 6) | 0.0431 (0.00557, n = 4) | 1.25 (0.135, n = 4) |
| 158 | 0.0454 (0.0102, n = 5) | 3.22 (0.527, n = 5) | 0.0374 (0.00374, n = 5) | 1.34 (0.0947, n = 5) |
| 159 | 4.6 | 0.039 | 0.33 | 0.176 |
| 160 | 21.0 (0.568, n = 2) | 0.00712 (0.00165, n = 2) | 0.0461 (0.00206, n = 2) | 1.24 (0.0824, n = 2) |
| 161 | 0.254 | 0.706 | 4.8 | 0.0121 |
| 162 | 4.56 | 0.0393 | 36 | 0.00161 |
| 163 | 0.121 | 1.29 | 0.0316 | 1.54 |
| 164 | 3.09 | 0.0581 | 15.6 | 0.00373 |
| 165 | 1.04 | 0.172 | 5.81 | 0.01 |
| 166 | 0.355 | 0.504 | 4.08 | 0.0143 |
| 167 | 0.617 | 0.291 | 1.2 | 0.0487 |
| 168 | 0.572 | 0.313 | 1.8 | 0.0323 |
| 169 | 0.86 | 0.122 | 3.37 | 0.0136 |
| 170 | 0.569 | 0.185 | 10.4 | 0.00438 |
| 171 | 0.223 | 0.471 | 0.75 | 0.0609 |
| 172 | 1.05 | 0.1 | 1.2 | 0.038 |
| 173 | 0.586 | 0.179 | 1.23 | 0.0373 |
| 174 | 0.217 | 0.483 | 0.472 | 0.0968 |
| 175 | 0.0881 | 1.19 | 1.11 | 0.0412 |
| 176 | 0.523 | 0.201 | 1.07 | 0.0427 |
| 177 | 1.4 | 0.0749 | 6.79 | 0.00673 |
| 178 | 3.08 | 0.0341 | 13.1 | 0.00349 |
| 179 | 1.83 | 0.0575 | 2.7 | 0.0169 |
| 180 | 0.79 | 0.133 | 2.16 | 0.0212 |
| 181 | 0.0459 (0.0122, n = 5) | 4.10 (0.698, n = 5) | 0.0592 (0.00966, n = 6) | 0.718 (0.0586, n = 6) |
| 182 | 0.0442 (0.0133, n = 5) | 4.37 (0.940, n = 5) | 0.0463 (0.00578, n = 6) | 0.873 (0.0433, n = 6) |
| 183 | 0.0615 (0.0175, n = 5) | 3.10 (0.600, n = 5) | 0.0551 (0.0125, n = 5) | 0.843 (0.121, n = 5) |
| 184 | 0.0477 | 2.45 | 0.392 | 0.135 |
| 185 | 0.632 | 0.185 | 7.16 | 0.00739 |
| 186 | 0.0939 | 0.572 | | |
| 187 | 0.0371 (0.00593, n = 6) | 4.61 (0.839, n = 6) | 0.0577 (0.00695, n = 6) | 0.702 (0.0431, n = 6) |
| 188 | 0.121 | 0.969 | 0.13 | 0.408 |
| 189 | 0.0775 (0.0140, n = 5) | 2.41 (0.314, n = 5) | 0.0608 (0.00976, n = 6) | 0.668 (0.0450, n = 6) |
| 190 | 0.738 | 0.158 | 0.0241 | 2.2 |
| 191 | 0.0645 (0.0139, n = 3) | 2.53 (0.131, n = 3) | 0.0356 (0.00490, n = 3) | 1.60 (0.182, n = 3) |
| 192 | 0.0615 (0.0139, n = 5) | 2.83 (0.340, n = 5) | 0.0289 (0.00261, n = 5) | 1.73 (0.0510, n = 5) |
| 193 | 0.336 | 0.538 | 0.162 | 0.359 |
| 194 | 0.423 | 0.427 | 0.284 | 0.205 |
| 195 | 0.193 | 0.936 | 0.0966 | 0.602 |
| 196 | 0.277 | 0.653 | 0.175 | 0.332 |
| 197 | 0.211 | 0.855 | 0.248 | 0.189 |
| 198 | >30.0 | <0.00602 | 0.139 | 0.337 |
| 199 | >30.0 | <0.00602 | 0.0422 | 1.11 |
| 200 | 12.3 | 0.0146 | 0.0818 | 0.573 |
| 201 | >30.0 | <0.00602 | 0.0385 | 1.22 |
| 202 | 0.0392 (0.00958, n = 3) | 4.79 (0.700, n = 3) | 0.0608 (0.00408, n = 2) | 0.712 (0.0866, n = 2) |
| 203 | 0.0387 (0.00465, n = 4) | 4.95 (0.383, n = 4) | 0.0679 (0.0116, n = 3) | 0.671 (0.130, n = 3) |

TABLE 3-continued

Functional activation of hGLP-1R, hGIPR, hGcgR in the presence of 0.1% Casein.

| Example or comparator | hGIPR cAMP Rel EC$_{50}$ nM (SEM, n) | hGIPR cAMP EC$_{50}$ ratio (SEM, n) | hGLP1R cAMP Rel EC$_{50}$ nM (SEM, n) | hGLP1R cAMP EC$_{50}$ ratio (SEM, n) |
|---|---|---|---|---|
| 204 | 0.0424 (0.0132, n = 3) | 4.58 (1.01, n = 3) | 0.0654 (0.0166, n = 2) | 0.689 (0.207, n = 2) |
| 205 | 0.0281 (0.000581, n = 2) | 5.71 (0.519, n = 2) | 0.0261 (0.00703, n = 3) | 1.46 (0.102, n = 3) |
| 206 | 0.0409 (0.00271, n = 2) | 4.75 (0.0828, n = 2) | 0.0270 (0.00477, n = 3) | 1.42 (0.139, n = 3) |
| 207 | 0.0395 (0.0103, n = 3) | 4.76 (0.715, n = 3) | 0.0359 (0.00622, n = 2) | 1.23 (0.275, n = 2) |
| 208 | 0.0371 (0.00797, n = 4) | 5.33 (0.808, n = 4) | 0.0753 (0.00608, n = 3) | 0.587 (0.0362, n = 3) |
| 209 | 0.0308 (0.00636, n = 5) | 5.73 (0.721, n = 5) | 0.0374 (0.00451, n = 4) | 1.12 (0.108, n = 4) |
| 210 | 0.0383 (0.0124, n = 4) | 5.40 (1.22, n = 4) | 0.0432 (0.00554, n = 3) | 1.03 (0.118, n = 3) |
| 211 | 0.0442 (0.00939, n = 5) | 4.59 (0.656, n = 5) | 0.0337 (0.00481, n = 4) | 1.28 (0.203, n = 4) |
| 212 | 0.0501 (0.0132, n = 4) | 4.17 (0.999, n = 4) | 0.0572 (0.00467, n = 3) | 0.771 (0.0330, n = 3) |
| 213 | 0.0523 (0.0140, n = 4) | 3.87 (0.721, n = 4) | 0.0710 (0.0146, n = 4) | 0.694 (0.110, n = 4) |
| 214 | 0.0251 (0.00459, n = 4) | 6.92 (0.628, n = 4) | 0.0221 (0.00364, n = 5) | 1.74 (0.122, n = 5) |
| 215 | 0.0525 (0.00720, n = 3) | 3.53 (0.379, n = 3) | 0.0529 (0.00177, n = 2) | 0.813 (0.0175, n = 2) |
| 216 | 0.0401 (0.0151, n = 3) | 4.91 (1.22, n = 3) | 0.0327 (0.00291, n = 2) | 1.31 (0.0447, n = 2) |
| 217 | 0.0563 (0.0165, n = 3) | 3.41 (0.665, n = 3) | 0.0383 (0.00448, n = 2) | 1.14 (0.193, n = 2) |
| 218 | 0.0413 (0.00450, n = 3) | 4.43 (0.113, n = 3) | 0.0423 (0.00335, n = 2) | 1.02 (0.137, n = 2) |
| 219 | 0.0341 (0.00595, n = 5) | 5.86 (0.825, n = 5) | 0.0403 (0.00221, n = 4) | 1.03 (0.0601, n = 4) |
| 220 | 0.0315 (0.00564, n = 5) | 6.30 (0.786, n = 5) | 0.0312 (0.00267, n = 4) | 1.36 (0.176, n = 4) |
| 221 | 0.0445 (0.0102, n = 4) | 4.50 (0.773, n = 4) | 0.0570 (0.0101, n = 3) | 0.795 (0.138, n = 3) |
| 222 | 0.0306 (0.00648, n = 4) | 5.84 (0.924, n = 4) | 0.0248 (0.00375, n = 5) | 1.55 (0.110, n = 5) |
| 223 | 0.0670 (0.00561, n = 2) | 2.93 (0.487, n = 2) | 0.0363 (0.00532, n = 3) | 0.962 (0.0435, n = 3) |
| 224 | 0.0545 (0.00995, n = 3) | 3.52 (0.580, n = 3) | 0.0349 (0.00788, n = 4) | 1.06 (0.145, n = 4) |
| 225 | 0.101 (0.0194, n = 2) | 1.99 (0.536, n = 2) | 0.0670 (0.0107, n = 3) | 0.523 (0.0355, n = 3) |
| 226 | 0.0461 (0.00446, n = 2) | 4.27 (0.762, n = 2) | 0.0284 (0.00805, n = 3) | 1.25 (0.167, n = 2) |
| 227 | 0.0414 (0.00954, n = 2) | 4.73 (0.688, n = 2) | 0.0329 (0.00627, n = 3) | 1.07 (0.0870, n = 3) |
| 228 | 0.0503 (0.00265, n = 2) | 3.86 (0.119, n = 2) | 0.0282 (0.00274, n = 2) | 1.10 (0.218, n = 2) |
| 229 | 4.79 | 0.0298 | 2.11 | 0.0139 |
| 230 | 0.0431 | 3.31 | 0.0491 | 0.599 |
| 231 | 0.0253 | 5.64 | 0.0611 | 0.481 |
| 232 | 0.027 | 5.28 | 0.0724 | 0.406 |
| 233 | 0.0288 | 4.95 | 0.0549 | 0.535 |
| 234 | 0.0372 | 3.83 | 0.0926 | 0.317 |
| 235 | 0.0372 | 3.83 | 0.136 | 0.216 |
| 236 | 0.0249 (0.00475, n = 5) | 6.76 (0.804, n = 5) | 0.0231 (0.00333, n = 5) | 1.65 (0.260, n = 5) |
| 237 | 0.0883 | 2.16 | 0.0187 | 2.34 |
| 238 | 0.0296 | 7.33 | 0.0241 | 1.15 |
| 239 | 0.0353 (0.00282, n = 4) | 5.27 (0.434, n = 4) | 0.0376 (0.00836, n = 4) | 0.987 (0.213, n = 4) |
| 240 | 0.0223 | 9.73 | 0.0393 | 0.706 |
| 241 | 0.0257 (0.00164, n = 3) | 7.12 (0.471, n = 3) | 0.0175 (0.00373, n = 3) | 1.89 (0.340, n = 3) |
| 242 | 0.0333 (0.00196, n = 3) | 5.58 (0.823, n = 3) | 0.0164 (0.00209, n = 3) | 1.96 (0.186, n = 3) |
| 243 | 0.0214 (0.00212, n = 3) | 8.69 (1.21, n = 3) | 0.0265 (0.00423, n = 3) | 1.22 (0.158, n = 3) |
| 244 | 0.0225 (0.00136, n = 3) | 8.27 (1.30, n = 3) | 0.0252 (0.00415, n = 3) | 1.29 (0.174, n = 3) |
| 245 | 0.0552 | 2.82 | 0.0222 | 1.55 |
| 246 | 0.0258 (0.00180, n = 6) | 6.36 (0.340, n = 6) | 0.0144 (0.00106, n = 5) | 2.56 (0.216, n = 5) |
| 247 | 0.0622 | 2.58 | 0.0491 | 0.614 |
| 248 | 0.0328 (0.000561, n = 2) | 5.08 (0.118, n = 2) | 0.0428 (0.00493, n = 2) | 0.800 (0.00908, n = 2) |
| 249 | 0.0437 (0.00337, n = 2) | 3.84 (0.449, n = 2) | 0.0446 (0.0131, n = 2) | 0.778 (0.129, n = 2) |
| 250 | 0.0376 | 4.27 | 0.0306 | 0.985 |
| 251 | 0.0292 | 5.12 | 0.081 | 1.37 |
| 252 | 0.093 | 1.61 | 0.0483 | 1.44 |
| 253 | 0.219 | 0.684 | 0.109 | 0.638 |
| 254 | 0.215 | 0.695 | 0.0553 | 1.26 |
| 255 | 0.102 | 1.47 | 0.0407 | 1.71 |
| 256 | 0.643 | 0.233 | 0.0506 | 1.38 |
| 257 | 0.474 | 0.316 | 0.0779 | 0.895 |
| 258 | 2.43 | 0.0616 | 0.174 | 0.401 |
| 259 | 0.257 | 0.582 | 0.145 | 0.482 |
| 260 | 0.617 | 0.242 | 0.408 | 0.171 |
| 261 | 0.16 | 0.936 | 0.0948 | 0.75 |
| 262 | 0.13 | 1.15 | 0.0943 | 0.754 |
| 263 | 0.317 | 0.473 | 0.0785 | 0.906 |
| 264 | 0.0196 (0.00197, n = 2) | 8.40 (1.51, n = 2) | 0.0229 (0.00180, n = 2) | 3.19 (0.327, n = 2) |
| 265 | 0.0229 (0.00918, n = 2) | 7.56 (2.21, n = 2) | 0.0223 (0.00115, n = 2) | 3.27 (0.0894, n = 2) |
| 266 | 0.0442 (0.0109, n = 6) | 2.82 (0.430, n = 6) | 0.0883 (0.0104, n = 6) | 0.627 (0.103, n = 6) |
| 267 | 0.108 (0.0203, n = 5) | 1.50 (0.0726, n = 5) | 0.0540 (0.0118, n = 5) | 0.974 (0.256, n = 5) |

TABLE 3-continued

Functional activation of hGLP-1R, hGIPR, hGcgR in the presence of 0.1% Casein.

| Example or comparator | hGIPR cAMP Rel EC$_{50}$ nM (SEM, n) | hGIPR cAMP EC$_{50}$ ratio (SEM, n) | hGLP1R cAMP Rel EC$_{50}$ nM (SEM, n) | hGLP1R cAMP EC$_{50}$ ratio (SEM, n) |
|---|---|---|---|---|
| 268 | 0.239 (0.00366, n = 3) | 0.851 (0.0652, n = 3) | 0.0572 (0.0135, n = 5) | 0.935 (0.247, n = 5) |
| 269 | 0.257 (0.0546, n = 3) | 0.825 (0.187, n = 3) | 0.0595 (0.0158, n = 3) | 0.828 (0.202, n = 3) |
| 270 | 0.328 (0.0226, n = 3) | 0.627 (0.0795, n = 3) | 0.128 (0.0355, n = 4) | 0.400 (0.132, n = 4) |
| 271 | 0.334 (0.0609, n = 3) | 0.614 (0.0761, n = 3) | 0.0352 (0.00104, n = 2) | 1.35 (0.0587, n = 2) |
| 272 | 0.0464 (0.0119, n = 6) | 2.97 (0.286, n = 6) | 0.0435 (0.0117, n = 4) | 1.19 (0.355, n = 4) |
| 273 | 0.0790 (0.0165, n = 5) | 2.15 (0.333, n = 5) | 0.0352 (0.0230, n = 3) | 1.85 (0.845, n = 3) |
| 274 | >30.0 | <0.00741 | 14.5 (5.14, n = 2) | 0.00353 (0.000807, n = 2) |
| 275 | >30.0 | <0.00741 | 14.0 (0.390, n = 2) | 0.00357 (0.000336, n = 2) |
| 276 | 0.0757 | 1.43 | 0.108 (0.0236, n = 2) | 0.491 (0.117, n = 2) |
| 277 | 0.0554 | 2.02 | 0.133 | 0.536 |
| 278 | 0.293 | 0.845 | 0.123 (0.0121, n = 2) | 0.517 (0.0592, n = 2) |
| 279 | 0.564 | 0.439 | 0.11 | 0.461 |
| 280 | 0.204 | 1.53 | 0.0767 | 0.663 |
| 281 | 0.166 | 1.87 | 0.16 | 0.318 |
| 282 | 0.323 | 0.962 | 0.247 | 0.23 |
| 283 | 0.301 | 1.03 | 0.155 | 0.329 |
| 284 | 0.113 | 2.74 | 0.0462 | 1.1 |
| 285 | 0.0884 | 3.52 | 0.072 | 0.706 |
| 286 | 0.184 | 1.69 | 0.0602 | 0.845 |
| 287 | 0.15 | 2.08 | 0.112 | 0.455 |
| 288 | 0.0732 (0.0140, n = 7) | 1.20 (0.268, n = 7) | 0.172 (0.0288, n = 4) | 0.393 (0.128, n = 4) |
| 289 | 0.0228 (0.00219, n = 5) | 4.13 (0.741, n = 5) | 0.0544 (0.00661, n = 6) | 1.33 (0.325, n = 6) |
| 290 | 0.0629 (0.0118, n = 5) | 1.09 (0.176, n = 5) | 0.179 (0.0336, n = 6) | 0.279 (0.0844, n = 6) |
| 291 | 0.118 (0.0226, n = 4) | 0.746 (0.0858, n = 4) | 0.150 (0.0253, n = 5) | 0.188 (0.0294, n = 5) |
| 292 | 0.0682 (0.0192, n = 2) | 1.10 (0.0631, n = 2) | 0.183 (0.0328, n = 2) | 0.143 (0.0191, n = 2) |
| 293 | 0.0562 (0.00736, n = 2) | 1.36 (0.278, n = 2) | 0.132 (0.000967, n = 2) | 0.197 (0.00743, n = 2) |
| 294 | 0.183 | 0.75 | 0.185 | 0.249 |
| 295 | 0.281 | 0.481 | 0.116 | 0.398 |
| 296 | 0.198 | 0.564 | 0.0867 | 0.82 |
| 297 | 0.0451 (0.00597, n = 4) | 3.00 (0.569, n = 4) | 0.111 (0.0151, n = 5) | 0.445 (0.0482, n = 5) |
| 298 | 0.0430 (0.00578, n = 6) | 2.87 (0.349, n = 6) | 0.0957 (0.0139, n = 7) | 0.507 (0.0734, n = 7) |
| 299 | 0.932 (0.507, n = 2) | 0.146 (0.0780, n = 2) | 2.54 (0.629, n = 4) | 0.0244 (0.00551, n = 4) |
| 300 | 0.0234 (0.00482, n = 7) | 5.38 (1.40, n = 7) | 0.0867 (0.0105, n = 9) | 0.636 (0.0568, n = 9) |
| 301 | 0.0346 (0.00764, n = 12) | 4.11 (0.921, n = 11) | 0.0441 (0.00684, n = 7) | 1.61 (0.433, n = 7) |
| 302 | 0.0308 (0.00225, n = 8) | 3.78 (0.554, n = 7) | 0.0275 (0.00247, n = 6) | 1.96 (0.175, n = 6) |
| 303 | 0.0254 (0.00381, n = 9) | 4.20 (1.10, n = 9) | 0.104 (0.0157, n = 6) | 0.602 (0.0702, n = 6) |
| 304 | 0.0296 (0.00440, n = 7) | 2.68 (0.425, n = 7) | 0.191 (0.0386, n = 5) | 0.481 (0.151, n = 5) |
| 305 | 0.0225 (0.00306, n = 7) | 4.28 (0.953, n = 7) | 0.107 (0.0149, n = 6) | 0.685 (0.0980, n = 6) |
| 306 | 0.0191 (0.00502, n = 4) | 3.97 (0.582, n = 4) | 0.0711 (0.0202, n = 4) | 0.912 (0.339, n = 4) |
| 307 | 0.0285 (0.00345, n = 5) | 2.48 (0.481, n = 5) | 0.0437 (0.00943, n = 4) | 1.29 (0.238, n = 4) |
| 308 | 0.0262 (0.00432, n = 8) | 4.06 (1.01, n = 8) | 0.0392 (0.00818, n = 4) | 1.45 (0.307, n = 4) |
| 309 | 0.0389 (0.00473, n = 4) | 1.64 (0.313, n = 4) | 0.0330 (0.00555, n = 3) | 1.27 (0.312, n = 3) |
| 310 | 0.0176 (0.00109, n = 4) | 5.56 (1.23, n = 4) | 0.0283 (0.00985, n = 3) | 1.43 (0.262, n = 3) |
| 311 | 0.0334 (0.00431, n = 4) | 3.50 (0.928, n = 4) | 0.0393 (0.0132, n = 3) | 1.04 (0.220, n = 3) |
| 312 | 0.0207 (0.00251, n = 5) | 4.76 (1.32, n = 5) | 0.0262 (0.00799, n = 3) | 1.53 (0.342, n = 3) |
| 313 | 0.0233 (0.00223, n = 2) | 2.87 (0.830, n = 2) | 0.0388 (0.00647, n = 3) | 0.867 (0.197, n = 3) |
| 314 | 0.0290 (0.0123, n = 2) | 2.81 (0.669, n = 2) | 0.0290 (0.00867, n = 3) | 1.48 (0.476, n = 3) |
| 315 | 0.0408 (0.00771, n = 4) | 2.06 (0.452, n = 4) | 0.0651 (0.0141, n = 4) | 1.00 (0.245, n = 4) |
| 316 | 0.0240 (0.00478, n = 7) | 3.75 (0.723, n = 7) | 0.122 (0.00791, n = 6) | 0.644 (0.146, n = 6) |
| 317 | 0.0948 (0.0240, n = 4) | 1.01 (0.478, n = 4) | 0.172 (0.00643, n = 3) | 0.333 (0.104, n = 3) |
| 318 | 0.0547 (0.00365, n = 4) | 1.69 (0.536, n = 4) | 0.124 (0.0271, n = 4) | 0.482 (0.188, n = 4) |
| 319 | 0.0540 (0.0220, n = 4) | 2.77 (2.07, n = 4) | 0.113 (0.00689, n = 3) | 0.522 (0.171, n = 3) |
| 320 | 0.161 | 0.241 | 0.397 | 0.224 |
| 321 | 0.0752 | 0.517 | 0.204 | 0.437 |
| 322 | 0.146 | 0.266 | 0.711 | 0.125 |
| 323 | 0.0251 (0.00551, n = 4) | 3.24 (0.508, n = 4) | 0.0597 (0.00797, n = 4) | 1.32 (0.527, n = 4) |
| 324 | 0.0374 (0.00637, n = 4) | 2.13 (0.185, n = 4) | 0.0926 (0.0147, n = 4) | 0.798 (0.264, n = 4) |

TABLE 3-continued

Functional activation of hGLP-1R, hGIPR, hGcgR in the presence of 0.1% Casein.

| Example or comparator | hGIPR cAMP Rel EC$_{50}$ nM (SEM, n) | hGIPR cAMP EC$_{50}$ ratio (SEM, n) | hGLP1R cAMP Rel EC$_{50}$ nM (SEM, n) | hGLP1R cAMP EC$_{50}$ ratio (SEM, n) |
|---|---|---|---|---|
| 325 | 0.0301 (0.00366, n = 5) | 2.65 (0.180, n = 5) | 0.0586 (0.0119, n = 5) | 1.16 (0.224, n = 5) |
| 326 | 0.0754 | 1.5 | 0.0369 | 1.4 |
| 327 | 0.0548 (0.0274, n = 2/3) | 1.47 (0.273, n = 2/3) | 0.27 | 0.191 |
| 328 | 0.0965 | 0.94 | 0.117 | 0.575 |
| 329 | 0.132 | 0.687 | 0.125 | 0.535 |
| 330 | 0.0919 | 0.562 | 0.199 | 0.255 |
| 331 | 0.0547 (0.0162, n = 2) | 1.40 (0.145, n = 2) | 0.0929 (0.0237, n = 2) | 0.808 (0.277, n = 2) |
| 332 | 0.0745 (0.0143, n = 3) | 0.949 (0.0533, n = 3) | 0.184 (0.0348, n = 3) | 0.345 (0.0711, n = 3) |
| 333 | 0.0492 | 2.31 | 0.131 | 0.487 |
| 334 | 0.0718 | 0.844 | 0.303 | 0.151 |
| 335 | 0.0477 | 1.27 | 0.122 | 0.374 |
| 336 | 0.0312 | 1.95 | 0.0874 | 0.523 |
| 337 | 0.0515 | 1.18 | 0.173 | 0.265 |
| 338 | 0.0472 | 1.29 | 0.174 | 0.262 |
| 339 | 0.0219 (0.00722, n = 3) | 3.18 (0.768, n = 3) | 0.0986 (0.0180, n = 4) | 0.574 (0.231, n = 4) |
| 340 | 0.0823 (0.0288, n = 3) | 0.852 (0.312, n = 3) | 0.252 (0.00594, n = 4) | 0.183 (0.0554, n = 4) |
| 341 | 0.238 | 0.213 | 0.373 | 0.0674 |
| 342 | 0.159 | 0.32 | 0.127 | 0.198 |
| 343 | 0.0422 | 1.84 | 0.124 | 0.662 |
| 344 | 0.0433 | 1.79 | 0.044 | 1.86 |
| 345 | 0.0649 | 2.16 | 0.035 | 0.937 |
| 346 | 0.144 (0.0284, n = 2) | 0.604 (0.00648, n = 2) | 0.128 (0.0378, n = 3) | 0.210 (0.0493, n = 3) |
| 347 | 0.0827 | 0.872 | 0.102 (0.0247, n = 2) | 0.245 (0.0142, n = 2) |
| 348 | 0.193 | 0.373 | 0.113 (0.00703, n = 2) | 0.224 (0.0269, n = 2) |
| 349 | 0.117 (0.00129, n = 2) | 0.756 (0.131, n = 2) | 0.121 (0.0287, n = 3) | 0.214 (0.0378, n = 3) |
| 350 | 0.189 | 0.741 | 0.107 | 0.307 |
| 351 | 0.298 | 0.47 | 0.149 | 0.22 |
| 352 | 0.127 (0.0116, n = 2) | 0.815 (0.193, n = 2) | 0.142 (0.0267, n = 3) | 0.201 (0.0439, n = 3) |
| 353 | 0.497 | 0.145 (0.0881, n = 2) | 1.09 | 0.0231 (0.00235, n = 2) |
| 354 | 0.233 (0.0309, n = 2) | 0.441 (0.0871, n = 2) | 0.540 (0.126, n = 3) | 0.0517 (0.00657, n = 3) |
| 355 | 0.685 (0.318, n = 2) | 0.111 (0.0498, n = 2) | 0.896 (0.00185, n = 2) | 0.0285 (0.00509, n = 2) |
| 356 | 0.386 | 0.364 | 0.506 | 0.0647 |
| 357 | 0.384 | 0.366 | 0.181 | 0.181 |
| 358 | 0.183 (0.0347, n = 2) | 0.662 (0.0284, n = 2) | 0.117 (0.0257, n = 2) | 0.260 (0.0901, n = 2) |
| 359 | 0.172 (0.0235, n = 2) | 0.706 (0.00679, n = 2) | 0.131 (0.0201, n = 2) | 0.227 (0.0647, n = 2) |
| 360 | 0.197 | 0.53 | 0.145 | 0.171 |
| 361 | 0.401 | 0.261 | 0.955 | 0.0259 |
| 362 | 0.302 (n = 1/2) | 0.347 (n = 1/2) | 0.365 (0.0425, n = 2) | 0.0805 (0.0202, n = 2) |
| 363 | 0.145 (0.0185, n = 2) | 0.835 (0.0159, n = 2) | 0.208 (0.0485, n = 2) | 0.146 (0.0522, n = 2) |
| 364 | 0.351 (0.0809, n = 2) | 0.347 (0.0290, n = 2) | 1.00 (0.213, n = 2) | 0.0303 (0.0103, n = 2) |
| 365 | 0.0678 | 0.784 | 0.175 | 0.155 |
| 366 | 0.0889 | 0.598 | 0.366 | 0.074 |
| 367 | 0.0179 | 5.85 | 0.0641 | 0.386 |
| 368 | 0.0757 | 0.109 | 0.108 | 0.299 |
| 369 | 0.166 | 0.499 | 0.101 | 0.319 |
| 370 | 0.117 | 0.704 | 0.186 | 0.172 |
| 371 | 0.135 | 0.393 | 0.132 | 0.206 |
| 372 | 0.0781 | 0.68 | 0.365 | 0.0741 |
| 373 | 0.185 | 0.287 | 0.436 | 0.0621 |
| 374 | 0.0468 | 1.76 | 0.190 | 0.169 |
| 375 | 0.0471 | 1.13 | 0.152 | 0.178 |
| 376 | 0.0723 | 0.734 | 0.170 | 0.159 |
| 377 | 0.0544 | 0.976 | 0.136 | 0.199 |
| 378 | 0.067 | 0.793 | 0.191 | 0.142 |
| 379 | 0.079 | 0.672 | 0.238 | 0.114 |
| 380 | 0.142 | 0.374 | 0.236 | 0.115 |

As demonstrated by data in Table 3, Example compounds stimulate cAMP from human GLP-1R and GIPR in the presence of 0.1% casein.

In Vivo Studies

Pharmacokinetics in Male CD-1 Mice

The pharmacokinetics of select Examples are evaluated following a single subcutaneous administration of 200 nMol/kg to male CD-1 mice. Blood samples are collected over 168 hours and resulting individual plasma concentrations are used to calculate pharmacokinetic parameters. Plasma (K$_3$ EDTA) concentrations are determined using a qualified LC/MS method that measures the intact mass of the Examples. Each Example and an analog as an internal standard are extracted from 100% mouse plasma using immunoaffinity based precipitation with anti-GIP/GLP1 antibodies. Instruments are combined for LC/MS detection. Mean pharmacokinetic parameters are shown in Table 4.

TABLE 4

Mean Pharmacokinetic Parameters of peptides Following a Single Subcutaneous Administration of 200 nMol/kg to Male CD-1 mice (N = 2/timepoint non-serial sampling).

| Example | $T_{1/2}$ (hr) | $T_{max}$ (hr) | $C_{max}$/D (kg * nmol/L/nmol) | AUCINF_D_obs (hr * kg * nmol/L/nmol) | Cl/F (mL/hr/Kg) |
|---|---|---|---|---|---|
| Example 1 | 17.54 | 12 | 4.84 | 135.61 | 7.37 |
| Example 2 | 7.55 | 6 | 5.4 | 77.23 | 12.95 |
| Example 3 | 15.04 | 6 | 4.42 | 158.49 | 6.31 |

Abbreviations:
$T_{1/2}$ = half-life,
$T_{max}$ = time to maximal concentration,
$C_{max}$ = maximal plasma concentration,
AUCINF_D_obs = AUCinf divided by dose,
CL/F = clearance/bioavailability.
Notes:
Data are the mean, where n = 2/timepoint/group.

Results from this study for Examples tested are consistent with an extended pharmacokinetic profile.

Pharmacokinetics in Male Cynomolgus Monkeys

The pharmacokinetics of select Examples are evaluated following a single subcutaneous administration of 50 nMol/kg to male cynomolgus monkeys. Blood samples are collected over 336 hours and resulting individual plasma concentrations are used to calculate pharmacokinetic parameters. Peptide plasma ($K_3$ EDTA) concentrations are determined using a qualified LC/MS method that measured the intact mass of the compound. Each peptide and an analog as an internal standard are extracted from 100% cynomolgus monkey plasma using immunoaffinity based precipitation with anti-GIP/GLG1 antibodies. Instruments are combined for LC/MS detection. Mean pharmacokinetic parameters are shown in Table 5.

TABLE 5

Mean Pharmacokinetic Parameters of peptides Following a Single Subcutaneous Administration of 50 nMol/kg to Male Cynomolgus Monkeys.

| Example | $T_{1/2}$ (hr) | $T_{max}$ (hr) | $C_{max}$/D (kg * nmol/L/nmol) | AUCINF_D_obs (hr * kg * nmol/L/nmol) | Cl/F (mL/hr/Kg) |
|---|---|---|---|---|---|
| Example 1 | 125.0 | 18 | 6.5 | 1458 | 0.69 |
| Example 2 | 102.1 | 24 | 11.7 | 2059 | 0.49 |
| Example 3 | 180.6 | 30 | 11.38 | 3420 | 0.29 |

Abbreviations:
$T_{1/2}$ = half-life,
$T_{max}$ = time to maximal concentration,
$C_{max}$ = maximal plasma concentration,
AUCINF_D_obs = AUCinf divided by dose,
CL/F = clearance/bioavailability.
Notes:
Data are the mean, where n = 2/group.
Notes:
Data are the mean, where n = 2/group.
As seen in Table 5, results from this study for Example peptides tested are consistent with an extended pharmacokinetic profile.

Pharmacokinetics in Male Sprague Dawley Rats Following Subcutaneous or Intrajejunal Administration The pharmacokinetics of select Examples are evaluated following a single subcutaneous (SC) administration of 50 nMol/kg (dissolved in PBS, pH 7.4) or single 1 μmol/kg (mixed with 250 mM sodium decanoate ("C10") and 12 mg/mL soybean trypsin inhibitor (SBTI)) intrajejunal (IJ) administration to male Sprague Dawley rats. Blood samples are collected over 168 hours following SC administration and 72 hours following IJ dosing. Pharmacokinetic parameters are calculated using individual plasma concentrations. A qualified LC/MS method that measures the intact mass of the Example is used to determine plasma ($K_3$ EDTA) concentrations. Each Example is tested with an analog peptide as an internal standard. Immunoaffinity based precipitation with anti-GIP/GLP1 antibodies is used to extract each test peptide and analog. Mean pharmacokinetic parameters for the Examples are shown in Table 6 and Table 7.

TABLE 6

Mean (+/− SD) Pharmacokinetic Parameters of peptides Following a Single Subcutaneous Administration of 50 nMol/kg to Male Sprague Dawley rats.

| Example | $T_{1/2}$ (hr) | $T_{max}$ (hr) | $C_{max}$/D (kg * nmol/L/nmol) | AUCINF_D_obs (hr * kg * nmol/L/nmol) | Cl/F (mL/hr/Kg) |
|---|---|---|---|---|---|
| Example 1 | 44.7 (6.2) | 21.3 (4.6) | 3.34 (0.22) | 294.2 (30.0) | 3.42 (0.33) |
| Example 2 | 20.3 (0.9) | 14.7 (2.3) | 5.19 (0.20) | 231.7 (9.6) | 4.32 (0.17) |
| Example 3 | 32.1 (1.9) | 21.3 (4.6) | 4.71 (0.50) | 371.8 (21.8) | 2.70 (0.16) |

Abbreviations:
$T_{1/2}$ = half-life,
$T_{max}$ = time to maximal concentration,
$C_{max}$ = maximal plasma concentration,
AUCINF_D_obs = AUCinf divided by dose,
CL/F = clearance/bioavailability.
Notes:
Data are the mean, where n = 3/group (Table 6)
As seen in table 6, results from this study using these Example peptides are consistent with an extended pharmacokinetic profile.

TABLE 7

Mean (+/− SD) Pharmacokinetic Parameters of peptides Following a Single Intrajejunal Administration of 1 μmol/kg to Male Sprague Dawley rats.

| Example | $T_{max}$ (hr) | $C_{max}$/D (kg * nmol/L/nmol) | AUCINF_D_obs (hr * kg * nmol/L/nmol) |
|---|---|---|---|
| Example 1 | 1.33 (0.82) | 0.08 (0.05) | 1.31 (0.85) |
| Example 2 | 0.25 (0.13) | 0.56 (0.40) | 6.6 (4.4) |
| Example 3 | 0.33 (0) | 0.47 (0.16) | 8.45 (3.1) |

Data are the mean, where n=3/group n=6/group (Table 7).

As illustrated by results in Table 7, these Examples are consistent with an exposure following intrajejunal administration. Intrajejunal exposure in this assay supports that the Examples may be suitable for oral formulation and administration.

In Vivo Effect on Insulin Secretion in Male Wistar Rats

Male Wistar rats with femoral artery and femoral vein canulas (Envigo, Indianapolis, Ind.) (280-320 grams) are single-housed in polycarbonate cages with filter tops. Rats maintained on a 12:12 h light-dark cycle (lights on at 6:00 A. M.) at 21° C. and receive food and deionized water ad libitum. Rats are randomized by body weight and dosed 1.5 ml/kg s.c. at doses of 0.04, 0.1, 0.3, 1, 3, and 10 nmol/kg 16 hours prior to glucose administration then fasted. Animals are weighed and anesthetized with sodium pentobarbital dosed i.p. (65 mg/kg, 30 mg/ml). A time 0 blood sample is collected into EDTA tubes after which glucose is administered i.v. (0.5 mg/kg, 5 ml/kg). Blood samples are collected for glucose and insulin levels at time 2, 4, 6, 10, 20 and 30 min post intravenous administration of glucose. Plasma glucose levels are determined using a clinical chemistry analyzer. Plasma insulin is determined using an electrochemiluminescence assay (Meso Scale, Gaithersburg, Md.). Glucose and insulin AUC are examined compared to the vehicle control with n=5 animals per group. Results are presented (SEM)(N).

TABLE 8

The effect of Example compounds on insulin secretion during intravenous glucose tolerance test.
Dose (nmol/kg, s.c.)

| Example | 0.0 | 0.04 | 0.1 | 0.3 | 1.0 | 3 | 10 |
|---|---|---|---|---|---|---|---|
| 1 | 31.3 (2.8) (5) | 32.2 (5.7) (5) | 31.5 (4.5) (5) | 24.7 (3.0) (5) | 35.1 (4.0) (5) | 43.5 (4.9) (5) | 63.9 (6.5) (5) |
| 2 | 18.9 (4.3) (5) | 32.8 (3.9) (5) | 49.1 (4.8) (5) | 82.2 (21.1) (5) | 110.9 (23.1) (5) | 108.2 (20.2) (5) | 77.3 (8.8) (5) |
| 3 | 18.5 (1.0) (5) | 26.0 (3.4) (5) | 24.6 (3.9) (5) | 44.9 (9.6) (5) | 60.1 (4.0) (5) | 95.5 (18.4) (5) | 87.7 (7.9) (5) |
| 4 | 33.7 (5.3, 5) | 34.0 (3.4, 5) | 42.0 (3.8, 5) | 86.3 (4.5, 5) | 90.2 (9.2, 5) | 108.7 (9.8, 5) | 114.6 (16.1, 5) |
| 5 | 24.4 (3.0, 5) | 28.2 (4.2, 5) | 40.2 (6.0, 5) | 41.1 (2.7, 5) | 44.1 (4.5, 5) | 54.3 (11.9, 5) | 94.2 (10.1, 5) |

The data provided by Table 8 demonstrate a dose dependent increase in insulin secretion.

TABLE 9 ivGTT Insulin Secretion shown by the following data:
Insulin secretion (ivGTT)

| Example | (ED$_{50}$, nmol/kg) (SEM, n) |
|---|---|
| 1 | >10 |
| 2 | 0.1 (0.05, 5) |
| 3 | 0.7 (0.3, 5) |
| 4 | 0.2 (0.05, 5) |
| 5 | 3 < ED$_{50}$ < 10 |

The data provided by Table 9 demonstrate dose dependent increase in insulin secretion.

Studies in Diet-Induced Obese C57/Bl6 Mice

C57/Bl6 diet-induced obese (DIO) male mice (Taconic, Germantown, N.Y.) weighing 41-50 g are used. Animals are individually housed in a temperature-controlled (24° C.) facility with a 12 hour light/dark photoperiod (lights off at 10:00 A M and lights on at 10:00 PM), with free access to food and water. After 2 week acclimatization to the facility, mice are randomized to treatment groups (n=6/group) based on body weight so each group has similar starting mean body weight.

Mice are treated with either vehicle (40 mM Tris-HCl at pH 8.0) or several peptides between the dose ranges of 0.03 nmol/kg to 10 nmol/kg. Treatments are subcutaneously administered to ad libitum fed DIO mice 30-90 minutes prior to the onset of the dark cycle daily (QD) for 14 days. During the course of the study, body weight and food intake are monitored daily.

All data are expressed as mean±SEM of 5-6 rats per group. Statistical analyses are assessed by one-way ANOVA followed by Dunnett's multiple comparison test to compare treatment groups to vehicle group or each other. Significant differences are identified at p<0.05.

$$\text{Percent Body Weight} = \frac{\text{Body weight after 14-day treatment}}{\text{Body weight before treatment started}} \times 100$$

"0" dose group represents the vehicle-treated mice during each study. All data are expressed as mean±SEM of 5-6 mice per group. Statistical analyses are assessed by one-way ANOVA followed by Dunnett's multiple comparison test to compare treatment groups to '0' dose (vehicle). *Significant differences are identified at p<0.05. Body weight change after treatment with Example compounds after 15 days. "Δ from vehicle" refers to difference between body weight at day 15 between test and vehicle groups. "% change" refers to percent decrease in body weight between days 1 and 15 in test groups. Percent decrease in body weight for animals receiving vehicle is recorded, and is less than about 1% in each study. The Δ from vehicle and % change data are statistically significantly different (p<0.05) than control for all Examples at all doses tested.

The samples are diluted 100 times using dilution buffer (1:1 of 1% TFA in 50% ACN: 50 mM Tris pH8) and ready for analysis using mass spectrometry (MS).

Sample preparation when pig small intestinal fluid (pSIF) is used:

Peptides are diluted to a concentration of 0.4 mg/mL in 90% pig small intestinal fluid. After the mixing, 20 μL are immediately removed (time 0 for the time point of pre-incubation). The mixture is then incubated at 37° C. at 150 rpm. Twenty μL of each sample are removed and placed into a new tube at 30, 45, and 60 min. At each time point (0, 30, 45, 60), the reaction is quenched by 1% TFA in 50% ACN at 1:1. The sample is centrifuged at 20,000×g for 20 min at 4° C. The supernatant is diluted 100 times using dilution buffer (1:1 of 1% TFA in 50% ACN: 50 mM Tris pH 8) and ready for analysis using mass spectrometry (MS).

MS Conditions: The liquid chromatography separation is carried out on a Waters Acquity UPLC using mobile phase A (0.1% formic acid in water) and B (0.1% formic acid in acetonitrile and an ACQUITY UPLC Protein BEH C4 Column (300 Å, 1.7 μm, 1 mm×50 mm) at 40° C. The gradient is 5% of B during 0-1.5, 5-90% of B during 1.5-1.8, 90-95% of B during 1.8-3.0, 95-95% of B during 3.0-3.5, 95-5% of B during 3.5-4.0, and 5-5% of B during 4.0-5.0. The MS analysis is carried out on a Waters Xevo G2-XS QTOF. The data is acquired using MSe Continuum in the range of 50-2000 m/z in positive and sensitivity mode. The data analysis is performed using MassLynx.

TABLE 10

The effect of GIP/GLP-1 receptor co-agonists on percent body weight in diet-induced obese mice after 14-day of treatment.

| Peptide | Dose (nmol/kg, s.c., QD) | | | | | | |
|---|---|---|---|---|---|---|---|
| | 0 | 0.03 | 0.1 | 0.3 | 1 | 3 | 10 |
| Example 1 | 99.2 ± 0.8 | 96.2 ± 1.2 | 95.6 ± 0.9 | 86.7 ± 1.3* | 86.3 ± 1.9* | 74.0 ± 3.8* | 64.7 ± 2.6* |
| Example 2 | 100.5 ± 1.4 | 101.5 ± 0.2 | 95.0 ± 1.2 | 86.5 ± 0.8* | 76.4 ± 4.0* | 76.4 ± 2.4* | 68.1 ± 3.1* |
| Example 3 | 98.0 ± 0.7 | 99.1 ± 1.3 | 95.6 ± 1.3 | 93.0 ± 1.1 | 85.6 ± 0.8* | 75.9 ± 4.3* | 73.6 ± 1.7* |
| Example 4 | 98.3 ± 1.1 | 96.6 ± 0.5 | 94.7 ± 1.8 | 88.5 ± 1.2* | 76.9 ± 1.4* | 66.6 ± 3.9* | 64.5 ± 2.2* |
| Example 5 | 98.3 ± 1.1 | 96.0 ± 1.3 | 96.7 ± 1.1 | 94.1 ± 1.8 | 82.4 ± 1.6* | 83.8 ± 1.6* | 74.9 ± 2.3* |
| Example 104 | 99.2 ± 0.8 | 94.0 ± 0.6 | 94.1 ± 0.8 | 89.0 ± 0.9* | 82.7 ± 1.5* | 70.8 ± 4.2* | 71.3 ± 4.1* |
| Example 123 | 99.2 ± 0.8 | 94.7 ± 0.9 | 90.5 ± 1.6* | 86.5 ± 1.1* | 81.3 ± 2.0* | 75.1 ± 1.8* | 68.6 ± 1.9* |

As illustrated by data provided in Table 10 above, Example compounds tested in the assay dose-dependently reduce body weight in the studies described.

Proteolytic Stability Assay

The proteolytic stability assay is a useful for assessing potential for oral delivery of peptides. The stability of peptides are compared in 1% rat small intestinal fluid (rSIF). The amount of intact peptide is measured for a sample peptide at 0, 3, 15, and 30 minutes to assess proteolytic stability. The amount of intact peptide for a sample peptide is measured in 90% pig small intestinal fluid (pSIF) at 0, 30, 45, and 60 minutes to assess the proteolytic stability.

Sample preparation when rat small intestinal fluid (rSIF) is used:

Peptides are prepared at 0.4 mg/mL in 50 mM Tris pH8.0. Rat small intestinal fluid is added at a ratio of 1% (v/v). The mixture is incubated at 37° C. at 150 rpm. Thirty μL of each sample are removed and placed into a new tube before the rSIF is added and at 3, 15, and 60 min. At each time point, the reaction was quenched by 1% TFA in 50% ACN at 1:1.

TABLE 11

The percentage of each peptide not cleaved at different time points using rSIF.

| | 0 min | 3 min | 15 min | 60 min |
|---|---|---|---|---|
| Example 1 | 100 | 82.4 | 41.4 | 1.6 |
| Example 2 | 100 | 75.5 | 18.3 | 0.3 |
| Example 3 | 100 | 68.8 | 25.8 | 0.3 |
| Example 4 | 100 | 97.9 | 99.3 | 89.4 |
| Example 69 | 100 | 2.2 | 0.0 | 0.0 |

The proteolytic peptide results provided in Table 11 suggest that the peptide of Example 4 may be suitable for oral formulation and delivery.

TABLE 12

The percentage of each peptide not cleaved at different time points using pSIF.

|  | 0 min | 30 min | 45 min | 60 min |
|---|---|---|---|---|
| Example 4 | 100 | 73.4 | 56.4 | 60.0 |
| Example 5 | 100 | 76.9 | 56.8 | 60.7 |

The proteolytic peptide results provided in Table 12 suggest that both the peptides of Examples 4 and 5 may be suitable for oral formulation and delivery.

In Vivo Studies

The purpose of this study is to determine the relative potential for clinical immunogenicity of a compound.

Methods:

CD8+ T cell depleted peripheral blood mononuclear cells are prepared and labeled with Carboxyfluorescein Diacetate Succinimidyl Ester (CFSE, Invitrogen) from a cohort of 10 healthy donors. Samples are tested in triplicate with 2.0 mL media control, keyhole limpet hemocyanin ("KLH") (0.33 µM), anti-chemokine receptor type 4 ("CD4+") (0.33 µM), and a compound of Examples 1, 2, and 3 (10 µM). Cultures are incubated for 7 days at 37° C. with 5% $CO_2$. On day 7, samples are analyzed by flow cytometry using High Throughput Sampler (HTS). Data is analyzed using FlowJo® Software (FlowJo, LLC, TreeStar).

Results and Discussion

All donors produce a positive T cell response against KLH (100%). Analysis of the frequency and magnitude of the CD4+ T cell response for Example compounds is shown in Table 13.

TABLE 13

CD4+ T Cell Responses for Example compounds and Positive Control (KLH).

|  | % Donor Response | Median Response Strength in positive donors (CDI) |
|---|---|---|
| KLH | 100% (n = 11) | 391 (n = 10) |
| Example 1 (GG-212) | 9% (n = 11) | 0.7 (n = 1) |
| Example 2 (GG-353) | 22% (n = 9) | 3.68 (n = 2) |
| Example 3 (GG-362) | 0% (n = 9) | NA (n = 0) |
| Example 4 (GG-427) | 0% (n = 9) | NA (n = 0) |
| Example 288 (GG-709) | 10% (n = 10) | 5.42 (n = 1) |
| Example 289 (GG-731) | 0% (n = 10) | NA (n = 0) |
| Example 301 (GG-650) | 0% (n = 10) | NA (n = 0) |
| Example 303 (GG-679) | 0% (n = 10) | NA (n = 0) |
| Example 316 (GG-698) | 0% (n = 10) | NA (n = 0) |

Cell Division Index ("CDI"): proportion of divided CD4+ T cells to the total number of CD4+ T cells in stimulated versus unstimulated samples.

These data show that the frequency of positive CD+ T cell response (CDI>2.5) was low for the compounds of Examples 1, 2, 3, 4, 288, 289, 301, 303 and 316, and the magnitude of the response in the few positive donors was low (CDI<6), indicating a low risk of immunogenicity using the CD4+ T cell assay.

GLP-1R HEK293 Cell Membrane [$^{35}$S]GTPγS Binding Assay

The GLP-1 receptor is a G-protein coupled receptor that increases GTP-bound $G\alpha_s$ upon ligand induced receptor activation. The potency of peptides to stimulate-GLP-1R induced activation of $G\alpha_s$ is determined using preparations of purified membranes from HEK293 cells expressing the human GLP-1R. The assay is performed similarly to that as previously described (Bueno et al., J. Biol. Chem., (2016) 291, 10700 and Willard et al., Mol. Pharmacol. (2012) 82, 1066). The test peptides are solubilized in DMSO and diluted in reaction buffer containing 5 µg of membrane in 20 mM HEPES pH 7.4, 50 mM NaCl, 5 mM $MgCl_2$, 40 µg/ml saponin, 0.1% BSA, and 500 pM $^{35}$S-labeled GTPγS for 30 minutes at room temperature. Reactions are terminated by addition of 0.2% Nonidet P-40 detergent containing rabbit anti-Gas polyclonal antibody and 0.5 mg of anti-rabbit polyvinyltoluene beads. Mixtures are developed for 30 minutes, centrifuged at 80×g for 10 minutes, and counted for 1 minute/well using a MicroBeta TriLux instrument. Peptide concentration-response curves are fit to a four-parameter logistic model to calculate potency as an $EC_{50}$. Data normalization to % stimulation is performed using DMSO and GLP-1(7-36) as minimum and maximum controls for the receptor (Campbell et al, Assay Guidance Manual 2017). The potency of a sample peptide to stimulate GIPR induced activation of $G\alpha_s$ is reported in the Table 14. Assay results identify a peptide that is a partial agonist on the GLP-1R with respect to GLP-1R induced activation of $G\alpha_s$.

GLP-1R CHO Cell β-Arrestin Recruitment Assay

Activated G-protein coupled receptors can interact with the β-arrestin family of signalling proteins. The potency of peptides for GLP-1R induced arrestin recruitment is determined using the PathHunter Enzyme Fragment Complementation approach substantially as described (von Degenfeld et al., FASEB J., 2007 (14):3819-26 and Hamdouchi et al., J. Med Chem., 2016 59(24): 10891-10916). CHO-K1 cells expressing Pro-Link-tagged Human GLP-1R and enzyme-acceptor-tagged β-arrestin-2 may be obtained from DiscoveRx and prepared as assay-ready frozen cells. Test peptides are solubilized in DMSO and serial dilutions are performed using the Echo acoustic dispenser (LabCyte). Assay media is the PathHunter Cell Assay Buffer (DiscoveRx) containing 0.1% w/v hydrolyzed Casein (Sigma). 100 nl of peptide is dispensed into 10 µl of assay media in a 384 well plate and then 10 µl of cells in assay media are added to give 5000 cells per well. Plates are incubated for 90 minutes in a 37'C/5% C02 incubator and 10 µl of PathHunter detection reagent is added (DiscoveRx) and plates are incubated at room temperature for 60 minutes. Luminescence signal is measured. Peptide concentration-response curves fit to a four-parameter logistic model to calculate potency as an $EC_{50}$. Data normalization to % stimulation is performed using DMSO and GLP-1(7-36) as minimum and maximum controls (Campbell et al, Assay Guidance Manual 2017). The potency of a sample peptide to stimulate GLP-1R induced β-arrestin recruitment is reported in Table 14. The assay results identify a peptide that is a partial agonist on the GLP-1R with respect to β-arrestin-2 recruitment.

TABLE 14

| Example | hGLP1R GTPgS Rel EC50 nM (SEM, n) | hGLP1R GTPgS % Top (SEM, n) | hGLP1R B-Arrestin2 Rel EC50 uM (SEM, n) | hGLP1R B-Arrestin2% Top (SEM, n) |
|---|---|---|---|---|
|  | 0.475 (0.0322, n = 115) | 99.2 (0.659, n = 115) | 0.00274 (0.000359, n = 42) | 104 (3.45, n = 42) |
| 1 | 0.235 (0.0201, n = 5) | 91.1 (1.77, n = 5) | 0.005 | 105 |
| 2 | 0.642 (0.0294, n = 2) | 95.9 (0.553, n = 2) | 0.00882 (0.00269, n = 2) | 96.1 (0.742, n = 2) |
| 3 | 0.421 (0.181, n = 2) | 95.4 (2.20, n = 2) |  |  |
| 4 | 0.245 (0.0638, n = 3) | 86.9 (5.93, n = 3) | 0.00480 (0.000138, n = 2) | 92.4 (14.0, n = 2) |
| 5 | 0.196 (0.0375, n = 3) | 91.3 (6.90, n = 3) |  |  |
| 266 | 0.865 (0.328, n = 2) | 63.4 (1.31, n = 2) | 0.016 | 17.1 |
| 267 | 0.867 | 62.3 | 0.00901 | 16.5 |
| 272 | 0.651 (0.0427, n = 2) | 66.5 (0.741, n = 2) | >12.0 | ND |
| 298 | 1.03 | 57.3 |  |  |
| 300 | 0.405 | 85.6 | 0.0054 | 38.4 |
| 301 | 0.435 (0.0848, n = 3) | 91.4 (3.63, n = 3) | 0.00267 | 93.7 |
| 302 | 0.268 | 98.6 | 0.00219 | 98.4 |
| 303 | 0.547 (0.0998, n = 2) | 74.3 (2.99, n = 2) | 0.0179 | 47.7 |
| 304 | 0.561 | 77.1 |  |  |
| 305 | 0.389 | 76.3 |  |  |
| 306 | 0.378 | 76.1 |  |  |
| 315 | 0.601 | 44.2 | 0.0199 | 25.4 |
| 316 | 0.766 (0.0469, n = 2) | 56.7 (3.14, n = 2) | 0.00608 | 26.1 |
| 317 | 0.536 | 53.7 |  |  |
| 318 | 0.415 | 58.4 |  |  |
| 288 | 0.666 (0.104, n = 3) | 66.7 (4.09, n = 3) | 0.00674 (0.00278, n = 3) | 21.3 (1.94, n = 3) |
| 319 | 0.657 | 65.7 |  |  |
| 323 | 0.79 | 81.9 |  |  |
| 324 | 0.475 | 84.5 |  |  |
| 289 | 0.404 (0.0247, n = 3) | 83.7 (3.81, n = 3) | 0.0124 (0.00151, n = 3) | 51.3 (6.05, n = 3) |
| 325 | 0.414 | 97.9 |  |  |
| 326 | 0.663 | 61.6 |  |  |
| 327 | 0.287 | 75.6 | 0.00379 | 41.6 |
| 328 | 0.481 | 66.3 |  |  |
| 329 | 0.343 | 83.6 | 0.00473 | 63.4 |
| 330 | 1.05 (0.275, n = 2) | 47.8 (1.16, n = 2) | >10.9 | ND |
| 331 | 0.375 (0.0274, n = 4) | 80.9 (2.54, n = 4) | 0.0128 | 44.3 |
| 332 | 0.453 (0.0479, n = 4) | 81.5 (4.65, n = 4) | 0.0171 | 45.6 |
| 333 | 0.442 (0.00535, n = 2) | 83.4 (0.439, n = 2) | 0.0548 | 58.2 |
| 334 | 0.432 | 70.2 | >10.3 | ND |
| 335 | 0.285 | 89.3 | 0.00531 | 73 |
| 336 | 0.377 | 90.2 | 0.00778 | 82.5 |
| 290 | 0.466 (0.0664, n = 9) | 66.2 (3.12, n = 9) | 0.0238 (0.00530, n = 4) | 20.0 (1.15, n = 4) |
| 337 | 0.322 | 59.5 | 0.0174 | 34.1 |
| 338 |  |  | 0.0189 | 47 |
| 339 | 0.326 (0.0357, n = 3) | 74.1 (7.97, n = 3) | 0.0107 (0.00238, n = 2) | 44.0 (2.40, n = 2) |
| 340 | 0.450 (0.0182, n = 5) | 67.4 (5.12, n = 5) | 0.0107 (0.00711, n = 4) | 20.1 (2.31, n = 4) |
| 341 | 0.496 | 78.9 | 0.0188 | 21.9 |
| 342 | 0.414 | 77.2 | 0.035 | 20.7 |
| 343 | 0.522 | 74.9 | 0.0455 | 41.4 |
| 344 | 0.423 | 85.8 | 0.0343 | 46 |
| 345 | 0.684 | 62 | 0.00308 (0.000666, n = 2) | 74.7 (2.86, n = 2) |
| 346 | 0.737 (0.201, n = 3) | 56.6 (3.94, n = 3) | 0.00325 (0.00105, n = 3) | 19.3 (0.767, n = 3) |
| 347 | 0.759 | 46.9 | 0.00542 (0.00152, n = 2) | 24.6 (2.81, n = 2) |

TABLE 14-continued

| | | | | |
|---|---|---|---|---|
| 348 | 0.66 | 47.7 | 0.00346 (n = ½) | 19.8 |
| 349 | 0.464 (0.0290, n = 4) | 64.5 (1.68, n = 4) | 0.0151 (0.00111, n = 2) | 18.4 (0.337, n = 2) |
| 350 | 0.589 | 64.1 | 0.0108 | 21.8 |
| 351 | 0.563 | 66.5 | 0.0196 | 23.5 |
| 352 | 0.552 (0.0267, n = 2) | 63.5 (1.51, n = 2) | 0.00421 (n = ½) | 17.4 |
| 353 | 1.96 | 63.1 | 0.559 (0.108, n = 2) | 23.0 (0.408, n = 2) |
| 291 | 0.466 (0.0476, n = 6) | 65.0 (2.15, n = 6) | >10.0 (n = ¼) | ND |
| 354 | 0.967 | 53.3 | 0.255 (n = ½) | 22.7 |
| 355 | 1.76 | 50.6 | 0.363 | 18.3 |
| 356 | | | >10.5 | ND |
| 357 | | | 0.118 | 18.2 |
| 358 | 0.414 (0.00356, n = 2) | 72.3 (1.27, n = 2) | 0.00938 (0.00413, n = 3) | 21.4 (2.47, n = 3) |
| 359 | 0.496 | 69.7 | 0.0841 | 28.4 |
| 360 | | | 0.0395 | 25.8 |
| 361 | | | 0.269 (n = ½) | 20.2 |
| 362 | | | >11.0 | ND |
| 363 | 0.943 | 69.6 | 0.135 | 22.1 |
| 364 | | | >12.0 | ND |
| 292 | 0.429 (0.0190, n = 4) | 71.5 (3.33, n = 4) | 0.00774 (0.00199, n = 4) | 29.0 (3.96, n = 4) |
| 293 | 0.368 (0.0304, n = 4) | 70.6 (0.715, n = 4) | 0.00719 (0.00168, n = 4) | 29.5 (6.23, n = 4) |
| 365 | 0.464 (0.0178, n = 3) | 66.9 (1.35, n = 3) | 0.00703 (0.00233, n = 4) | 20.8 (1.78, n = 4) |
| 366 | 0.409 (0.0308, n = 3) | 67.6 (3.55, n = 3) | 0.00557 (0.00363, n = 2) | 21.2 (0.163, n = 2) |
| 367 | 0.289 | 89.7 | 0.00666 (0.00118, n = 2) | 70.6 (8.61, n = 2) |
| 368 | 0.495 | 68.9 | 0.0479 (0.0205, n = 2) | 21.3 (4.03, n = 2) |
| 369 | 0.381 | 58.8 | 0.0414 (n = ½) | 19.9 |
| 370 | 0.428 | 63.7 | 0.00990 (0.00149, n = 2) | 23.0 (0.470, n = 2) |
| 371 | 0.27 | 62.5 | 0.0142 (0.00333, n = 2) | 21.7 (0.711, n = 2) |
| 372 | 0.379 | 69.1 | 0.00981 (0.00630, n = 2) | 32.9 (1.65, n = 2) |
| 373 | 0.336 | 65.6 | 0.00954 (0.00348, n = 2) | 22.9 (5.88, n = 2) |
| 374 | 0.345 | 67.1 | 0.0218 | 34.7 |
| 375 | 0.419 | 70.4 | 0.0114 | 24.2 |
| 376 | 0.326 | 72.6 | 0.0123 | 25.6 |
| 377 | 0.356 | 68.4 | 0.00532 | 16.7 |
| 378 | 0.359 | 68.6 | >10.2 | ND |
| 379 | 0.239 | 71 | 0.0181 | 31.9 |
| 380 | 0.188 | 66.8 | 0.0137 | 35 |
| 381 | 0.273 | 73.6 | 0.0155 | 25.8 |
| Comparator Tirzepatide | 0.442 (se = 0.0311, n = 9( | 62.9 (se = 1.28, n = 9) | >10.5 (n = ⅓) | ND |

| Example | hGLP1R B-Arrestin2 Rel EC50 uM (SEM, n) | hGLP1R B-Arrestin2 % Top (SEM, n) |
|---|---|---|
| | 0.00274 (0.000359, n = 42) | 104 (3.45, n = 42) |
| 1 | 0.005 | 105 |
| 2 | 0.00882 (0.00269, n = 2) | 96.1 (0.742, n = 2) |
| 3 | | |
| 4 | 0.00480 (0.000138, n = 2) | 92.4 (14.0, n = 2) |
| 266 | 0.016 | 17.1 |
| 267 | 0.00901 | 16.5 |
| 272 | >12.0 | ND |
| 300 | 0.0054 | 38.4 |
| 301 | 0.00267 | 93.7 |
| 302 | 0.00219 | 98.4 |
| 303 | 0.0179 | 47.7 |
| 315 | 0.0199 | 25.4 |

TABLE 14-continued

| | | |
|---|---|---|
| 316 | 0.00608 | 26.1 |
| 288 | 0.00674 | 21.3 |
| | (0.00278, n = 3) | (1.94, n = 3) |
| 289 | 0.0124 | 51.3 |
| | (0.00151, n = 3) | (6.05, n = 3) |
| 327 | 0.00379 | 41.6 |
| 329 | 0.00473 | 63.4 |
| 330 | >10.9 | ND |
| 331 | 0.0128 | 44.3 |
| 332 | 0.0171 | 45.6 |
| 333 | 0.0548 | 58.2 |
| 334 | >10.3 | ND |
| 335 | 0.00531 | 73 |
| 336 | 0.00778 | 82.5 |
| 290 | 0.0238 | 20.0 |
| | (0.00530, n = 4) | (1.15, n = 4) |
| 337 | 0.0174 | 34.1 |
| 338 | 0.0189 | 47 |
| 339 | 0.0107 | 44.0 |
| | (0.00238, n = 2) | (2.40, n = 2) |
| 340 | 0.0107 | 20.1 |
| | (0.00711, n = 4) | (2.31, n = 4) |
| 341 | 0.0188 | 21.9 |
| 342 | 0.035 | 20.7 |
| 343 | 0.0455 | 41.4 |
| 344 | 0.0343 | 46 |
| 345 | 0.00308 | 74.7 |
| | (0.000666, n = 2) | (2.86, n = 2) |
| 346 | 0.00325 | 19.3 |
| | (0.00105, n = 3) | (0.767, n = 3) |
| 347 | 0.00542 | 24.6 |
| | (0.00152, n = 2) | (2.81, n = 2) |
| 348 | 0.00346 | 19.8 |
| | (n = ½) | |
| 349 | 0.0151 | 18.4 |
| | (0.00111, n = 2) | (0.337, n = 2) |
| 350 | 0.0108 | 21.8 |
| 351 | 0.0196 | 23.5 |
| 352 | 0.00421 | 17.4 |
| | (n = ½) | |
| 353 | 0.559 | 23.0 |
| | (0.108, n = 2) | (0.408, n = 2) |
| 291 | >10.0 | ND |
| | (n = ¼) | |
| 354 | 0.255 | 22.7 |
| | (n = ½) | |
| 355 | 0.363 | 18.3 |
| 356 | >10.5 | ND |
| 357 | 0.118 | 18.2 |
| 358 | 0.00938 | 21.4 |
| | (0.00413, n = 3) | (2.47, n = 3) |
| 359 | 0.0841 | 28.4 |
| 360 | 0.0395 | 25.8 |
| 361 | 0.269 | 20.2 |
| | (n = ½) | |
| 362 | >11.0 | ND |
| 363 | 0.135 | 22.1 |
| 364 | >12.0 | ND |
| 292 | 0.00774 | 29.0 |
| | (0.00199, n = 4) | (3.96, n = 4) |
| 293 | 0.00719 | 29.5 |
| | (0.00168, n = 4) | (6.23, n = 4) |
| 365 | 0.00703 | 20.8 |
| | (0.00233, n = 4) | (1.78, n = 4) |
| 366 | 0.00557 | 21.2 |
| | (0.00363, n = 2) | (0.163, n = 2) |
| 367 | 0.00666 | 70.6 |
| | (0.00118, n = 2) | (8.61, n = 2) |
| 368 | 0.0479 | 21.3 |
| | (0.0205, n = 2) | (4.03, n = 2) |
| 369 | 0.0414 | 19.9 |
| | (n = ½) | |
| 370 | 0.00990 | 23.0 |
| | (0.00149, n = 2) | (0.470, n = 2) |
| 371 | 0.0142 | 21.7 |
| | (0.00333, n = 2) | (0.711, n = 2) |
| 372 | 0.00981 | 32.9 |
| | (0.00630, n = 2) | (1.65, n = 2) |
| 373 | 0.00954 | 22.9 |
| | (0.00348, n = 2) | (5.88, n = 2) |

TABLE 14-continued

| | | |
|---|---|---|
| 374 | 0.0218 | 34.7 |
| 375 | 0.0114 | 24.2 |
| 376 | 0.0123 | 25.6 |
| 377 | 0.00532 | 16.7 |
| 378 | >10.2 | ND |
| 379 | 0.0181 | 31.9 |
| 380 | 0.0137 | 35 |
| 381 | 0.0155 | 25.8 |

Composition for Oral Administration

A peptide is dissolved in Tris buffer (pH 8.0, 50 mM). A Permeation enhancer ("PE") is prepared as follows: C10 is dissolved in Tris buffer (pH 8.0, 50 mM), LC, DPC, C12-maltoside and Rhamnolipid are each dissolved in phosphate buffered saline ("PBS") (1×, pH 7.2). A solution of peptide, a PE, and a protease inhibitor is mixed to reach a final peptide concentration of 300 uM, PE at 100 mM (5% w/v for Rhamnolipid) and 1% (v/v) for the protease inhibitor.

A peptide is incubated at 37° C. in 1% (v/v) rat small intestinal fluid or 50% (v/v) pig small intestinal fluid with and without a peptidase inhibitor. At different time points, samples are taken out, followed by quenching with 1% TFA in 50% ACN/water to stop the enzyme activity. The intact peptide at different time points is analyzed by high-performance liquid chromatography (HPLC) equipped with an ultraviolet (UV) detector or LC-MS/MS and normalized to the amount of peptide before mixing with the enzyme solution. A study using a peptide of Example 2 and a peptide of Example 4 are reported in Table 15.

TABLE 15

| | | % peptide intact | | | |
|---|---|---|---|---|---|
| Recombinant protease inhibitor (concentration) | Small intestinal fluid | 0 min | 15 min | 30 min | 60 min |
| rSBTI (5 mg/mL) + Peptide (Example 4) | 50% v/v pig | 100.00 | 96.96 | 96.28 | 88.57 |
| Peptide Example 4 (no PI; control) | 50% v/v pig | 100.00 | 72.52 | 41.44 | 18.98 |
| rSBTI (5 mg/mL) + Peptide Example 2 | 50% v/v pig | 100.00 | 103.02 | 112.69 | 87.33 |
| Peptide Example 2 (no PI; control) | 50% v/v pig | 100.00 | 2.42 | 1.90 | 3.09 |
| rSBTCI (0.5 mg/mL) + Peptide Example 2 | 50% v/v pig | 100.00 | 131.71 | 126.53 | 123.70 |

Table 15 results support that an oral formulation composition for a peptide of Example 4 may be prepared using a PE and no PI.

Oral Formulation Composition

Examples of formulation compositions for a peptide of this invention are provided by Table 16. The formulation compositions for peptides of this invention are in no way limited by the examples provided.

TABLE 16

| Formulation | Formulation composition | Concentration |
|---|---|---|
| 1 | Peptide (Example 1; or Example 4 or Example 3) | 2.4 mg/mL |
| | C10 | 250 mM |
| | SBTI | 75 mg/mL |
| 2 | Peptide (Example 1) | 2.4 mg/mL |
| | LC | 500 mM |
| | Citric acid | 500 mM |
| 3 | Peptide (Example 1) | 2.4 mg/mL |
| | NaTDC | 250 mM |
| | SBTI | 75 mg/mL |
| 4 | Peptide (Example 1, Example 2, or Example 4) | 2.4 mg/mL |
| | C10 | 250 mM |
| | SBTI | 12 mg/mL |

TABLE 16-continued

| Formulation | Formulation composition | Concentration |
|---|---|---|
| 5 | Peptide (Example 1 or Example 2) | 2.4 mg/mL |
| | C10 | 125 mM |
| | SBTI | 12 mg/mL |
| 6 | Peptide (Example 1) | 2.4 mg/mL |
| | C10 | 125 mM |
| | SBTI | 24 mg/mL |
| 7 | Peptide (Example 4) | 2.4 mg/mL |
| | C10 | 250 mM |
| | SFTI | 12 mg/mL |

The effect of formulation composition on a peptide exposure is evaluated in rats via intrajejunal (IJ) administration using liquid formulations. To prepare liquid formulations for a rat IJ administration, a peptide, C10 or NaTDC and SBTI is dissolved in 50 mM Tris buffer pH 8.0 and mixed to achieve final desired concentration. For LC/citric acid formulation, LC and citric acid are dissolved in water and mixed with a peptide dissolved in Tris buffer. Formulation compositions provided in Table 16 may be administered as an oral composition.

Enteric Capsules

An enteric capsule composition may be desired for certain peptides of this invention and may be prepared using methods for example, as set forth by Table 17. Enteric compositions may be prepared by blending ingredients together and filling the blend in enteric capsules.

An enteric composition of Table 17 is prepared adding half of the stated amount of sodium decanoate to a mortar. SBTI (for Examples 382-385) or SFTI (for Examples 386 and 387), and a peptide (peptides of Examples 1-4), as shown in Table 17. A remaining half of the sodium decanoate is added. A mixture is gently blended together using pestle, and spatula. If desired, additional mixing using pestle provides a homogenous blend. A capsule may be manually filled by individually weighing the required amount of blend, filling in capsules, and securely closing the capsule caps to the capsule bodies.

Dissolution testing of a single capsule is completed using known methods. A peptide of this invention may be formulated as an entric oral composition.

TABLE 17

Composition of Individual Enteric Capsule for Formulation

| Peptide Component | Enteric Example 382 | Enteric Example 383 | Enteric Example 384 | Enteric Example 385 | Enteric Example 386 | Enteric Example 387 |
|---|---|---|---|---|---|---|
| Example 2 | 12.50 | | | | 12.50 | |
| Example 4 | | 12.50 | | | | 12.50 |
| Example 1 | | | 12.50 | | | |
| Example 3 | | | | 12.50 | | |
| Sodium decanoate (C10) | 250.00 | 250.00 | 250.00 | 250.00 | 250.00 | 250.00 |
| SBTI | 62.50 | 62.50 | 62.50 | 62.50 | | |
| SFTI | | | | | 62.50 | 62.50 |
| Total Capsule Fill Weight | 325.00 | 325.00 | 325.00 | 325.00 | 325.00 | 325.00 |
| Capsule Size | Size 00 | Size 00 | Size 00 | Size 00 | Size 00 | Size 00 |

Amino Acid Sequences

GIP (Human)
SEQ ID NO: 1
YAEGTFISDYSIAMDKIHQQDFVNWLLAQKGKKNDWKHNITQ

GLP-1 (7-36) (Human)
SEQ ID NO: 2
HAEGTFTSDVSSYLEGQAAKEFIAWLVKGR-NH$_2$

SEQ ID NO: 3
R$_1$X$_1$X$_2$X$_3$GTX$_6$TSDX$_{10}$X$_{11}$X$_{12}$X$_{13}$X$_{14}$DX$_{16}$X$_{17}$AX$_{19}$X$_{20}$X$_{21}$X$_{22}$X$_{23}$X$_{24}$X$_{25}$X$_{26}$X$_{27}$X$_{28}$X$_{29}$X$_{30}$X$_{31}$

SEQ ID NO: 4
PX$_{32}$X$_{33}$X$_{34}$-R$_2$

SEQ ID NO: 5
PX$_{32}$X$_{33}$X$_{34}$X$_{35}$X$_{36}$X$_{37}$X$_{38}$X$_{39}$-R$_2$

SEQ ID NO: 6
PX$_{32}$X$_{33}$X$_{34}$X$_{35}$X$_{36}$X$_{37}$X$_{38}$X$_{39}$X$_{40}$-R$_2$

SEQ ID NO: 7
K[(2-[2-(2-Amino-ethoxy)-ethoxy]-acetyl)$_2$-(γ-Glu)-CO-(CH$_2$)$_q$-CO$_2$H]X$_{32}$X$_{33}$X$_{34}$-R$_2$ SEQ ID NO: 8
K[(2-[2-(2-Amino-ethoxy)-ethoxy]-acetyl)$_2$-(γ-Glu)-CO-(CH$_2$)$_q$-CO$_2$H]X$_{32}$X$_{33}$X$_{34}$X$_{35}$X$_{36}$X$_{37}$X$_{38}$X$_{39}$-R$_2$ SEQ ID NO: 9
K[(2-[2-(2-Amino-ethoxy)-ethoxy]-acetyl)$_2$-(γ-Glu)-CO-(CH$_2$)$_q$-CO$_2$H]X$_{32}$X$_{33}$X$_{34}$X$_{35}$X$_{36}$X$_{37}$X$_{38}$X$_{39}$X$_{40}$-R$_2$

Example 1

SEQ ID NO: 10
Y-Aib-EGT-αMeF(2F)-TSDYSI-αMeL-LDEK((2-[2-(2-Amino-ethoxy)-ethoxy]-acetyl)$_2$-(γ-Glu)-CO-(CH$_2$)$_{18}$-CO$_2$H)AQ-Aib-EFI-(D-Glu)-YLIEGGPSSGAPPPS-NH$_2$

Example 2

SEQ ID NO: 11
Y-Aib-EGT-αMeF(2F)-TSDYSI-αMeL-LD-Orn-K((2-[2-(2-Amino-ethoxy)-ethoxy]-acetyl)$_2$-(γ-Glu)-CO-(CH$_2$)$_{16}$-CO$_2$H)AQ-Aib-EFI-(D-Glu)-YLIEGGPSSGAPPPS-NH$_2$

Example 3

SEQ ID NO: 12
Y-Aib-EGT-αMeF(2F)-TSDYSI-αMeL-LD-Orn-K((2-[2-(2-Amino-ethoxy)-ethoxy]-acetyl)$_2$-(γ-Glu)-CO-(CH$_2$)$_{18}$-CO$_2$H)AQ-Aib-EFI-(D-Glu)-YLIEGGPSSGAPPPS-NH$_2$

Example 4

SEQ ID NO: 13
Y-Aib-EGT-αMeF(2F)-TSD-4Pal-SI-αMeL-LD-Orn-K((2-[2-(2-Amino-ethoxy)-ethoxy]-acetyl)$_2$-(γ-Glu)-CO-(CH$_2$)$_{16}$-CO$_2$H)AQ-Aib-EFI-(D-Glu)-αMeY-LIEGGPSSGAPPPS-NH$_2$

Example 5

SEQ ID NO: 14
Y-Aib-EGT-αMeF(2F)-TSDVSI-αMeL-LD-Orn-K((2-[2-(2-Amino-ethoxy)-ethoxy]-acetyl)$_2$-(γ-Glu)-CO-(CH$_2$)$_{16}$-CO$_2$H)AQ-Aib-EFI-(D-Glu)-αMeY-LIEGGPSSGAPPPS-NH$_2$

SEQ ID NO: 297
PSSG-R$_2$

SEQ ID NO: 298
PSSGAPPPS-R$_2$

SEQ ID NO: 299
PSSG

SEQ ID NO: 300
PSSG-NH$_2$

SEQ ID NO: 301
PSSGAPPPS

SEQ ID NO: 302
PSSGAPPPS-NH$_2$

Legal Framework

The material in ASCII text file named "X21852 Sequence Listing", created on 09/19/2019 and of the size 440 KB, is hereby incorporated by reference.

SEQUENCE LISTING

<160> NUMBER OF SEQ ID NOS: 396

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic construct; Formula I
<220> FEATURE:
<221> NAME/KEY: VARIANT
<222> LOCATION: (1)..(1)
<223> OTHER INFORMATION: Xaa at position 1 is selected from the group
      consisting of Y, H, D-Tyr, F, desH, and desY, or Xaa at position 1
      and Xaa at position 2 combine to form desH-psi[NHCO]-Aib
<220> FEATURE:
<221> NAME/KEY: MOD_RES
<222> LOCATION: (1)..(1)
<223> OTHER INFORMATION: The N-terminus of Xaa at position 1 is modified
      with R1, wherein the modification is selected from the group
      consisting of Ac and absent.
<220> FEATURE:
<221> NAME/KEY: VARIANT
<222> LOCATION: (2)..(2)
<223> OTHER INFORMATION: Xaa at position 2 is selected from the group
      consisting of Aib, alpha-MeP, A, P, and D-Ala, or Xaa at position
      1 combines with Xaa at position 2 to form desH-psi[NHCO]-Aib
<220> FEATURE:
<221> NAME/KEY: VARIANT
<222> LOCATION: (3)..(3)
<223> OTHER INFORMATION: Xaa at position 3 is selected from the group of
      E, N, Aad, and cTA
<220> FEATURE:
<221> NAME/KEY: VARIANT
<222> LOCATION: (6)..(6)
<223> OTHER INFORMATION: Xaa at position 6 is selected from the group
      consisting of F, alpha-MeF, and alpha-MeF(2F)
<220> FEATURE:
<221> NAME/KEY: VARIANT
<222> LOCATION: (10)..(10)
<223> OTHER INFORMATION: Xaa at position 10 is selected from the group
      consisting of A, L, H, 3Pal, 4Pal, V, Y, E, alpha-MeF, alpha-MeF
      (2F), I, alpha-MeY, Q, D-His, D-Tyr, cTA, and K
<220> FEATURE:

```
<221> NAME/KEY: VARIANT
<222> LOCATION: (10)..(10)
<223> OTHER INFORMATION: when Xaa at position 10 is K, then K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: MISC_FEATURE
<222> LOCATION: (10)..(31)
<223> OTHER INFORMATION: When Xaa is
      K(2-[2-(2-amino-ethoxy)-ethoxy]-acetyl)2-(gamma-Glu)-CO-(CH2)q-CO
      2H at positions 10, 12, 13, 14, 16, 17, 19, 20, 21, 23, 24, 26,
      27, 28, 29, 30 or 31, q is 14, 15, 16, 17, 18, 19 or 20.
<220> FEATURE:
<221> NAME/KEY: VARIANT
<222> LOCATION: (11)..(11)
<223> OTHER INFORMATION: Xaa at position 11 is selected from the group
      consisting of S, alpha-MeS, or D-Ser
<220> FEATURE:
<221> NAME/KEY: VARIANT
<222> LOCATION: (12)..(12)
<223> OTHER INFORMATION: Xaa at position 12 is selected from the group
      consisting of I, S, D-Ile, and K
<220> FEATURE:
<221> NAME/KEY: MOD_RES
<222> LOCATION: (12)..(12)
<223> OTHER INFORMATION: when Xaa at position 12 is K, then K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (13)..(13)
<223> OTHER INFORMATION: Xaa at position 13 is selected from the group
      consisting of Nle, Aib, L, alpha-MeL, and K
<220> FEATURE:
<221> NAME/KEY: MOD_RES
<222> LOCATION: (13)..(13)
<223> OTHER INFORMATION: when Xaa at position 13 is K, then K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (14)..(14)
<223> OTHER INFORMATION: Xaa at position 14 is selected from the group
      consisting of L and K, wherein K is conjugated to a C16-C22 fatty
      acid wherein said fatty acid is optionally conjugated to said K
      via a linker
<220> FEATURE:
<221> NAME/KEY: VARIANT
<222> LOCATION: (16)..(16)
<223> OTHER INFORMATION: Xaa at position 16 is selected from the group
      consisting of E, Orn, Dab, Dap, S, T, H, Aib, alpha-MeK, R, and K
<220> FEATURE:
<221> NAME/KEY: MOD_RES
<222> LOCATION: (16)..(16)
<223> OTHER INFORMATION: when Xaa at position 16 is K, then K is
      optionally chemically modified by conjugation of the epsilon-amino
      group of the K side
      chain with (2-[2-(2-amino-ethoxy)-ethoxy]-acetyl)2-(gamma-Glu)-
      CO-(CH2)q-CO2H
<220> FEATURE:
<221> NAME/KEY: VARIANT
<222> LOCATION: (17)..(17)
<223> OTHER INFORMATION: Xaa at position 17 is selected from the group
      consisting of K, Q, I, and an amino acid conjugated to a C16-C22
      fatty acid wherein said fatty acid is optionally conjugated to
      said amino acid via a linker
<220> FEATURE:
<221> NAME/KEY: VARIANT
<222> LOCATION: (19)..(19)
<223> OTHER INFORMATION: Xaa at position 19 is selected from the group
      consisting of Q, A, and K
<220> FEATURE:
<221> NAME/KEY: MOD_RES
```

-continued

```
<222> LOCATION: (19)..(19)
<223> OTHER INFORMATION: when Xaa at position 19 is K, then K is
      chemically modified by conjugation of the epsilon-amino group of
      the K side chain with
      (2-[2-(2-amino-ethoxy)-ethoxy]-acetyl)2-(gamma-Glu)-
      CO-(CH2)q-CO2H
<220> FEATURE:
<221> NAME/KEY: VARIANT
<222> LOCATION: (20)..(20)
<223> OTHER INFORMATION: Xaa at position 20 is selected from the group
      consisting of Aib, Q, H, R, K, and alpha-MeK
<220> FEATURE:
<221> NAME/KEY: MOD_RES
<222> LOCATION: (20)..(20)
<223> OTHER INFORMATION: when Xaa at position 20 is K, then K is
      optionally chemically modified by conjugation of the epsilon-amino
      group of the K side chain with
      (2-[2-(2-amino-ethoxy)-ethoxy]-acetyl)2-(gamma-Glu)-
      CO-(CH2)q-CO2H
<220> FEATURE:
<221> NAME/KEY: VARIANT
<222> LOCATION: (21)..(21)
<223> OTHER INFORMATION: Xaa at position 21 is selected from the group
      consisting of H, Aad, D, Aib, T, A, E, I, and K
<220> FEATURE:
<221> NAME/KEY: MOD_RES
<222> LOCATION: (21)..(21)
<223> OTHER INFORMATION: when Xaa at position 21 is K, then K is
      chemically modified by conjugation of the epsilon-amino group of
      the K side chain with
      K(2-[2-(2-amino-ethoxy)-ethoxy]-acetyl)2-(gamma-Glu)-CO-(CH2)q-CO
      2H
<220> FEATURE:
<221> NAME/KEY: VARIANT
<222> LOCATION: (22)..(22)
<223> OTHER INFORMATION: Xaa at position 22 is selected from the group
      consisting of F and alpha-MeF
<220> FEATURE:
<221> NAME/KEY: VARIANT
<222> LOCATION: (23)..(23)
<223> OTHER INFORMATION: Xaa at position 23 is selected from the group
      consisting of I, L, A, G, F, H, E, V, and K
<220> FEATURE:
<221> NAME/KEY: MOD_RES
<222> LOCATION: (23)..(23)
<223> OTHER INFORMATION: when Xaa at position 23 is K, then K is
      chemically modified by conjugation of the epsilon-amino group of
      the K side chain with
      K(2-[2-(2-amino-ethoxy)-ethoxy]-acetyl)2-(gamma-Glu)-CO-(CH2)q-CO
      2H
<220> FEATURE:
<221> NAME/KEY: VARIANT
<222> LOCATION: (24)..(24)
<223> OTHER INFORMATION: Xaa at position 24 is selected from the group
      consisting of S, Aad, D-Glu, E, Aib, H, V, A, Q, D, P, and K
<220> FEATURE:
<221> NAME/KEY: MOD_RES
<222> LOCATION: (24)..(24)
<223> OTHER INFORMATION: when Xaa at position 24 is K, then K is
      chemically modified by conjugation of the epsilon-amino group of
      the K side chain with
      K(2-[2-(2-amino-ethoxy)-ethoxy]-acetyl)2-(gamma-Glu)-CO-(CH2)q-CO
      2H
<220> FEATURE:
<221> NAME/KEY: VARIANT
<222> LOCATION: (25)..(25)
<223> OTHER INFORMATION: Xaa at position 25 is selected from the group
      consisting of Y or alpha-MeY
<220> FEATURE:
<221> NAME/KEY: VARIANT
<222> LOCATION: (26)..(26)
<223> OTHER INFORMATION: Xaa at position 26 is selected from the group
      consisting of L, alpha-MeL, and K
<220> FEATURE:
<221> NAME/KEY: MOD_RES
<222> LOCATION: (26)..(26)
<223> OTHER INFORMATION: when Xaa at position 26 is K, then K is
      chemically modified by conjugation of the epsilon-amino group of
      the K side chain with
```

```
            (2-[2-(2-amino-ethoxy)-ethoxy]-acetyl)2-(gamma-Glu)-CO-(CH2)q-CO2
            H
<220> FEATURE:
<221> NAME/KEY: VARIANT
<222> LOCATION: (27)..(27)
<223> OTHER INFORMATION: Xaa at position 27 is selected from the group
      consisting of L, I, and K
<220> FEATURE:
<221> NAME/KEY: MOD_RES
<222> LOCATION: (27)..(27)
<223> OTHER INFORMATION: when Xaa at position 27 is K, then K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (28)..(28)
<223> OTHER INFORMATION: Xaa at position 28 is selected from the group
      consisting of E, A, S, D-Glu, and K
<220> FEATURE:
<221> NAME/KEY: MOD_RES
<222> LOCATION: (28)..(28)
<223> OTHER INFORMATION: when Xaa at position 28 is K, then K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (29)..(29)
<223> OTHER INFORMATION: Xaa at position 29 is selected from the group
      consisting of Aib, G, A, and K
<220> FEATURE:
<221> NAME/KEY: MOD_RES
<222> LOCATION: (29)..(29)
<223> OTHER INFORMATION: when Xaa at position 29 is K, then K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (30)..(30)
<223> OTHER INFORMATION: Xaa at position 30 is selected from the group
      consisting of C, G, G-R2, and K, wherein R2 is a modification of
      the C-terminal group, wherein the modification is NH2 or absent,
      wherein if X30 is G-R2, then X31 is absent.
<220> FEATURE:
<221> NAME/KEY: MOD_RES
<222> LOCATION: (30)..(30)
<223> OTHER INFORMATION: when Xaa at position 30 is K, then K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (31)..(31)
<223> OTHER INFORMATION: Xaa at position 31 is absent or is selected
      from the group consisting of SEQ ID NO:4, SEQ ID NO:5, SEQ ID:6,
      SEQ ID NO:7, SEQ ID NO:8, and SEQ ID NO:9
<220> FEATURE:
<221> NAME/KEY: MISC_FEATURE
<222> LOCATION: (31)..(31)
<223> OTHER INFORMATION: wherein no more than one of X10, X12, X13, X14,
      X16, X17, X19, X20, X21, X23, X24, X26, X27, X28, X29, X30, X31,
      X32, X33, X34, X35, X36, X37, X38, X39, and X40 may be a
      substituent that contains a fatty acid
<220> FEATURE:
<221> NAME/KEY: MISC_FEATURE
<222> LOCATION: (31)..(31)
<223> OTHER INFORMATION: wherein no more than one of X30, X34, X39, and
      X40 may be C
<220> FEATURE:
<221> NAME/KEY: MISC_FEATURE
<222> LOCATION: (31)..(31)
<223> OTHER INFORMATION: wherein if one of X30, X34, X39, and X40 is C,
      then none of X10, X12, X13, X14, X16, X17, X19, X20, X21, X23,
```

X24, X26, X27, X28, X29, X30, X31, X32, X33, X34, X35, X36, X37,
        X38, X39, and X40 is a substituent that contains a fatty acid
<220> FEATURE:
<221> NAME/KEY: MOD_RES
<222> LOCATION: (31)..(31)
<223> OTHER INFORMATION: Xaa at position 31 is modified with R2, wherein
        the modification is NH2 to form a C-terminal amide or absent

<400> SEQUENCE: 3

Xaa Xaa Xaa Gly Thr Xaa Thr Ser Asp Xaa Xaa Xaa Xaa Xaa Asp Xaa
1               5                   10                  15

Xaa Ala Xaa Xaa Xaa Xaa Xaa Xaa Xaa Xaa Xaa Xaa Xaa Xaa Xaa
            20                  25                  30

<210> SEQ ID NO 4
<211> LENGTH: 4
<212> TYPE: PRT
<213> ORGANISM: Artificial Sequence
<220> FEATURE:
<223> OTHER INFORMATION: Synthetic construct; SEQ ID NO:4 is PX32X33X34
<220> FEATURE:
<221> NAME/KEY: VARIANT
<222> LOCATION: (2)..(2)
<223> OTHER INFORMATION: Xaa at position 2 is S or K, wherein K is
        chemically modified by conjugation of the epsilon-amino group of
        the K side chain with
        (2-[2-(2-amino-ethoxy)-ethoxy]-acetyl)2-(gamma-Glu)-CO-(CH2)q-CO2
        H
<220> FEATURE:
<221> NAME/KEY: MISC_FEATURE
<222> LOCATION: (2)..(4)
<223> OTHER INFORMATION: wherein q is selected from the group consisting
        of 14, 15, 16, 17, 18, 19, and 20.
<220> FEATURE:
<221> NAME/KEY: VARIANT
<222> LOCATION: (3)..(3)
<223> OTHER INFORMATION: Xaa at position 3 is S or K, wherein K is
        chemically modified by conjugation of the epsilon-amino group of
        the K side chain with
        (2-[2-(2-amino-ethoxy)-ethoxy]-acetyl)2-(gamma-Glu)-CO-(CH2)q-CO2
        H
<220> FEATURE:
<221> NAME/KEY: VARIANT
<222> LOCATION: (4)..(4)
<223> OTHER INFORMATION: Xaa at position 4 is G, C or K, wherein K is
        chemically modified by conjugation of the epsilon-amino group of
        the K side chain with
        (2-[2-(2-amino-ethoxy)-ethoxy]-acetyl)2-(gamma-Glu)-
        CO-(CH2)q-CO2H
<220> FEATURE:
<221> NAME/KEY: MOD_RES
<222> LOCATION: (4)..(4)
<223> OTHER INFORMATION: The C-terminal group of Xaa at position 4 is
        modified with R2, wherein the modification is NH2 to form a
        C-terminal amide or absent

<400> SEQUENCE: 4

Pro Xaa Xaa Xaa
1

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct; SEQ ID NO:5 is
        PX32X33X34X35X36X37X38X39
<220> FEATURE:
<221> NAME/KEY: VARIANT
<222> LOCATION: (2)..(2)
<223> OTHER INFORMATION: Xaa at position 2 is S or K, wherein K is
        chemically modified by conjugation of the epsilon-amino group of
        the K side chain with
        (2-[2-(2-amino-ethoxy)-ethoxy]-acetyl)2-(gamma-Glu)-CO-(CH2)q-CO2

```
      H
<220> FEATURE:
<221> NAME/KEY: MISC_FEATURE
<222> LOCATION: (2)..(9)
<223> OTHER INFORMATION: wherein q is selected from the group consisting
      of 14, 15, 16, 17, 18, 19, and 20.
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2H
<220> FEATURE:
<221> NAME/KEY: VARIANT
<222> LOCATION: (5)..(5)
<223> OTHER INFORMATION: Xaa at position 5 is A or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (6)..(6)
<223> OTHER INFORMATION: Xaa at position 6 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (7)..(7)
<223> OTHER INFORMATION: Xaa at position 7 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (8)..(8)
<223> OTHER INFORMATION: Xaa at position 8 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (9)..(9)
<223> OTHER INFORMATION: Xaa at position 9 is C, S or K, wherein K is
      chemically modified by conjugation of the epsilon-amino group of
      the K side chain
      with (2-[2-(2-amino-ethoxy)-ethoxy]-acetyl)2-(gamma-Glu)-
      CO-(CH2)q-CO2H
<220> FEATURE:
<221> NAME/KEY: MOD_RES
<222> LOCATION: (9)..(9)
<223> OTHER INFORMATION: The C-terminal group of Xaa at position 9 is
      modified with R2, wherein the modification is NH2 to from a
      C-terminal amide or absent

<400> SEQUENCE: 5

Pro Xaa Xaa Xaa Xaa Xaa Xaa Xaa Xaa
1               5

<210> SEQ ID NO 6
<211> LENGTH: 10
<212> TYPE: PRT
<213> ORGANISM: Artificial Sequence
<220> FEATURE:
```

<223> OTHER INFORMATION: Synthetic Construct; SEQ ID NO:6 is
      PX32X33X34X35X36X37X38X39X40
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: MISC_FEATURE
<222> LOCATION: (2)..(10)
<223> OTHER INFORMATION: wherein q is selected from the group consisting
      of 14, 15, 16, 17, 18, 19, and 20.
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with
      (2-[2-(2-amino-ethoxy)-ethoxy]-acetyl)2-(gamma-Glu)-
      CO-(CH2)q-CO2H
<220> FEATURE:
<221> NAME/KEY: VARIANT
<222> LOCATION: (5)..(5)
<223> OTHER INFORMATION: Xaa at position 5 is A or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (6)..(6)
<223> OTHER INFORMATION: Xaa at position 6 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (7)..(7)
<223> OTHER INFORMATION: Xaa at position 7 is P or K, wherein K is
      chemically modified by conjugation of the epsilon-amino group of
      the K side chain with
      K(2-[2-(2-amino-ethoxy)-ethoxy]-acetyl)2-(gamma-Glu)-CO-(CH2)q-CO
      2H
<220> FEATURE:
<221> NAME/KEY: VARIANT
<222> LOCATION: (8)..(8)
<223> OTHER INFORMATION: Xaa at position 8 is P or K, wherein K is
      chemically modified by conjugation of the epsilon-amino group of
      the K side chain with
      K(2-[2-(2-amino-ethoxy)-ethoxy]-acetyl)2-(gamma-Glu)-CO-(CH2)q-CO
      2H
<220> FEATURE:
<221> NAME/KEY: VARIANT
<222> LOCATION: (9)..(9)
<223> OTHER INFORMATION: Xaa at position 9 is C, S or K, wherein K is
      chemically modified by conjugation of the epsilon-amino group of
      the K side chain with
      (2-[2-(2-amino-ethoxy)-ethoxy]-acetyl)2-(gamma-Glu)-
      CO-(CH2)q-CO2H
<220> FEATURE:
<221> NAME/KEY: VARIANT
<222> LOCATION: (10)..(10)
<223> OTHER INFORMATION: Xaa at position 10 is C or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H

```
<220> FEATURE:
<221> NAME/KEY: MOD_RES
<222> LOCATION: (10)..(10)
<223> OTHER INFORMATION: The C-terminal group of Xaa at position 10 is
      modified with R2, wherein the modification is NH2 to form a
      C-terminal amide or absent

<400> SEQUENCE: 6

Pro Xaa Xaa Xaa Xaa Xaa Xaa Xaa Xaa Xaa
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct; SEQ ID NO:7 is
      K[(2-[2-(2-amino-ethoxy)-ethoxy]-acetyl)2-(gamma-Glu)-CO-(CH2)q-C
      O2 H]X32X33X34
<220> FEATURE:
<221> NAME/KEY: MOD_RES
<222> LOCATION: (1)..(1)
<223> OTHER INFORMATION: K is chemically modified by conjugation of the
      epsilon-amino group of the K side chain with
      (2-[2-(2-amino-ethoxy)-ethoxy]-acetyl)2-(gamma-Glu)-CO-(CH2)q-CO2
      H
<220> FEATURE:
<221> NAME/KEY: MISC_FEATURE
<222> LOCATION: (1)..(1)
<223> OTHER INFORMATION: wherein q is selected from the group consisting
      of 14, 15, 16, 17, 18, 19, and 20
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with
      (2-[2-(2-amino-ethoxy)-ethoxy]-acetyl)2-(gamma-Glu)-
      CO-(CH2)q-CO2H
<220> FEATURE:
<221> NAME/KEY: MOD_RES
<222> LOCATION: (4)..(4)
<223> OTHER INFORMATION: The C-terminal group of Xaa at position 4 is
      modified with R2, wherein the modification is NH2 to form a
      C-terminal amide or absent

<400> SEQUENCE: 7

Lys Xaa Xaa Xaa
1

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct; SEQ ID NO:8 is
      K[(2-[2-(2-amino-ethoxy)-ethoxy]-acetyl)2-(gamma-Glu)-CO-(CH2)q-C
      O2H]X32X33X34X35X36X37X38X39
<220> FEATURE:
```

```
<221> NAME/KEY: MOD_RES
<222> LOCATION: (1)..(1)
<223> OTHER INFORMATION: K is chemically modified by conjugation of the
      epsilon-amino group of the K side chain with
      (2-[2-(2-amino-ethoxy)-ethoxy]-acetyl)2-(gamma-Glu)-CO-(CH2)q-CO2
      H
<220> FEATURE:
<221> NAME/KEY: MISC_FEATURE
<222> LOCATION: (1)..(1)
<223> OTHER INFORMATION: wherein q is selected from the group consisting
      of 14, 15, 16, 17, 18, 19, and 20
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with
      (2-[2-(2-amino-ethoxy)-ethoxy]-acetyl)2-(gamma-Glu)-
      CO-(CH2)q-CO2H
<220> FEATURE:
<221> NAME/KEY: VARIANT
<222> LOCATION: (5)..(5)
<223> OTHER INFORMATION: Xaa at position 5 is A or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (6)..(6)
<223> OTHER INFORMATION: Xaa at position 6 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (7)..(7)
<223> OTHER INFORMATION: Xaa at position 7 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (8)..(8)
<223> OTHER INFORMATION: Xaa at position 8 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (9)..(9)
<223> OTHER INFORMATION: Xaa at position 9 is C, S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: MOD_RES
<222> LOCATION: (9)..(9)
<223> OTHER INFORMATION: The C-terminal group of Xaa at position 9 is
      modified with R2, wherein the modification is NH2 to form a
```

C-terminal amide or absent

<400> SEQUENCE: 8

Lys Xaa Xaa Xaa Xaa Xaa Xaa Xaa Xaa
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct; SEQ ID NO:9 is
      K[(2-[2-(2-amino-ethoxy)-ethoxy]-acetyl)2-(gamma-Glu)-CO-(CH2)q-C
      O2H]X32X33X34X35X36X37X38X39X40
<220> FEATURE:
<221> NAME/KEY: MOD_RES
<222> LOCATION: (1)..(1)
<223> OTHER INFORMATION: K is chemically modified by conjugation of the
      epsilon-amino group of the K side chain with
      (2-[2-(2-amino-ethoxy)-ethoxy]-acetyl)2-(gamma-Glu)-CO-(CH2)q-CO2
      H
<220> FEATURE:
<221> NAME/KEY: MISC_FEATURE
<222> LOCATION: (1)..(1)
<223> OTHER INFORMATION: wherein q is selected from the group consisting
      of 14, 15, 16, 17, 18, 19, and 20
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with
      (2-[2-(2-amino-ethoxy)-ethoxy]-acetyl)2-(gamma-Glu)-
      CO-(CH2)q-CO2H
<220> FEATURE:
<221> NAME/KEY: VARIANT
<222> LOCATION: (5)..(5)
<223> OTHER INFORMATION: Xaa at position 5 is A or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (6)..(6)
<223> OTHER INFORMATION: Xaa at position 6 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (7)..(7)
<223> OTHER INFORMATION: Xaa at position 7 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (8)..(8)

```
<223> OTHER INFORMATION: Xaa at position 8 is P or K, wherein K is
      chemically modified by conjugation of the epsilon-amino group of
      the K side chain with
      (2-[2-(2-amino-ethoxy)-ethoxy]-acetyl)2-(gamma-Glu)-CO-(CH2)q-CO2
      H
<220> FEATURE:
<221> NAME/KEY: VARIANT
<222> LOCATION: (9)..(9)
<223> OTHER INFORMATION: Xaa at position 9 is C, S or K, wherein K is
      chemically modified by conjugation of the epsilon-amino group of
      the K side chain with
      (2-[2-(2-amino-ethoxy)-ethoxy]-acetyl)2-(gamma-Glu)-
      CO-(CH2)q-CO2H
<220> FEATURE:
<221> NAME/KEY: VARIANT
<222> LOCATION: (10)..(10)
<223> OTHER INFORMATION: Xaa at position 10 is C or K, wherein K is
      chemically modified by conjugation of the epsilon-amino group of
      the K side chain with
      (2-[2-(2-amino-ethoxy)-ethoxy]-acetyl)2-(gamma-Glu)-
      CO-(CH2)q-CO2H
<220> FEATURE:
<221> NAME/KEY: MOD_RES
<222> LOCATION: (10)..(10)
<223> OTHER INFORMATION: The C-terminal group of Xaa at position 10 is
      modified with R2, wherein the modification is NH2 to form a
      C-terminal amide or absent

<400> SEQUENCE: 9

Lys Xaa Xaa Xaa Xaa Xaa Xaa Xaa Xaa Xaa
1               5                   10

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: The Serine at position 39 is amidated

<400> SEQUENCE: 10

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30
```

```
Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: The Serine at position 39 is amidated

<400> SEQUENCE: 11

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
```

```
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (39)..(39)
<223> OTHER INFORMATION: The Serine at position 39 is amidated

<400> SEQUENCE: 12

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-MeY
```

```
<220> FEATURE:
<221> NAME/KEY: MOD_RES
<222> LOCATION: (39)..(39)
<223> OTHER INFORMATION: The Serine at position 39 is amidated

<400> SEQUENCE: 13

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Xaa Leu Ile Glu Gly Gly Pro Ser
                20                  25                  30

Ser Gly Ala Pro Pro Pro Ser
            35

<210> SEQ ID NO 14
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-MeY
<220> FEATURE:
<221> NAME/KEY: MOD_RES
<222> LOCATION: (39)..(39)
<223> OTHER INFORMATION: The Serine at position 39 is amidated

<400> SEQUENCE: 14

Tyr Xaa Glu Gly Thr Xaa Thr Ser Asp Val Ser Ile Xaa Leu Asp Xaa
1               5                   10                  15

Lys Ala Gln Xaa Glu Phe Ile Xaa Xaa Leu Ile Glu Gly Gly Pro Ser
                20                  25                  30

Ser Gly Ala Pro Pro Pro Ser
            35

<210> SEQ ID NO 15
<211> LENGTH: 39
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 15

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 16

Tyr Xaa Glu Gly Thr Phe Thr Ser Asp Tyr Ser Ile Leu Leu Asp Ser
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 17

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 18

Tyr Xaa Glu Gly Thr Phe Thr Ser Asp Tyr Ser Ile Leu Leu Asp Ser
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
```

```
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (24)..(24)
<223> OTHER INFORMATION: Lys at position 24 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 19

Tyr Xaa Glu Gly Thr Phe Thr Ser Asp Tyr Ser Ile Leu Leu Asp Ser
1               5                   10                  15

Ile Ala Gln Xaa Ala Phe Ile Lys Tyr Leu Leu Ala Xaa Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 20

Tyr Xaa Glu Gly Thr Phe Thr Ser Asp Tyr Ser Ile Leu Leu Asp Ser
1               5                   10                  15

Ile Ala Gln Xaa Ala Phe Ile Glu Tyr Leu Leu Lys Xaa Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 21

Tyr Xaa Glu Gly Thr Phe Thr Ser Asp Tyr Ser Ile Leu Leu Asp Lys
1               5                   10                  15

Ile Ala Gln Lys Ala Phe Ile Glu Tyr Leu Ile Glu Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (16)..(16)
<223> OTHER INFORMATION: Xaa at position 16 is Aib
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 22

Tyr Xaa Glu Gly Thr Phe Thr Ser Asp Tyr Ser Ile Leu Leu Asp Xaa
1               5                   10                  15

Ile Ala Gln Lys Ala Phe Ile Glu Tyr Leu Ile Glu Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
```

```
<222> LOCATION: (20)..(20)
<223> OTHER INFORMATION: Lys at position 20 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 23

Tyr Xaa Glu Gly Thr Phe Thr Ser Asp Tyr Ser Ile Leu Leu Asp Lys
1               5                   10                  15

Ile Ala Gln Lys Glu Phe Ile Gln Tyr Leu Leu Glu Xaa Gly Pro Ser
            20                  25                  30

Ser Gly Ala Pro Pro Pro Ser
            35

<210> SEQ ID NO 24
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 24

His Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Leu Glu Xaa Gly Pro Ser
            20                  25                  30

Ser Gly Ala Pro Pro Pro Ser
            35

<210> SEQ ID NO 25
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
```

```
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 25

His Xaa Glu Gly Thr Phe Thr Ser Asp Tyr Ser Ile Leu Leu Asp Lys
 1               5                  10                  15

Lys Ala Gln Xaa Ala Phe Ile Glu Tyr Leu Ile Glu Xaa Gly Pro Ser
            20                  25                  30

Ser Gly Ala Pro Pro Pro Ser
        35

<210> SEQ ID NO 26
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (34)..(34)
<223> OTHER INFORMATION: Ser at position 34 is amidated

<400> SEQUENCE: 26

His Xaa Glu Gly Thr Phe Thr Ser Asp Tyr Ser Ile Leu Leu Asp Lys
 1               5                  10                  15

Ile Ala Gln Lys Ala Phe Ile Glu Tyr Leu Leu Glu Xaa Gly Pro Ser
            20                  25                  30

Ser Gly

<210> SEQ ID NO 27
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
```

```
<221> NAME/KEY: MISC_FEATURE
<222> LOCATION: (13)..(13)
<223> OTHER INFORMATION: Xaa at position 13 is alpha-methyl-L
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      Dab-(2-[2-(2-Amino-ethoxy)-ethoxy]-acetyl)-Dab-(2-[2-(2-Amino-eth
      oxy)-ethoxy]-acetyl)-CO-(CH2)18-CO2H
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 27

His Xaa Glu Gly Thr Phe Thr Ser Asp Tyr Ser Ile Xaa Leu Asp Lys
1               5                   10                  15

Lys Ala Gln Xaa Ala Phe Ile Gln Tyr Leu Leu Ala Xaa Gly Pro Ser
            20                  25                  30

Ser Gly Ala Pro Lys Pro Ser
            35

<210> SEQ ID NO 28
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      Dab-(2-[2-(2-Amino-ethoxy)-ethoxy]-acetyl)-Dab-(2-[2-(2-Amino-eth
      oxy)-ethoxy]-acetyl)-CO-(CH2)18-CO2H
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 28

His Xaa Glu Gly Thr Phe Thr Ser Asp Tyr Ser Ile Xaa Leu Asp Lys
1               5                   10                  15

Lys Ala Gln Xaa Ala Phe Ile Gln Tyr Leu Leu Ala Xaa Gly Pro Ser
            20                  25                  30

Ser Gly Ala Pro Pro Pro Ser
            35
```

```
<210> SEQ ID NO 29
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 29

Tyr Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
<221> NAME/KEY: MOD_RES
<222> LOCATION: (39)..(39)
<223> OTHER INFORMATION: Ser at position 39 is amidated

<400> SEQUENCE: 30

Tyr Xaa Glu Gly Thr Phe Thr Ser Asp Tyr Ser Ile Xaa Leu Asp Glu
1               5                   10                  15
```

```
Lys Ala Gln Xaa Ala Phe Ile Glu Tyr Leu Leu Glu Gly Gly Pro Ser
            20                  25                  30

Ser Gly Ala Pro Pro Pro Ser
            35

<210> SEQ ID NO 31
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 31

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Leu Glu Xaa Gly Pro Ser
            20                  25                  30

Ser Gly Ala Pro Pro Pro Ser
            35

<210> SEQ ID NO 32
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (10)..(10)
<223> OTHER INFORMATION: Lys at position 10 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated
```

```
<400> SEQUENCE: 32

Tyr Xaa Glu Gly Thr Phe Thr Ser Asp Lys Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 33
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (11)..(11)
<223> OTHER INFORMATION: Lys at position 11 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 33

Tyr Xaa Glu Gly Thr Phe Thr Ser Asp Tyr Lys Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 34
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (12)..(12)
<223> OTHER INFORMATION: Lys at position 12 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 34

Tyr Xaa Glu Gly Thr Phe Thr Ser Asp Tyr Ser Lys Leu Leu Asp Lys
```

```
1               5                   10                  15
Ile Ala Gln Xaa Ala Phe Ile Glu Tyr Leu Ile Glu Gly Gly Pro Ser
            20                  25                  30

Ser Gly Ala Pro Pro Pro Ser
            35
```

<210> SEQ ID NO 35
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (13)..(13)
<223> OTHER INFORMATION: Lys at position 13 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 35

```
Tyr Xaa Glu Gly Thr Phe Thr Ser Asp Tyr Ser Ile Lys Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser
            35
```

<210> SEQ ID NO 36
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (14)..(14)
<223> OTHER INFORMATION: Lys at position 14 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 36

```
Tyr Xaa Glu Gly Thr Phe Thr Ser Asp Tyr Ser Ile Leu Lys Asp Lys
1               5                   10                  15

Ile Ala Gln Xaa Ala Phe Ile Glu Tyr Leu Ile Glu Gly Gly Pro Ser
```

```
                20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (15)..(15)
<223> OTHER INFORMATION: Lys at position 15 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 37

Tyr Xaa Glu Gly Thr Phe Thr Ser Asp Tyr Ser Ile Leu Leu Lys Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (16)..(16)
<223> OTHER INFORMATION: Lys at position 16 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 38

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser
```

<210> SEQ ID NO 39
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (18)..(18)
<223> OTHER INFORMATION: Lys at position 18 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 39

Tyr Xaa Glu Gly Thr Phe Thr Ser Asp Tyr Ser Ile Leu Leu Asp Lys
1               5                   10                  15

Ile Lys Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 40
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (19)..(19)
<223> OTHER INFORMATION: Lys at position 19 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 40

Tyr Xaa Glu Gly Thr Phe Thr Ser Asp Tyr Ser Ile Leu Leu Asp Lys
1               5                   10                  15

Ile Ala Lys Xaa Ala Phe Ile Glu Tyr Leu Ile Glu Gly Gly Pro Ser
            20                  25                  30

Ser Gly Ala Pro Pro Pro Ser
        35

```
<210> SEQ ID NO 41
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (21)..(21)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 41

Tyr Xaa Glu Gly Thr Phe Thr Ser Asp Tyr Ser Ile Leu Leu Asp Lys
1               5                   10                  15

Ile Ala Gln Xaa Lys Phe Ile Glu Tyr Leu Ile Glu Gly Gly Pro Ser
            20                  25                  30

Ser Gly Ala Pro Pro Pro Ser
            35

<210> SEQ ID NO 42
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (23)..(23)
<223> OTHER INFORMATION: Lys at position 23 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 42

Tyr Xaa Glu Gly Thr Phe Thr Ser Asp Tyr Ser Ile Leu Leu Asp Lys
1               5                   10                  15

Ile Ala Gln Xaa Ala Phe Lys Glu Tyr Leu Ile Glu Gly Gly Pro Ser
            20                  25                  30

Ser Gly Ala Pro Pro Pro Ser
            35

<210> SEQ ID NO 43
<211> LENGTH: 39
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (24)..(24)
<223> OTHER INFORMATION: Lys at position 24 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 43

Tyr Xaa Glu Gly Thr Phe Thr Ser Asp Tyr Ser Ile Leu Leu Asp Lys
1               5                   10                  15

Ile Ala Gln Xaa Ala Phe Ile Lys Tyr Leu Ile Glu Gly Gly Pro Ser
            20                  25                  30

Ser Gly Ala Pro Pro Pro Ser
        35

<210> SEQ ID NO 44
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (26)..(26)
<223> OTHER INFORMATION: Lys at position 26 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 44

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Lys Ile Glu Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Synthetic Construct
```

<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (27)..(27)
<223> OTHER INFORMATION: Lys at position 27 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 45

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Lys Glu Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 46

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Lys Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)

<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (29)..(29)
<223> OTHER INFORMATION: Lys at position 29 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 47

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Lys Gly Pro Ser
            20                  25                  30

Ser Gly Ala Pro Pro Pro Ser
        35

<210> SEQ ID NO 48
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Lys at position 30 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 48

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Lys Pro Ser
            20                  25                  30

Ser Gly Ala Pro Pro Pro Ser
        35

<210> SEQ ID NO 49
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE

```
<222> LOCATION: (20)..(20)
<223> OTHER INFORMATION: Xaa at position 20 is Aib
<220> FEATURE:
<221> NAME/KEY: MOD_RES
<222> LOCATION: (31)..(31)
<223> OTHER INFORMATION: Lys at position 31 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 49

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Lys Ser
            20                  25                  30

Ser Gly Ala Pro Pro Pro Ser
            35

<210> SEQ ID NO 50
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (32)..(32)
<223> OTHER INFORMATION: Lys at position 32 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 50

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Lys
            20                  25                  30

Ser Gly Ala Pro Pro Pro Ser
            35

<210> SEQ ID NO 51
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
```

```
<221> NAME/KEY: MOD_RES
<222> LOCATION: (33)..(33)
<223> OTHER INFORMATION: Lys at position 33 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 51

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Lys Gly Ala Pro Pro Ser
        35

<210> SEQ ID NO 52
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Lys at position 34 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 52

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Lys Ala Pro Pro Ser
        35

<210> SEQ ID NO 53
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (35)..(35)
<223> OTHER INFORMATION: Lys at position 35 is chemically modified by
```

```
           conjugation of the epsilon-amino group of the Lys side chain with
           (2-[2-(2-amino-ethoxy)-ethoxy]-acetyl)2-(gamma-Glu)-CO-(CH2)18-CO
           2H
<220> FEATURE:
<221> NAME/KEY: MOD_RES
<222> LOCATION: (39)..(39)
<223> OTHER INFORMATION: Ser at position 39 is amidated

<400> SEQUENCE: 53

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Lys Pro Pro Ser
        35

<210> SEQ ID NO 54
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (36)..(36)
<223> OTHER INFORMATION: Lys at position 36 is chemically modified by
           conjugation of the epsilon-amino group of the Lys side chain with
           (2-[2-(2-amino-ethoxy)-ethoxy]-acetyl)2-(gamma-Glu)-CO-(CH2)18-CO
           2H
<220> FEATURE:
<221> NAME/KEY: MOD_RES
<222> LOCATION: (39)..(39)
<223> OTHER INFORMATION: Ser at position 39 is amidated

<400> SEQUENCE: 54

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Lys Pro Pro Ser
        35

<210> SEQ ID NO 55
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (37)..(37)
<223> OTHER INFORMATION: Lys at position 37 is chemically modified by
           conjugation of the epsilon-amino group of the Lys side chain with
           (2-[2-(2-amino-ethoxy)-ethoxy]-acetyl)2-(gamma-Glu)-CO-(CH2)18-CO
           2H
```

```
<220> FEATURE:
<221> NAME/KEY: MOD_RES
<222> LOCATION: (39)..(39)
<223> OTHER INFORMATION: Ser at position 39 is amidated

<400> SEQUENCE: 55

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Lys Pro Ser
        35

<210> SEQ ID NO 56
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (38)..(38)
<223> OTHER INFORMATION: Lys at position 38 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 56

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Lys Ser
        35

<210> SEQ ID NO 57
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Lys at position 39 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
```

<223> OTHER INFORMATION: Lys at position 39 is amidated

<400> SEQUENCE: 57

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Lys
        35

<210> SEQ ID NO 58
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (40)..(40)
<223> OTHER INFORMATION: Lys at position 40 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (40)..(40)
<223> OTHER INFORMATION: Lys at position 40 is amidated

<400> SEQUENCE: 58

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser Lys
        35                  40

<210> SEQ ID NO 59
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 59

```
Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly

<210> SEQ ID NO 60
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 60

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly
            20                  25                  30

<210> SEQ ID NO 61
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 61

Tyr Xaa Glu Gly Thr Phe Thr Ser Asp Tyr Ser Ile Xaa Leu Asp Ser
1               5                   10                  15
```

```
Lys Ala Gln Xaa Ala Phe Ile Glu Tyr Leu Ile Glu Gly Gly Pro Ser
                20                  25                  30

Ser Gly Ala Pro Pro Pro Ser
        35
```

<210> SEQ ID NO 62
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 62

```
His Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
        35
```

<210> SEQ ID NO 63
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 63

```
His Xaa Glu Gly Thr Phe Thr Ser Asp Tyr Ser Ile Xaa Leu Asp Lys
```

```
                1               5                  10                  15
Lys Ala Gln His Ala Phe Ile Glu Tyr Leu Ile Glu Gly Gly Pro Ser
                20                 25                  30

Ser Gly Ala Pro Pro Ser
                35

<210> SEQ ID NO 64
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 64

His Xaa Glu Gly Thr Phe Thr Ser Asp Tyr Ser Ile Xaa Leu Asp Glu
1               5                   10                  15

Lys Ala Gln His Ala Phe Ile Glu Tyr Leu Ile Glu Gly Gly Pro Ser
                20                  25                  30

Ser Gly Ala Pro Pro Ser
                35

<210> SEQ ID NO 65
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 65

Tyr Xaa Glu Gly Thr Phe Thr Ser Asp Tyr Ser Ile Xaa Leu Asp Glu
1               5                   10                  15

Lys Ala Gln His Ala Phe Ile Glu Tyr Leu Ile Glu Gly Gly Pro Ser
```

```
                    20                  25                  30

Ser Gly Ala Pro Pro Ser
        35

<210> SEQ ID NO 66
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 66

Tyr Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Ser
        35

<210> SEQ ID NO 67
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 67

Tyr Xaa Glu Gly Thr Phe Thr Ser Asp Tyr Ser Ser Leu Leu Asp Lys
1               5                   10                  15
```

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 68
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 68

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:

```
<221> NAME/KEY: MOD_RES
<222> LOCATION: (39)..(39)
<223> OTHER INFORMATION: Ser at position 39 is amidated

<400> SEQUENCE: 69

Tyr Xaa Glu Gly Thr Phe Thr Ser Asp Tyr Ser Ile Xaa Leu Asp Xaa
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 70

Tyr Xaa Glu Gly Thr Phe Thr Ser Asp Tyr Ser Ile Xaa Leu Asp Ser
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 71
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
```

```
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 71

Tyr Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Glu Gly Gly
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 72

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Ile Glu Gly Gly
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
```

```
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 73

Tyr Xaa Glu Gly Thr Phe Thr Ser Asp Tyr Ser Ile Xaa Leu Asp Ser
1               5                   10                  15

Lys Ala Gln Xaa Ala Phe Ile Glu Tyr Leu Ile Glu Gly Gly
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 74

Tyr Xaa Glu Gly Thr Phe Thr Ser Asp Tyr Ser Ile Xaa Leu Asp Thr
1               5                   10                  15

Lys Ala Gln Xaa Ala Phe Ile Glu Tyr Leu Ile Glu Gly Gly
            20                  25                  30

<210> SEQ ID NO 75
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
```

```
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 75

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 76
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (22)..(22)
<223> OTHER INFORMATION: Xaa at position 22 is alpha-methyl-Phe
<220> FEATURE:
<221> NAME/KEY: MOD_RES
<222> LOCATION: (39)..(39)
<223> OTHER INFORMATION: Ser at position 39 is amidated

<400> SEQUENCE: 76

Tyr Xaa Glu Gly Thr Phe Thr Ser Asp Tyr Ser Ile Leu Leu Asp Lys
1               5                   10                  15

Lys Ala Gln Xaa Ala Xaa Ile Glu Tyr Leu Ile Glu Gly Gly Pro Ser
            20                  25                  30

Ser Gly Ala Pro Pro Pro Ser
        35

<210> SEQ ID NO 77
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (11)..(11)
<223> OTHER INFORMATION: Xaa at position 11 is alpha-methyl-Ser
<220> FEATURE:
<221> NAME/KEY: MOD_RES
<222> LOCATION: (17)..(17)
<223> OTHER INFORMATION: Lys at position 17 is chemically modified by
```

```
            conjugation of the epsilon-amino group of the Lys side chain with
            (2-[2-(2-amino-ethoxy)-ethoxy]-acetyl)2-(gamma-Glu)-CO-(CH2)18-CO
            2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 77

Tyr Xaa Glu Gly Thr Phe Thr Ser Asp Tyr Xaa Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 78
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
            conjugation of the epsilon-amino group of the Lys side chain with
            (2-[2-(2-amino-ethoxy)-ethoxy]-acetyl)2-(gamma-Glu)-CO-(CH2)18-CO
            2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 78

Tyr Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 79
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
```

<223> OTHER INFORMATION: Xaa at position 2 is Aib
<220> FEATURE:
<221> NAME/KEY: MOD_RES
<222> LOCATION: (10)..(10)
<223> OTHER INFORMATION: Lys at position 10 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 79

Tyr Xaa Glu Gly Thr Phe Thr Ser Asp Lys Ser Ile Leu Leu Asp Lys
1               5                   10                  15

Ile Ala Gln Xaa Ala Phe Ile Glu Tyr Leu Ile Glu Gly Gly
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (14)..(14)
<223> OTHER INFORMATION: Lys at position 14 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 80

Tyr Xaa Glu Gly Thr Phe Thr Ser Asp Tyr Ser Ile Leu Lys Asp Lys
1               5                   10                  15

Ile Ala Gln Xaa Ala Phe Ile Glu Tyr Leu Ile Glu Gly Gly
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (21)..(21)
<223> OTHER INFORMATION: Lys at position 21 is chemically modified by -continued

```
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (30)..(30)
<223> OTHER INFORMATION: Gly at position 30 is amidated

<400> SEQUENCE: 81

Tyr Xaa Glu Gly Thr Phe Thr Ser Asp Tyr Ser Ile Leu Leu Asp Lys
1               5                   10                  15

Ile Ala Gln Xaa Lys Phe Ile Glu Tyr Leu Ile Glu Gly Gly
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (30)..(30)
<223> OTHER INFORMATION: Gly at position 30 is amidated

<400> SEQUENCE: 82

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Lys Gly Gly
            20                  25                  30

<210> SEQ ID NO 83
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
```

```
<222> LOCATION: (22)..(22)
<223> OTHER INFORMATION: Xaa at position 22 is alpha-methyl-Phe
<220> FEATURE:
<221> NAME/KEY: MOD_RES
<222> LOCATION: (39)..(39)
<223> OTHER INFORMATION: Ser at position 39 is amidated

<400> SEQUENCE: 83

Tyr Xaa Glu Gly Thr Phe Thr Ser Asp Tyr Ser Ile Xaa Leu Asp Lys
1               5                   10                  15

Lys Ala Gln Xaa Ala Xaa Ile Glu Tyr Leu Ile Glu Gly Gly Pro Ser
            20                  25                  30

Ser Gly Ala Pro Pro Pro Ser
        35

<210> SEQ ID NO 84
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (26)..(26)
<223> OTHER INFORMATION: Xaa at position 26 is alpha-methyl-Leu
<220> FEATURE:
<221> NAME/KEY: MOD_RES
<222> LOCATION: (39)..(39)
<223> OTHER INFORMATION: Ser at position 39 is amidated

<400> SEQUENCE: 84

Tyr Xaa Glu Gly Thr Phe Thr Ser Asp Tyr Ser Ile Xaa Leu Asp Lys
1               5                   10                  15

Lys Ala Gln Xaa Ala Phe Ile Glu Tyr Xaa Ile Glu Gly Gly Pro Ser
            20                  25                  30

Ser Gly Ala Pro Pro Pro Ser
        35

<210> SEQ ID NO 85
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
```

```
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (22)..(22)
<223> OTHER INFORMATION: Xaa at position 22 is alpha-methyl-Phe
<220> FEATURE:
<221> NAME/KEY: MOD_RES
<222> LOCATION: (39)..(39)
<223> OTHER INFORMATION: Ser at position 39 is amidated

<400> SEQUENCE: 85

Tyr Xaa Glu Gly Thr Xaa Thr Ser Asp Tyr Ser Ile Xaa Leu Asp Lys
1               5                   10                  15

Lys Ala Gln Xaa Ala Xaa Ile Glu Tyr Leu Ile Glu Gly Gly Pro Ser
                20                  25                  30

Ser Gly Ala Pro Pro Pro Ser
            35

<210> SEQ ID NO 86
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (19)..(19)
<223> OTHER INFORMATION: Xaa at position 19 is Aib
<220> FEATURE:
<221> NAME/KEY: MOD_RES
<222> LOCATION: (37)..(37)
<223> OTHER INFORMATION: Lys at position 37 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (38)..(38)
<223> OTHER INFORMATION: Ser at position 38 is amidated

<400> SEQUENCE: 86

Tyr Xaa Glu Gly Thr Phe Thr Ser Asp Tyr Ser Ile Leu Leu Lys Ile
1               5                   10                  15

Ala Gln Xaa Ala Phe Ile Glu Tyr Leu Ile Glu Gly Gly Pro Ser Ser
                20                  25                  30

Gly Ala Pro Pro Lys Ser
            35

<210> SEQ ID NO 87
<211> LENGTH: 39
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 87

Xaa Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 88
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MOD_RES
<222> LOCATION: (1)..(1)
<223> OTHER INFORMATION: The N-terminal amino is acetylated
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 88

Xaa Ala Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35
```

```
<210> SEQ ID NO 89
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 89

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
            35

<210> SEQ ID NO 90
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (11)..(11)
<223> OTHER INFORMATION: Xaa at position 11 is D-Ser
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 90

Tyr Xaa Glu Gly Thr Phe Thr Ser Asp Tyr Xaa Ile Leu Leu Asp Lys
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
            35
```

```
<210> SEQ ID NO 91
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (12)..(12)
<223> OTHER INFORMATION: Xaa at position 12 is D-Ile
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 91

Tyr Xaa Glu Gly Thr Phe Thr Ser Asp Tyr Ser Xaa Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 92
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (28)..(28)
<223> OTHER INFORMATION: Xaa at position 28 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 92

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Xaa Gly Gly Pro Ser
            20                  25                  30
```

Ser Gly Ala Pro Pro Pro Ser
        35

<210> SEQ ID NO 93
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 93

Tyr Xaa Glu Gly Thr Phe Thr Ser Asp Tyr Ser Ile Leu Leu Asp Lys
1               5                   10                  15

Lys Ala Gln Xaa Ala Phe Ile Xaa Tyr Leu Ile Glu Gly Gly Pro Ser
            20                  25                  30

Ser Gly Ala Pro Pro Pro Ser
        35

<210> SEQ ID NO 94
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 94

Tyr Xaa Glu Gly Thr Phe Thr Ser Asp Ala Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 95
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 95

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Ala Gly Pro Ser
            20                  25                  30

Ser Gly Ala Pro Pro Pro Ser
        35

<210> SEQ ID NO 96
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 96

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 97
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 97

Tyr Pro Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 98
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (3)..(3)
<223> OTHER INFORMATION: Xaa at position 3 is Aad
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 98

Tyr Xaa Xaa Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

```
<210> SEQ ID NO 99
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 99

Tyr Xaa Asn Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 100
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (3)..(3)
<223> OTHER INFORMATION: Xaa at position 3 is gamma-Glu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 100

Tyr Xaa Xaa Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35
```

```
<210> SEQ ID NO 101
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (10)..(10)
<223> OTHER INFORMATION: Lys at position 10 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 101

Tyr Xaa Glu Gly Thr Xaa Thr Ser Asp Lys Ser Ile Leu Leu Asp Lys
1               5                   10                  15

Ile Ala Gln Xaa Ala Phe Ile Glu Tyr Leu Ile Glu Gly Gly
            20                  25                  30

<210> SEQ ID NO 102
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (14)..(14)
<223> OTHER INFORMATION: Lys at position 14 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (30)..(30)
<223> OTHER INFORMATION: Gly at position 30 is amidated

<400> SEQUENCE: 102

Tyr Xaa Glu Gly Thr Xaa Thr Ser Asp Tyr Ser Ile Leu Lys Asp Lys
1               5                   10                  15

Ile Ala Gln Xaa Ala Phe Ile Glu Tyr Leu Ile Glu Gly Gly
            20                  25                  30
```

```
<210> SEQ ID NO 103
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (21)..(21)
<223> OTHER INFORMATION: Lys at position 21 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (30)..(30)
<223> OTHER INFORMATION: Gly at position 30 is amidated

<400> SEQUENCE: 103

Tyr Xaa Glu Gly Thr Xaa Thr Ser Asp Tyr Ser Ile Leu Leu Asp Lys
1               5                   10                  15

Ile Ala Gln Xaa Lys Phe Ile Glu Tyr Leu Ile Glu Gly Gly
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (30)..(30)
<223> OTHER INFORMATION: Gly at position 30 is amidated

<400> SEQUENCE: 104

Tyr Xaa Glu Gly Thr Xaa Thr Ser Asp Tyr Ser Ile Leu Leu Asp Lys
1               5                   10                  15

Ile Ala Gln Xaa Ala Phe Ile Glu Tyr Leu Ile Lys Gly Gly
            20                  25                  30
```

```
<210> SEQ ID NO 105
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (10)..(10)
<223> OTHER INFORMATION: Lys at position 10 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 105

Tyr Xaa Glu Gly Thr Phe Thr Ser Asp Lys Ser Ile Xaa Leu Asp Lys
1               5                   10                  15

Ile Ala Gln Xaa Ala Phe Ile Glu Tyr Leu Ile Glu Gly Gly
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (30)..(30)
<223> OTHER INFORMATION: Gly at position 30 is amidated

<400> SEQUENCE: 106

Tyr Xaa Glu Gly Thr Phe Thr Ser Asp Tyr Ser Ile Xaa Leu Asp Lys
1               5                   10                  15

Ile Ala Gln Xaa Ala Phe Ile Glu Tyr Leu Ile Lys Gly Gly
            20                  25                  30

<210> SEQ ID NO 107
```

```
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 13 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 107

Tyr Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Glu Gly Gly
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 108

Tyr Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Gly Gly
            20                  25                  30
```

<210> SEQ ID NO 109
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 109

Tyr Xaa Glu Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

```
<400> SEQUENCE: 110

Tyr Xaa Glu Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 111

Tyr Xaa Glu Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
```

-continued

```
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 112

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 113

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly
            20                  25                  30

<210> SEQ ID NO 114
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa at position 1 combines with Xaa at position
      2 to form desHis-psi[NHCO]-Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
```

```
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 114

Xaa Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 115
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa at position 1 combines with Xaa at position
      2 to form desHis-Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 115

Xaa Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 116
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Des-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
```

```
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 116

Xaa Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 117
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-AOC-(gamma-Glu)-CO-(CH2)18
      -CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 117

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 118
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      AOC-(2-[2-(2-amino-ethoxy)-ethoxy]-acetyl)-(gamma-Glu)-CO-(CH2)18
      -CO2H
<220> FEATURE:
<221> NAME/KEY: MISC_FEATURE
<222> LOCATION: (20)..(20)
```

<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 118

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 119
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(gamma-Glu)-(Trx)-CO-(CH2)
      18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 119

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 120
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(Trx)-(gamma-Glu)-CO-(CH2)
      18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 120

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 121
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(epsilon-Lys)-(gamma-Glu)-
      CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 121

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 122
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

```
<400> SEQUENCE: 122

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 123
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(epsilon-Lys)-(epsilon-Lys
      )-CO-(CH2)18-CO2H
<220> FEATURE:
<221> NAME/KEY: MISC_FEATURE
<222> LOCATION: (20)..(20)
<223> OTHER INFORMATION: Xaa at position 2 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 123

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 124
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
```

```
<220> FEATURE:
<221> NAME/KEY: MOD_RES
<222> LOCATION: (39)..(39)
<223> OTHER INFORMATION: Ser at position 39 is amidated

<400> SEQUENCE: 124

Tyr Xaa Glu Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 125
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 125

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly Pro Ser
            20                  25                  30

Ser Gly Ala Pro Pro Pro Ser
            35

<210> SEQ ID NO 126
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
```

```
<222> LOCATION: (13)..(13)
<223> OTHER INFORMATION: Xaa at position 13 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 126

Tyr Xaa Glu Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 127
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 127

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly Pro Ser
            20                  25                  30

Ser Gly Ala Pro Pro Pro Ser
            35

<210> SEQ ID NO 128
<211> LENGTH: 39
<212> TYPE: PRT
```

-continued

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 128

Phe Xaa Glu Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
                35

<210> SEQ ID NO 129
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (3)..(3)
<223> OTHER INFORMATION: Xaa at position 3 is cTA
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
```

<223> OTHER INFORMATION: Ser at position 39 is amidated

<400> SEQUENCE: 129

Tyr Xaa Xaa Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 130
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 130

Tyr Xaa Glu Gly Thr Xaa Thr Ser Asp Tyr Ser Ile Xaa Leu Asp Glu
1               5                   10                  15

Lys Ala Gln Gln Ala Phe Ile Glu Tyr Leu Ile Glu Gly Gly Pro Ser
            20                  25                  30

Ser Gly Ala Pro Pro Pro Ser
        35

<210> SEQ ID NO 131
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with

```
        (2-[2-(2-amino-ethoxy)-ethoxy]-acetyl)2-(gamma-Glu)-CO-(CH2)18-CO
        2H
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 131

Tyr Xaa Glu Gly Thr Xaa Thr Ser Asp Tyr Ser Ile Xaa Leu Asp Glu
1               5                   10                  15

Lys Ala Gln Gln Ala Phe Ile Glu Tyr Leu Ile Glu Xaa Gly Pro Ser
            20                  25                  30

Ser Gly Ala Pro Pro Pro Ser
        35

<210> SEQ ID NO 132
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 132

Tyr Xaa Glu Gly Thr Xaa Thr Ser Asp Tyr Ser Ile Xaa Leu Asp Lys
1               5                   10                  15

Lys Ala Gln Xaa Glu Phe Ile Glu Tyr Leu Ile Glu Gly Gly Pro Ser
            20                  25                  30

Ser Gly

<210> SEQ ID NO 133
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
```

```
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 133

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly Pro Ser
            20                  25                  30

Ser Gly

<210> SEQ ID NO 134
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)2-CO-(CH2)18-C
      O2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 134

Tyr Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35
```

```
<210> SEQ ID NO 135
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 135

Tyr Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Ala Gly Pro Ser
            20                  25                  30

Ser Gly Ala Pro Pro Pro Ser
            35

<210> SEQ ID NO 136
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 136
```

```
Tyr Xaa Glu Gly Thr Xaa Thr Ser Asp Ile Ser Ile Leu Leu Asp Lys
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
            35

<210> SEQ ID NO 137
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 137

Tyr Xaa Glu Gly Thr Xaa Thr Ser Asp His Ser Ile Leu Leu Asp Lys
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
            35

<210> SEQ ID NO 138
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
```

```
<222> LOCATION: (39)..(39)
<223> OTHER INFORMATION: Ser at position 39 is amidated

<400> SEQUENCE: 138

Tyr Xaa Glu Gly Thr Xaa Thr Ser Asp Leu Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 139
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 139

Tyr Xaa Glu Gly Thr Xaa Thr Ser Asp Glu Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 140
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (10)..(10)
<223> OTHER INFORMATION: Xaa at position 10 is alpha-methyl-Phe
<220> FEATURE:
<221> NAME/KEY: MOD_RES
<222> LOCATION: (17)..(17)
<223> OTHER INFORMATION: Lys at position 17 is chemically modified by
``` conjugation of the epsilon-amino group of the Lys side chain with
(2-[2-(2-amino-ethoxy)-ethoxy]-acetyl)2-(gamma-Glu)-CO-(CH2)18-CO
2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 140

Tyr Xaa Glu Gly Thr Xaa Thr Ser Asp Xaa Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 141
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (10)..(10)
<223> OTHER INFORMATION: Xaa at position 10 is 3Pal
<220> FEATURE:
<221> NAME/KEY: MOD_RES
<222> LOCATION: (17)..(17)
<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)18-CO
2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 141

Tyr Xaa Glu Gly Thr Xaa Thr Ser Asp Xaa Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 142
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)

```
<223> OTHER INFORMATION: Xaa at position 1 is DesTyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 142

Xaa Xaa Glu Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 143
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is DesTyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated
```

-continued

<400> SEQUENCE: 143

Xaa Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly Pro Ser
                20                  25                  30

Ser Gly Ala Pro Pro Pro Ser
        35

<210> SEQ ID NO 144
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 144

His Xaa Asn Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
        35

<210> SEQ ID NO 145
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 145

Tyr Xaa Glu Gly Thr Phe Thr Ser Asp Ala Ser Ile Leu Leu Asp Lys

```
                        1               5                  10                 15
Lys Ala Gln Xaa Ala Phe Ile Glu Tyr Leu Ile Glu Ala Gly Pro Ser
                        20                 25                 30

Ser Gly Ala Pro Pro Ser
              35

<210> SEQ ID NO 146
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (21)..(21)
<223> OTHER INFORMATION: Xaa at position 21 is Aad
<220> FEATURE:
<221> NAME/KEY: MOD_RES
<222> LOCATION: (39)..(39)
<223> OTHER INFORMATION: Ser at position 39 is amidated

<400> SEQUENCE: 146

Tyr Xaa Glu Gly Thr Xaa Thr Ser Asp Tyr Ser Ile Xaa Leu Asp Lys
1               5                  10                 15

Lys Ala Gln Xaa Xaa Phe Ile Glu Tyr Leu Ile Glu Gly Gly Pro Ser
                        20                 25                 30

Ser Gly Ala Pro Pro Ser
              35

<210> SEQ ID NO 147
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
```

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 147

Tyr Xaa Glu Gly Thr Xaa Thr Ser Asp Tyr Ser Ile Xaa Leu Asp Lys
1               5                   10                  15

Lys Ala Gln Xaa Ser Phe Ile Glu Tyr Leu Ile Glu Gly Gly Pro Ser
            20                  25                  30

Ser Gly Ala Pro Pro Pro Ser
        35

<210> SEQ ID NO 148
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 148

Tyr Xaa Glu Gly Thr Xaa Thr Ser Asp Tyr Ser Ile Xaa Leu Asp Lys
1               5                   10                  15

Lys Ala Gln Xaa Thr Phe Ile Glu Tyr Leu Ile Glu Gly Gly Pro Ser
            20                  25                  30

Ser Gly Ala Pro Pro Pro Ser
        35

<210> SEQ ID NO 149
<211> LENGTH: 39
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 149

Tyr Xaa Glu Gly Thr Xaa Thr Ser Asp Tyr Ser Ile Xaa Leu Asp Lys
1               5                  10                  15

Lys Ala Gln Xaa Asp Phe Ile Glu Tyr Leu Ile Glu Gly Gly Pro Ser
            20                  25                  30

Ser Gly Ala Pro Pro Pro Ser
        35

<210> SEQ ID NO 150
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 150

Tyr Xaa Glu Gly Thr Xaa Thr Ser Asp Tyr Ser Ile Xaa Leu Asp Lys
1               5                  10                  15

Lys Ala Gln Xaa Ile Phe Ile Glu Tyr Leu Ile Glu Gly Gly Pro Ser
```

```
                    20                  25                  30

Ser Gly Ala Pro Pro Ser
        35

<210> SEQ ID NO 151
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 2 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 151

Tyr Xaa Glu Gly Thr Xaa Thr Ser Asp Tyr Ser Ile Xaa Leu Asp Lys
1               5                   10                  15

Lys Ala Gln Xaa His Phe Ile Glu Tyr Leu Ile Glu Gly Gly Pro Ser
            20                  25                  30

Ser Gly Ala Pro Pro Ser
        35

<210> SEQ ID NO 152
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
```

```
<222> LOCATION: (20)..(20)
<223> OTHER INFORMATION: Xaa at position 20 is Aib
<220> FEATURE:
<221> NAME/KEY: MISC_FEATURE
<222> LOCATION: (21)..(21)
<223> OTHER INFORMATION: Xaa at position 21 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 152

Tyr Xaa Glu Gly Thr Xaa Thr Ser Asp Tyr Ser Ile Xaa Leu Asp Lys
 1               5                  10                  15

Lys Ala Gln Xaa Xaa Phe Ile Glu Tyr Leu Ile Glu Gly Gly Pro Ser
             20                  25                  30

Ser Gly Ala Pro Pro Pro Ser
             35

<210> SEQ ID NO 153
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (21)..(21)
<223> OTHER INFORMATION: Xaa at position 21 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 153

Tyr Xaa Glu Gly Thr Xaa Thr Ser Asp Tyr Ser Ile Xaa Leu Asp Lys
 1               5                  10                  15

Lys Ala Gln His Xaa Phe Ile Glu Tyr Leu Ile Glu Gly Gly Pro Ser
             20                  25                  30

Ser Gly Ala Pro Pro Pro Ser
             35

<210> SEQ ID NO 154
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
```

```
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 154

Tyr Xaa Glu Gly Thr Xaa Thr Ser Asp Ala Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 155
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 155

Tyr Xaa Glu Gly Thr Xaa Thr Ser Asp Tyr Ser Ile Xaa Leu Asp Glu
1               5                   10                  15

Lys Ala Gln Xaa Glu Phe Ile Gln Tyr Leu Ile Glu Gly Gly Pro Ser
            20                  25                  30

Ser Gly Ala Pro Pro Pro Ser
```

<210> SEQ ID NO 156
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is Aad
<220> FEATURE:
<221> NAME/KEY: MOD_RES
<222> LOCATION: (39)..(39)
<223> OTHER INFORMATION: Ser at position 39 is amidated

<400> SEQUENCE: 156

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 157
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:

```
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 157

Tyr Xaa Glu Gly Thr Xaa Thr Ser Asp Tyr Ser Ile Xaa Leu Asp Glu
1               5                   10                  15

Lys Ala Gln Xaa Glu Phe Ile Ala Tyr Leu Ile Glu Gly Gly Pro Ser
                20                  25                  30

Ser Gly Ala Pro Pro Pro Ser
            35

<210> SEQ ID NO 158
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 158

Tyr Xaa Glu Gly Thr Xaa Thr Ser Asp Tyr Ser Ile Xaa Leu Asp Glu
1               5                   10                  15

Lys Ala Gln Xaa Glu Phe Ile Val Tyr Leu Ile Glu Gly Gly Pro Ser
                20                  25                  30

Ser Gly Ala Pro Pro Pro Ser
            35

<210> SEQ ID NO 159
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
```

<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 159

Tyr Xaa Glu Gly Thr Xaa Thr Ser Asp Tyr Ser Ile Xaa Leu Asp Glu
1               5                   10                  15

Lys Ala Gln Xaa Glu Phe Ile Ser Tyr Leu Ile Glu Gly Gly Pro Ser
                20                  25                  30

Ser Gly Ala Pro Pro Pro Ser
            35

<210> SEQ ID NO 160
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 160

Tyr Xaa Glu Gly Thr Xaa Thr Ser Asp Tyr Ser Ile Xaa Leu Asp Glu
1               5                   10                  15

Lys Ala Gln Xaa Glu Phe Ile Pro Tyr Leu Ile Glu Gly Gly Pro Ser
                20                  25                  30

Ser Gly Ala Pro Pro Pro Ser
            35

-continued

<210> SEQ ID NO 161
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 161

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 162
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib

```
<220> FEATURE:
<221> NAME/KEY: MOD_RES
<222> LOCATION: (39)..(39)
<223> OTHER INFORMATION: Ser at position 39 is amidated

<400> SEQUENCE: 162

Tyr Xaa Glu Gly Thr Xaa Thr Ser Asp Tyr Ser Ile Xaa Leu Asp Glu
1               5                   10                  15

Lys Ala Gln Xaa Glu Phe Ile His Tyr Leu Ile Glu Gly Gly Pro Ser
                20                  25                  30

Ser Gly Ala Pro Pro Pro Ser
            35

<210> SEQ ID NO 163
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 163

Tyr Xaa Glu Gly Thr Xaa Thr Ser Asp His Ser Ile Xaa Leu Asp Glu
1               5                   10                  15

Lys Ala Gln Xaa Glu Phe Ile Glu Tyr Leu Ile Glu Gly Gly Pro Ser
                20                  25                  30

Ser Gly Ala Pro Pro Pro Ser
            35

<210> SEQ ID NO 164
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
```

```
<222> LOCATION: (10)..(10)
<223> OTHER INFORMATION: Xaa at position 10 is cTA
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 164

Tyr Xaa Glu Gly Thr Xaa Thr Ser Asp Xaa Ser Ile Xaa Leu Asp Glu
1               5                   10                  15

Lys Ala Gln Xaa Glu Phe Ile Glu Tyr Leu Ile Glu Gly Gly Pro Ser
            20                  25                  30

Ser Gly Ala Pro Pro Pro Ser
        35

<210> SEQ ID NO 165
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 2Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 165

Tyr Xaa Glu Gly Thr Xaa Thr Ser Asp Xaa Ser Ile Xaa Leu Asp Glu
1               5                   10                  15

Lys Ala Gln Xaa Glu Phe Ile Glu Tyr Leu Ile Glu Gly Gly Pro Ser
            20                  25                  30
```

```
Ser Gly Ala Pro Pro Pro Ser
        35

<210> SEQ ID NO 166
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 3Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 166

Tyr Xaa Glu Gly Thr Xaa Thr Ser Asp Xaa Ser Ile Xaa Leu Asp Glu
1               5                   10                  15

Lys Ala Gln Xaa Glu Phe Ile Glu Tyr Leu Ile Glu Gly Gly Pro Ser
            20                  25                  30

Ser Gly Ala Pro Pro Pro Ser
        35

<210> SEQ ID NO 167
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
```

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 167

Tyr Xaa Glu Gly Thr Xaa Thr Ser Asp Xaa Ser Ile Xaa Leu Asp Glu
1               5                   10                  15

Lys Ala Gln Xaa Glu Phe Ile Glu Tyr Leu Ile Glu Gly Gly Pro Ser
                20                  25                  30

Ser Gly Ala Pro Pro Pro Ser
            35

<210> SEQ ID NO 168
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 168

Tyr Xaa Glu Gly Thr Xaa Thr Ser Asp Xaa Ser Ile Xaa Leu Asp Glu
1               5                   10                  15

Lys Ala Gln Xaa Glu Phe Ile Glu Tyr Leu Ile Glu Gly Gly Pro Ser
                20                  25                  30

Ser Gly Ala Pro Pro Pro Ser
            35

<210> SEQ ID NO 169
<211> LENGTH: 39
<212> TYPE: PRT
```

<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 169

Tyr Xaa Glu Gly Thr Xaa Thr Ser Asp Xaa Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly Ala Pro Pro Ser
        35

<210> SEQ ID NO 170
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)2-CO-(CH2)18-C
      O2H
<220> FEATURE:
<221> NAME/KEY: MISC_FEATURE
<222> LOCATION: (20)..(20)

```
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 170

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly

<210> SEQ ID NO 171
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)2-CO-(CH2)18-C
      O2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 171

Tyr Xaa Glu Gly Thr Xaa Thr Ser Asp His Ser Ile Xaa Leu Asp Glu
1               5                   10                  15

Lys Ala Gln Xaa Thr Phe Ile Xaa His Leu Ile Glu Gly Gly Pro Ser
            20                  25                  30

Ser Gly

<210> SEQ ID NO 172
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
```

```
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 172

His Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly Pro Ser
            20                  25                  30

Ser Gly Ala Pro Pro Pro Ser
        35

<210> SEQ ID NO 173
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (28)..(28)
<223> OTHER INFORMATION: Xaa at position 28 is D-Glu
<220> FEATURE:
<221> NAME/KEY: MOD_RES
<222> LOCATION: (39)..(39)
<223> OTHER INFORMATION: Ser at position 39 is amidated
```

<400> SEQUENCE: 173

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Xaa Gly Gly Pro Ser
                20                  25                  30

Ser Gly Ala Pro Pro Pro Ser
            35

<210> SEQ ID NO 174
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Phe
<220> FEATURE:
<221> NAME/KEY: MISC_FEATURE
<222> LOCATION: (28)..(28)
<223> OTHER INFORMATION: Xaa at position 28 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 174

Tyr Xaa Glu Gly Thr Xaa Thr Ser Asp His Ser Ile Xaa Leu Asp Glu
1               5                   10                  15

Lys Ala Gln Xaa Thr Phe Ile Xaa Xaa Leu Ile Xaa Gly Gly Pro Ser
                20                  25                  30

Ser Gly Ala Pro Pro Pro Ser
            35

<210> SEQ ID NO 175
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)

```
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (30)..(30)

<400> SEQUENCE: 175

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly
            20                  25                  30

<210> SEQ ID NO 176
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 176

Tyr Xaa Glu Gly Thr Xaa Thr Ser Asp His Ser Ile Xaa Leu Asp Glu
1               5                   10                  15
```

Lys Ala Gln Xaa Thr Phe Ile Xaa Tyr Leu Ile Glu Gly Gly Pro Ser
            20                  25                  30

Ser Gly

<210> SEQ ID NO 177
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 177

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly Ala Pro Pro Ser
        35

<210> SEQ ID NO 178
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by conjugation of the epsilon-amino group of the Lys side chain with
(2-[2-(2-amino-ethoxy)-ethoxy]-acetyl)2-(gamma-Glu)-CO-(CH2)16-CO
2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 178

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
                20                  25                  30

Ser Gly Ala Pro Pro Pro Ser
            35

<210> SEQ ID NO 179
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)14-CO
2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 179

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
                20                  25                  30

Ser Gly Ala Pro Pro Pro Ser
            35

<210> SEQ ID NO 180

```
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 180

Tyr Xaa Glu Gly Thr Xaa Thr Ser Asp His Ser Ile Xaa Leu Asp Xaa
1               5                   10                  15

Lys Ala Gln Xaa Thr Phe Ile Xaa Tyr Leu Ile Glu Gly Gly Pro Ser
            20                  25                  30

Ser Gly Ala Pro Pro Ser
        35

<210> SEQ ID NO 181
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
```

```
           conjugation of the epsilon-amino group of the Lys side chain with
           (2-[2-(2-amino-ethoxy)-ethoxy]-acetyl)2-(gamma-Glu)-CO-(CH2)18-CO
           2H
<220> FEATURE:
<221> NAME/KEY: MISC_FEATURE
<222> LOCATION: (20)..(20)
<223> OTHER INFORMATION: Xaa at position 20 is a Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 181

Tyr Xaa Glu Gly Thr Xaa Thr Ser Asp His Ser Ile Xaa Leu Asp Xaa
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 182
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dap
<220> FEATURE:
<221> NAME/KEY: MOD_RES
<222> LOCATION: (17)..(17)
<223> OTHER INFORMATION: Lys at position 17 is chemically modified by
           conjugation of the epsilon-amino group of the Lys side chain with
           (2-[2-(2-amino-ethoxy)-ethoxy]-acetyl)2-(gamma-Glu)-CO-(CH2)18-CO
           2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 182

Tyr Xaa Glu Gly Thr Xaa Thr Ser Asp His Ser Ile Xaa Leu Asp Xaa
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
```

```
<210> SEQ ID NO 183
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 183

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 184
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)18-
      CO2H
<220> FEATURE:
<221> NAME/KEY: MISC_FEATURE
```

```
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 184

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 185
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 185

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 186
<211> LENGTH: 39
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 186

Tyr Xaa Glu Gly Thr Xaa Thr Ser Asp His Ser Ile Xaa Leu Asp Glu
1               5                   10                  15

Lys Ala Gln Xaa His Phe Ile Xaa Tyr Leu Ile Glu Gly Gly Pro Ser
            20                  25                  30

Ser Gly Ala Pro Pro Pro Ser
            35

<210> SEQ ID NO 187
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)14-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
```

<222> LOCATION: (39)..(39)
<223> OTHER INFORMATION: Ser at position 39 is amidated

<400> SEQUENCE: 187

Tyr Xaa Glu Gly Thr Xaa Thr Ser Asp His Ser Ile Xaa Leu Asp Glu
1               5                   10                  15

Lys Ala Gln Xaa His Phe Ile Xaa Tyr Leu Ile Glu Gly Gly Pro Ser
            20                  25                  30

Ser Gly Ala Pro Pro Pro Ser
        35

<210> SEQ ID NO 188
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 188

Tyr Xaa Glu Gly Thr Xaa Thr Ser Asp His Ser Ile Xaa Leu Asp Glu
1               5                   10                  15

Lys Ala Gln Xaa His Phe Ile Xaa Tyr Leu Ile Glu Gly Gly Pro Ser
            20                  25                  30

Ser Gly

<210> SEQ ID NO 189
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:

```
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (30)..(30)
<223> OTHER INFORMATION: Gly at position 30 is amidated

<400> SEQUENCE: 189

Tyr Xaa Glu Gly Thr Xaa Thr Ser Asp His Ser Ile Xaa Leu Asp Glu
1               5                   10                  15

Lys Ala Gln Xaa His Phe Ile Xaa Tyr Leu Ile Glu Gly Gly
            20                  25                  30

<210> SEQ ID NO 190
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 3Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 190

Tyr Xaa Glu Gly Thr Xaa Thr Ser Asp Xaa Ser Ile Xaa Leu Asp Glu
1               5                   10                  15
```

-continued

Lys Ala Gln Xaa Glu Phe Ile Xaa Tyr Leu Ile Glu Gly Gly Pro Ser
                20                  25                  30

Ser Gly Ala Pro Pro Pro Ser
        35

<210> SEQ ID NO 191
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 191

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
        35

<210> SEQ ID NO 192
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu

```
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 192

Tyr Xaa Glu Gly Thr Xaa Thr Ser Asp Leu Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 193
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is D-Tyr
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 193

Tyr Xaa Glu Gly Thr Xaa Thr Ser Asp Xaa Ser Ile Xaa Leu Asp Glu
1               5                   10                  15
```

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 194
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is D-His
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 194

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 195
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is alpha-methyl-Tyr

```
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 195

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 196
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 196

Tyr Xaa Glu Gly Thr Xaa Thr Ser Asp Gln Ser Ile Xaa Leu Asp Glu
1               5                   10                  15
```

```
Lys Ala Gln Xaa Glu Phe Ile Xaa Tyr Leu Ile Glu Gly Gly Pro Ser
            20              25                  30

Ser Gly Ala Pro Pro Pro Ser
        35

<210> SEQ ID NO 197
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 3Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 197

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20              25                  30

Ser Gly Ala Pro Pro Pro Ser
        35

<210> SEQ ID NO 198
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
```

```
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 198

Tyr Xaa Glu Gly Thr Xaa Thr Ser Asp Xaa Ser Ile Xaa Leu Asp Glu
 1               5                  10                  15

Lys Ala Gln Xaa Glu Phe Ile Xaa Tyr Leu Ile Glu Gly Gly Pro Ser
             20                  25                  30

Ser Gly Ala Pro Pro Pro Ser
             35

<210> SEQ ID NO 199
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 3Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 199
```

-continued

```
His Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35
```

<210> SEQ ID NO 200
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 200

```
Tyr Xaa Glu Gly Thr Xaa Thr Ser Asp Val Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35
```

<210> SEQ ID NO 201
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu

```
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 201

Tyr Xaa Glu Gly Thr Xaa Thr Ser Asp Ala Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 202
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 202

Tyr Xaa Glu Gly Thr Phe Thr Ser Asp Tyr Ser Ile Leu Leu Asp Glu
1               5                   10                  15

Lys Ala Gln Gln Ala Phe Ile Glu Tyr Leu Ile Glu Gly Gly Pro Ser
            20                  25                  30

Ser Gly Ala Pro Pro Pro Ser
        35

<210> SEQ ID NO 203
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
```

<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 203

Tyr Xaa Glu Gly Thr Phe Thr Ser Asp Tyr Ser Ile Leu Leu Asp Glu
1               5                   10                  15

Lys Ala Gln His Ala Phe Ile Glu Tyr Leu Ile Glu Gly Gly Pro Ser
            20                  25                  30

Ser Gly Ala Pro Pro Pro Ser
        35

<210> SEQ ID NO 204
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 204

Tyr Xaa Glu Gly Thr Phe Thr Ser Asp Tyr Ser Ile Leu Leu Asp Arg
1               5                   10                  15

Lys Ala Gln Gln Ala Phe Ile Glu Tyr Leu Ile Glu Gly Gly Pro Ser
            20                  25                  30

Ser Gly Ala Pro Pro Pro Ser
        35

<210> SEQ ID NO 205
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 205

-continued

```
Tyr Xaa Glu Gly Thr Phe Thr Ser Asp Tyr Ser Ile Leu Leu Asp Arg
1               5                   10                  15

Lys Ala Gln His Ala Phe Ile Glu Tyr Leu Ile Glu Gly Gly Pro Ser
            20                  25                  30

Ser Gly Ala Pro Pro Pro Ser
        35
```

<210> SEQ ID NO 206
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MOD_RES
<222> LOCATION: (34)..(34)
<223> OTHER INFORMATION: Gly at position 34 is amidated

<400> SEQUENCE: 206

```
Tyr Xaa Glu Gly Thr Phe Thr Ser Asp Tyr Ser Ile Leu Leu Asp Glu
1               5                   10                  15

Lys Ala Gln Gln Ala Phe Ile Glu Tyr Leu Ile Glu Gly Gly Pro Ser
            20                  25                  30

Ser Gly
```

<210> SEQ ID NO 207
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MOD_RES
<222> LOCATION: (34)..(34)
<223> OTHER INFORMATION: Gly at position 34 is amidated

<400> SEQUENCE: 207

```
Xaa Xaa Glu Gly Thr Phe Thr Ser Asp Tyr Ser Ile Leu Leu Asp Glu
1               5                   10                  15

Lys Ala Gln Gln Ala Phe Ile Glu Tyr Leu Ile Glu Gly Gly Pro Ser
            20                  25                  30

Ser Gly
```

<210> SEQ ID NO 208
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is DesTyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 208

Xaa Xaa Glu Gly Thr Phe Thr Ser Asp Tyr Ser Ile Leu Leu Asp Glu
1               5                   10                  15

Lys Ala Gln Gln Ala Phe Ile Glu Tyr Leu Ile Glu Gly Gly Pro Ser
            20                  25                  30

Ser Gly Ala Pro Pro Pro Ser
        35

<210> SEQ ID NO 209
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is DesTyr
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 209

Xaa Ala Glu Gly Thr Phe Thr Ser Asp Tyr Ser Ile Leu Leu Asp Glu
1               5                   10                  15

Lys Ala Gln Gln Ala Phe Ile Glu Tyr Leu Ile Glu Gly Gly Pro Ser
            20                  25                  30

Ser Gly Ala Pro Pro Pro Ser
        35

<210> SEQ ID NO 210
<211> LENGTH: 39
<212> TYPE: PRT
<213> ORGANISM: Artificial Sequence
<220> FEATURE:
<223> OTHER INFORMATION: Synthetic Construct

```
<220> FEATURE:
<221> NAME/KEY: MISC_FEATURE
<222> LOCATION: (1)..(1)
<223> OTHER INFORMATION: Xaa at position 1 is DesHis
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 210

Xaa Xaa Glu Gly Thr Phe Thr Ser Asp Tyr Ser Ile Leu Leu Asp Glu
1               5                   10                  15

Lys Ala Gln Gln Ala Phe Ile Glu Tyr Leu Ile Glu Gly Gly Pro Ser
            20                  25                  30

Ser Gly Ala Pro Pro Pro Ser
        35

<210> SEQ ID NO 211
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-(2-[2-(2-Amino
      -ethoxy)-ethoxy]-acetyl)-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 211

Tyr Xaa Glu Gly Thr Xaa Thr Ser Asp Xaa Ser Ile Xaa Leu Asp Lys
1               5                   10                  15
```

Lys Ala Gln Xaa Glu Phe Ile Xaa Tyr Leu Ile Glu Gly Gly Pro Ser
            20              25                  30

Ser Gly Ala Pro Pro Pro Ser
        35

<210> SEQ ID NO 212
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 212

Tyr Xaa Glu Gly Thr Xaa Thr Ser Asp Xaa Ser Ile Xaa Leu Asp Lys
1               5                   10                  15

Lys Ala Gln Xaa Glu Phe Ile Xaa Tyr Leu Ile Glu Gly Gly Pro Ser
            20              25                  30

Ser Gly Ala Pro Pro Pro Ser
        35

<210> SEQ ID NO 213
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal

```
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 213

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
        35

<210> SEQ ID NO 214
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)16-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 214
```

```
Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
            35

<210> SEQ ID NO 215
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 215

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
            35

<210> SEQ ID NO 216
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
```

```
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 216

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 217
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)14-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 217

Tyr Xaa Glu Gly Thr Xaa Thr Ser Asp Tyr Ser Ile Xaa Leu Asp Glu
```

```
1               5                   10                  15
Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 218
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 218

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 219
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
```

```
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dap
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 219

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
        35

<210> SEQ ID NO 220
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-(2-[2-(2-Amino
      -ethoxy)-ethoxy]-acetyl)-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 220

Tyr Xaa Glu Gly Thr Xaa Thr Ser Asp Tyr Ser Ile Xaa Leu Asp Lys
```

```
  1               5                  10                  15
Lys Ala Gln Xaa Glu Phe Ile Xaa Tyr Leu Ile Glu Gly Gly Pro Ser
            20                  25                  30

Ser Gly Ala Pro Pro Ser
            35

<210> SEQ ID NO 221
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 221

Tyr Xaa Glu Gly Thr Xaa Thr Ser Asp Tyr Ser Ile Xaa Leu Asp Lys
  1               5                  10                  15

Lys Ala Gln Xaa Glu Phe Ile Xaa Tyr Leu Ile Glu Gly Gly Pro Ser
            20                  25                  30

Ser Gly Ala Pro Pro Ser
            35

<210> SEQ ID NO 222
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
```

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 222

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 223
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)16-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 223

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35
```

```
<210> SEQ ID NO 224
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 224

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
                35

<210> SEQ ID NO 225
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
```

```
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 225

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 226
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 226

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 227
<211> LENGTH: 39
<212> TYPE: PRT
<213> ORGANISM: Artificial Sequence
<220> FEATURE:
```

<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dap
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 227

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
        35

<210> SEQ ID NO 228
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:

```
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 228

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly

<210> SEQ ID NO 229
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (30)..(30)
<223> OTHER INFORMATION: Gly at position 30 is amidated

<400> SEQUENCE: 229

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly
            20                  25                  30

<210> SEQ ID NO 230
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
```

```
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 230

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
            35

<210> SEQ ID NO 231
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 alpha-methyl-Tyr
<220> FEATURE:
<221> NAME/KEY: MOD_RES
<222> LOCATION: (39)..(39)
<223> OTHER INFORMATION: Ser at position 39 is amidated
```

-continued

<400> SEQUENCE: 231

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Xaa Leu Ile Glu Gly Gly Pro Ser
                20                  25                  30

Ser Gly Ala Pro Pro Pro Ser
        35

<210> SEQ ID NO 232
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 232

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Xaa Leu Ile Glu Gly Gly Pro Ser
                20                  25                  30

Ser Gly Ala Pro Pro Pro Ser
        35

<210> SEQ ID NO 233
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)

```
<223> OTHER INFORMATION: Xaa at position 13 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 233

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
            35

<210> SEQ ID NO 234
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 234

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30
```

Ser Gly Ala Pro Pro Pro Ser
        35

<210> SEQ ID NO 235
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 235

Tyr Xaa Glu Gly Thr Xaa Thr Ser Asp Tyr Ser Ile Leu Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 236
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib

```
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 236

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 237
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
     conjugation of the epsilon-amino group of the Lys side chain with
     (2-[2-(2-amino-ethoxy)-ethoxy]-acetyl)2-(gamma-Glu)-CO-(CH2)18-CO
     2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 237

Tyr Xaa Glu Gly Thr Xaa Thr Ser Asp Tyr Ser Ile Xaa Leu Asp Lys
1               5                   10                  15

Lys Ala Gln Xaa Glu Phe Ile Xaa Tyr Leu Ile Glu Gly Gly Pro Ser
            20                  25                  30

Ser Gly

<210> SEQ ID NO 238
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
```

<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (12)..(12)
<223> OTHER INFORMATION: Xaa at position 12 is alpha-methyl-Leu
<220> FEATURE:
<221> NAME/KEY: MOD_RES
<222> LOCATION: (16)..(16)
<223> OTHER INFORMATION: Lys at position 16 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (19)..(19)
<223> OTHER INFORMATION: Xaa at position 19 is Aib
<220> FEATURE:
<221> NAME/KEY: MISC_FEATURE
<222> LOCATION: (23)..(23)
<223> OTHER INFORMATION: Xaa at position 23 is D-Glu
<220> FEATURE:
<221> NAME/KEY: MOD_RES
<222> LOCATION: (38)..(38)
<223> OTHER INFORMATION: Ser at position 39 is amidated

<400> SEQUENCE: 238

Tyr Xaa Glu Gly Thr Xaa Thr Ser Asp Tyr Ser Xaa Leu Asp Glu Lys
1               5                   10                  15

Ala Gln Xaa Glu Phe Ile Xaa Tyr Leu Ile Glu Gly Gly Pro Ser Ser
            20                  25                  30

Gly Ala Pro Pro Pro Ser
        35

<210> SEQ ID NO 239
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated -continued

<400> SEQUENCE: 239

Tyr Xaa Glu Gly Thr Xaa Thr Ser Asp Tyr Ser Ile Xaa Leu Asp His
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 240
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 240

Tyr Xaa Glu Gly Thr Xaa Thr Ser Asp Tyr Ser Ile Xaa Leu Asp Lys
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 241
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)

<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 241

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 242
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:

```
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 242

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 243
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 243

Tyr Xaa Glu Gly Thr Xaa Thr Ser Asp Xaa Ser Ile Leu Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 244
<211> LENGTH: 39
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 244

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Ser
        35

<210> SEQ ID NO 245
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
```

```
       conjugation of the epsilon-amino group of the Lys side chain with
       (2-[2-(2-amino-ethoxy)-ethoxy]-acetyl)2-(gamma-Glu)-CO-(CH2)16-CO
       2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 245

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Xaa Leu Ile Glu Gly Gly Pro Ser
            20                  25                  30

Ser Gly Ala Pro Pro Pro Ser
        35

<210> SEQ ID NO 246
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
       conjugation of the epsilon-amino group of the Lys side chain with
       (2-[2-(2-amino-ethoxy)-ethoxy]-acetyl)2-(gamma-Glu)-CO-(CH2)16-CO
       2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 246
```

Tyr Xaa Glu Gly Thr Xaa Thr Ser Asp Ala Ser Ile Xaa Leu Asp Xaa
1               5                   10                  15

Lys Ala Gln Xaa Glu Phe Ile Xaa Xaa Leu Ile Glu Gly Gly Pro Ser
            20                  25                  30

Ser Gly Ala Pro Pro Ser
        35

<210> SEQ ID NO 247
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 247

Tyr Xaa Glu Gly Thr Xaa Thr Ser Asp Leu Ser Ile Xaa Leu Asp Xaa
1               5                   10                  15

Lys Ala Gln Xaa Glu Phe Ile Xaa Xaa Leu Ile Glu Gly Gly Pro Ser
            20                  25                  30

Ser Gly Ala Pro Pro Ser
        35

<210> SEQ ID NO 248
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib

```
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 248

Tyr Xaa Glu Gly Thr Xaa Thr Ser Asp Xaa Ser Ile Xaa Leu Asp Xaa
1               5                   10                  15

Lys Ala Gln Xaa Thr Phe Ile Xaa Xaa Leu Ile Glu Gly Gly Pro Ser
            20                  25                  30

Ser Gly Ala Pro Pro Pro Ser
        35

<210> SEQ ID NO 249
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
```

```
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 249

Tyr Xaa Glu Gly Thr Xaa Thr Ser Asp Xaa Ser Ile Xaa Leu Asp Xaa
1               5                   10                  15

Lys Ala Gln Xaa Ala Phe Ile Xaa Xaa Leu Ile Glu Gly Gly Pro Ser
            20                  25                  30

Ser Gly Ala Pro Pro Pro Ser
            35

<210> SEQ ID NO 250
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
```

<223> OTHER INFORMATION: Ser at position 39 is amidated

<400> SEQUENCE: 250

Tyr Xaa Glu Gly Thr Xaa Thr Ser Asp Val Ser Ile Xaa Leu Asp Xaa
1               5                   10                  15

Lys Ala Gln Xaa Thr Phe Ile Xaa Xaa Leu Ile Glu Gly Gly Pro Ser
            20                  25                  30

Ser Gly Ala Pro Pro Pro Ser
        35

<210> SEQ ID NO 251
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 251

Tyr Xaa Glu Gly Thr Xaa Thr Ser Asp Val Ser Ile Xaa Leu Asp Xaa
1               5                   10                  15

Lys Ala Gln Xaa Ala Phe Ile Xaa Xaa Leu Ile Glu Gly Gly Pro Ser
            20                  25                  30

Ser Gly Ala Pro Pro Pro Ser
        35

<210> SEQ ID NO 252
<211> LENGTH: 39
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 252

Tyr Xaa Glu Gly Thr Xaa Thr Ser Asp Leu Ser Ile Xaa Leu Asp Xaa
1               5                   10                  15

Lys Ala Gln Xaa Thr Phe Ile Xaa Xaa Leu Ile Glu Gly Gly Pro Ser
            20                  25                  30

Ser Gly Ala Pro Pro Pro Ser
        35

<210> SEQ ID NO 253
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
```

```
                                2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 253

Tyr Xaa Glu Gly Thr Xaa Thr Ser Asp Leu Ser Ile Xaa Leu Asp Xaa
1               5                   10                  15

Lys Ala Gln Xaa Ala Phe Ile Xaa Xaa Leu Ile Glu Gly Gly Pro Ser
            20                  25                  30

Ser Gly Ala Pro Pro Pro Ser
            35

<210> SEQ ID NO 254
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 254

Tyr Xaa Glu Gly Thr Xaa Thr Ser Asp Ala Ser Ile Xaa Leu Asp Xaa
```

```
                1               5                   10                  15
Lys Ala Gln Xaa Thr Phe Ile Xaa Xaa Leu Ile Glu Gly Gly Pro Ser
            20                  25                  30

Ser Gly Ala Pro Pro Ser
            35
```

<210> SEQ ID NO 255
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 255

```
Tyr Xaa Glu Gly Thr Xaa Thr Ser Asp Ala Ser Ile Xaa Leu Asp Xaa
1               5                   10                  15

Lys Ala Gln Xaa Ala Phe Ile Xaa Xaa Leu Ile Glu Gly Gly Pro Ser
            20                  25                  30

Ser Gly Ala Pro Pro Ser
            35
```

<210> SEQ ID NO 256
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE

```
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 256

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 257
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated
```

<400> SEQUENCE: 257

Tyr Xaa Glu Gly Thr Xaa Thr Ser Asp Tyr Ser Ile Leu Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 258
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is Nle
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 258

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 259
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE

```
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 259

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 260
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
```

```
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 260

Tyr Xaa Glu Gly Thr Xaa Thr Ser Asp Xaa Ser Ile Xaa Leu Asp Xaa
1               5                   10                  15

Lys Ala Gln Xaa Ala Phe Ile Xaa Xaa Leu Ile Glu Gly Gly Pro Ser
            20                  25                  30

Ser Gly Ala Pro Pro Pro Ser
        35

<210> SEQ ID NO 261
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 261

Tyr Xaa Glu Gly Thr Xaa Thr Ser Asp Xaa Ser Ile Xaa Leu Asp Xaa
1               5                   10                  15
```

Lys Ala Gln Xaa Ala Phe Ile Xaa Xaa Leu Ile Ala Gly Gly Pro Ser
            20                  25                  30

Ser Gly Ala Pro Pro Pro Ser
        35

<210> SEQ ID NO 262
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 262

Tyr Xaa Glu Gly Thr Phe Thr Ser Asp Tyr Ser Ile Leu Leu Asp Lys
1               5                   10                  15

Lys Ala Gln Ala Ala Phe Ile Glu Tyr Leu Ile Glu Gly Gly Pro Ser
            20                  25                  30

Ser Gly Ala Pro Pro Pro Ser
        35

<210> SEQ ID NO 263
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 263

Tyr Xaa Glu Gly Thr Phe Thr Ser Asp Tyr Ser Ile Leu Leu Asp Lys
1               5                   10                  15

Lys Ala Gln Gln Ala Phe Ile Glu Tyr Leu Ile Glu Gly Gly Pro Ser
            20                  25                  30

Ser Gly Ala Pro Pro Pro Ser
        35

<210> SEQ ID NO 264
<211> LENGTH: 39
<212> TYPE: PRT

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 264

Tyr Xaa Glu Gly Thr Phe Thr Ser Asp Tyr Ser Ile Leu Leu Asp Lys
1               5                  10                  15

Lys Ala Gln His Ala Phe Ile Glu Tyr Leu Ile Glu Gly Gly Pro Ser
            20                  25                  30

Ser Gly Ala Pro Pro Pro Ser
        35

<210> SEQ ID NO 265
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 265

Tyr Xaa Glu Gly Thr Phe Thr Ser Asp Tyr Ser Ile Leu Leu Asp Lys
1               5                  10                  15

Lys Ala Gln Lys Ala Phe Ile Glu Tyr Leu Ile Glu Gly Gly Pro Ser
            20                  25                  30

Ser Gly Ala Pro Pro Pro Ser
        35

<210> SEQ ID NO 266
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
```

-continued

```
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 266

Tyr Xaa Glu Gly Thr Phe Thr Ser Asp Tyr Ser Ile Leu Leu Asp Lys
1               5                   10                  15

Lys Ala Gln Arg Ala Phe Ile Glu Tyr Leu Ile Glu Gly Gly Pro Ser
            20                  25                  30

Ser Gly Ala Pro Pro Pro Ser
        35

<210> SEQ ID NO 267
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 267

Tyr Xaa Glu Gly Thr Phe Thr Ser Asp Tyr Ser Ile Leu Leu Asp Glu
1               5                   10                  15

Lys Ala Gln Lys Ala Phe Ile Glu Tyr Leu Ile Glu Gly Gly Pro Ser
            20                  25                  30

Ser Gly Ala Pro Pro Pro Ser
        35

<210> SEQ ID NO 268
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated
```

<400> SEQUENCE: 268

Tyr Xaa Glu Gly Thr Phe Thr Ser Asp Tyr Ser Ile Leu Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 269
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (39)..(39)
<223> OTHER INFORMATION: Ser at position 39 is amidated

<400> SEQUENCE: 269

Tyr Xaa Glu Gly Thr Phe Thr Ser Asp His Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 270
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 270

Tyr Xaa Glu Gly Thr Phe Thr Ser Asp Tyr Ser Ile Leu Leu Asp Lys
1               5                   10                  15

Lys Ala Gln Glu Ala Phe Ile Glu Tyr Leu Ile Glu Gly Gly Pro Ser

Ser Gly Ala Pro Pro Pro Ser
        35

<210> SEQ ID NO 271
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 271

Tyr Xaa Glu Gly Thr Phe Thr Ser Asp Tyr Ser Ile Leu Leu Asp Lys
1               5                   10                  15

Lys Ala Gln Thr Ala Phe Ile Glu Tyr Leu Ile Glu Gly Gly Pro Ser
            20                  25                  30

Ser Gly Ala Pro Pro Pro Ser
        35

<210> SEQ ID NO 272
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MOD_RES
<222> LOCATION: (39)..(39)
<223> OTHER INFORMATION: Ser at position 39 is amidated

<400> SEQUENCE: 272

Tyr Xaa Glu Gly Thr Phe Thr Ser Asp Tyr Ser Ile Leu Leu Asp Lys
1               5                   10                  15

Lys Ala Gln Ser Ala Phe Ile Glu Tyr Leu Ile Glu Gly Gly Pro Ser
            20                  25                  30

Ser Gly Ala Pro Pro Pro Ser
        35

<210> SEQ ID NO 273
<211> LENGTH: 34
<212> TYPE: PRT
<213> ORGANISM: Artificial Sequence
<220> FEATURE:

```
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (34)..(34)
<223> OTHER INFORMATION: Gly at position 34 is amidated

<400> SEQUENCE: 273

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Xaa Leu Ile Glu Gly Gly Pro Ser
            20                  25                  30

Ser Gly

<210> SEQ ID NO 274
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
```

```
<221> NAME/KEY: MISC_FEATURE
<222> LOCATION: (16)..(16)
<223> OTHER INFORMATION: Xaa at position 13 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (30)..(30)
<223> OTHER INFORMATION: Gly at position 30 is amidated

<400> SEQUENCE: 274

Tyr Xaa Glu Gly Thr Xaa Thr Ser Asp Xaa Ser Ile Xaa Leu Asp Xaa
 1               5                  10                  15

Lys Ala Gln Xaa Glu Phe Ile Xaa Xaa Leu Ile Glu Gly Gly
            20                  25                  30

<210> SEQ ID NO 275
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 275

Tyr Xaa Glu Gly Thr Phe Thr Ser Asp Tyr Ser Ile Leu Leu Asp Lys
 1               5                  10                  15

Lys Ala Gln Xaa Ala Phe Ile Glu Tyr Leu Ile Glu Gly Gly Pro Ser
            20                  25                  30

Ser Gly

<210> SEQ ID NO 276
<211> LENGTH: 30
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 276

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly
            20                  25                  30

<210> SEQ ID NO 277
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 277

Tyr Xaa Glu Gly Thr Phe Thr Ser Asp Tyr Ser Ile Leu Leu Asp Glu
1               5                   10                  15

Lys Ala Gln Xaa Ala Phe Ile Glu Tyr Leu Ile Glu Gly Gly Pro Ser
            20                  25                  30

Ser Gly

<210> SEQ ID NO 278
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
```

<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)16-CO
2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (30)..(30)
<223> OTHER INFORMATION: Gly at position 30 is amidated

<400> SEQUENCE: 278

Tyr Xaa Glu Gly Thr Phe Thr Ser Asp Tyr Ser Ile Leu Leu Asp Glu
1               5                   10                  15

Lys Ala Gln Xaa Ala Phe Ile Glu Tyr Leu Ile Glu Gly Gly
            20                  25                  30

<210> SEQ ID NO 279
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)16-CO
2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 279

Tyr Xaa Glu Gly Thr Phe Thr Ser Asp Tyr Ser Ile Leu Leu Asp Lys
1               5                   10                  15

Lys Ala Gln Xaa Glu Phe Ile Glu Tyr Leu Ile Glu Gly Gly Pro Ser
            20                  25                  30

Ser Gly

<210> SEQ ID NO 280
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)16-CO
2H
<220> FEATURE:
<221> NAME/KEY: MISC_FEATURE
<222> LOCATION: (20)..(20)

<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 280

Tyr Xaa Glu Gly Thr Phe Thr Ser Asp Tyr Ser Ile Leu Leu Asp Lys
1               5                   10                  15

Lys Ala Gln Xaa Glu Phe Ile Glu Tyr Leu Ile Glu Gly Gly
            20                  25                  30

<210> SEQ ID NO 281
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
    conjugation of the epsilon-amino group of the Lys side chain with
    (2-[2-(2-amino-ethoxy)-ethoxy]-acetyl)2-(gamma-Glu)-CO-(CH2)16-CO
    2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 281

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Ala Gly Gly Pro Ser
            20                  25                  30

Ser Gly

<210> SEQ ID NO 282
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
    conjugation of the epsilon-amino group of the Lys side chain with
    (2-[2-(2-amino-ethoxy)-ethoxy]-acetyl)2-(gamma-Glu)-CO-(CH2)16-CO
    2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 282

```
Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Ala Gly Gly
            20                  25                  30
```

<210> SEQ ID NO 283
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MOD_RES
<222> LOCATION: (34)..(34)
<223> OTHER INFORMATION: Gly at position 34 is amidated

<400> SEQUENCE: 283

```
Tyr Xaa Glu Gly Thr Phe Thr Ser Asp Tyr Ser Ile Leu Leu Asp Lys
1               5                   10                  15

Lys Ala Gln Pro Ala Phe Ile Glu Tyr Leu Ile Glu Gly Gly Pro Ser
            20                  25                  30

Ser Gly
```

<210> SEQ ID NO 284
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MOD_RES
<222> LOCATION: (30)..(30)
<223> OTHER INFORMATION: Gly at position 30 is amidated

<400> SEQUENCE: 284

```
Tyr Xaa Glu Gly Thr Phe Thr Ser Asp Tyr Ser Ile Leu Leu Asp Lys
1               5                   10                  15

Lys Ala Gln Pro Ala Phe Ile Glu Tyr Leu Ile Glu Gly Gly
            20                  25                  30
```

<210> SEQ ID NO 285
<211> LENGTH: 39
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 285

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
            35

<210> SEQ ID NO 286
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 286

Tyr Xaa Glu Gly Thr Xaa Thr Ser Asp Tyr Ser Ile Xaa Leu Asp Glu
1               5                   10                  15

Gln Ala Gln Xaa Glu Phe Ile Xaa Tyr Leu Ile Glu Gly Gly Pro Ser
                20                  25                  30

Ser Gly Ala Pro Pro Pro Ser
            35
```

```
<210> SEQ ID NO 287
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (40)..(40)
<223> OTHER INFORMATION: Cys at position 40 is amidated

<400> SEQUENCE: 287

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Ser Cys
        35                  40

<210> SEQ ID NO 288
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (40)..(40)
<223> OTHER INFORMATION: Cys at position 40 is amidated

<400> SEQUENCE: 288

Tyr Xaa Glu Gly Thr Xaa Thr Ser Asp Tyr Ser Ile Xaa Leu Asp Glu
1               5                   10                  15
```

Gln Ala Gln Xaa Glu Phe Ile Xaa Tyr Leu Ile Glu Gly Gly Pro Ser
            20                  25                  30

Ser Gly Ala Pro Pro Pro Ser Cys
        35                  40

<210> SEQ ID NO 289
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 289

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 290
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)

<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 290

Tyr Xaa Glu Gly Thr Xaa Thr Ser Asp Tyr Ser Ile Xaa Leu Asp Xaa
1               5                   10                  15

Gln Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 291
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (40)..(40)
<223> OTHER INFORMATION: Cys at position 40 is amidated

<400> SEQUENCE: 291

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser Cys
        35                  40

<210> SEQ ID NO 292
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib

```
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (40)..(40)
<223> OTHER INFORMATION: Cys at position 40 is amidated

<400> SEQUENCE: 292

Tyr Xaa Glu Gly Thr Xaa Thr Ser Asp Tyr Ser Ile Xaa Leu Asp Xaa
1               5                   10                  15

Gln Ala Gln Xaa Glu Phe Ile Xaa Tyr Leu Ile Glu Gly Gly Pro Ser
            20                  25                  30

Ser Gly Ala Pro Pro Pro Ser Cys
        35                  40

<210> SEQ ID NO 293
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated
```

<400> SEQUENCE: 293

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Xaa Leu Ile Glu Gly Gly Pro Ser
            20                  25                  30

Ser Gly Ala Pro Pro Ser
        35

<210> SEQ ID NO 294
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: mod
<222> LOCATION: (39)..(39)
<223> OTHER INFORMATION: Ser at position 39 is amidated

<400> SEQUENCE: 294

Tyr Xaa Glu Gly Thr Xaa Thr Ser Asp Xaa Ser Ile Xaa Leu Asp Xaa
1               5                   10                  15

Gln Ala Gln Xaa Glu Phe Ile Xaa Xaa Leu Ile Glu Gly Gly Pro Ser
            20                  25                  30

Ser Gly Ala Pro Pro Ser
        35

<210> SEQ ID NO 295
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:

```
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (40)..(40)
<223> OTHER INFORMATION: Cys at position 40 is amidated

<400> SEQUENCE: 295

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Xaa Leu Ile Glu Gly Gly Pro Ser
            20                  25                  30

Ser Gly Ala Pro Pro Pro Ser Cys
        35                  40

<210> SEQ ID NO 296
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
```

```
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (40)..(40)
<223> OTHER INFORMATION: Cys at position 40 is amidated

<400> SEQUENCE: 296

Tyr Xaa Glu Gly Thr Xaa Thr Ser Asp Xaa Ser Ile Xaa Leu Asp Xaa
1               5                   10                  15

Gln Ala Gln Xaa Glu Phe Ile Xaa Xaa Leu Ile Glu Gly Gly Pro Ser
            20                  25                  30

Ser Gly Ala Pro Pro Pro Ser Cys
        35                  40

<210> SEQ ID NO 297
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: The C-terminal Gly is modified with R2 to
      provide PSSG-R2, wherein the modification is NH2 or absent.

<400> SEQUENCE: 297

Pro Ser Ser Gly
1

<210> SEQ ID NO 298
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: The C-terminal Ser is modified with R2 to
      provide PSSGAPPPS-R2, wherein the modification is NH2 or absent.

<400> SEQUENCE: 298

Pro Ser Ser Gly Ala Pro Pro Pro Ser
1               5

<210> SEQ ID NO 299
<211> LENGTH: 4
<212> TYPE: PRT
<213> ORGANISM: Artificial Sequence
<220> FEATURE:
<223> OTHER INFORMATION: Synthetic Construct

<400> SEQUENCE: 299

Pro Ser Ser Gly
1

<210> SEQ ID NO 300
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Gly at position 4 is amidated
```

```
<400> SEQUENCE: 300

Pro Ser Ser Gly
1

<210> SEQ ID NO 301
<211> LENGTH: 9
<212> TYPE: PRT
<213> ORGANISM: Artificial Sequence
<220> FEATURE:
<223> OTHER INFORMATION: Synthetic Construct

<400> SEQUENCE: 301

Pro Ser Ser Gly Ala Pro Pro Pro Ser
1               5

<210> SEQ ID NO 302
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Ser at position 9 is amidated

<400> SEQUENCE: 302

Pro Ser Ser Gly Ala Pro Pro Pro Ser
1               5

<210> SEQ ID NO 303
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 303

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Ala Gly Gly Pro Ser
            20                  25                  30

Ser Gly Ala Pro Pro Pro Ser
            35

<210> SEQ ID NO 304
<211> LENGTH: 39
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 304

Tyr Xaa Glu Gly Thr Phe Thr Ser Asp Tyr Ser Ile Xaa Leu Asp Lys
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
            35

<210> SEQ ID NO 305
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 305

Xaa Xaa Glu Gly Thr Phe Thr Ser Asp Tyr Ser Ile Xaa Leu Asp Lys
1               5                   10                  15

Lys Ala Gln Xaa Glu Phe Ile Glu Tyr Leu Ile Ala Gly Gly Pro Ser
            20                  25                  30
```

```
Ser Gly Ala Pro Pro Pro Ser
        35

<210> SEQ ID NO 306
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 306

Xaa Xaa Glu Gly Thr Phe Thr Ser Asp Tyr Ser Ile Xaa Leu Asp Xaa
1               5                   10                  15

Lys Ala Gln Xaa Ala Phe Ile Xaa Tyr Leu Ile Ala Gly Gly Pro Ser
            20                  25                  30

Ser Gly Ala Pro Pro Pro Ser
        35

<210> SEQ ID NO 307
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
```

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 307

Xaa Xaa Glu Gly Thr Phe Thr Ser Asp Tyr Ser Ile Xaa Leu Asp Lys
1               5                   10                  15

Lys Ala Gln Xaa Glu Phe Ile Glu Xaa Leu Ile Ala Gly Gly Pro Ser
            20                  25                  30

Ser Gly Ala Pro Pro Pro Ser
        35

<210> SEQ ID NO 308
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 308

Xaa Xaa Glu Gly Thr Phe Thr Ser Asp Tyr Ser Ile Xaa Leu Asp Xaa
1               5                   10                  15

Lys Ala Gln Xaa Glu Phe Ile Glu Xaa Leu Ile Ala Gly Gly Pro Ser
            20                  25                  30
```

```
Ser Gly Ala Pro Pro Pro Ser
            35

<210> SEQ ID NO 309
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MOD_RES
<222> LOCATION: (30)..(30)
<223> OTHER INFORMATION: Gly at position 30 is amidated

<400> SEQUENCE: 309

Tyr Xaa Glu Gly Thr Phe Thr Ser Asp Tyr Ser Ile Leu Leu Asp Lys
1               5                   10                  15

Lys Ala Gln Gln Ala Phe Ile Glu Tyr Leu Ile Glu Gly Gly
            20                  25                  30

<210> SEQ ID NO 310
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MOD_RES
<222> LOCATION: (30)..(30)
<223> OTHER INFORMATION: Gly at position 30 is amidated

<400> SEQUENCE: 310

Tyr Xaa Glu Gly Thr Phe Thr Ser Asp Tyr Ser Ile Leu Leu Asp Lys
1               5                   10                  15

Lys Ala Gln His Ala Phe Ile Glu Tyr Leu Ile Glu Gly Gly
            20                  25                  30

<210> SEQ ID NO 311
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
```

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MOD_RES
<222> LOCATION: (34)..(34)
<223> OTHER INFORMATION: Gly at position 34 is amidated

<400> SEQUENCE: 311

Tyr Xaa Glu Gly Thr Phe Thr Ser Asp Tyr Ser Ile Leu Leu Asp Lys
1               5                   10                  15

Lys Ala Gln Lys Ala Phe Ile Glu Tyr Leu Ile Glu Gly Gly Pro Ser
            20                  25                  30

Ser Gly

<210> SEQ ID NO 312
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 312

Tyr Xaa Glu Gly Thr Phe Thr Ser Asp Tyr Ser Ile Leu Leu Asp Lys
1               5                   10                  15

Lys Ala Gln Xaa Glu Phe Ile Glu Tyr Leu Ile Ala Gly Gly
            20                  25                  30

<210> SEQ ID NO 313
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
```

```
<222> LOCATION: (34)..(34)
<223> OTHER INFORMATION: Gly at position 34 is amidated

<400> SEQUENCE: 313

Tyr Xaa Glu Gly Thr Phe Thr Ser Asp Tyr Ser Ile Leu Leu Asp Lys
1               5                   10                  15
Lys Ala Gln Xaa Ala Phe Val Glu Tyr Leu Ile Glu Gly Gly Pro Ser
            20                  25                  30
Ser Gly

<210> SEQ ID NO 314
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 314

Tyr Xaa Glu Gly Thr Phe Thr Ser Asp Tyr Ser Ile Leu Leu Asp Lys
1               5                   10                  15
Lys Ala Gln Xaa Ala Phe Leu Glu Tyr Leu Ile Glu Gly Gly Pro Ser
            20                  25                  30
Ser Gly

<210> SEQ ID NO 315
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
```

<223> OTHER INFORMATION: Gly at position 34 is amidated

<400> SEQUENCE: 315

Tyr Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly

<210> SEQ ID NO 316
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 316

Tyr Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly

<210> SEQ ID NO 317
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib

```
<220> FEATURE:
<221> NAME/KEY: MOD_RES
<222> LOCATION: (34)..(34)
<223> OTHER INFORMATION: Gly at position 34 is amidated

<400> SEQUENCE: 317

Tyr Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly

<210> SEQ ID NO 318
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 318

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly

<210> SEQ ID NO 319
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
```

```
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 319

Tyr Xaa Glu Gly Thr Phe Thr Ser Asp Tyr Ser Ile Xaa Leu Asp Lys
1               5                   10                  15

Lys Ala Gln Xaa Glu Phe Ile Glu Tyr Leu Ile Glu Gly Gly Pro Ser
            20                  25                  30

Ser Gly

<210> SEQ ID NO 320
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 320

Tyr Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Ala Gly Gly Pro Ser
            20                  25                  30

Ser Gly

<210> SEQ ID NO 321
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
```

```
        (2-[2-(2-amino-ethoxy)-ethoxy]-acetyl)2-(gamma-Glu)-CO-(CH2)16-CO
        2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 321

Tyr Xaa Glu Gly Thr Phe Thr Ser Asp Tyr Ser Ile Xaa Leu Asp Lys
1               5                   10                  15

Lys Ala Gln Xaa Glu Phe Ile Glu Tyr Leu Ile Ala Gly Gly Pro Ser
            20                  25                  30

Ser Gly

<210> SEQ ID NO 322
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
        conjugation of the epsilon-amino group of the Lys side chain with
        (2-[2-(2-amino-ethoxy)-ethoxy]-acetyl)2-(gamma-Glu)-CO-(CH2)16-CO
        2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 322

Tyr Xaa Glu Gly Thr Xaa Thr Ser Asp Tyr Ser Ile Leu Leu Asp Glu
1               5                   10                  15

Lys Ala Gln Xaa Ala Phe Ile Glu Tyr Leu Ile Glu Gly Gly Pro Ser
            20                  25                  30

Ser Gly

<210> SEQ ID NO 323
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
```

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 323

Tyr Xaa Glu Gly Thr Xaa Thr Ser Asp Tyr Ser Ile Leu Leu Asp Lys
1               5                   10                  15

Lys Ala Gln Xaa Glu Phe Ile Glu Tyr Leu Ile Glu Gly Gly Pro Ser
            20                  25                  30

Ser Gly

<210> SEQ ID NO 324
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 324

Tyr Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Ala Gly Gly Pro Ser
            20                  25                  30

Ser Gly

<210> SEQ ID NO 325
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
```

```
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 325

Tyr Xaa Glu Gly Thr Xaa Thr Ser Asp Tyr Ser Ile Leu Leu Asp Lys
1               5                   10                  15

Lys Ala Gln Xaa Glu Phe Ile Glu Tyr Leu Ile Ala Gly Gly Pro Ser
            20                  25                  30

Ser Gly

<210> SEQ ID NO 326
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 326

Tyr Xaa Glu Gly Thr Xaa Thr Ser Asp Tyr Ser Ile Leu Leu Asp Glu
1               5                   10                  15

Lys Ala Gln Xaa Ala Phe Ile Glu Tyr Leu Ile Glu Gly Gly Pro Ser
            20                  25                  30

Ser Gly

<210> SEQ ID NO 327
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
```

```
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 327

Tyr Xaa Glu Gly Thr Xaa Thr Ser Asp Tyr Ser Ile Leu Leu Asp Lys
1               5                   10                  15

Lys Ala Gln Xaa Glu Phe Ile Glu Tyr Leu Ile Glu Gly Gly Pro Ser
            20                  25                  30

Ser Gly

<210> SEQ ID NO 328
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 328

Tyr Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Ala Gly Gly Pro Ser
            20                  25                  30

Ser Gly

<210> SEQ ID NO 329
<211> LENGTH: 34
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 329

Tyr Xaa Glu Gly Thr Xaa Thr Ser Asp Tyr Ser Ile Leu Leu Asp Lys
1               5                   10                  15

Lys Ala Gln Xaa Glu Phe Ile Glu Tyr Leu Ile Ala Gly Gly Pro Ser
            20                  25                  30

Ser Gly

<210> SEQ ID NO 330
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 330

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 331
<211> LENGTH: 39
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 331

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Ala Gly Gly Pro Ser
            20                  25                  30

Ser Gly Ala Pro Pro Pro Ser
        35

<210> SEQ ID NO 332
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 332

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Ala Gly Gly Pro Ser
            20                  25                  30

Ser Gly

<210> SEQ ID NO 333
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
```

-continued

```
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 333

Tyr Xaa Glu Gly Thr Phe Thr Ser Asp Tyr Ser Ile Leu Leu Asp Lys
1               5                   10                  15

Lys Ala Gln Xaa Glu Phe Ile Glu Tyr Leu Ile Ala Gly Gly Pro Ser
            20                  25                  30

Ser Gly

<210> SEQ ID NO 334
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 334

Tyr Xaa Glu Gly Thr Phe Thr Ser Asp Tyr Ser Ile Leu Leu Asp Lys
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
        35

<210> SEQ ID NO 335
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
```

```
            (2-[2-(2-amino-ethoxy)-ethoxy]-acetyl)2-(gamma-Glu)-CO-(CH2)16-CO
            2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 335

Tyr Xaa Glu Gly Thr Phe Thr Ser Asp Tyr Ser Ile Leu Leu Asp Lys
1               5                   10                  15

Lys Ala Gln Xaa Asp Phe Ile Glu Tyr Leu Ile Glu Gly Gly Pro Ser
            20                  25                  30

Ser Gly

<210> SEQ ID NO 336
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 336

Tyr Xaa Glu Gly Thr Phe Thr Ser Asp Tyr Ser Ile Leu Leu Asp Lys
1               5                   10                  15

Lys Ala Gln Xaa Thr Phe Ile Glu Tyr Leu Ile Glu Gly Gly Pro Ser
            20                  25                  30

Ser Gly

<210> SEQ ID NO 337
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
```

<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 337

Tyr Xaa Glu Gly Thr Phe Thr Ser Asp Tyr Ser Ile Leu Leu Asp Lys
1               5                   10                  15

Lys Ala Gln Xaa His Phe Ile Glu Tyr Leu Ile Glu Gly Gly Pro Ser
            20                  25                  30

Ser Gly

<210> SEQ ID NO 338
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 338

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 339
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO

```
                                    2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 339

Tyr Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Ala Gly Gly Pro Ser
            20                  25                  30

Ser Gly Ala Pro Pro Pro Ser
        35

<210> SEQ ID NO 340
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 340

Tyr Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 341
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
```

```
         (2-[2-(2-amino-ethoxy)-ethoxy]-acetyl)2-(gamma-Glu)-CO-(CH2)18-CO
         2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 341

Phe Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 342
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 342

Phe Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 343
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
```

<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 343

Phe Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Glu Ala Gly Pro Ser
            20                  25                  30

Ser Gly Ala Pro Pro Pro Ser
            35

<210> SEQ ID NO 344
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 344

Xaa Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 345
<211> LENGTH: 39
<212> TYPE: PRT
<213> ORGANISM: Artificial Sequence
<220> FEATURE:

<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
    conjugation of the epsilon-amino group of the Lys side chain with
    (2-[2-(2-amino-ethoxy)-ethoxy]-acetyl)2-(gamma-Glu)-CO-(CH2)18-CO
    2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 345

Tyr Xaa Glu Gly Thr Phe Thr Ser Asp Tyr Ser Ile Leu Leu Asp Glu
1               5                   10                  15

Lys Ala Gln Xaa Ala Phe Ile Glu Tyr Leu Ile Ala Gly Gly Pro Ser
            20                  25                  30

Ser Gly Ala Pro Pro Pro Ser
        35

<210> SEQ ID NO 346
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
    conjugation of the epsilon-amino group of the Lys side chain with
    (2-[2-(2-amino-ethoxy)-ethoxy]-acetyl)2-(gamma-Glu)-CO-(CH2)18-CO
    2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 346

Tyr Xaa Glu Gly Thr Phe Thr Ser Asp Tyr Ser Ile Xaa Leu Asp Glu
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
        35

<210> SEQ ID NO 347
<211> LENGTH: 39
<212> TYPE: PRT
<213> ORGANISM: Artificial Sequence -continued

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 2 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 347

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Ile Ala Gly Gly Pro Ser
                20                  25                  30

Ser Gly Ala Pro Pro Pro Ser
            35

<210> SEQ ID NO 348
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 348

Tyr Xaa Glu Gly Thr Phe Thr Ser Asp Tyr Ser Ile Xaa Leu Asp Lys
1               5                   10                  15

Lys Ala Gln Xaa Glu Phe Ile Glu Tyr Leu Ile Glu Gly Gly Pro Ser
                20                  25                  30

Ser Gly Ala Pro Pro Pro Ser
            35
```

```
<210> SEQ ID NO 349
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 349

Xaa Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 350
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
```

<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 350

Xaa Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 351
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 351

Xaa Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 352
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:

```
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 352

Phe Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Ala Gly Gly Pro Ser
            20                  25                  30

Ser Gly Ala Pro Pro Pro Ser
            35

<210> SEQ ID NO 353
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 353

Phe Xaa Glu Gly Thr Phe Thr Ser Asp Tyr Ser Ile Xaa Leu Asp Lys
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
            35

<210> SEQ ID NO 354
<211> LENGTH: 39
<212> TYPE: PRT
<213> ORGANISM: Artificial Sequence
<220> FEATURE:
<223> OTHER INFORMATION: Synthetic Construct
```

-continued

```
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(gamma-Glu)-CO-(CH2)18-CO2
      H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 354

Tyr Xaa Glu Gly Thr Phe Thr Ser Asp Tyr Ser Ile Xaa Leu Asp Lys
1               5                   10                  15

Lys Ala Gln Xaa Glu Phe Ile Glu Tyr Leu Ile Ala Gly Gly Pro Ser
                20                  25                  30

Ser Gly Ala Pro Pro Pro Ser
        35

<210> SEQ ID NO 355
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 355

Xaa Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Ala Gly Gly Pro Ser
                20                  25                  30

Ser Gly Ala Pro Pro Pro Ser
```

```
<210> SEQ ID NO 356
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 356

Xaa Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Ile Ala Gly Gly Pro Ser
            20                  25                  30

Ser Gly Ala Pro Pro Ser
        35

<210> SEQ ID NO 357
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
```

```
<221> NAME/KEY: MOD_RES
<222> LOCATION: (39)..(39)
<223> OTHER INFORMATION: Ser at position 39 is amidated

<400> SEQUENCE: 357

Xaa Xaa Glu Gly Thr Phe Thr Ser Asp Tyr Ser Ile Xaa Leu Asp Glu
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
            35

<210> SEQ ID NO 358
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 358

Tyr Xaa Glu Gly Thr Phe Thr Ser Asp Tyr Ser Ile Xaa Leu Asp Glu
1               5                   10                  15

Lys Ala Gln Xaa Ala Phe Ile Xaa Tyr Leu Ile Ala Gly Gly Pro Ser
            20                  25                  30

Ser Gly Ala Pro Pro Pro Ser
            35

<210> SEQ ID NO 359
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
```

<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)18-CO
2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 359

Tyr Xaa Glu Gly Thr Phe Thr Ser Asp Tyr Ser Ile Xaa Leu Asp Glu
1               5                   10                  15

Lys Ala Gln Xaa Asp Phe Ile Glu Tyr Leu Ile Ala Gly Gly Pro Ser
            20                  25                  30

Ser Gly Ala Pro Pro Pro Ser
        35

<210> SEQ ID NO 360
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)18-CO
2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 360

Xaa Xaa Glu Gly Thr Xaa Thr Ser Asp Tyr Ser Ile Xaa Leu Asp Lys
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
        35

<210> SEQ ID NO 361
<211> LENGTH: 39
<212> TYPE: PRT
<213> ORGANISM: Artificial Sequence

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 361

Xaa Xaa Glu Gly Thr Phe Thr Ser Asp Tyr Ser Ile Xaa Leu Asp Xaa
1               5                   10                  15

Lys Ala Gln Xaa Ala Phe Ile Glu Tyr Leu Ile Ala Gly Gly Pro Ser
            20                  25                  30

Ser Gly Ala Pro Pro Pro Ser
        35

<210> SEQ ID NO 362
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
```

```
<220> FEATURE:
<221> NAME/KEY: MOD_RES
<222> LOCATION: (39)..(39)
<223> OTHER INFORMATION: Ser at position 39 is amidated

<400> SEQUENCE: 362

Xaa Xaa Glu Gly Thr Phe Thr Ser Asp Tyr Ser Ile Xaa Leu Asp Xaa
1               5                   10                  15

Lys Ala Gln Xaa Ala Phe Ile Glu Tyr Leu Ile Ala Gly Gly Pro Ser
            20                  25                  30

Ser Gly Ala Pro Pro Pro Ser
            35

<210> SEQ ID NO 363
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dap
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 363

Xaa Xaa Glu Gly Thr Phe Thr Ser Asp Tyr Ser Ile Xaa Leu Asp Xaa
1               5                   10                  15

Lys Ala Gln Xaa Ala Phe Ile Glu Tyr Leu Ile Ala Gly Gly Pro Ser
            20                  25                  30

Ser Gly Ala Pro Pro Pro Ser
            35

<210> SEQ ID NO 364
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
```

<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 364

Xaa Xaa Glu Gly Thr Phe Thr Ser Asp Tyr Ser Ile Xaa Leu Asp Xaa
1               5                   10                  15

Lys Ala Gln Xaa Glu Phe Ile Glu Tyr Leu Ile Ala Gly Gly Pro Ser
                20                  25                  30

Ser Gly Ala Pro Pro Pro Ser
            35

<210> SEQ ID NO 365
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 365

Xaa Xaa Glu Gly Thr Phe Thr Ser Asp Tyr Ser Ile Xaa Leu Asp Xaa

```
                1               5                  10                 15
Lys Ala Gln Xaa Glu Phe Ile Glu Tyr Leu Ile Ala Gly Gly Pro Ser
                20                  25                 30

Ser Gly Ala Pro Pro Ser
        35

<210> SEQ ID NO 366
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dap
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 366

Xaa Xaa Glu Gly Thr Phe Thr Ser Asp Tyr Ser Ile Xaa Leu Asp Xaa
1               5                   10                  15

Lys Ala Gln Xaa Glu Phe Ile Glu Tyr Leu Ile Ala Gly Gly Pro Ser
                20                  25                 30

Ser Gly Ala Pro Pro Ser
        35

<210> SEQ ID NO 367
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
```

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 367

Xaa Xaa Glu Gly Thr Phe Thr Ser Asp Tyr Ser Ile Xaa Leu Asp Lys
1               5                   10                  15

Lys Ala Gln Xaa Ala Phe Ile Xaa Tyr Leu Ile Ala Gly Gly Pro Ser
            20                  25                  30

Ser Gly Ala Pro Pro Pro Ser
            35

<210> SEQ ID NO 368
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 368

Xaa Xaa Glu Gly Thr Phe Thr Ser Asp Tyr Ser Ile Xaa Leu Asp Lys
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35
```

<210> SEQ ID NO 369
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 369

Xaa Xaa Glu Gly Thr Phe Thr Ser Asp Tyr Ser Ile Xaa Leu Asp Xaa
1               5                   10                  15

Lys Ala Gln Xaa Glu Phe Ile Xaa Tyr Leu Ile Ala Gly Gly Pro Ser
            20                  25                  30

Ser Gly Ala Pro Pro Pro Ser
        35

<210> SEQ ID NO 370
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 370

Xaa Xaa Glu Gly Thr Phe Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 371
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 371

Xaa Xaa Glu Gly Thr Phe Thr Ser Asp Tyr Ser Ile Xaa Leu Asp Lys
1               5                   10                  15

Lys Ala Gln Xaa Ala Phe Ile Xaa Tyr Leu Ile Glu Gly Gly Pro Ser
            20                  25                  30

Ser Gly Ala Pro Pro Pro Ser
        35
```

```
<210> SEQ ID NO 372
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 372

Xaa Xaa Glu Gly Thr Phe Thr Ser Asp Tyr Ser Ile Xaa Leu Asp Xaa
1               5                   10                  15

Lys Ala Gln Xaa Ala Phe Ile Xaa Tyr Leu Ile Glu Gly Gly Pro Ser
            20                  25                  30

Ser Gly Ala Pro Pro Pro Ser
        35

<210> SEQ ID NO 373
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
```

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 373

Xaa Xaa Glu Gly Thr Phe Thr Ser Asp Tyr Ser Ile Xaa Leu Asp Xaa
1               5                   10                  15

Lys Ala Gln Xaa Ala Phe Val Glu Tyr Leu Ile Ala Gly Gly Pro Ser
            20                  25                  30

Ser Gly Ala Pro Pro Pro Ser
            35

<210> SEQ ID NO 374
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 374

Xaa Xaa Glu Gly Thr Phe Thr Ser Asp Tyr Ser Ile Xaa Leu Asp Xaa
1               5                   10                  15

Lys Ala Gln Xaa Glu Phe Val Glu Tyr Leu Ile Ala Gly Gly Pro Ser
            20                  25                  30

Ser Gly Ala Pro Pro Pro Ser
            35

<210> SEQ ID NO 375
<211> LENGTH: 39
<212> TYPE: PRT
```

<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 375

Xaa Xaa Glu Gly Thr Phe Thr Ser Asp Tyr Ser Ile Xaa Leu Asp Xaa
1               5                   10                  15

Lys Ala Gln Xaa Ala Phe Val Glu Tyr Leu Ile Glu Gly Gly Pro Ser
            20                  25                  30

Ser Gly Ala Pro Pro Pro Ser
        35

<210> SEQ ID NO 376
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)

<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 376

Xaa Xaa Glu Gly Thr Phe Thr Ser Asp Tyr Ser Ile Xaa Leu Asp Lys
1               5                   10                  15

Lys Ala Gln Xaa Ala Phe Val Xaa Tyr Leu Ile Ala Gly Gly Pro Ser
            20                  25                  30

Ser Gly Ala Pro Pro Pro Ser
            35

<210> SEQ ID NO 377
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 377

Xaa Xaa Glu Gly Thr Phe Thr Ser Asp Tyr Ser Ile Xaa Leu Asp Xaa
1               5                   10                  15

Lys Ala Gln Xaa Ala Phe Val Xaa Tyr Leu Ile Ala Gly Gly Pro Ser
            20                  25                  30

Ser Gly Ala Pro Pro Pro Ser
            35

<210> SEQ ID NO 378
<211> LENGTH: 39
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 378

Xaa Xaa Glu Gly Thr Phe Thr Ser Asp Tyr Ser Ile Xaa Leu Asp Xaa
1               5                  10                  15

Lys Ala Gln Xaa Ala Phe Ile Xaa Tyr Leu Ile Ala Gly Gly Pro Ser
            20                  25                  30

Ser Gly Ala Pro Pro Ser
        35

<210> SEQ ID NO 379
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
```

<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 379

Xaa Xaa Glu Gly Thr Phe Thr Ser Asp Tyr Ser Ile Xaa Leu Asp Xaa
1               5                   10                  15

Lys Ala Gln Xaa Ala Phe Val Xaa Tyr Leu Ile Ala Gly Gly Pro Ser
            20                  25                  30

Ser Gly Ala Pro Pro Pro Ser
            35

<210> SEQ ID NO 380
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 380

Xaa Xaa Glu Gly Thr Phe Thr Ser Asp Tyr Ser Ile Xaa Leu Asp Lys
1               5                   10                  15

Lys Ala Gln Xaa Ala Phe Ile Glu Xaa Leu Ile Ala Gly Gly Pro Ser
            20                  25                  30

Ser Gly Ala Pro Pro Pro Ser
            35

<210> SEQ ID NO 381
<211> LENGTH: 39
<212> TYPE: PRT
<213> ORGANISM: Artificial Sequence
<220> FEATURE:
<223> OTHER INFORMATION: Synthetic Construct
<220> FEATURE:

<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 381

Xaa Xaa Glu Gly Thr Phe Thr Ser Asp Tyr Ser Ile Xaa Leu Asp Xaa
1               5                   10                  15

Lys Ala Gln Xaa Ala Phe Ile Glu Xaa Leu Ile Ala Gly Gly Pro Ser
            20                  25                  30

Ser Gly Ala Pro Pro Pro Ser
        35

<210> SEQ ID NO 382
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)

<223> OTHER INFORMATION: Ser at position 39 is amidated

<400> SEQUENCE: 382

Tyr Xaa Glu Gly Thr Phe Thr Ser Asp Tyr Ser Ile Xaa Leu Asp Lys
1               5                   10                  15

Lys Ala Gln Xaa Glu Phe Ile Glu Xaa Leu Ile Ala Gly Gly Pro Ser
            20                  25                  30

Ser Gly Ala Pro Pro Pro Ser
        35

<210> SEQ ID NO 383
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 383

Xaa Xaa Glu Gly Thr Phe Thr Ser Asp Tyr Ser Ile Xaa Leu Asp Xaa
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
        35

<210> SEQ ID NO 384
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:

```
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 384

Xaa Xaa Glu Gly Thr Phe Thr Ser Asp Tyr Ser Ile Xaa Leu Asp Xaa
1               5                   10                  15

Lys Ala Gln Xaa Asp Phe Ile Glu Tyr Leu Ile Ala Gly Gly Pro Ser
            20                  25                  30

Ser Gly Ala Pro Pro Pro Ser
        35

<210> SEQ ID NO 385
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 385

Xaa Xaa Glu Gly Thr Phe Thr Ser Asp Tyr Ser Ile Xaa Leu Asp Xaa
1               5                   10                  15

Lys Ala Gln Xaa Glu Phe Ile Glu Tyr Leu Ile Ala Gly Gly Pro Ser
```

Ser Gly

<210> SEQ ID NO 386
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(gamma-Glu)-CO-(CH2)18-CO2
      H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 386

Xaa Xaa Glu Gly Thr Phe Thr Ser Asp Tyr Ser Ile Xaa Leu Asp Xaa
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
        35

<210> SEQ ID NO 387
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(gamma-Glu)-CO-(CH2)18-CO2

```
                                      H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 387

Xaa Xaa Glu Gly Thr Phe Thr Ser Asp Tyr Ser Ile Xaa Leu Asp Lys
1               5                   10                  15

Lys Ala Gln Xaa Glu Phe Ile Glu Xaa Leu Ile Ala Gly Gly Pro Ser
            20                  25                  30

Ser Gly Ala Pro Pro Pro Ser
            35

<210> SEQ ID NO 388
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(gamma-Glu)-CO-(CH2)18-CO2
      H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 388

Xaa Xaa Glu Gly Thr Phe Thr Ser Asp Tyr Ser Ile Xaa Leu Asp Lys
1               5                   10                  15

Lys Ala Gln Xaa Ala Phe Ile Glu Xaa Leu Ile Ala Gly Gly Pro Ser
            20                  25                  30

Ser Gly Ala Pro Pro Pro Ser
            35

<210> SEQ ID NO 389
<211> LENGTH: 39
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 389

Xaa Xaa Glu Gly Thr Phe Thr Ser Asp Tyr Ser Ile Xaa Leu Asp Lys
 1               5                  10                  15

Lys Ala Gln Xaa Glu Phe Ile Glu Xaa Leu Ile Ala Gly Gly Pro Ser
            20                  25                  30

Ser Gly Ala Pro Pro Pro Ser
            35

<210> SEQ ID NO 390
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
```

<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 390

Xaa Xaa Glu Gly Thr Phe Thr Ser Asp Tyr Ser Ile Xaa Leu Asp Xaa
1               5                   10                  15

Lys Ala Gln Xaa Glu Phe Ile Glu Xaa Leu Ile Ala Gly Gly Pro Ser
            20                  25                  30

Ser Gly Ala Pro Pro Pro Ser
        35

<210> SEQ ID NO 391
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 391

Xaa Xaa Glu Gly Thr Phe Thr Ser Asp Tyr Ser Ile Xaa Leu Asp Lys
1               5                   10                  15

Lys Ala Gln Xaa Ala Phe Ile Glu Xaa Leu Ile Ala Gly Gly Pro Ser
            20                  25                  30

Ser Gly Ala Pro Pro Pro Ser
        35

<210> SEQ ID NO 392
<211> LENGTH: 39
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 392

Xaa Xaa Glu Gly Thr Phe Thr Ser Asp Tyr Ser Ile Xaa Leu Asp Xaa
1               5                   10                  15

Lys Ala Gln Xaa Ala Phe Ile Glu Xaa Leu Ile Ala Gly Gly Pro Ser
            20                  25                  30

Ser Gly Ala Pro Pro Pro Ser
        35

<210> SEQ ID NO 393
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(gamma-Glu)-CO-(CH2)18-CO2
      H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
```

<223> OTHER INFORMATION: Ser at position 39 is amidated

<400> SEQUENCE: 393

Xaa Xaa Glu Gly Thr Phe Thr Ser Asp Tyr Ser Ile Xaa Leu Asp Lys
1               5                   10                  15

Lys Ala Gln Xaa Glu Phe Ile Glu Tyr Leu Ile Ala Gly Gly Pro Ser
            20                  25                  30

Ser Gly Ala Pro Pro Pro Ser
        35

<210> SEQ ID NO 394
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 394

Xaa Xaa Glu Gly Thr Phe Thr Ser Asp Tyr Ser Ile Xaa Leu Asp Lys
1               5                   10                  15

Lys Ala Gln Xaa Glu Phe Ile Glu Xaa Leu Ile Glu Gly Gly Pro Ser
            20                  25                  30

Ser Gly Ala Pro Pro Pro Ser
        35

<210> SEQ ID NO 395
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:

```
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 395

Xaa Xaa Glu Gly Thr Phe Thr Ser Asp Tyr Ser Ile Xaa Leu Asp Xaa
1               5                   10                  15

Lys Ala Gln Xaa Glu Phe Ile Glu Xaa Leu Ile Glu Gly Gly Pro Ser
                20                  25                  30

Ser Gly Ala Pro Pro Pro Ser
            35

<210> SEQ ID NO 396
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is D-Tyr
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-CO
      2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 396
```

-continued

```
Xaa Xaa Glu Gly Thr Phe Thr Ser Asp Tyr Ser Ile Xaa Leu Asp Glu
1           5                   10              15

Lys Ala Gln Xaa Ala Phe Ile Glu Xaa Leu Ile Ala Gly Gly Pro Ser
            20              25                  30

Ser Gly Ala Pro Pro Pro Ser
        35
```

We claim:

1. A compound wherein the compound is any one of the amino acid sequences selected from the group consisting of SEQ ID NO:10, SEQ ID NO:11, SEQ ID NO:12, SEQ ID NO:13, and SEQ ID NO:14, or a pharmaceutically acceptable salt thereof.

2. A compound as claimed by claim 1 wherein the compound is SEQ ID NO:13, or a pharmaceutically acceptable salt thereof.

3. A compound as claimed by claim 1 wherein the compound is SEQ ID NO:10, or a pharmaceutically acceptable salt thereof.

4. A compound as claimed by claim 1 wherein the compound is SEQ ID NO:11, or a pharmaceutically acceptable salt thereof.

5. A compound as claimed by claim 1 wherein the compound is SEQ ID NO:12, or a pharmaceutically acceptable salt thereof.

6. A compound as claimed by claim 1 wherein the compound is SEQ ID NO:14, or a pharmaceutically acceptable salt thereof.

7. A pharmaceutical composition comprising any one of the compounds as claimed by claim 1, or a pharmaceutically acceptable salt thereof, and at least one pharmaceutically acceptable carrier, diluent, or excipient.

8. A method of treating type 2 diabetes mellitus or obesity comprising; administering an effective amount of any one of the compounds as claimed by claim 1, or a pharmaceutically acceptable salt thereof, to a patient in need thereof.

9. A method of treating type 2 diabetes or obesity comprising administering an effective amount of a compound of the amino acid sequence SEQ ID NO:13, or a pharmaceutically acceptable salt thereof, to a patient in need thereof.

10. A method of providing therapeutic weight loss, comprising administering an effective amount of any one of the compounds as claimed by claim 1, or a pharmaceutically acceptable salt thereof, to a subject in need thereof.

* * * * *

UNITED STATES PATENT AND TRADEMARK OFFICE
CERTIFICATE OF CORRECTION

PATENT NO. : 11,084,861 B2  
APPLICATION NO. : 16/518468  
DATED : August 10, 2021  
INVENTOR(S) : Milata Mary Abraham et al.

It is certified that error appears in the above-identified patent and that said Letters Patent is hereby corrected as shown below:

On the Title Page

Item (56) Column 2, Line 12 Delete "tiral;" and insert -- trial; --, therefor.

Item (56) Column 2, Line 18 Delete "Translationl" and insert -- Translational --, therefor.

In the Claims

In Claim 8, Column 570, Line 19 Delete "comprising;" and insert -- comprising --, therefor.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*